(12) United States Patent
Schenkel et al.

(10) Patent No.: US 12,398,146 B2
(45) Date of Patent: *Aug. 26, 2025

(54) HETEROBICYCLIC AMIDES AS INHIBITORS OF CD38

(71) Applicant: Boehringer Ingelheim International GmbH, Ingelheim (DE)

(72) Inventors: Laurie B. Schenkel, Cambridge, MA (US); Melissa Marie Vasbinder, Cambridge, MA (US); Kevin Wayne Kuntz, Cambridge, MA (US); Nicholas Robert Perl, Cambridge, MA (US); Jennifer Downing, Cambridge, MA (US)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/638,989

(22) Filed: Apr. 18, 2024

(65) Prior Publication Data

US 2024/0368167 A1 Nov. 7, 2024

Related U.S. Application Data

(63) Continuation of application No. 18/074,746, filed on Dec. 5, 2022, now Pat. No. 11,987,584, which is a continuation of application No. 16/942,857, filed on Jul. 30, 2020, now Pat. No. 11,535,621.

(60) Provisional application No. 63/034,750, filed on Jun. 4, 2020, provisional application No. 62/951,604, filed on Dec. 20, 2019, provisional application No. 62/880,923, filed on Jul. 31, 2019.

(51) Int. Cl.
| | |
|---|---|
| C07D 487/04 | (2006.01) |
| A61P 35/00 | (2006.01) |
| C07D 403/10 | (2006.01) |
| C07D 417/10 | (2006.01) |
| C07D 471/04 | (2006.01) |
| C07D 473/32 | (2006.01) |
| C07D 495/04 | (2006.01) |
| C07D 513/04 | (2006.01) |

(52) U.S. Cl.
CPC ............ *C07D 487/04* (2013.01); *A61P 35/00* (2018.01); *C07D 403/10* (2013.01); *C07D 417/10* (2013.01); *C07D 471/04* (2013.01); *C07D 473/32* (2013.01); *C07D 495/04* (2013.01); *C07D 513/04* (2013.01)

(58) Field of Classification Search
CPC .. C07D 417/10; C07D 417/04; C07D 487/04; C07D 403/10; C07D 471/04; C07D 473/32; C07D 495/04; C07D 513/04; A61P 35/00
See application file for complete search history.

(56) References Cited

U.S. PATENT DOCUMENTS

| | | | |
|---|---|---|---|
| 11,535,621 | B2 | 12/2022 | Schenkel et al. |
| 11,952,377 | B2 | 4/2024 | Downing et al. |
| 11,987,584 | B2 | 5/2024 | Schenkel et al. |
| 2013/0245016 | A1 | 9/2013 | Knight et al. |
| 2014/0256739 | A1 | 9/2014 | Bassil et al. |
| 2017/0260164 | A1 | 9/2017 | Becherer et al. |
| 2018/0273527 | A1 | 9/2018 | Krogstad et al. |
| 2021/0032251 | A1 | 2/2021 | Schenkel et al. |
| 2022/0242862 | A1 | 8/2022 | Downing et al. |
| 2024/0279224 | A1 | 8/2024 | Downing et al. |

FOREIGN PATENT DOCUMENTS

| | | |
|---|---|---|
| CN | 101679432 | 3/2010 |
| CN | 103998036 | 8/2014 |
| CN | 105017221 A | 11/2015 |
| JP | 2015-501784 A | 1/2015 |
| JP | 2016-514147 A | 5/2016 |
| JP | 2018-501215 A | 1/2018 |
| WO | WO 2011/081205 A1 | 7/2011 |
| WO | WO 2012/005805 A1 | 1/2012 |
| WO | WO 2012/075080 | 6/2012 |
| WO | WO 2012/080729 A2 | 6/2012 |
| WO | WO 2012/118812 A2 | 9/2012 |
| WO | WO 2013/039988 A1 | 3/2013 |
| WO | WO 2013/067296 | 5/2013 |
| WO | WO 2013/067302 A1 | 5/2013 |
| WO | WO 2013/188848 A2 | 12/2013 |
| WO | WO 2014/037340 A1 | 3/2014 |
| WO | WO 2014/159837 | 10/2014 |
| WO | WO 2016/087975 | 6/2016 |
| WO | WO 2017/053604 | 3/2017 |
| WO | WO 2018/151830 | 8/2018 |
| WO | WO 2019/020643 | 1/2019 |
| WO | WO 2019/067623 | 4/2019 |
| WO | WO 2021/021986 | 2/2021 |
| WO | WO 2021/087087 | 5/2021 |
| WO | WO 2021/207186 | 10/2021 |

(Continued)

OTHER PUBLICATIONS

Barbosa et al., "The enzyme CD38 (a NAD glycohydrolase, EC 3.2.2.5) is necessary for the development of diet-induced obesity," The FASEB Journal, Nov. 2007, 21(13):3629-3639.

(Continued)

*Primary Examiner* — Rebecca L Anderson
(74) *Attorney, Agent, or Firm* — Fish & Richardson P.C.

(57) ABSTRACT

The present invention relates to heterobicyclic amides and related compounds which are inhibitors of CD38 and are useful in the treatment of cancer.

53 Claims, 16 Drawing Sheets

(56) References Cited

FOREIGN PATENT DOCUMENTS

WO  WO 2022/165114  8/2022

OTHER PUBLICATIONS

Baruch et al., "Stromal CD38 regulates outgrowth of primary melanoma and generation of spontaneous metastasis," Oncotarget, Aug. 7, 2018, 9(61):31797-811.

Becherer et al., "Discovery of 4-Amino-8-quinoline Carboxamides as Novel, Submicromolar Inhibitors of NAD-Hydrolyzing Enzyme CD38," Journal of Medicinal Chemistry, Aug. 12, 2015, 58(17):7021-7056.

Bengsch et al., "Epigenomic-Guided Mass Cytometry Profiling Reveals Disease-Specific Features of Exhausted CD8 T Cells," Immunity., May 15, 2018, 48(5): 1029-1045.

Berge et al., "Pharmaceutical Salts," Journal of Pharmaceutical Science, Jan. 1977, 66(1):1-19.

Blacher et al., "Inhibition of glioma progression by a newly discovered CD38 inhibitor," Int. J. Cancer, Mar. 15, 2015, 136(6):1422-1433.

Bu et al., "CD38 knockout suppresses tumorigenesis in mice and clonogenic growth of human lung cancer cells," Carcinogenesis, Feb. 2018, 39(2):242-251.

Camacho-Pereira et al., "CD38 Dictates Age-Related NAD Decline and Mitochondrial Dysfunction through an SIRT3-Dependent Mechanism," Cell Metabolism, Jun. 14, 2016, 23(6):1127-39.

Ceni et al., "Evidence for an intracellular ADP-ribosyl cyclase/ NAD+-glycohydrolase in brain from CD38-deficient mice, " The Journal of Biological Chemistry, Oct. 17, 2003, 278(42):40670-40678.

Chatterjee et al., "CD38-NAD + Axis Regulates Immunotherapeutic Anti-Tumor T Cell Response," Cell Metabolism, Jan. 9, 2018, 27(1):85-100 (Author Manuscript).

Chen et al., "CD38-Mediated Immunosuppression as a Mechanism of Tumor Cell Escape from PD-1/PD-LI Blockade," Cancer Discovery, Sep. 2018, 8(9):1157-1175.

Chen et al., "Targeted disruption of CD38 accelerates autoimmune diabetes in NOD/Lt mice by enhancing autoimmunity in an ADP-ribosyltransferase 2-dependent fashion," The Journal of Immunology, Apr. 15, 2006, 176(8):4590-4599.

Chevrier et al., "An Immune Atlas of Clear Cell Renal Cell Carcinoma," Cell, May 4, 2017, 169(4):736-749, 33 pages.

Chini et al., "CD38 ecto-enzyme in immune cells is induced during aging and regulates NAD+ and NMN levels," Nature Metabolism, Nov. 2020, 2(11): 1284-1304.

Chini et al., "The Pharmacology of CD38/NADase: An Emerging Target in Cancer and Diseases of Aging," Trends Pharmacol. Sci., Apr. 2018, 39(4): 424-436 (Author Manuscript).

Covarrubias et al., "Senescent cells promote tissue NAD+ decline during ageing via the activation of CD38+ macrophages," Nature Metabolism, Nov. 2020, 2(11):1265-1283.

Deaglio et al., "Human CD38 (ADP-ribosyl cyclase) is a counter-receptor of CD31, an Ig superfamily member," The Journal of Immunology, Jan. 1998, 160(1):395-402.

Deaton et al., "2,4-Diamino-8-quinazoline carboxamides as novel, potent inhibitors of the NAD hydrolyzing enzyme CD38: Exploration of the 2-position structure-activity relationships," Bioorganic & Medicinal Chemistry, May 1, 2018, 26(8):2107-2150.

Deshpande et al., "Altered airway responsiveness in CD38-deficient mice," Am. J. Respir. Cell Mal. Biol., Feb. 2005, 32(2):149-56.

Deshpande et al., "CD38 in the pathogenesis of allergic airway disease: Potential therapeutic targets," Pharmacology & Therapeutics, Apr. 2017, 172:116-126.

Feng et al., "Targeting CD38 Suppresses Induction and Function of T Regulatory Cells to Mitigate Immunosuppression in Multiple Myeloma," Clinical Cancer Research, Aug. 1, 2017, 23(15):4290-4300 (Author manuascript).

Ferretti et al., "Canonical and non-canonical adenosinergic pathways," Immunol. Lett., Mar. 2018, 205:25-30.

Frerichs et al., "CD38-targeting antibodies in multiple myeloma: mechanisms of action and clinical experience," Expert Rev. Clin. Immunol., Feb. 21, 2018, 14(3):197-206 (accepted manuscript).

Fukushi et al., "Identification of cyclic ADP-ribose-dependent mechanisms in pancreatic muscarinic Ca(2+) signaling using CD38 knock-out mice, " The Journal of Biological Chemistry, Jan. 5, 2001, 276(1):649-55.

Galon et al., "Approaches to treat immune hot, altered and cold tumours with combination immunotherapies," Nat. Rev. Drug Discov., Mar. 2019, 18(3):197-218.

Golub et al., "Molecular classification of cancer: class discovery and class prediction by gene expression monitoring, " Science, Oct. 15, 1999, 286(5439):531-537.

Haag et al., "Extracellular NAD and ATP: Partners in immune cell modulation," Purinergic Signal., Mar. 2007, 3(1-2):71-81.

Haffner et al., "Discovery, Synthesis, and Biological Evaluation of Thiazoloquin(az)olin(on)es as Potent CD38 Inhibitors," Journal of Medicinal Chemistry, Apr. 2015, 58:3548-3571.

Hashimoto et al., "CD8 T Cell Exhaustion in Chronic Infection and Cancer; Opportunities for Interventions," Annu. Rev. Med., Jan. 2018, 69:301-318, 22 pages.

Hay et al., "Discovery and Optimization of Small-Molecule Ligands for the CBP/p300 Bromodomains—Supporting Information," Journal of the American Chemical Society, Jun. 19, 2014, S1-S99.

Hay et al., "Discovery and Optimization of Small-Molecule Ligands for the CBP/p300 Bromodomains," Journal of the American Chemical Society, Jul. 2014, 136(26):9308-9319.

Hogan et al., "The Multi-faceted Ecto-enzyme CD38: Roles in Immunomodulation, Cancer, Aging, and Metabolic Diseases, " Front. Immunol., May 31, 2019, 10:1187.

Horenstein et al., "A CD38/CD203a/CD73 ectoenzymatic pathway independent of CD39 drives a novel adenosinergic loop in human T lymphocytes," Oncoimmunology, Sep. 2013, 2(9):e26246.

Hubert et al., "Extracellular NAD+ shapes the Foxp3+ regulatory T cell compartment through the ART2-P2X7 pathway," J. Exp. Med., Nov. 22, 2010, 207(12):2561-8.

International Preliminary Report on Patentability in International Appln. No. PCT/US2020/044156, mailed on Feb. 1, 2022, 8 pages.

International Preliminary Report on Patentability in International Appln. No. PCT/US2022/014221, mailed on Aug. 10, 2023, 9 pages.

International Search Report and Written Opinion in International Appln. No. PCT/US2020/044156, mailed on Oct. 15, 2020, 14 pages.

International Search Report and Written Opinion in International Appln. No. PCT/US2022/014221, mailed on Apr. 12, 2022, 13 pages.

Karakasheva et al., "CD38+ M-MDSC expansion characterizes a subset of advanced colorectal cancer patients," JCI Insight, Mar. 22, 2018, 3(6):1-8.

Karakasheva et al., "CD38-Expressing Myeloid-Derived Suppressor Cells Promote Tumor Growth in a Murine Model of Esophageal Cancer," Cancer. Res., Oct. 1, 2015, 75(19):4074-4085 (Author Manuscript).

Kato et al., "CD38 disruption impairs glucose-induced increases in cyclic ADP-ribose, [Ca2+]i, and insulin secretion," The Journal of Biological Chemistry, Jan. 22, 1999, 274(4):1869-72.

Krejcik et al., "Daratumumab depletes CD38+ immune regulatory cells, promotes T-cell expansion, and skews T-cell repertoire in multiple myeloma," Blood, Jul. 21, 2016, 128(3):384-394.

Lala et al., "A Role of nitric oxide in tumor progression: lessons from experimental tumors," Cancer and Metastasis Reviews, Mar. 1998, 17(1):91-106.

Langley et al., "CD38 dependent NAD+ depletion contributes to oligodendrocyte loss and inhibition of myelin regeneration," BioRxiv, Jun. 12, 2020, 86 pages.

Lavin et al., "Innate Immune Landscape in Early Lung Adenocarcinoma by Paired Single-Cell Analyses," Cell, May 4, 2017, 169(4):750-765 (Author Manuscript).

(56) References Cited

OTHER PUBLICATIONS

Levy et al., "CD38 deficiency in the tumor microenvironment attenuates glioma progression and modulates features of tumor-associated microglia/macrophages," Neuro. Oncol., Aug. 2012, 14(8):1037-1049.
Liao et al., "CD38 enhances the proliferation and inhibits the apoptosis of cervical cancer cells by affecting the mitochondria functions," Mol. Carcinog., May 20, 2017, 56(10):2245-2257 (Accepted article).
Lv et al., "NAD+ Metabolism Maintains Inducible PD-L1 Expression to Drive Tumor Immune Evasion," Cell Metabolism, Jan. 2021, 33(1):110-127.
Mitsui-Saito et al., "CD38 gene disruption inhibits the contraction induced by alpha-adrenoceptor stimulation in mouse aorta," J. Vet. Med. Sci., Dec. 1, 2003, 65(12):1325-30.
Office Action in Chinese Appln. No. 202080066542.2, mailed on Aug. 30, 2023, 18 pages (with English translation).
Office Action in Chinese Appln. No. 202080066542.2, mailed on Mar. 18, 2024, 11 pages (with English translation).
Office Action in Indian Appln. No. 202227005086, mailed on Mar. 7, 2024, 5 pages.
Office Action in Taiwanese Appln. No. 109125742, mailed on Mar. 4, 2024, 10 pages (with English translation).
Partida-Sanchez et al., "Cyclic ADP-ribose production by CD38 regulates intracellular calcium release, extracellular calcium influx and chemotaxis in neutrophils and is required for bacterial clearance in vivo, " Nat. Med., Nov. 2001, 7(11):1209-16.
Partida-Sanchez et al., "Regulation of dendritic cell trafficking by the ADP-ribosyl cyclase CD38: impact on the development of humoral immunity," Immunity., Mar. 2004, 20:279-91.
Patton et al., "The PI3K p110δ regulates expression of CD38 on regulatory T cells," PLoS One, Mar. 2011, 6(3):e17359.
Peclat et al., "The NADase enzyme CD38: an emerging pharmacological target for systemic sclerosis, systemic lupus erythematosus and rheumatoid arthritis," Current opinion in rheumatology, Nov. 2020, 32(6):488-496.
Preugschat, "The base exchange reaction of NAD+ glycohydrolase: identification of novel heterocyclic alternative substrates," Archives of Biochemistry and Biophysics, Nov. 15, 2008, 479(2):114-20.
Quarona et al., "CD38 and CD157: a long journey from activation markers to multifunctional moleculesm," Cytometry Part B: Clinical Cytometry, Jul. 2013, 84B(4):207-217.
Sahoo et al., "Boolean analysis identifies CD38 as a biomarker of aggressive localized prostate cancer," Oncotarget, Jan. 5, 2018, 9(5):6550-61.
Scully et al., "Synthesis and Evaluation of Thiazoloquinolinones with Linkers to Enable Targeting of CD38," ACS Medicinal Chemistry Letters, Dec. 22, 2016, 8(2):196-200.
Shi et al., "Targeting CD38-dependent NAD+ metabolism to mitigate multiple organ fibrosis," iScience, Jan. 22, 2021, 24(1):101902, 39 pages.
STN International Web 20190506X160136-RBNI, May 6, 2019, 52 pages.
STN International Web 2019507X162614-RBN2, May 7, 2019, 64 pages.
STN International Web 20201118X163715-RBN3, Nov. 18, 2020, 56 pages.
STN Registry No. 1092314-22-1, "1H-Imidazo[4,5-c]pyridine-4-carboxam.ide, N-cyclohexyl-2-methyl-1-(tetrahydro-1,1-dioxido-3-thienyl)-6-(2-thienyl)(CA Index Name)," File Registry on STN, Dec. 31, 2008, 3 pages.
Sun et al., "Disordered osteoclast formation and function in a CD38 (ADP-ribosyl cyclase)-deficient mouse establishes an essential role for CD38 in bone resorption," The FASEB Journal, Mar. 2003, 17(3):369-75.
Takahashi et al., "Deficit of CD38/cyclic ADP-ribose is differentially compensated in hearts by gender," Biochemical and Biophysical Research Communications, Dec. 12, 2003, 312(2):434-40.
Van de Donk et al., "CD38 Antibodies in Multiple Myeloma: Mechanisms of Action and Modes of Resistance," Front. Immunol., Sep. 20, 2018, 9:2134, 12 pages.
Verma et al., "PD-1 blockade in subprimed CD8 cells induces dysfunctional PD-1+CD38hi cells and anti-PD-1 resistance," Nature Immunology, Sep. 2019, 20(9):1231-1243.
Wu et al., "CD38-expressing macrophages drive age-related NAD+ decline," Nature Metabolism, Nov. 2020, 2:1186-1187.
Xing et al., "Synthesis and Structure-Activity Relationship (SAR) Studies of Novel Pyrazolopyridine Derivatives as Inhibitors of Enterovirus Replication," Journal of Medicinal Chemistry, Feb. 22, 2018, 61(4):1688-1703.
Zhang et al., "Prognostic Values of CD38 + CD101 + PD1 + CD8 + T Cells in Pancreatic Cancer," Immunol. Invest., Jul. 2019, 48(5):466-79.
Zhao et al., "Determinants of the membrane orientation of a calcium signaling enzyme CD38," Biochimica et Biophysica Acta, Nov. 4, 2014, 1853(9):2095-2103.
Zhu et al., "Subcellular compartmentalization of NAD + and its role in cancer: A sereNADe of metabolic melodies, " Pharmacology & Therapeutics, Aug. 2019, 200:27-41 (Author Manuscript).
Office Action in Japanese Appln. No. 2022-506169, mailed on Jul. 23, 2024, 12 pages (with English translation).
Office Action in Japanese Appln. No. 2023-544674, mailed on Aug. 6, 2024, 16 pages (with English translation).
Zuo et al., "Discovery of structurally diverse small-molecule compounds with broad antiviral activity against enteroviruses," Antimicrobial Agents Chemotherapy, Mar. 2016, 60(3):1615-26.
Ommen et al., "2020 AHA/ACC Guideline for the Diagnosis and Treatment of Patients With Hypertrophic Cardiomyopathy," Circulation, Dec. 2020, 142:e558-e631.
Office Action in Mexican Appln. No. MX/a/2022/001019, mailed on Jan. 15, 2025, 14 pages (with English translation).
Office Action in Saudi Arabian Appln. No. 523450071, mailed on Mar. 16, 2025, 18 pages (with English translation).

HETEROBICYCLIC AMIDES AS INHIBITORS OF CD38

FIELD OF THE INVENTION

The present invention relates to heterobicyclic amides and related compounds which are inhibitors of CD38 and are useful in the treatment of cancer.

BACKGROUND OF THE INVENTION

CD38 (cluster of differentiation 38) is a member of the ADP-ribosyl cyclase family that is widely expressed on the surface of multiple cell types and is responsible for the degradation of nicotinamide adenine dinucleotide ($NAD^+$). CD38 was first characterized as a surface antigen on immune cells as an activation marker, located on the plasma membrane and on the membranes of intracellular organelles (Quarona, V., et al. *Cytometry B Clin Cytom* 84(4): 207-217 (2013)). Human CD38 contains 300 amino acid residues comprising a short N-terminal fragment, a single-pass transmembrane helix, and a C-terminal catalytic domain. CD38 is generally classified as a type II membrane protein; however, it has also been reported as existing in a type III orientation (Zhao Y Z et al. *Biochim Biophys Acta* 1853(9): 2095-2103 (2012)). CD38 converts $NAD^+$ to ADP-ribose (ADPR) or cyclic ADPR (cADPR) and nicotinamide (Chini E N et al. *Trends Pharmacol Sci* 39(4): 424-436 (2018)). While $NAD^+$ is recognized as the major substrate for CD38, it is also known to have other substrates such as nicotinamide adenine dinucleotide phosphate ($NADP^+$) and nicotinamide mononucleotide ($NMN^+$). Under some conditions, CD38 can also catalyze base exchange reactions with these same substrates (Preugschat, F et al. *Arch Biochem Biophys*, 479: 114-20 (2008)). This CD38-dependent $NAD^+$ metabolism regulates levels of extracellular and intracellular metabolites, intracellular $Ca^{2+}$, and signal transduction pathways (Horenstein, A L, et al. *Oncoimmunology* 2(9): e26246 (2013)); Chini E N et al. 2018). CD38 also functions as a receptor, and the receptor-ligand activity of CD38 regulates development, activation, and differentiation of multiple immune cell types (Quorona B et al. 2013), and CD31/PECAM-1 has been reported to be a ligand for CD38 (Deaglio S, *J Immunol,* 160: 395-402 (1998)).

CD38 exerts diverse physiological functions, and characterization of CD38 knockout (KO) mice has clarified the various roles played by this protein. CD38 KO mice are characterized by large decreases in endogenous cADPR levels in all tissues/organs analyzed except the brain (Partida-Sanchez S et al. *Nat Med,* 7: 1209-16 (2001); Ceni C et al. *J Biol Chem* 278(42): 40670-40678 (2003)) In the pancreatic islets, loss of CD38 impairs glucose-induced production of cADPR, intracellular $Ca^{2+}$, and insulin secretion (Kato J et al. *J Biol Chem,* 274: 1869-72 (1999)). CD38 KO also impairs acetylcholine-induced accumulation of cADPR in acinar cells, leading to marked alteration of $Ca^{2+}$ signaling patterns (Fukushi Y et al. *J Biol Chem,* 276: 649-55 (2001)). Likewise, in neutrophils, cADPR production has been shown to regulate both intracellular $Ca^{2+}$ release and extracellular $Ca^{2+}$ influx during chemotaxis and is required for bacterial clearance in vivo (Partida-Sanchez S et al. *Nat Med,* 7: 1209-16 (2001)). CD38 KO mice also show other defects, including disordered osteoclast formation and function (Sun L et al. *FASEB J,* 17: 369-75 (2003)), altered airway responsiveness (Deshpande D A et al. *Am J Respir Cell MolBiol,* 32: 149-56 (2005)), impairment of dendritic cell trafficking and reduced humoral immune response (Partida-Sanchez S et al. *Immunity,* 20: 279-91 (2004)), inhibition of α-adrenoceptor-stimulated contraction in the aorta (Mitsui-Saito M et al. *J Vet Med Sci,* 65: 1325-30 (2003)), and cardiac hypertrophy (Takahashi J et al. *Biochem Biophys Res Commun,* 312: 434-40 (2003)). These findings clearly demonstrate the diverse biological roles played by CD38.

CD38 expression has also been associated with the immunosuppressive functions of regulatory T (Treg) cells, tumor-associated macrophages (TAMs) and myeloid-derived suppressive cells (MDSCs) (Feng X et al. *Clin Cancer Res* 23(15): 4290-4300 (2017); Krejcik J et al. *Blood* 128(3): 384-394 (2016); Chevrier S et al. *Cell* 169(4): 736-749 e718 (2017); Levy A *Neuro Oncol* 14(8): 1037-1049 (2012)). CD38 KO Treg cells are remarkably sensitive to $NAD^+$-induced cell death due to their inability to consume $NAD^+$ (Chen J et al. *J Immunol* 176(8): 4590-4599 (2006); Hubert, S B et al. *J Exp Med,* 207: 2561-8 (2010)). Conversely, Tregs with high CD38 expression are more suppressive than other subsets with lower or no CD38 expression (Krejcik et al. 2016; Patton D T et al. *PLoS One* 6(3): e17359 (2011)). Likewise, $CD38^{high}$ MDSCs possess greater capacity to suppress activated T cells. The activity of such $CD38^{high}$ MDSCs promoted esophageal tumor growth in mice, an effect that could be inhibited by CD38 blockade (Karakasheva T A et al. *Cancer Res* 75(19): 4074-4085 (2015)). The expansion of functional $CD38^+$ MDSCs has also been described in colorectal cancer, especially in patients who have previously undergone therapy (Karakasheva T A et al. *JCI Insight* 3(6) (2018)). Broad systems immunology approaches have revealed the association of CD38-expressing tumor-infiltrating lymphocytes (TILs) with poor prognosis in clear cell renal cell carcinoma (ccRCC) and early lung adenocarcinoma (Chevrier S et al. 2017; Lavin Y et al. *Cell* 169(4): 750-765 e717 (2017)). In ccRCC, it was determined that CD38 was co-expressed with other markers of T cell exhaustion, whereas in lung adenocarcinoma, $CD38^{high}$ Treg cells were enriched in the tumor microenvironment (TME) (Chevrier S et al. 2017; Lavin Y et al. 2017). High co-expression of CD38 and CD101 on TILs in tumor tissue was correlated with poor survival of pancreatic cancer patients (Zhang M et al. *Immunol Invest,* 48: 466-79 (2019)). A study looking into exhausted T cell populations in humans with chronic infection and various cancers identified CD38 as a T cell exhaustion marker, and the presence of such exhausted T cells was linked to more severe disease from HIV infection and dysfunctional TILs in lung cancer (Bengsch B et al. *Immunity* 48(5): 1029-1045 e1025 (2018)). CD38 also dictates the metabolic fitness of T cells, and the inhibition of CD38 expression on T cells upregulates $NAD^+$ and activates T cells by promoting glutaminolysis, enhancing oxidative phosphorylation, and altering mitochondrial dynamics (Chatterjee S et al. 2018). This study further demonstrated that inhibition of CD38 prevented T cell exhaustion and thereby boosted the efficacy of adoptive T cell therapy (Chatterjee S et al. *Cell Metab* 27(1): 85-100 e108 (2018)).

The role of CD38 in tumorigenesis and immune suppression is an active field of research, with multiple studies associating CD38 with tumor progression. CD38 was shown to promote cervical cancer cell growth by reducing levels of reactive oxygen species and inhibiting apoptosis (Liao S et al. *Mol Carcinog* 56(10): 2245-2257 (2017)), and loss of CD38 in human lung adenocarcinoma cells inhibited cell growth, invasion, and xenograft growth in nude mice (Bu X et al. *Carcinogenesis* 39(2): 242-251 (2017)). CD38 KO mice are more resistant to tumor growth and were shown to efficiently reject B16-F10 melanoma tumors (Baruch B B et al. *Oncotarget,* 9: 31797-811 (2018)). Similarly, targeting CD38 expression or its activity in the TME inhibited glioma progression and prolonged the lifespan of glioma-bearing mice (Blacher E et al. *Int J Cancer* 136(6): 1422-1433 (2013)). CD38 has also been identified as a biomarker of aggressive localized prostate cancer (Sahoo D et al. *Oncotarget,* 9: 6550-61 (2018)).

Recent research has investigated the role of CD38 in an ecto-enzyme cascade that generates immunosuppressive adenosine from $NAD^+$. In addition to CD38, this cascade includes ectonucleotide pyrophosphatase/phosphodiesterase 1 (ENPP1) and the 5'-ectonucleotidase CD73. CD38 generates ADPR that is further hydrolyzed by ENPP1 to produce AMP, and the subsequent conversion of AMP to adenosine is regulated by CD73 (Ferretti E et al. *Immunol Lett* 205: 25-30 (2019)). This non-canonical adenosine generation pathway, which relies on CD38, occurs independently of ATP, and bypasses CD39 (Horenstein A L et al. 2013), plays a major role in creating an immunosuppressive TME, wherein dying cells provide $NAD^+$ that is eventually converted to adenosine (Haag F et al. *Purinergic Signal* 3(1-2): 71-81 (2007); Zhu Y et al. *Pharmacol Ther* 200: 27-41 (2019)).

Furthermore, a recent study demonstrated that cancer cells acquire resistance to immune checkpoint inhibitors that target programmed cell death protein 1 (PD-1) or its ligand (PD-L1) via upregulation of CD38, which blocks $CD8^+$ T cell function through adenosine receptor signaling (Chen L et al. *Cancer Discov* 8(9): 1156-1175 (2018)). CD38 blockade subsequently restored $CD8^+$ T cell proliferation, antitumor cytokine secretion, and cytotoxic capabilities. Pathologic analysis of lung cancer specimens revealed positive immunohistochemical staining for CD38 on tumor cells in 15-23% of cases, and bioinformatic analyses of datasets from non-small cell lung cancer (NSCLC) and melanoma patients revealed a strong correlation between CD38 expression and an inflamed TME (Chen L et al. 2018).

CD38 is one of the main enzymes responsible for the age-related $NAD^+$ decline that occurs in mammals (Hogan K A et al. *Front Immunol* 10: 1187 (2019)). CD38 KO mice are consistently protected from this progressive deficit and age-related metabolic dysfunction (Camacho-Pereira J et al. *Cell Metab,* 23: 1127-39 (2016)). Inhibition of CD38 likewise reversed age-related $NAD^+$ decline and ameliorated several metabolic, structural, and molecular features of aging in chronologically aged and progeroid mice (Camacho-Pereira J et al. 2016). CD38 KO mice are also protected from diet-induced obesity, liver steatosis, and glucose intolerance due to enhanced energy expenditure (Barbosa M T et al. *FASEB J* 21(13): 3629-3639 (2007)).

CD38 is a cell-surface marker for multiple myeloma and these cells are specifically susceptible to CD38 depletion, thus CD38 offers a useful therapeutic target for this malignancy (Chini E N et al. 2018). Clinical trials have demonstrated that CD38-targeting antibodies are specifically effective in relapsed/refractory multiple myeloma patients (Frerichs K A et al. *Expert Rev Clin Immunol,* 14: 197-206 (2018); van de Donk NWCJ et al. *Front Immunol,* 9: 2134 (2018)), and the anti-CD38 antibody daratumumab has been approved by the FDA for multiple myeloma treatment. Several other therapeutic antibodies against CD38 are now in clinical development for multiple myeloma and other cancers (van de Donk NWCJ 2018).

The literature is replete with references reporting the potential therapeutic benefits of inhibiting abnormal expression or activity of CD38. For example, the following diseases are characterized by abnormal expression or activity of CD38: non-small cell lung cancer, melanoma, checkpoint therapy treated and/or resistant cancers, and adenosine-dependent tumors (Chen L et al. "CD38-mediated immunosuppression as a mechanism of tumor cell escape from PD-1/PD-L1 blockade." *Cancer Discov.* 8, 1156-1175 (2018)); lung cancer (adenocarcinoma) (Bu X et al. "CD38 knockout suppresses tumorigenesis in mice and clonogenic growth of human lung cancer cells." *Carcinogenesis* 39, 242-251 (2018)); cervical cancer (Liao S et al. "CD38 enhances the proliferation and inhibits the apoptosis of cervical cancer cells by affecting the mitochondria functions." *Mol. Carcinog.* 56, 2245-2257 (2017)); glioma (Blacher E et al. "Inhibition of glioma progression by a newly discovered CD38 inhibitor." *Int. J. Cancer* 136, 1422-1433 (2015)); colorectal cancer (Karakasheva T A et al. "CD38+M-MDSC expansion characterizes a subset of advanced colorectal cancer patients." *JCI Insight* 3, 1-8 (2018)); esophageal cancer (Karakasheva T A et al. "CD38-expressing myeloid-derived suppressor cells promote tumor growth in a murine model of esophageal cancer." *Cancer Res.* 75, 4074-4085 (2015)); clear cell renal cell carcinoma (Chevrier S et al. "An immune atlas of clear cell renal cell carcinoma." *Cell* 169, 736-749 (2017)); prostate cancer (Sahoo D et al. "Boolean analysis identifies CD38 as a biomarker of aggressive localized prostate cancer." *Oncotarget* 9, 6550-6561 (2018)); treg-infiltrated tumors (Lavin Y et al. "Innate immune landscape in early lung adenocarcinoma by paired single-cell analyses." *Cell* 169, 750-757.e15 (2017)); MDSC-infiltrated tumors (Karakasheva T A et al. "CD38+ M-MDSC expansion characterizes a subset of advanced colorectal cancer patients." *JCI Insight* 3, 1-8 (2018)); HIV/AIDS (Bengsch B et al. "Epigenomic-guided mass cytometry profiling reveals disease-specific features of exhausted resource epigenomic-guided mass cytometry profiling reveals disease-specific features of exhausted CD8 T cells." *Cell* 48, 1029-1045 (2018)); adoptive T cell therapy (Chatterjee S et al. "CD38-$NAD^+$ axis regulates immunotherapeutic anti-tumor T cell response." *Cell Metab.* 27, 85-100.e8 (2018)); pancreatic cancer (Zhang M et al. "Prognostic values of $CD38^+$ $CD101^+$ $PD1^+$ $CD8^+$ T cells in pancreatic cancer." *Immunol. Invest.* 48, 466-479 (2019)); and multiple myeloma (Chini E N et al. "The Pharmacology of CD38/NADase: An Emerging Target in Cancer and Diseases of Aging." *Trends Pharmacol. Sci.* 39, 424-436 (2018)).

In summation, CD38 is a multifunctional enzyme and signaling receptor that plays important functions in cancer progression, the creation of an immunosuppressive TME, metabolic fitness of T cells, and the modulation of $NAD^+$ levels in aging and other physiological conditions. The inhibition of CD38 in various disease states—including tumor growth—has already shown clinical promise, and the development of potent and selective small-molecule inhibitors will create therapeutic options for other conditions characterized by abnormal expression or activity of CD38. The compounds, compositions, and methods described herein will help meet these and other needs.

SUMMARY OF THE INVENTION

The present invention provides a compound of Formula I:

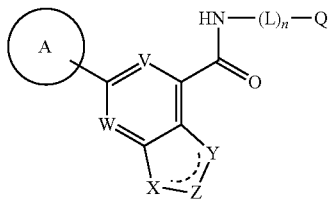

or a pharmaceutically acceptable salt thereof, wherein constituent members are defined herein.

The present invention is also directed to a pharmaceutical composition comprising a compound of Formula I, or a pharmaceutically acceptable salt thereof, and at least one pharmaceutically acceptable carrier.

The present invention is also directed to a method of inhibiting a function of CD38 by contacting the CD38 with a compound of Formula I, or a pharmaceutically acceptable salt thereof.

The present invention is also directed to a method of treating a disease associated with abnormal activity or expression of CD38 by administering a therapeutically effective amount of a compound of Formula I, or a pharmaceutically acceptable salt thereof, to a patient in need thereof.

The present invention is further directed to a compound of the invention, or a pharmaceutically acceptable salt thereof, for use in the treatment of a disease associated with abnormal activity or expression of CD38.

The present invention is further directed to use of a compound of the invention, or a pharmaceutically acceptable salt thereof, in the manufacture of a medicament for use in therapy.

DETAILED DESCRIPTION

Figure 1A:
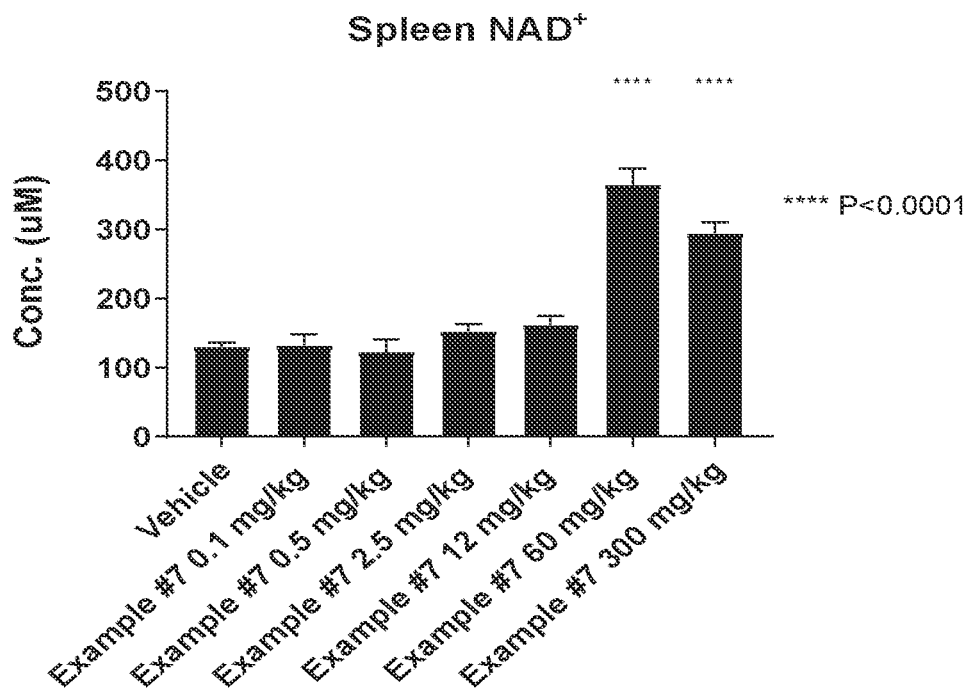
FIG. 1A is a graph of the concentration of $NAD^+$ in the spleen at a single time point after dosing with various amounts of Example 7.

The present invention relates to a CD38-inhibiting compound of Formula I:

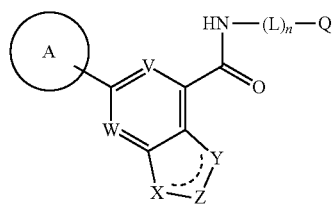

or a pharmaceutically acceptable salt thereof, wherein:
V is N or $CR^V$, wherein $R^V$ is H, halo, or $C_{1-4}$ alkyl;
W is N or $CR^W$, wherein $R^W$ is H, halo, or $C_{1-4}$ alkyl;
the moiety represented by:

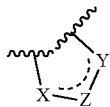

is selected from:

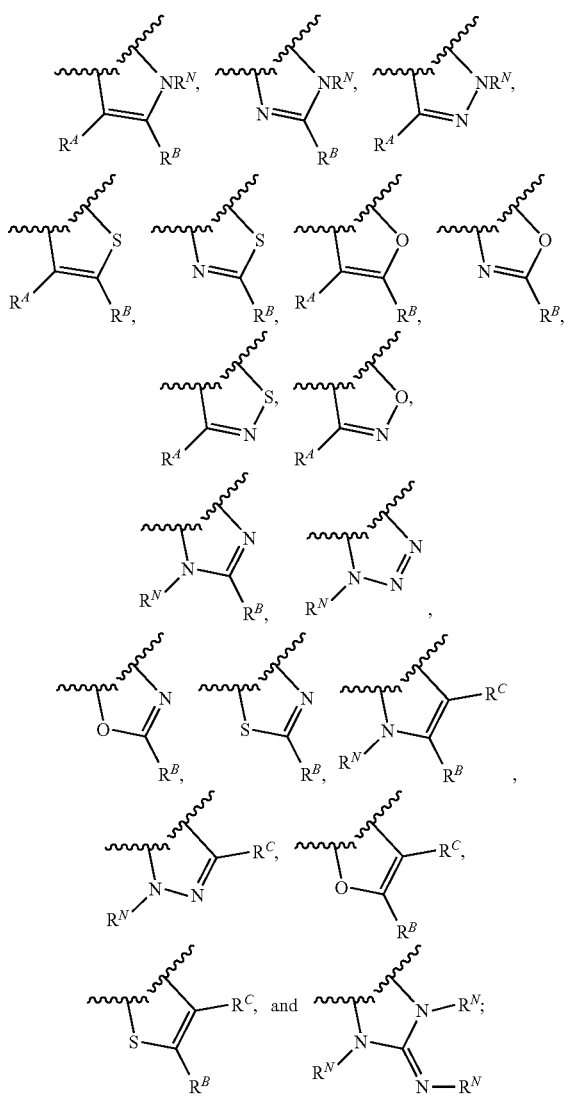

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substitutents independently selected from halo and $C_{1-4}$ alkyl;

each $R^N$ is independently selected from H, $C_{1-4}$ alkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^N$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^{c1}C(O)R^{b1}$, $NR^cC(O)OR^a$, $NR^cC(O)NR^cR^d$; $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^A$, $R^B$, and $R^C$ is independently selected from H, halo, $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^A$, $R^B$, and $R^C$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^{c1}C(O)R^{b1}$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

L is a $C_{1-4}$ alkylene linker;
n is 0 or 1;
Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2 NR^{c1}R^{d1}$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein Q is other than H when n is 0;
each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each Cy¹ is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{e2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{e2}$S(O)$_2$R$^{b2}$, NR$^{e2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$ NR$^{c2}$R$^{d2}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from Cy², Cy²-C$_{1-4}$ alkyl, halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^c$ and R$^d$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$ NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$, or R$^{c1}$ and R$^{d1}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^a$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^{c2}$ and R$^{d2}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^a$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each Cy² is C$_{6-10}$ aryl, C$_{3-7}$ cycloalkyl, 5-10 membered heteroaryl, or 4-10 membered heterocycloalkyl, each optionally substituted by 1, 2, 3, or 4 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl are each optionally substituted with 1, 2, or 3 substituents independently selected from OH, CN, amino, halo, C$_{1-6}$ alkyl, C$_{1-6}$ alkylamino, di(C$_{1-6}$ alkyl)amino, C$_{1-6}$ alkoxy, C$_{1-6}$ haloalkyl, and C$_{1-6}$ haloalkoxy;

each R$^c$, R$^{c2}$, R$^{e2}$, and R$^{e3}$ is independently selected from H, C$_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups; and with the proviso that when:

V is CH;

W is CH;

the moiety represented by:

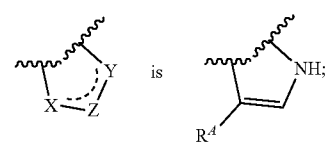

n is 0; and

Q is cyclohexyl optionally substituted with 1, 2, 3, 4, or 5 substituents independently selected from Cy¹, Cy¹-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, N$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

then Ring A is other than:

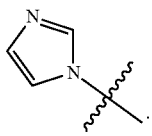 [SMILES: *n1ccnc1]

In some embodiments:
V is N or CR$^V$, wherein R$^V$ is H, halo, or C$_{1-4}$ alkyl;
W is N or CR$^W$, wherein R$^W$ is H, halo, or C$_{1-4}$ alkyl;
the moiety represented by:

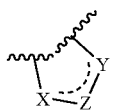

is selected from:

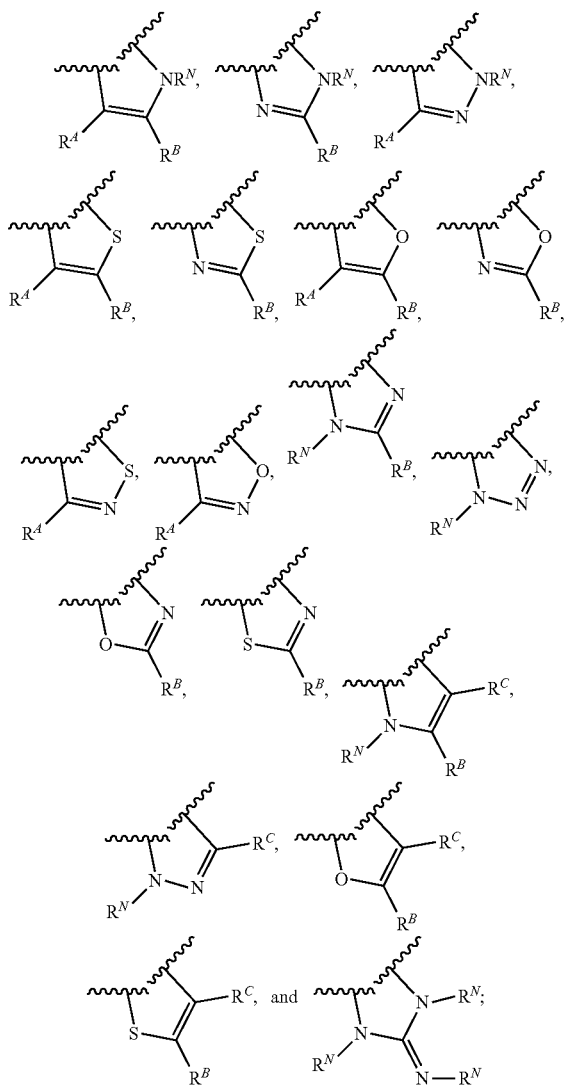

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and C$_{1-4}$ alkyl;

each R$^N$ is independently selected from H, C$_{1-4}$ alkyl, C$_{6-10}$ aryl, C$_{3-7}$ cycloalkyl, 5-10 membered heteroaryl, or 4-10 membered heterocycloalkyl, wherein said C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, and 4-10 membered heterocycloalkyl of R$^N$ are each optionally substituted with 1, 2, 3, 4, or 5 substituents independently selected from Cy, Cy-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$ C(=NR$^e$)NR$^c$R$^d$, NR$^c$C(=NR$^e$)NR$^c$R$^d$, NR$^c$R$^d$, NR$^{c1}$C(O)R$^{b1}$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^A$, R$^B$, and R$^C$ is independently selected from H, halo, C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, or 4-10 membered heterocycloalkyl, wherein said C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, and 4-10 membered heterocycloalkyl of R$^A$, R$^B$, and R$^C$ are each optionally substituted with 1, 2, 3, 4, or 5 substituents independently selected from Cy, Cy-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^{c1}$C(O)R$^{b1}$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

L is a C$_{1-4}$ alkylene linker;

n is 0 or 1;

Q is H, C$_{1-10}$ alkyl, C$_{2-10}$ alkenyl, C$_{2-10}$ alkynyl, C$_{1-10}$ haloalkyl, C$_{6-10}$ aryl, C$_{3-14}$ cycloalkyl, 5-14 membered heteroaryl, or 4-14 membered heterocycloalkyl, wherein said C$_{1-10}$ alkyl, C$_{2-10}$ alkenyl, C$_{2-10}$ alkynyl, C$_{1-10}$ haloalkyl, C$_{6-10}$ aryl, C$_{3-14}$ cycloalkyl, 5-14 membered heteroaryl, and 4-14 membered heterocycloalkyl of Q are each optionally substituted with 1, 2, 3, 4, or 5 substituents independently selected from Cy$^1$, Cy$^1$-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$R$^{c1}$R$^{d1}$, wherein the C$_{1-6}$ alkyl is optionally substituted by 1, 2, or 3 substituents independently selected from OH, CN, C$_{1-6}$ alkoxy, and NR$^{c1}$C(O)R$^{b1}$;

wherein Q is other than H when n is 0;

each Cy is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C (O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each Cy$^1$ is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{e2}$S(O)$_2$R$^{b2}$, NR$^{e2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$ NR$^{c2}$R$^{d2}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from Cy$^2$, Cy$^2$-C$_{1-4}$ alkyl, halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O) NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^c$ and R$^d$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O) OR$^3$, OC(O)R$^{b3}$, OC(O)NR$^{c3}$R$^{d3}$, NR$^{c3}$R$^{d3}$, NR$^{c3}$C(O) R$^{b3}$ NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

or R$^{c1}$ and R$^{d1}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O) OR$^3$, OC(O)R$^{b3}$, OC(O)NR$^{c3}$R$^{d3}$, NR$^{c3}$R$^{d3}$, NR$^{c3}$C(O) R$^{b3}$, NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

or R$^{c2}$ and R$^{d2}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O) OR$^3$, OC(O)R$^{b3}$, OC(O)NR$^{c3}$R$^{d3}$, NR$^{c3}$R$^{d3}$, NR$^{c3}$C(O) R$^{b3}$, NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

each Cy$^2$ is C$_{6-10}$ aryl, C$_{3-7}$ cycloalkyl, 5-10 membered heteroaryl, or 4-10 membered heterocycloalkyl, each optionally substituted by 1, 2, 3, or 4 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl are each optionally substituted with 1, 2, or 3 substituents independently selected from OH, CN, amino, halo, C$_{1-6}$ alkyl, C$_{1-6}$ alkylamino, di(C$_{1-6}$ alkyl)amino, C$_{1-6}$ alkoxy, C$_{1-6}$ haloalkyl, and C$_{1-6}$ haloalkoxy;

each R$^e$, R$^{e1}$, R$^{e2}$, and R$^{e3}$ is independently selected from H, C$_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups; and with the proviso that when:

V is CH;

W is CH;

the moiety represented by:

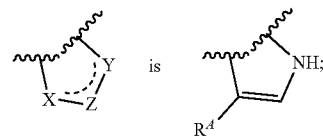

n is 0; and

Q is cyclohexyl optionally substituted with 1, 2, 3, 4, or 5 substituents independently selected from Cy$^1$, Cy$^1$-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O) NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O) NR$^{c1}$R$^{d1}$, NR$^{c1}$S(O)R$^{b1}$, NR$^{c1}$S(O)$_2$R$^{b1}$, NR$^{c1}$S(O)$_2$ NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

then Ring A is other than:

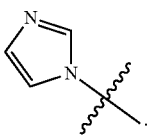 [SMILES: *n1ccnc1]

In some embodiments:
V is N or CR$^V$, wherein R$^V$ is H, halo, or C$_{1-4}$ alkyl;
W is N or CR$^W$, wherein R$^W$ is H, halo, or C$_{1-4}$ alkyl;
the moiety represented by:

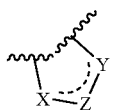

is selected from:

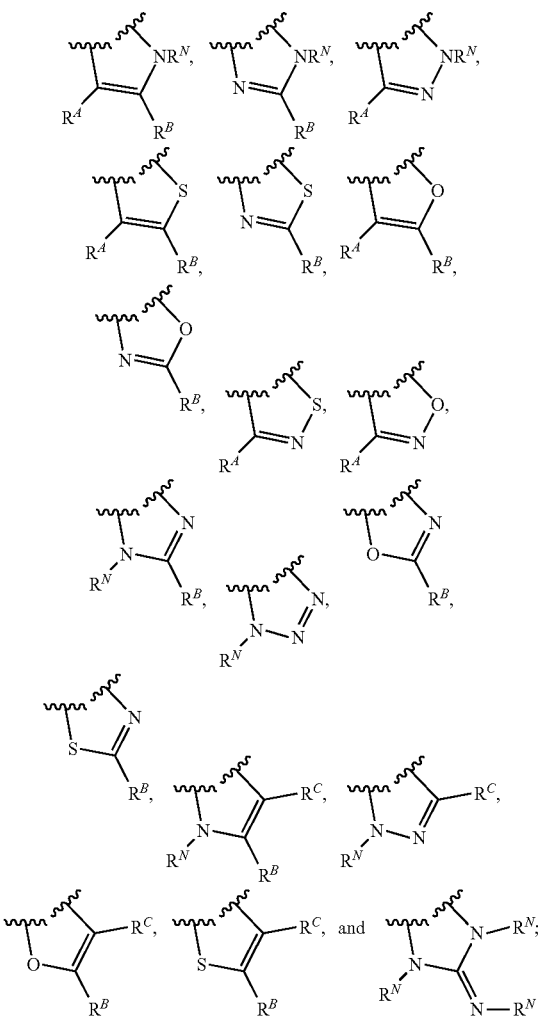

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and C$_{1-4}$ alkyl;

each R$^N$ is independently selected from H, C$_{1-4}$ alkyl, C$_{6-10}$ aryl, C$_{3-7}$ cycloalkyl, 5-10 membered heteroaryl, or 4-10 membered heterocycloalkyl, wherein said C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, and 4-10 membered heterocycloalkyl of R$^N$ are each optionally substituted with 1, 2, 3, 4, or 5 substituents independently selected from Cy, Cy-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$ C(=NR$^e$)NR$^c$R$^d$, NR$^c$C(=NR$^e$)NR$^c$R$^d$, NR$^c$R$^d$, NR$^{c1}$C(O)R$^{b1}$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each R$^A$, R$^B$, and R$^C$ is independently selected from H, halo, C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, or 4-10 membered heterocycloalkyl, wherein said C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, and 4-10 membered heterocycloalkyl of R$^A$, R$^B$, and R$^C$ are each optionally substituted with 1, 2, 3, 4, or 5 substituents independently selected from Cy, Cy-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$NR$^c$R$^d$, NR$^{c1}$C(O)R$^{b1}$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$ S(O)R$^b$, S(O)NR$^c$R$^d$, S(O)$_2$R$^b$, and S(O)$_2$NR$^c$R$^d$;

L is a C$_{1-4}$ alkylene linker;

n is 0 or 1;

Q is H, C$_{1-10}$ alkyl, C$_{2-10}$ alkenyl, C$_{2-10}$ alkynyl, C$_{1-10}$ haloalkyl, C$_{6-10}$ aryl, C$_{3-14}$ cycloalkyl, 5-14 membered heteroaryl, or 4-14 membered heterocycloalkyl, wherein said C$_{1-10}$ alkyl, C$_{2-10}$ alkenyl, C$_{2-10}$ alkynyl, C$_{1-10}$ haloalkyl, C$_{6-10}$ aryl, C$_{3-14}$ cycloalkyl, 5-14 membered heteroaryl, and 4-14 membered heterocycloalkyl of Q are each optionally substituted with 1, 2, 3, 4, or 5 substituents independently selected from Cy$^1$, Cy$^1$-C$_{1-4}$ alkyl, halo, C$_{1-6}$ alkyl, C$_{2-6}$ alkenyl, C$_2$-6 alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$ NR$^{c1}$R$^{d1}$;

wherein Q is other than H when n is 0;

each Cy is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, C(=NR$^e$)NR$^c$R$^d$, NR$^c$C(=NR$^e$)NR$^c$R$^d$, NR$^c$R$^d$, NR$^c$C(O)R$^b$, NR$^c$C(O)OR$^a$, NR$^c$C(O)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$;

each Cy$^1$ is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$ $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$ $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^a$, $OC(O)R^{b3}$, $OC(O)NR^{c3}R^{d3}$, $NR^{c3}R^{d3}$, $NR^{c3}C(O)R^{b3}$ $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$ $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)R^{b3}$ $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups; and with the proviso that when:

V is CH;

W is CH;

the moiety represented by:

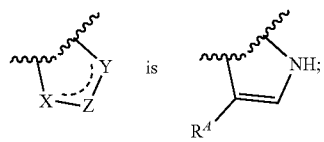 is n is 0; and

Q is cyclohexyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$ $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$ $S(O)_2R^{b1}$, and $S(O)_2NR^{c1}R^{d1}$;

then Ring A is other than:

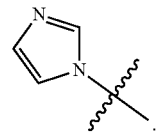 [SMILES: *n1ccnc1]

In some embodiments, the moiety represented by:

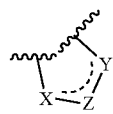

is selected from:

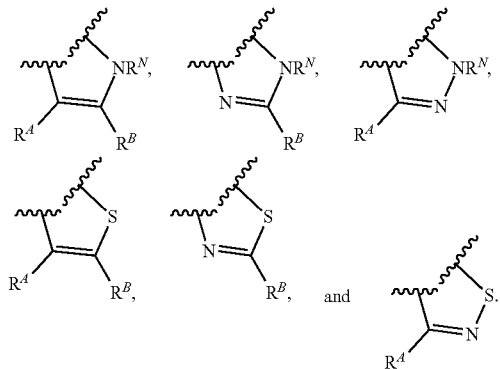

In some embodiments, the moiety represented by:

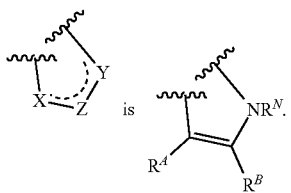

In some embodiments, the moiety represented by:

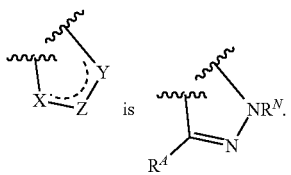

In some embodiments, each $R^A$, $R^B$, and $R^C$ is independently selected from H and $C_{1-4}$ alkyl. In some embodiments, $R^A$ is H. In some embodiments, $R^B$ is H. In some embodiments, $R^C$ is H.

In some embodiments, V is N.

In some embodiments, V is $CR^V$. In some embodiments, V is CH.

In some embodiments, W is N.

In some embodiments, W is $CR^W$. In some embodiments, W is CH.

In some embodiments, V is N and W is N. In some embodiments, V is N and W is $CR^W$.

In some embodiments, V is $CR^V$ and W is N. In some embodiments, V is $CR^V$ and W is $CR^W$.

In some embodiments, at least one of V and W is N.

In some embodiments, Ring A is selected from:

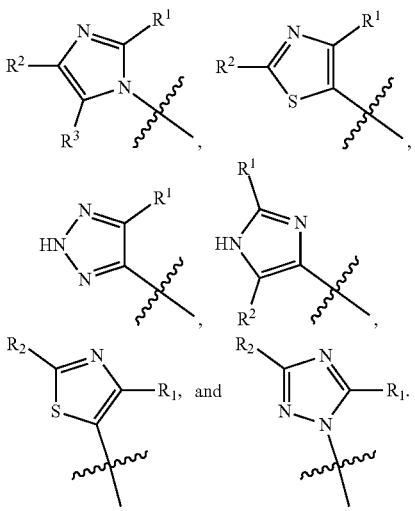

In some embodiments, ring A is

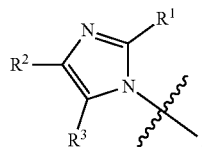

In some embodiments, $R^1$, $R^2$, and $R^3$ are each independently selected from H and $C_{1-4}$ alkyl. In some embodiments, $R^1$, $R^2$, and $R^3$ are each H.

In some embodiments, Q is $C_{1-10}$ alkyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{1-4}$ alkyl, $C_{1-4}$ haloalkyl, phenyl, $C_{3-7}$ cycloalkyl, 5-10 membered heteroaryl, or 4-10 membered heterocycloalkyl, wherein said $C_{1-4}$ alkyl, phenyl, $C_{3-10}$ cycloalkyl, 5-10 membered heteroaryl, or 4-10 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl are optionally substituted by 1, 2, or 3 substituents independently selected from OH, CN, $C_{1-6}$ alkoxy, and $NR^{c1}C(O)R^{b1}$.

In some embodiments, Q is $C_{1-10}$ alkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is $C_{1-10}$ alkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{1-10}$ alkyl or $C_{1-10}$ haloalkyl, wherein said $C_{1-10}$ alkyl is optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{1-4}$ alkyl.

In some embodiments, Q is selected from $C_{1-4}$ alkyl and $C_{1-4}$ haloalkyl.

In some embodiments, Q is phenyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is phenyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is phenyl optionally substituted with 1 or 2 substituents independently selected from halo, $C_{1-6}$ alkyl, $C_{1-6}$ haloalkyl, CN, and $OR^{a1}$, wherein the $C_{1-6}$ alkyl is optionally substituted by CN.

In some embodiments, Q is phenyl optionally substituted with 1 or 2 substituents independently selected from halo, $C_{1-6}$ haloalkyl, and $OR^{a1}$.

In some embodiments, Q is $C_{3-14}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is $C_{3-14}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is $C_{4-7}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is cyclohexyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is $C_314$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{4-7}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_2$-6 alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is $C_{4-7}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is $C_{4-7}$ cycloalkyl optionally substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, and $NR^{c1}C(O)R^{b1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is $C_{4-7}$ cycloalkyl optionally substituted with 1 or 2 substituents independently selected from $C_{1-6}$ haloalkyl, $OR^{a1}$, and $NR^{c1}R^{d1}$.

In some embodiments, Q is $C_{4-7}$ cycloalkyl optionally substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is $C_{4-7}$ cycloalkyl optionally substituted with 1 or 2 substituents independently selected from $C_{1-6}$ alkyl, $C_{1-6}$ haloalkyl, $OR^{a1}$, and $NR^{c1}R^{d1}$ wherein the $C_{1-6}$ alkyl is optionally substituted by 1 or 2 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is cyclohexyl optionally substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is cyclohexyl optionally substituted with 1 or 2 substituents independently selected from $C_{1-6}$ alkyl, $C_{1-6}$ haloalkyl, $OR^{a1}$, and $NR^{c1}R^{d1}$, wherein the $C_{1-6}$ alkyl is optionally substituted by 1 or 2 substituents independently selected from OH, CN, $C_{1-6}$ alkoxy, $C(O)NR^{c1}R^{d1}$, $NR^{c1}R^{d1}$ and $NR^{c1}C(O)R^{b1}$.

In some embodiments, Q is $C_{4-7}$ cycloalkyl substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is cyclohexyl substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

In some embodiments, Q is cyclohexyl substituted with $C_{1-6}$ alkyl, wherein the $C_{1-6}$ alkyl is optionally substituted by 1 or 2 substituents independently selected from OH, CN, $C_{1-6}$ alkoxy, $C(O)NR^{c1}R^{d1}$, $NR^{c1}R^{d1}$ and $NR^{c1}C(O)R^{b1}$.

In some embodiments, Q is 5-14 membered heteroaryl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is 5-14 membered heteroaryl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is 5-14 membered heteroaryl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$ $NR^{c1}S(O)R^{b1}$, $NR^{c1}S(O)_2R^{b1}$, $NR^{c}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl and $C_{2-6}$ alkynyl are optionally substituted by 1, 2, or 3 substituents independently selected from OH, CN, $C_{1-6}$ alkoxy, $NR^{c1}R^{d1}$ and $NR^{c1}C(O)R^{b1}$.

In some embodiments, Q is 5- or 6-membered heteroaryl optionally substituted with $Cy^1$, halo, $C_{1-6}$ alkyl, or $OR^{a1}$, wherein the $C_{1-6}$ alkyl is optionally substituted by $C_{1-6}$ alkoxy.

In some embodiments, Q is 5- or 6-membered heteroaryl optionally substituted with $Cy^1$, halo, $C_{1-6}$ alkyl, or $OR^{a1}$, wherein the $C_{1-6}$ alkyl is optionally substituted by methoxy.

In some embodiments, Q is 5- or 6-membered heteroaryl optionally substituted with $OR^{a1}$.

In some embodiments, Q is 5- or 6-membered heteroaryl optionally substituted with $Cy^1$, halo, $C_{1-6}$ alkyl, $C_{2-6}$ alkynyl, $C_{1-6}$ haloalkyl, or $OR^{a1}$, wherein said $C_{1-6}$ alkyl and $C_{2-6}$ alkynyl are optionally substituted by $C_{1-6}$ alkoxy or $NR^{c1}R^{d1}$.

In some embodiments, Q is 4-14 membered heterocycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is 4-14 membered heterocycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$.

In some embodiments, Q is 5-10-membered heterocycloalkyl optionally substituted with 1 or 2 substituents independently selected from $Cy^1$, $C_{1-6}$ alkyl, $C_{1-6}$ haloalkyl, $C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is 5-10-membered heterocycloalkyl optionally substituted with 1 or 2 substituents independently selected from $Cy^1$, halo, $C_{1-6}$ alkyl, $C_{1-6}$ haloalkyl, $C(O)R^{b1}$, and $S(O)_2R^{b1}$.

In some embodiments, Q is 5- or 6-membered heterocycloalkyl optionally substituted with 1 or 2 substituents independently selected from $Cy^1$, $C_{1-6}$ alkyl, $C_{1-6}$ haloalkyl, $C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

In some embodiments, Q is 5- or 6-membered heterocycloalkyl optionally substituted with 1 or 2 substituents independently selected from $Cy^1$, halo, $C_{1-6}$ alkyl, $C_{1-6}$ haloalkyl, $C(O)R^{b1}$, and $S(O)_2R^{b1}$.

In some embodiments, Q is 5- or 6-membered heterocycloalkyl optionally substituted with 1 or 2 substituents independently selected from $Cy^1$, $C_{1-6}$ alkyl, $C_{1-6}$ haloalkyl, $C(O)R^{b1}$, and $S(O)_2R^{b1}$.

In some embodiments, Q is 9- or 10-membered heterocycloalkyl optionally substituted with $C_{1-6}$ alkyl, wherein the $C_{1-6}$ alkyl is optionally substituted by $C_{1-6}$ alkoxy.

In some embodiments, Q is 9- or 10-membered heterocycloalkyl optionally substituted with $C_{1-6}$ alkyl or $C(O)R^{b1}$, wherein the $C_{1-6}$ alkyl is optionally substituted by $C_{1-6}$ alkoxy.

In some embodiments, Q is 9- or 10-membered heterocycloalkyl optionally substituted with $C_{1-6}$ alkyl, wherein the $C_{1-6}$ alkyl is optionally substituted by methoxy.

In some embodiments, each $Cy^1$ is independently selected from phenyl, morpholinyl, piperidinyl, and isothiazolidinyl-1,1-dione, wherein the piperidinyl is optionally substituted by 4-6 membered heterocycloalkyl. In some embodiments, each $Cy^1$ is independently selected from phenyl, morpholinyl, piperidinyl, and isothiazolidinyl-1,1-dione, wherein the piperidinyl is optionally substituted by morpholinyl.

In some embodiments, each $Cy^1$ is independently selected from phenyl, cyclopropyl, azetidinyl, pyrrolidinyl, morpholinyl, piperidinyl, piperazinyl, and isothiazolidinyl-1,1-dione, each optionally substituted by 1 or 2 substituents independently selected from halo, OH, and 4-6 membered heterocycloalkyl.

In some embodiments, each $Cy^1$ is independently selected from phenyl, cyclopropyl, azetidinyl, pyrrolidinyl, morpholinyl, piperidinyl, piperazinyl, and isothiazolidinyl-1,1-dione, each optionally substituted by 1 or 2 substituents independently selected from $C_{1-6}$ alkyl, halo, OH, CN, and 4-6 membered heterocycloalkyl.

In some embodiments, each $Cy^1$ is independently selected from phenyl, cyclopropyl, azetidinyl, pyrrolidinyl, morpholinyl, piperidinyl, piperazinyl, and isothiazolidinyl-1,1-dione, each optionally substituted by 1 or 2 substituents independently selected from halo, OH, and morpholinyl.

In some embodiments, each $Cy^1$ is independently selected from phenyl, cyclopropyl, azetidinyl, pyrrolidinyl, morpholinyl, piperidinyl, piperazinyl, and isothiazolidinyl-1,1-dione, each optionally substituted by 1 or 2 substituents independently selected from methyl, F, OH, CN, and morpholinyl.

In some embodiments, L is a methylene linker.

In some embodiments, L is an ethylene linker.

In some embodiments, n is 0.

In some embodiments, n is 1.

In some embodiments, each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, and 4-10 membered heterocycloalkyl-$C_{1-4}$ alkyl, wherein said $C_{1-6}$ alkyl and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from CN, $OR^{a3}$, $C(O)NR^{c3}R^{d3}$, and $NR^{c3}R^{d3}$.

In some embodiments, each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, and 4-10 membered heterocycloalkyl-$C_{1-4}$ alkyl, wherein said $C_{1-6}$ alkyl and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, or 3 substituents independently selected from CN, $OR^{a3}$, $C(O)NR^{c3}R^{d3}$, and $NR^{c3}R^{d3}$.

In some embodiments, each $R^{a3}$, $R^{b3}$, $R^{c3}$, and $R^{d3}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, or 3 substituents independently selected from OH, di($C_{1-6}$ alkyl)amino, and $C_{1-6}$ alkoxy.

In some embodiments, each $R^{a3}$, $R^{b3}$, $R^{c3}$, and $R^{d3}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, or 3 substituents independently selected from OH, dimethylamino, and methoxy.

In some embodiments:

V is N or $CR^V$, wherein $R^V$ is H, halo, or $C_{1-4}$ alkyl;

W is N or $CR^W$, wherein $R^W$ is H, halo, or $C_{1-4}$ alkyl;

the moiety represented by:

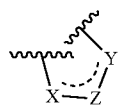

is selected from:

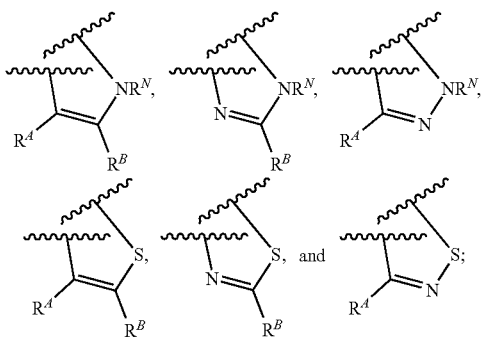

each $R^N$ is independently selected from H and $C_{1-4}$ alkyl;
each $R^A$, $R^B$, and $R^C$ is independently selected from H and $C_{1-4}$ alkyl;
Ring A is selected from:

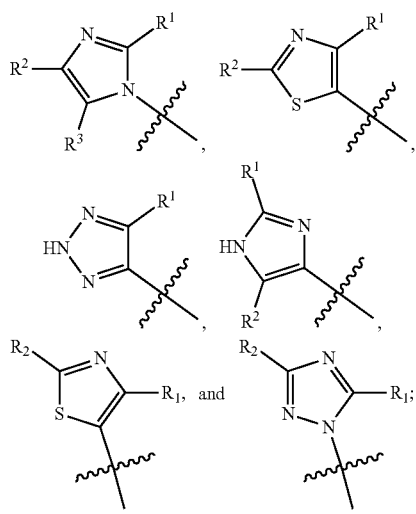

$R^1$, $R^2$, and $R^3$ are each independently selected from H and $C_{1-4}$ alkyl;
L is methylene;
n is 0 or 1;
Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, C(O)$R^{b1}$, C(O)NR$^{c1}$R$^{d1}$, C(O)OR$^{a1}$, OC(O)R$^{b1}$, OC(O) NR$^{c1}$R$^{d1}$, C(=NR$^{e1}$)NR$^{c1}$R$^{d1}$, NR$^{c1}$C(=NR$^{e1}$) NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$ R$^{b1}$, and S(O)$_2$NR$^{c1}$R$^{d1}$, wherein the $C_{1-6}$ alkyl is optionally substituted by 1, 2, or 3 substituents independently selected from OH, CN, $C_{1-6}$ alkoxy, and NR$^{c1}$C(O)R$^{b1}$;

wherein Q is other than H when n is 0;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, C(O)R$^{b2}$, C(O) NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$ NR$^{c2}$C(O) NR$^{c2}$R$^{d2}$, NR$^{c2}$S(O)R$^{b2}$, NR$^{c2}$S(O)$_2$R$^{b2}$, NR$^{c2}$S(O)$_2$ NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$—$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, OR$^3$, SR$^{a3}$, C(O)R$^{b3}$, C(O) NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C (O)OR$^{a3}$, C(=NR$^{e3}$)NR$^{c3}$R$^{d3}$, NR$^{c3}$C(=NR$^{e3}$) NR$^{c3}$R$^{d3}$, S(O)R$^{b3}$, S(O)NR$^{c3}$R$^{d3}$, S(O)$_2$R$^{b3}$, NR$^{c3}$S (O)$_2$R$^{b3}$, NR$^{c3}$S(O)$_2$NR$^{c3}$R$^{d3}$, and S(O)$_2$NR$^{c3}$R$^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, OR$^{a3}$, SR$^{a3}$, C(O)R$^{b3}$, C(O)NR$^{c3}$R$^{d3}$, C(O) OR$^3$, OC(O)R$^{b3}$, OC(O)NR$^{c3}$R$^{d3}$, NR$^{c3}$R$^{d3}$, NR$^{c3}$C(O) R$^{b3}$ NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, OR$^{a3}$, SR$^{a3}$, C(O)R$^{b3}$, C(O)NR$^{c3}$R$^{d3}$, C(O) OR$^3$, OC(O)R$^{b3}$, OC(O)NR$^{c3}$R$^{d3}$, NR$^{c3}$R$^{d3}$, NR$^{c3}$C(O) R$^{b3}$ NR$^{c3}$C(O)NR$^{c3}$R$^{d3}$, NR$^{c3}$C(O)OR$^{a3}$, C(=NR$^{e3}$) NR$^{c3}$R$^{d3}$, NR$^{c3}$C(=NR$^{e3}$)NR$^{c3}$R$^{d3}$, S(O)R$^{b3}$, S(O) NR$^{c3}$R$^{d3}$, S(O)$_2$R$^{b3}$, NR$^{c3}$S(O)$_2$R$^{b3}$, NR$^{c3}$S(O)$_2$ NR$^{c3}$R$^{d3}$, and S(O)$_2$NR$^{c3}$R$^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkylamino, di($C_{1-6}$ alkyl)amino, $C_{1-6}$ alkoxy, $C_{1-6}$ haloalkyl, and $C_{1-6}$ haloalkoxy;

each $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups; and with the proviso that when:
V is CH;
W is CH;
the moiety represented by:

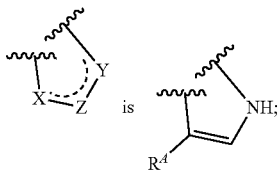

is

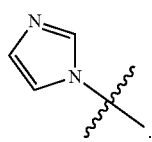 [SMILES: *n1ccnc1]

n is 0; and
Q is cyclohexyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $N^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

then Ring A is other than:

In some embodiments:
V is N or $CR^V$, wherein $R^V$ is H, halo, or $C_{1-4}$ alkyl;
W is N or $CR^W$, wherein $R^W$ is H, halo, or $C_{1-4}$ alkyl;
the moiety represented by:

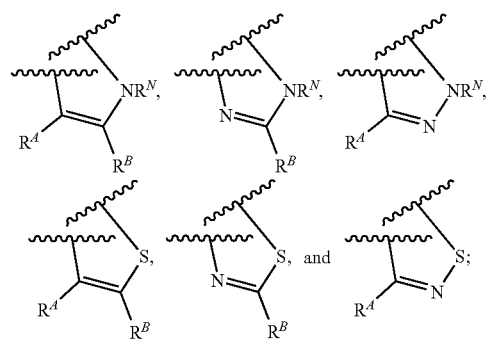

is selected from:

each $R^N$ is independently selected from H and $C_{1-4}$ alkyl;
each $R^A$, $R^B$, and $R^C$ is independently selected from H and $C_{1-4}$ alkyl;
Ring A is selected from:

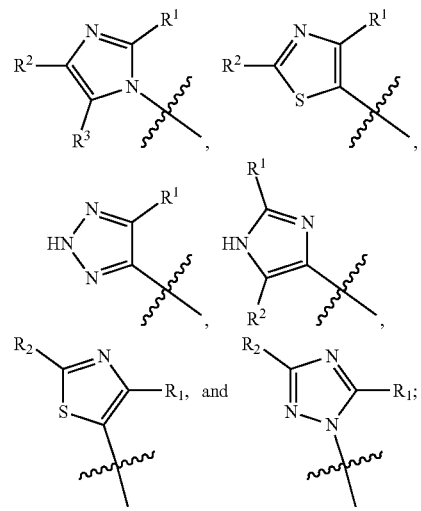

$R^1$, $R^2$, and $R^3$ are each independently selected from H and $C_{1-4}$ alkyl;
L is methylene;
n is 0 or 1;
Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, C(O)

$R^{b1}$, C(O)$NR^{c1}R^{d1}$, C(O)$OR^{a1}$, OC(O)$R^{b1}$, OC(O) $NR^{c1}R^{d1}$, C(=$NR^{e1}$)$NR^{c1}R^{d1}$, $NR^{c1}$C(=$NR^{e1}$) $NR^{c1}R^{d1}$, $NR^{c1}$C(O)$R^{b1}$, $NR^{c1}$C(O)$OR^{a1}$, $NR^{c1}$C(O) $NR^{c1}R^{d1}$, $NR^{c1}$S(O)$R^{b1}$, $NR^{c1}$S(O)$_2R^{b1}$N, $NR^{c1}$S(O)$_2$ $NR^{c1}R^{d1}$, S(O)$R^{b1}$, S(O)$NR^{c1}R^{d1}$, S(O)$_2R^{b1}$, and S(O)$_2$ $NR^{c1}R^{d1}$;

wherein Q is other than H when n is 0;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, NO$_2$, $OR^{a2}$, $SR^{a2}$, C(O)$R^{b2}$, C(O)$NR^{c2}R^{d2}$, C(O)$OR^{a2}$, OC(O)$R^{b2}$, OC(O)$NR^{c2}R^{d2}$, C(=$NR^{e2}$)$NR^{c2}R^{d2}$, $NR^{c2}$C(=$NR^{e2}$) $NR^{c2}R^{d2}$, $NR^{c2}R^{d2}$, $NR^{c2}$C(O)$R^{b2}$, $NR^{c2}$C(O)$OR^{a2}$ $NR^{c2}$C(O)$NR^{c2}R^{d2}$, $NR^{c2}$S(O)$R^{b2}$, $NR^{c2}$S(O)$_2R^{b2}$, $NR^{c2}$S(O)$_2NR^{c2}R^{d2}$, S(O)$R^{b2}$, S(O)$NR^{c2}R^{d2}$, S(O)$_2$ $R^{b2}$, and S(O)$_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$—$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^3$, $SR^{a3}$, C(O)$R^{b3}$, C(O)$NR^{c3}R^{d3}$, C(O)$OR^3$, OC(O)$R^{b3}$, OC(O)$NR^{c3}R^{d3}$, $NR^{c3}R^{d3}$, $NR^{c3}$C(O)$R^{b3}$ $NR^{c3}$C(O)$NR^{c3}R^{d3}$, $NR^{c3}$C(O)$OR^{a3}$, C(=$NR^{e3}$)$NR^{c3}R^{d3}$, $NR^{c3}$C(=$NR^{e3}$)$NR^{c3}R^{d3}$, S(O) $R^{b3}$, S(O)$NR^{c3}R^{d3}$, S(O)$_2R^{b3}$, $NR^{c3}$S(O)$_2R^{b3}$, $NR^{c3}$S (O)$_2NR^{c3}R^{d3}$, and S(O)$_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, C(O)$R^{b3}$, C(O)$NR^{c3}R^{d3}$, C(O) $OR^3$, OC(O)$R^{b3}$, OC(O)$NR^{c3}R^{d3}$, $NR^{c3}R^{d3}$, $NR^{c3}$C(O) $R^{b3}$ $NR^{c3}$C(O)$NR^{c3}R^{d3}$, $NR^{c3}$C(O)$OR^{a3}$, C(=$NR^{e3}$) $NR^{c3}R^{d3}$, $NR^{c3}$C(=$NR^{e3}$)$NR^{c3}R^{d3}$, S(O)$R^{b3}$, S(O) $NR^{c3}R^{d3}$, S(O)$_2R^{b3}$, $NR^{c3}$S(O)$_2R^{b3}$, $NR^{c3}$S(O)$_2$ $NR^{c3}R^{d3}$, and S(O)$_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, C(O)$R^{b3}$, C(O)$NR^{c3}R^{d3}$, C(O) $OR^3$, OC(O)$R^{b3}$, OC(O)$NR^{c3}R^{d3}$, $NR^{c3}R^{d3}$, $NR^{c3}$C(O) $R^{b3}$, $NR^{c3}$C(O)$NR^{c3}R^{d3}$, $NR^{c3}$C(O)$OR^3$, C(=$NR^{e3}$) $NR^{c3}R^{d3}$, $NR^{c3}$C(=$NR^{e3}$)$NR^{c3}R^{d3}$, S(O)$R^{b3}$, S(O) $NR^{c3}R^{d3}$, S(O)$_2R^{b3}$, $NR^{c3}$S(O)$_2R^{b3}$, $NR^{c3}$S(O)$_2$ $NR^{c3}R^{d3}$, and S(O)$_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, C(O)$R^{b3}$, C(O)$NR^{c3}R^{d3}$, C(O)$OR^{a3}$, OC(O)$R^{b3}$, OC(O)$NR^{c3}R^{d3}$, $NR^{c3}R^{d3}$, $NR^{c3}$C(O)$R^{b3}$, $NR^{c3}$C(O)$NR^{c3}R^{d3}$, $NR^{c3}$C(O)$OR^{a3}$, C(=$NR^{e3}$) $NR^{c3}R^{d3}$, $NR^{c3}$C(=$NR^{e3}$)$NR^{c3}R^{d3}$, S(O)$R^{b3}$, S(O) $NR^{c3}R^{d3}$, S(O)$_2R^{b3}$, $NR^{c3}$S(O)$_2R^{b3}$, $NR^{c3}$S(O)$_2$ $NR^{c3}R^{d3}$, and S(O)$_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups; and with the proviso that when:

V is CH;

W is CH;

the moiety represented by:

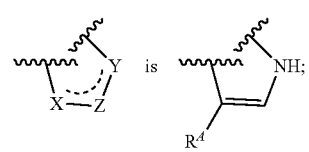

is n is 0; and

Q is cyclohexyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, NO$_2$, $OR^{a1}$, $SR^{a1}$, C(O)$R^{b1}$, C(O) $NR^{c1}R^{d1}$, C(O)$OR^{a1}$, OC(O)$R^{b1}$, OC(O)$NR^{c1}R^{d1}$, C(=$NR^{e1}$)$NR^{c1}R^{d1}$, $NR^{c1}$C(=$NR^{e1}$)$NR^{c1}R^{d1}$, $NR^{c1}R^{d1}$, $NR^{c1}$C(O)$R^{b1}$, $NR^{c1}$C(O)$OR^{a1}$, $NR^{c1}$C(O) $NR^{c1}R^{d1}$, $NR^{c1}$S(O)$R^{b1}$, $NR^{c1}$S(O)$_2R^{b1}$, $NR^{c1}$S(O)$_2$ $NR^{c1}R^{d1}$, S(O)$R^{b1}$, S(O)$NR^{c1}R^{d1}$, S(O)$_2R^{b1}$, and S(O)$_2$ $NR^{c1}R^{d1}$;

then Ring A is other than:

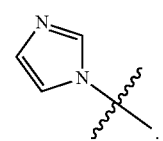 [SMILES: *n1ccnc1]

In some embodiments:
V is N or $CR^V$, wherein $R^V$ is H, halo, or $C_{1-4}$ alkyl;
W is N or $CR^W$, wherein $R^W$ is H, halo, or $C_{1-4}$ alkyl;
wherein at least one of V and W is N;
the moiety represented by:

is selected from:

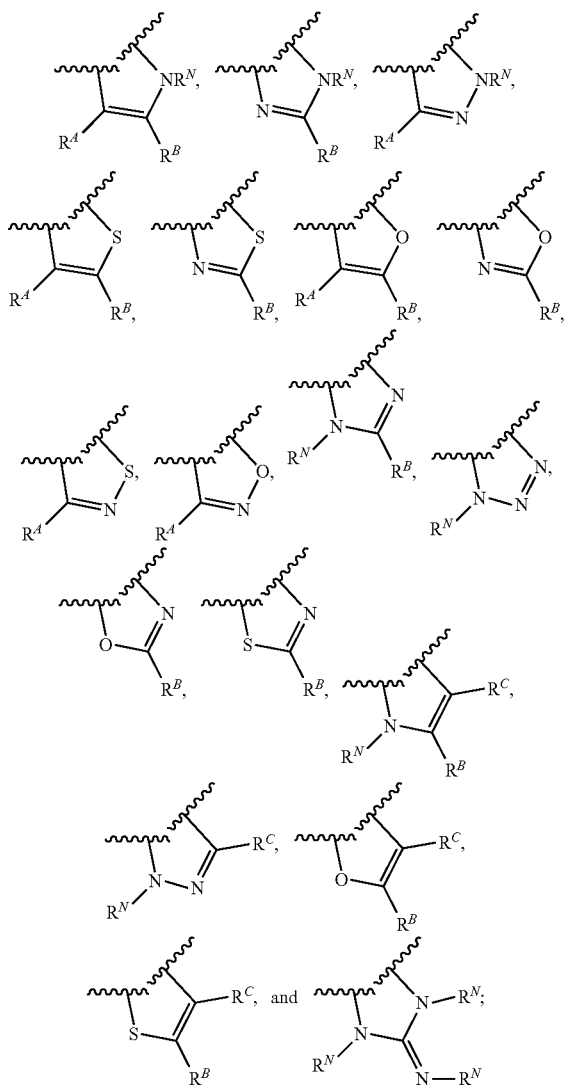

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and $C_{1-4}$ alkyl;

each $R^N$ is independently selected from H, $C_{1-4}$ alkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^N$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^{c1}C(O)R^{b1}$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $R^A$, $R^B$, and $R^C$ is independently selected from H, halo, $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^A$, $R^B$, and $R^C$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

L is a $C_{1-4}$ alkylene linker;

n is 0 or 1;

Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^cR^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2 NR^{c1}R^{d1}$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$w $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein Q is other than H when n is 0;

each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each Cy¹ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)$ $NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^a$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^a$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^3$, $OC(O)R^{b3}$, $OC(O)NR^{c3}R^{d3}$, $NR^{c3}R^{d3}$, $NR^{c3}C(O)$ $R^{b3}$ $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkylamino, di($C_{1-6}$ alkyl)amino, $C_{1-6}$ alkoxy, $C_{1-6}$ haloalkyl, and $C_{1-6}$ haloalkoxy;

each $R^e$, $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

In some embodiments:

V is N or $CR^V$, wherein $R^V$ is H, halo, or $C_{1-4}$ alkyl;

W is N or $CR^W$, wherein $R^W$ is H, halo, or $C_{1-4}$ alkyl;

the moiety represented by:

is selected from:

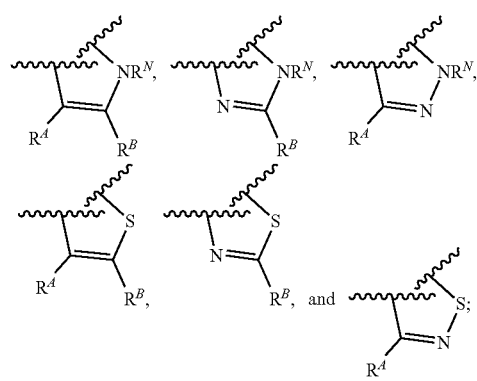

Ring A is selected from:

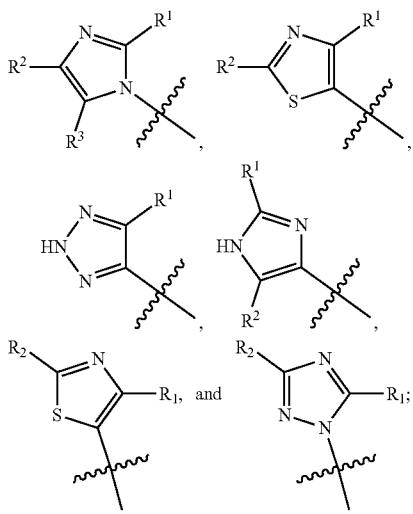

each $R^N$ is independently selected from H and $C_{1-4}$ alkyl;
each $R^A$ and $R^B$ is independently selected from H and $C_{1-4}$ alkyl;
$R^1$, $R^2$, and $R^3$ are each independently selected from H and $C_{1-4}$ alkyl;
L is a $C_{1-4}$ alkylene linker;
n is 0 or 1;
Q is $C_{1-4}$ alkyl, $C_{1-4}$ haloalkyl, phenyl, $C_{3-7}$ cycloalkyl, 5-10 membered heteroaryl, or 4-10 membered heterocycloalkyl, wherein said $C_{1-4}$ alkyl, phenyl, $C_{3-10}$ cycloalkyl, 5-10 membered heteroaryl, or 4-10 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl are optionally substituted by 1, 2, or 3 substituents independently selected from OH, CN, $C_{1-6}$ alkoxy, and $NR^cC(O)R^{b1}$;
each $Cy^1$ is independently selected from phenyl, cyclopropyl, azetidinyl, pyrrolidinyl, morpholinyl, piperidinyl, piperazinyl, and isothiazolidinyl-1,1-dione, each optionally substituted by 1 or 2 substituents independently selected from halo, OH, and morpholinyl;
each $R^{a1}$, $R^{b1}$, $R^{c1}$, and $R^{d1}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{a1}$, $R^{b1}$, $R^{c1}$, and $R^{d1}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^a$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, and $C_{1-6}$ haloalkyl, wherein said $C_{1-6}$ alkyl and $C_{1-6}$ haloalkyl are each optionally substituted with 1, 2, or 3 substituents independently selected from OH, di($C_{1-6}$ alkyl)amino, and $C_{1-6}$ alkoxy;

each $R^{e1}$ and $R^{e3}$ is independently selected from H, $C_{1-4}$ alkyl, and CN;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups;

with the proviso that when:
V is CH;
W is CH;
the moiety represented by:

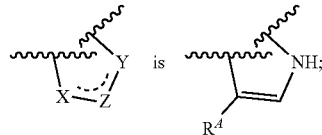

n is 0; and
Q is cyclohexyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^cR^d$, $S(O)R^{b1}$, $S(O)NR^{c1}R^{d1}$, $S(O)_2R^{b1}$, and $S(O)_2NR^{c1}R^{d1}$;

then Ring A is other than:

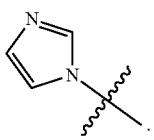 [SMILES: *n1ccnc1]

In some embodiments, provided herein is a compound of Formula IIa:

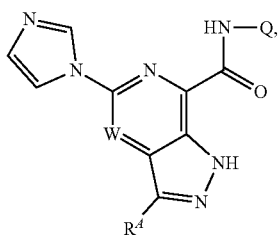

or a pharmaceutically acceptable salt thereof.

In some embodiments, provided herein is a compound of Formula IIb:

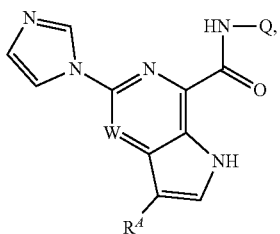

or a pharmaceutically acceptable salt thereof.

In some embodiments, provided herein is a compound of Formula IIIa:

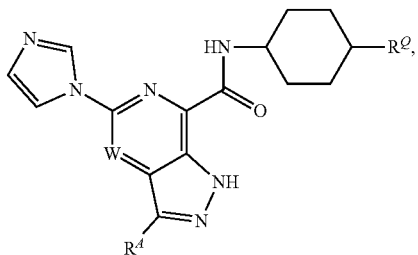

or a pharmaceutically acceptable salt thereof, wherein $R^Q$ is $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$ and $NR^{c1}C(O)R^{b1}$.

In some embodiments, provided herein is a compound of Formula IIb:

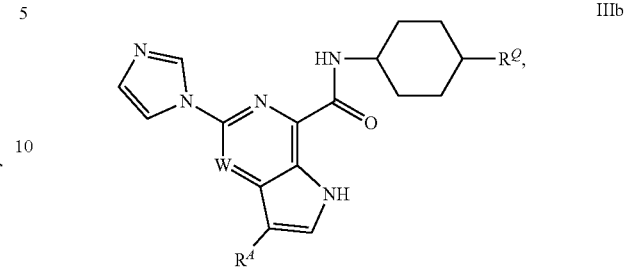

or a pharmaceutically acceptable salt thereof, wherein $R^Q$ is $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$ and $NR^{c1}C(O)R^{b1}$.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, the term "alkylene," employed alone or in combination with other terms, refers to a linking alkyl group.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or Cl.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the haloalkoxy group has 1 to 6 or 1 to 4 carbon atoms. An example haloalkoxy group is —OCF$_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —N(alkyl)$_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5]octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl," employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Where the heterocycloalkyl group includes a fused aromatic ring, the heterocycloalkyl group can be attached to the main structure though either the aromatic or non-aromatic ring. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-azaspiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl," employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl," employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b]thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl," employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution. Tautomeric forms can also include methyltropic tautomers, which result from the swapping of a single bond with an adjacent double bond together with the concomitant migration of a methyl group. Methyltropic tautomers can include, for example, 2-methyl-2H-pyrazolo[3,4-c]pyridine and 1-methyl-1H-pyrazolo[3,4-c]pyridine.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term, "compound," as used herein is meant to include all stereoisomers, geometric isomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of a compound of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "RT", as used herein, are understood in the art, and refer generally to a temperature, e.g. a reaction temperature, that is about the temperature of the room in which the reaction is carried out, for example, a temperature from about 20° C. to about 30° C.

Compounds of Formula I can be prepared according to numerous preparatory routes known in the literature. Example synthetic methods for preparing compounds of the invention are provided in the Schemes below. Unless noted otherwise, all substituents are as defined herein.

Scheme 1

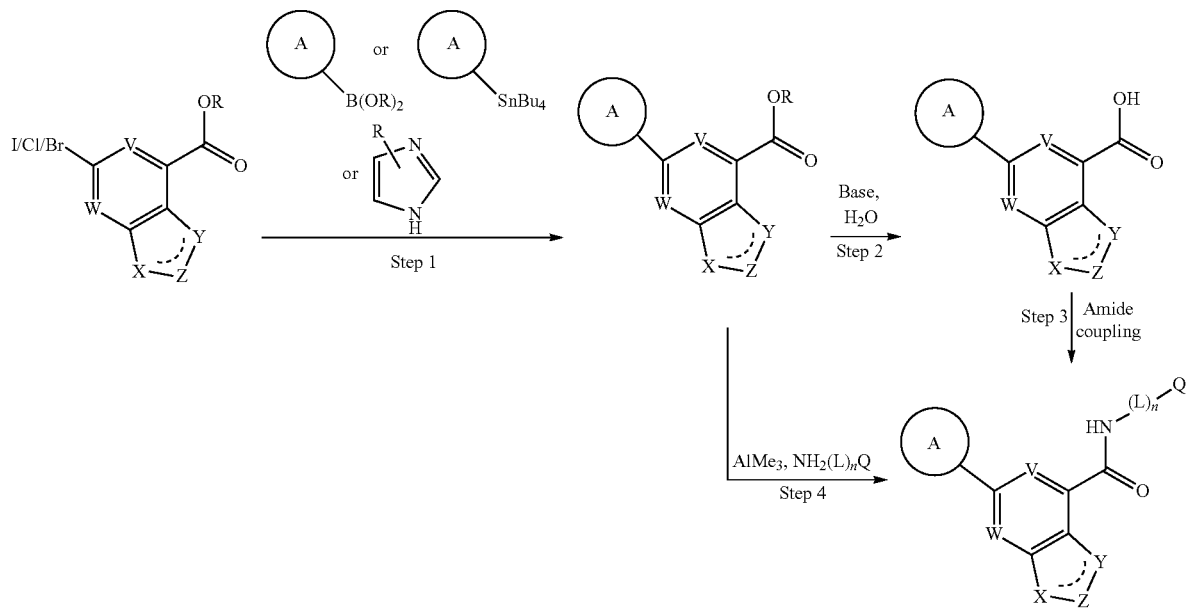

Scheme 1 shows the synthesis of analogs following a general route that utilizes well-established chemistry. Substituted haloaromatic esters can be coupled with a 5-membered heteroaromatic ring via several different methods known to one skilled in the art (Step 1). These include coupling an aromatic tributylstannane in the presence of a Pd catalyst such as $Pd(PPh_3)_2Cl_2$ in a polar solvent such as DMF at elevated temperature, coupling a boronic acid or boronic ester in the presence of a Pd/Cu catalyst such as $Pd(dppf)Cl_2$ and CuI and a base such as sodium carbonate or cesium fluoride in a solvent such as DMF, and coupling a substituted imidazole in the presence of a Pd catalyst such as $Pd_2dba_3$, a ligand such as tBuXPhos, and a base such as $K_3PO_4$ in a non-polar solvent such as toluene at elevated temperature. The resulting esters can be hydrolyzed by a base such as sodium hydroxide in the presence of water to give carboxylic acids (Step 2), which can then be converted to the desired amide analogs by coupling amines $NH_2(L)_nQ$ using amide coupling reagents such as HATU in the presence of a base such as diisopropylethylamine in a polar solvent such as DMF (Step 3). Alternatively the substituted ester products of Step 1 can be converted directly to the desired amide analogs by treating with amines $NH_2(L)_nQ$ in the presence of trimethylaluminum in a nonpolar solvent such as toluene (Step 4).

Scheme 2

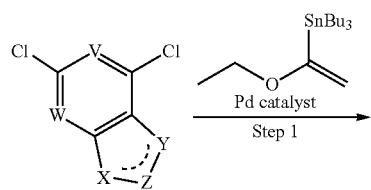

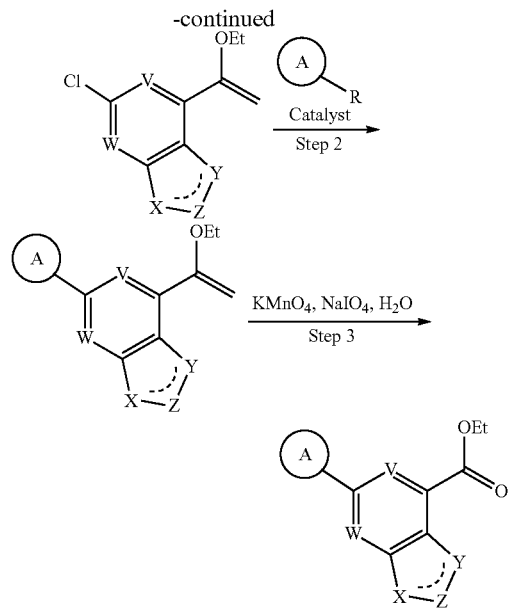

Scheme 2 shows the synthesis of substituted aromatic ester intermediates following a route that utilizes well-established chemistry. Aromatic dichlorides, which may be commercially available or can be made via routes known to one skilled in the art, can be converted to enol ethers by coupling to tributyl(1-ethoxyvinyl)stannane in the presence of a Pd catalyst such as $Pd(PPh_3)Cl_2$ in a polar solvent such as DMF at elevated temperature (Step 1). A 5-membered heteroaromatic may be introduced (Step 2) using coupling conditions described in Scheme 1, Step 1. Treatment of the enol ethers with $KMnO_4$, $NaIO_4$ and water in a nonpolar solvent such as dioxane at room temperature gives substituted esters (Step 3), which can then be converted to amide analogs using the conditions described in Scheme 1, Steps 2 and 3, or Step 4.

Scheme 3

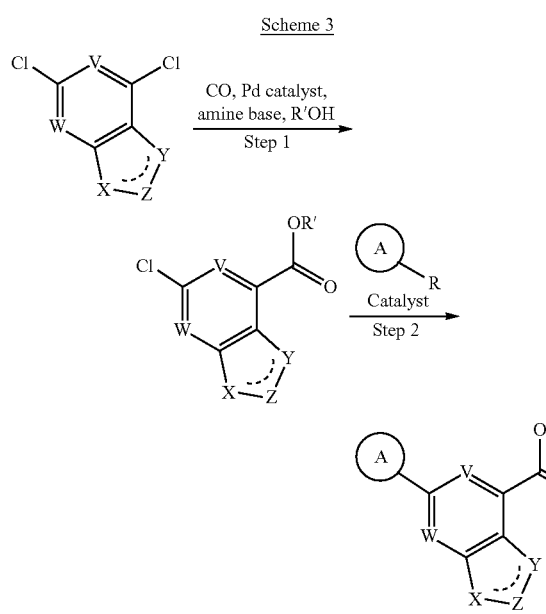

Scheme 3 shows an alternative route to substituted aromatic esters, which can be prepared from aromatic dichlorides by first treating with carbon monoxide in the presence of a Pd catalyst such as Pd(dppf)Cl$_2$, an amine base such as triethylamine, and an alcohol such as methanol in a polar solvent such as DMF at elevated temperature (Step 1). The resulting chloroesters can then be coupled with a 5-membered heteroaromatic ring using the coupling conditions described in Scheme 1, Step 1.

Scheme 4

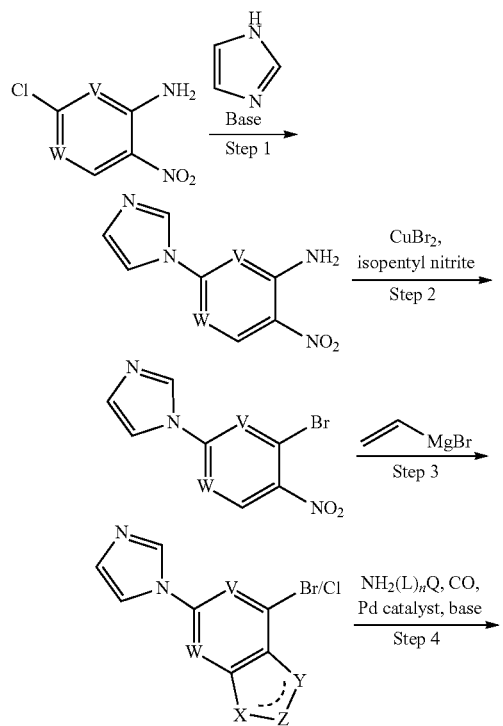

Scheme 4 shows a synthetic route to imidazole substituted amide analogs. Beginning from a commercially available chloro-nitroheteroaromatic amine, an imidazole ring can be introduced by treatment with imidazole in the presence of a base such as K$_2$CO$_3$ in a polar solvent such as DMF at elevated temperature (Step 1). The amine can then be converted to a bromide by treatment with CuBr$_2$ and isopentyl nitrite in a polar solvent such as acetonitrile at elevated temperature (Step 2). Reacting with vinylmagnesium bromide in an aprotic solvent such as THF at low temperature (Step 3) followed by treatment with an amine in the presence of carbon monoxide, a Pd catalyst such as Pd(dppf)Cl$_2$, an amine base such as triethylamine in a polar solvent such as DMSO at elevated temperature (Step 4) provides imidazole substituted amide analogs.

Methods of Use

Compounds of the invention can inhibit the activity of CD38. For example, the compounds of the invention can be used to inhibit activity or a function of CD38 in a cell or in an individual or patient in need of inhibition of the enzyme by administering an inhibiting amount of a compound of the invention to the cell, individual, or patient. As used herein, the term "in a cell" includes both inside the cell membrane and on the surface of the cell membrane.

Compounds of the invention, as CD38 inhibitors, can increase levels of NAD$^+$. Accordingly, the present invention is further directed to a method of increasing the level of NAD$^+$ in a sample or in a patient, comprising contacting the sample or administering to the patient a compound of Formula I, or a pharmaceutically acceptable salt thereof, wherein the increased level of NAD$^+$ is relative to the level of NAD$^+$ prior to the contacting or administering.

The compounds of the invention are useful in the treatment of various diseases associated with abnormal expression or activity of CD38. For example, the compounds of the invention are useful in the treatment of cancer. In some embodiments, the cancers are characterized in having abnormal expression or activity of CD38, for example, elevated expression or activity, compared with normal cells. In some embodiments, the cancers treatable according to the present invention include breast, central nervous system, endometrium, kidney, large intestine, lung, oesophagus, ovary, pancreas, prostate, stomach, head and neck (upper aerodigestive), urinary tract, colon, and others.

The compounds of the invention are useful in the treatment of tumors with exhausted T cells (for example, see Hashimoto M, Kamphorst A O, Im S J, et al. CD8 T Cell Exhaustion in Chronic Infection and Cancer: Opportunities for Interventions. *Annu Rev Med.* 2018; 69: 301-318. doi: 10.1146/annurev-med-012017-043208) and tumors defined as hot, altered, and cold immune tumors based on immunoscore (for example, see Galon J, Bruni D. Approaches to treat immune hot, altered and cold tumours with combination immunotherapies. *Nat Rev Drug Discov.* 2019; 18(3):197-218. doi:10.1038/s41573-018-0007-y).

In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

In some embodiments, the cancer treatable by administration of the compounds of the invention is lung cancer.

In some embodiments, the cancer treatable by administration of the compounds of the invention is melanoma.

In some embodiments, the cancer treatable by administration of the compounds of the invention is colon cancer.

Other cancers treatable by the administration of the compounds of the invention include checkpoint therapy-treated cancers, checkpoint therapy-treated resistant cancers, adenosine-dependent tumors, Treg-infiltrated tumors, and MDSC-infiltrated tumors.

Other cancers treatable by the administration of the compounds of the invention include bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, glioma, head and neck cancer (upper aerodigestive cancer), intestinal cancers, Kaposi's sarcoma, kidney cancer, laryngeal cancer, liver cancer (e.g., hepatocellular carcinoma), lung cancer (e.g., non-small cell lung cancer, adenocarcinoma), melanoma, prostate cancer, rectal cancer, renal clear cell carcinoma, skin cancer, stomach cancer, testicular cancer, thyroid cancer, and uterine cancer.

In some embodiments, the cancer treatable by administration of the compounds of the invention is multiple myeloma, diffuse large B-cell lymphoma (DLBCL), hepatocellular carcinoma, bladder cancer, esophageal cancer, head and neck cancer (upper aerodigestive cancer), kidney cancer, prostate cancer, rectal cancer, stomach cancer, thyroid cancer, uterine cancer, and breast cancer.

Other cancers treatable by the administration of the compounds of the invention include checkpoint therapy-treated cancers, checkpoint therapy-treated resistant cancers, adenosine-dependent tumors, Treg-infiltrated tumors, and MDSC-infiltrated tumors.

The compounds of the invention can also be used to treat the following diseases or conditions: HIV/AIDS, adoptive T cell therapy, acute lung injury, acute respiratory distress syndrome (ARDS), hyperphosphatemia, alcohol intolerance, lupus, rheumatoid arthritis ataxia-telangiectasia, sleep disorders, epilepsy, exercise intolerance, hypertension, hypoxic pulmonary vasoconstriction, hansen's disease, tuberculosis, leishmaniasis, cardiac hypertrophy, congestive heart failure (CHF), muscular dystrophy, stroke, organ reperfusion injury, idiopathic pulmonary fibrosis, pancreatitis, cystic fibrosis, asthma, chronic obstructive pulmonary disease (COPD), Irritable Bowel Syndrome (IBS), colitis, gout, obesity, sarcopenic obesity, Metabolic Syndrome, end stage renal disease, dyslipidemia, hearing loss, liver disease, steatosis, nonalcoholic steatohepatitis (NASH/NAFLD), Alzheimer's disease, multiple sclerosis, neurocognitive disorders, optic neuropathy, postmenopausal osteoporosis, bipolar disorder, schizophrenia, Huntington's disease, diabetes, Hartnup disease, skin hyperpigmentation, diabetic neuropathy, radiation exposure, UV skin damage, psoriasis, periodontal disease, chronic lymphocytic leukemia, amyelotrophic lateral sclerosis, Parkinson's disease, Leber's hereditary amaurosisinsulin resistance, and type I diabetes.

The CD38 inhibitors of the invention may also have therapeutic utility in CD38-related disorders in disease areas such as cardiology, virology, neurodegeneration, inflammation, and pain, particularly where the diseases are characterized by overexpression or increased activity of CD38.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" CD38 or "contacting" a cell with a compound of the invention includes the administration of a compound of the present invention to an individual or patient, such as a human, having CD38, as well as, for example, introducing a compound of the invention into a sample containing a cellular or purified preparation containing CD38.

As used herein, the term "individual" or "patient," used interchangeably, refers to mammals, and particularly humans. The individual or patient can be in need of treatment.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease. In some embodiments, the invention is directed to a method of preventing a disease in a patient, by administering to the patient a therapeutically effective amount of a compound of Formula I, or a pharmaceutically acceptable salt thereof.

Combination Therapy

One or more additional pharmaceutical agents or treatment methods such as, for example, chemotherapeutics or other anti-cancer agents, immune enhancers, immunosuppressants, immunotherapies, radiation, anti-tumor and antiviral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Suitable agents for use in combination with the compounds of the present invention for the treatment of cancer further include agents that target adenosine signaling like A2aR and A2bR, inhibitors and nodes of adenosine generating pathway like CD39, CD73, and ENPP1 inhibitors, and agents that target generation of immunosuppressive amino acids and their products like IDO inhibitors and AHR inhibitors.

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to checkpoint or costimulatory molecules such as CTLA-4, PD-1, PD-L1 or 4-1BB, respectively, or antibodies to cytokines (IL-10, TGF-β, etc.). Exemplary cancer immunotherapy antibodies include pembrolizumab, ipilimumab, nivolumab, atezolizumab and durvalumab. Additional anti-cancer agent(s) include antibody therapeutics directed to surface molecules of hematological cancers such as ofatumumab, rituximab and alemtuzumab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, NJ), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, anti-cancer agents, vaccines, antibodies, immune enhancers, immune suppressants, anti-inflammatory agents and the like.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of CD38 according to one or more of the assays provided herein.

Equipment: $^1$H NMR Spectra were recorded at 300 or 400 MHz using a Bruker AVANCE 300 MHz/400 MHz spectrometer. NMR interpretation was performed using Bruker Topspin software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

1. LC (basic condition): Shimadzu LC-20AD, Binary Pump, Diode Array Detector. Column: Kinetex 2.6 m EVO C18 100A, 50*3.0 mm, 2.6 µm. Mobile phase: A: Water/5 mM $NH_4HCO_3$, B: Acetonitrile. Flow Rate: 1.2 mL/min at 40° C. Detector: 254 nm, 220 nm. Gradient stop time, 2.9 min. Timetable:

| T (min) | A (%) | B (%) |
| --- | --- | --- |
| 0.01 | 90 | 10 |
| 2.10 | 5 | 95 |
| 2.70 | 5 | 95 |
| 2.90 | 90 | 10 |

2. LC (Basic condition): Shimadzu LC-20ADXR, Binary Pump, Diode Array Detector. Column: Poroshell HPH—C18 50*3.0 mm, 2.7 µm. Mobile Phase A: 0.04% Ammonium hydroxide Mobile Phase B: Acetonitrile. Flow Rate: 1.2 mL/min at 40° C. Detector: 254 nm, 220 nm. Gradient stop time 3.0 min Timetable:

| T (min) | A (%) | B (%) |
| --- | --- | --- |
| 0.01 | 90 | 10 |
| 2.0 | 5 | 95 |
| 2.7 | 5 | 95 |
| 2.8 | 90 | 10 |

3. LC (acidic condition): Shimadzu LC-20AD, Binary Pump, Diode Array Detector. Column: Ascentis Express C18, 50*3.0 mm, 2.7 µm. Mobile phase: A: Water/0.05% TFA, B: Acetonitrile/0.05% TFA. Flow Rate: 1.5 mL/min at 40° C. Detector: 254 nm, 220 nm. Gradient stop time, 2.9 min. Timetable:

| T (min) | A (%) | B (%) |
| --- | --- | --- |
| 0.01 | 90 | 5 |
| 2.10 | 5 | 95 |
| 2.70 | 5 | 95 |
| 2.90 | 90 | 5 |

4. LC (Acidic condition): Shimadzu LC-30AD, Binary Pump, Diode Array Detector. Column: Accucore C18 50*2.1 mm, 2.6 μm. Mobile Phase A: Water/0.1%/FA Mobile Phase B: Acetonitrile/0.1% FA. Flow Rate: 1.0 mL/min at 40° C. Detector: 254 nm, 220 nm. Gradient stop time 3.0 min Timetable:

| T (min) | A (%) | B (%) |
| --- | --- | --- |
| 0.01 | 95 | 5 |
| 2.0 | 5 | 95 |
| 2.7 | 5 | 95 |
| 2.8 | 95 | 5 |

1. S:LCMS-2020, Quadrupole LC/MS, Ion Source: ES-API, TIC: 90~900 m/z, Fragmentor: 60, Drying gas flow: 15 L/min, Nebulizing Gas Flow: 1.5 L/min, Drying gas temperature: 250° C., Vcap: 1100V.
2. Sample preparation: samples were dissolved in ACN or methanol at 1~10 mg/mL, then filtered through a 0.22 μm filter membrane. Injection volume: 1~10 μL.

Definitions: ACN (acetonitrile); Ac$_2$O (acetic anhydride); AcOH (acetic acid); Boc (tert-butoxycarbonyl); Boc$_2$O (di-tert-butyl dicarbonate); BPO (benzoyl peroxide); conc (concentrated); CsF (cesium fluoride); CuI (copper iodide); CH$_3$CN (acetonitrile); CDCl$_3$ (deuterated chloroform); CD$_3$OD (deuterated methanol); DCM (dichloromethane); DEA (diethylamine); DIPEA or DIEA (N,N-diisopropylethylamine); DMF (N,N-dimethylformamide); DMAP (4-dimethyl aminopyridine); DMSO (dimethylsulfoxide); DMSO-d$_6$ (deuterated dimethylsulfoxide); eq (equivalent); dppf (bis(diphenylphosphino)ferrocene); EDCI (1-ethyl-3-(3-dimethylaminopropyl)carbodiimide); eq (equivalents); EtOAc (EtOAc); EtOH (ethanol); g (gram); h (hour); (HATU (1-[bis(dimethylamino)methylene]-1H-1,2,3-triazolo[4,5-b]pyridinium 3-oxide hexafluorophosphate); Hex (hexanes); HOAc (acetic acid); HOBt (hydroxybenzotriazole); $^1$H NMR (proton nuclear magnetic resonance); HCl (hydrochloric acid); Hz (hertz); IPA (iso-propyl alcohol); K$_2$CO$_3$ (potassium carbonate); KOAc (potassium acetate); L (liter); LCMS (liquid chromatography-mass spectrometry); M (molar); MeOH (methanol); mg (milligrams); MHz (megahertz); min (minutes); mL (milliliters), mmol (millimoles); NaCl (sodium chloride); NaH (sodium hydride); n-BuOH (1-butanol); NH$_4$Cl (ammonium chloride); NaN$_3$ (sodium azide); NBS (N-bromo succinimide); NIS (N-iodo succinimide); NMP (N-methyl-2-pyrrolidone); Pd(dppf)Cl$_2$ ([1,1'-Bis(diphenylphosphino)ferrocene]dichloropalladium(II)); Pd$_2$(dba)$_3$·CHCl$_3$ (Tris(dibenzylideneacetone)dipalladium (0)-chloroform adduct); Pd(OH)$_2$/C (Palladium hydroxide on carbon); prep-HPLC (preparative high-performance liquid chromatography); ppm (parts per million); RT (room temperature); SEM (2-(trimethylsilyl)ethoxymethyl); SEMCl (2-(trimethylsilyl)ethoxymethyl chloride); T3P (propanephosphonic acid anhydride); t-BuOH (tert-butyl alcohol); t-BuOK (potassium tert-butoxide); tBuXPhos (2-di-tert-butylphosphino-2',4',6'-triisopropylbiphenyl); TEA (triethylamine); THF (tetrahydrofuran); Ti(Oi-Pr)$_4$ (titanium IV isopropoxide); TsCl (tosyl chloride); tR (retention time); TFA (trifluoroacetic acid); TLC (thin layer chromatography); v/v (volume/volume); XPhos (2-Dicyclohexylphosphino-2',4',6'-triisopropylbiphenyl).

Synthesis of Intermediates

Int-A1: 5-Bromo-1-((2-(trimethylsilyl)ethoxy)methyl)-1H-benzo[d]imidazole-7-carboxylic acid

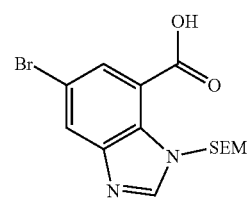 [SMILES: C[Si](C)(C)CCOCn1cnc2cc(Br)cc(C(=O)O)c21]

Step 1: Methyl 6-bromo-3H-benzimidazole-4-carboxylate

To a solution of methyl 2,3-diamino-5-bromo-benzoate (500 mg, 2.0 mmol, 1 eq) in 1M HCl (1.5 mL, 2.0 mmol, 1 eq) was added trimethoxymethane (5 mL, 2.0 mmol, 1 eq), and the mixture was stirred at RT for 1 h. The mixture was diluted with water (20 mL) and extracted with EtOAc (40 mL×3). The combined organic layers were dried over Na$_2$SO$_4$ and concentrated under reduced pressure. The residue was purified by silica gel chromatography (petroleum ether:EtOAc, 1:1) to afford the title compound (506 mg, 2.0 mmol, 97% yield) as a gray solid. LCMS: [M+H]$^+$ 256.9.

Step 2: Methyl 6-bromo-3-(2-trimethylsilylethoxymethyl)benzimidazole-4-carboxylate To a solution of methyl 6-bromo-3H-benzimidazole-4-carboxylate (1.5 g, 5.89 mmol, 1 eq) in anhydrous THF (15 mL) at 0° C. under a N$_2$ atmosphere was added NaH (212 mg, 8.82 mmol, 1.5 eq) slowly and the mixture was stirred at 0° C. for 1 h. SEMCl (824 mg, 7.06 mmol, 1.2 eq) was added and the mixture was stirred for a further 1.5 h. The reaction was quenched with water (30 mL) and the mixture was extracted with EtOAc (50 mL×3). The combined organic layers were dried over Na$_2$SO$_4$ and concentrated under reduced pressure. The residue was purified by silica gel chromatography (petroleum ether:EtOAc, 20:1 to 2:1) to afford the title compound (800 mg, 2.1 mmol, 35% yield). LCMS: [M+H]$^+$ 385.1.

Step 3: 6-Bromo-3-(2-trimethylsilylethoxymethyl) benzimidazole-4-carboxylic acid To a solution of methyl 6-bromo-3-(2-trimethylsilylethoxymethyl)benzimidazole-4-carboxylate (200 mg, 0.52 mmol, 1 eq) in THF (3 mL) was added a solution of lithium hydroxide (65 mg, 1.6 mmol, 3 eq) in water (1 mL). The mixture was stirred at 25° C. overnight. The mixture was adjusted to pH to 3-4 with 2 N HCl and was diluted with water (15 mL) and extracted with EtOAc (20 mL×3). The combined organic layers were dried over Na$_2$SO$_4$ and concentrated under reduced pressure to afford the title compound (180 mg, 0.5 mmol, 93% yield) as a brown solid. LCMS: [M+H]$^+$ 373.1.

Int-A2: 2-(1H-Imidazol-1-yl)-5H-pyrrolo[3,2-d]pyrimidine-4-carboxylic acid

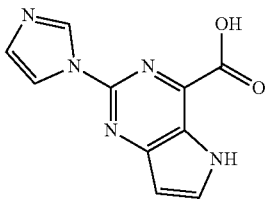 [SMILES: O=C(O)c1nc(-n2ccnc2)nc2cc[nH]c12]

Step 1: 2-Chloro-4-(1-ethoxyvinyl)-5H-pyrrolo[3,2-d]pyrimidine

Under nitrogen, a solution of 2,4-dichloro-5H-pyrrolo[3,2-d]pyrimidine (112 g, 597 mmol, 1 eq), tributyl(1-ethoxyethenyl)stannane (226 g, 627 mmol, 1.1 eq), and Pd(PPh$_3$)$_2$Cl$_2$ (42 g, 60 mmol, 0.1 eq) in DMF (900 mL) was stirred for 3 h at 70° C. The resulting solution was cooled to RT and quenched with saturated aqueous KF. The solids were filtered out, and the resulting solution was extracted with EtOAc. The organic layers were combined, dried over sodium sulfate and concentrated. The crude product was applied onto a silica gel column eluting with EtOAc:petroleum ether (1:5) to afford the title compound (105 g, 79% yield). LCMS: [M+H]$^+$ 224.1, 226.1.

Step 2: 4-(1-Ethoxyvinyl)-2-(1H-imidazol-1-yl)-5H-pyrrolo[3,2-d]pyrimidine

Under nitrogen, a solution of 2-chloro-4-(1-ethoxyethenyl)-5H-pyrrolo[3,2-d]pyrimidine (55.8 g, 249.3 mmol, 1.0 eq), 1H-imidazole (84.9 g, 1.25 mol, 5.00 eq), Pd$_2$(dba)$_3$CHCl$_3$ (38.7 g, 37.39 mmol, 0.15 eq), tBuXphos (26.5 g, 62.32 mmol, 0.25 eq), and K$_3$PO$_4$ (105.8 g, 498.53 mmol, 2.00 eq) in toluene (1 L) was stirred at 110° C. for 2 h. The resulting solution was quenched with water (500 mL), and extracted with EtOAc. The organic layers were combined, dried over Na$_2$SO$_4$ and concentrated under reduced pressure. The crude product was applied onto a silica gel column eluting with EtOAc:petroleum ether (1:1) to afford the title compound (54 g, 85% yield). LCMS: [M+H]$^+$ 256.1.

Step 3: Ethyl 2-(1H-imidazol-1-yl)-5H-pyrrolo[3,2-d]pyrimidine-4-carboxylate A solution of 4-(1-ethoxyvinyl)-2-(1H-imidazol-1-yl)-5H-pyrrolo[3,2-d]pyrimidine (54.0 g, 211.5 mmol, 1.0 eq), KMnO$_4$ (13.4 g, 84.61 mmol, 0.40 eq), and NaIO$_4$ (180.9 g, 846.13 mmol, 4.00 eq) in dioxane (1.1 L) and water (1.1 L) was stirred at 0° C. for 2 h. The reaction was quenched with water. The resulting solution was extracted with EtOAc. The organic layers were combined, dried over Na$_2$SO$_4$ and concentrated under reduced pressure to give the title compound (41.0 g, 76% yield) as a white solid. LCMS: [M+H]$^+$ 258.1.

Step 4: 2-(1H-Imidazol-1-yl)-5H-pyrrolo[3,2-d]pyrimidine-4-carboxylic acid

A solution of ethyl 2-(imidazol-1-yl)-5H-pyrrolo[3,2-d]pyrimidine-4-carboxylate (39 g, 152 mmol, 1.0 eq) and NaOH (12.1 g, 303 mmol, 2.00 eq) in H$_2$O (350 mL) and EtOH (350 mL) was stirred at RT for 2 h. The pH value of the solution was adjusted to 5 with conc. HCl. The solids were collected by filtration. The solids were further purified by slurrying in CH$_3$CN and filtering to afford the title compound (30.0 g, 86% yield) as a white solid. [M+H]$^+$ 230.1.

Int-A3: 2-Chloro-N-((1r,4r)-4-(2-methoxyethoxy)cyclohexyl)-5H-pyrrolo[3,2-d]pyrimidine-4-carboxamide

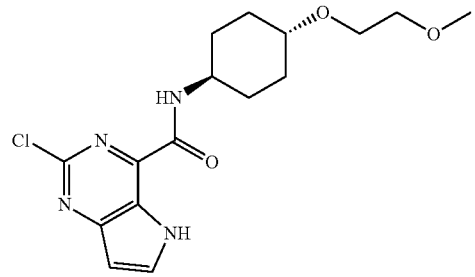 [SMILES: COCCO[C@H]1CC[C@H](NC(=O)c2nc(Cl)nc3cc[nH]c23)CC1]

Step 1: Ethyl 2-chloro-5H-pyrrolo[3,2-d]pyrimidine-4-carboxylate

A solution of NaIO$_4$ (20.2 g, 94.44 mmol, 4.0 eq) in H$_2$O (80 mL) was added to a solution of 2-chloro-4-(1-ethoxyethenyl)-5H-pyrrolo[3,2-d]pyrimidine (5.3 g, 23.47 mmol, 1.0 eq) in dioxane (100 mL). To this mixture was added a solution of KMnO$_4$ (1.48 g, 9.37 mmol, 0.40 eq) in H$_2$O (20 mL), and the resulting mixture was stirred for 1 h at 25° C. The solids were filtered out. The resulting solution was extracted with 4×100 mL of dichloromethane, and the combined organic layers were dried over sodium sulfate and concentrated under vacuum to afford the title compound (5 g, 94% yield) as a yellow solid. LCMS: [M+H]$^+$ 226.03.

Step 2: 2-Chloro-5H-pyrrolo[3,2-d]pyrimidine-4-carboxylic acid

A mixture of ethyl 2-chloro-5H-pyrrolo[3,2-d]pyrimidine-4-carboxylate (4.5 g, 19.94 mmol, 1.0 eq), lithium hydroxide hydrate (1.68 g, 40.04 mmol, 2.0 eq) in THF (30 mL) and H$_2$O (10 mL) was stirred for 2 h at 25° C. The resulting mixture was concentrated to remove THF, and the pH value was adjusted to 3 with 2 M HCl. The solids were collected by filtration to afford the title compound (2.3 g, 58% yield) as a yellow solid. LCMS: [M+H]$^+$ 198.00.

Step 3: 2-Chloro-N-((1r,4r)-4-(2-methoxyethoxy)cyclohexyl)-5H-pyrrolo[3,2-d]pyrimidine-4-carboxamide A solution of 2-chloro-5H-pyrrolo[3,2-d]pyrimidine-4-carboxylic acid (2.3 g, 11.64 mmol, 1.0 eq), DIPEA (4.49 g, 34.74 mmol, 2.9 eq), HATU (5.30 g, 13.94 mmol, 1.2 eq) and Int B1 (2.40 g, 13.85 mmol, 1.2 eq) in DMF (20 mL) was stirred for 2 h at 25° C. The reaction was quenched with water and extracted with 3×100 mL of dichloromethane. The organic layers were combined, dried over sodium sulfate and concentrated under vacuum. The crude product was purified by re-crystallization from MeOH to afford the title compound (2.4 g, 58% yield) as a yellow solid. LCMS: [M+H]+ 353.13.

Int-A4: 5-(1H-imidazol-1-yl)-1H-pyrazolo[4,3-d]pyrimidine-7-carboxylic acid

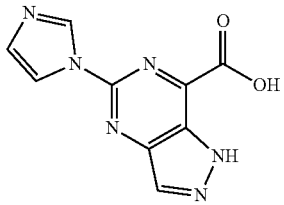 [SMILES: O=C(O)c1nc(-n2ccnc2)nc2cn[nH]c12]

Step 1: methyl 1-(4-methoxybenzyl)-4-nitro-1H-pyrazole-3-carboxylate

A solution of methyl 4-nitro-1H-pyrazole-3-carboxylate (100 g, 584.4 mmol, 1 equiv), K$_2$CO$_3$ (185.8 g, 1.34 mmol, 2.3 equiv), and 1-(chloromethyl)-4-methoxy-benzene (111.7 g, 713.0 mmol, 1.2 equiv) in DMF (1.10 L) was stirred for 4 h at 50° C. After completion, the reaction was quenched with H$_2$O (1.5 L) and extracted with ethyl acetate (3×1.2 L). The organic layers were combined and washed with 3×300 ml of brine. The mixture was dried over anhydrous sodium sulfate and then concentrated under vacuum. The crude product was purified by silica gel column eluting with ethyl acetate/petroleum ether (1:3) to afford the title compound (170.0 g, 99%) as yellow oil. LCMS: [M+H]+ 292.15

Step 2: 1-(4-methoxybenzyl)-4-nitro-1H-pyrazole-3-carboxamide

A solution of methyl 1-(4-methoxybenzyl)-4-nitro-1H-pyrazole-3-carboxylate (170 g, 584.19 mmol, 1.0 equiv) in NH$_3$/MeOH (7 M, 800 mL) was stirred for 16 h at RT. After concentrating under vacuum, the crude product was slurried in H$_2$O and then filtered and rinsed to afford the title compound (149.0 g, 92.2%) as a white solid. LCMS: [M+H]+ 277.10.

Step 3: 4-amino-1-(4-methoxybenzyl)-1H-pyrazole-3-carboxamide

Under an H$_2$ atmosphere, a solution of 1-(4-methoxybenzyl)-4-nitro-1H-pyrazole-3-carboxamide (80 g, 289.8 mmol, 1 equiv), Pd/C (20.0 g) in DCM (1.2 L) and EtOH (1.6 L) was stirred for 2 h at RT. The solids were filtered out. The resulting mixture was concentrated under vacuum to afford the title compound (79.2 g, % yield) as a pink solid. LCMS: [M+H]+ 247.15.

Step 4: 5-chloro-2-(4-methoxybenzyl)-2H-pyrazolo[4,3-d]pyrimidin-7(6H)-one

To the solution of 4-amino-1-(4-methoxybenzyl)-1H-pyrazole-3-carboxamide (260 g, 1.06 mol, 1 equiv) in 1,4-dioxane (5.0 L) was added slowly thiophosgene (265.4 g, 2.32 mol, 2.2 equiv) at RT. The mixture was stirred for 4 h at 95° C. After concentrating under vacuum, the crude product was slurried in petroleum ether/EtOAc (2:1, 800 ml) and then filtered and rinsed to afford the title compound (257 g, 83%) as a yellow solid. LCMS [M+H]+: 291.10.

Step 5: 5-(1H-imidazol-1-yl)-2-(4-methoxybenzyl)-2H-pyrazolo[4,3-d]pyrimidin-7(6H)-one Under an N$_2$ atmosphere, a solution of 5-chloro-2-(4-methoxybenzyl)-2H-pyrazolo[4,3-d]pyrimidin-7(6H)-one (257 g, 886.2 mmol, 1 equiv), imidazole (211 g, 3.1 mol, 3.5 equiv), Pd$_2$(dba)$_3$·CHCl$_3$ (55 g, 53.14 mmol, 0.06 equiv), and 2-di-tert-butylphosphino-2',4',6'-triisopropylbiphenyl (34 g, 80.1 mmol, 0.09 equiv) in toluene (4500 mL) was stirred for 2 h at 110° C. After completion, the solids were collected by filtration and slurried in 600 mL of MeOH and then filtered and rinsed to afford the title compound (200 g, 70%) as a brown solid.

Step 6: 7-chloro-5-(1H-imidazol-1-yl)-2-(4-methoxybenzyl)-2H-pyrazolo[4,3-d]pyrimidine A solution of 5-(1H-imidazol-1-yl)-2-(4-methoxybenzyl)-2H-pyrazolo[4,3-d]pyrimidin-7(6H)-one (63 g, 195.4 mmol, 1 equiv), SOCl$_2$ (500 mL, 6.89 mol, 35.26 equiv), DMF (20 mL) was stirred for 2.5 h at 90° C. The resulting mixture was concentrated under vacuum. The resulting solution was diluted with 1000 mL of DCM and 200 mL H$_2$O. The pH value of the solution was adjusted to 8.0 with saturated aqueous Na$_2$CO$_3$. The resulting solution was extracted with 3×500 mL of DCM. The organic layers were combined, dried over anhydrous sodium sulfate and concentrated under vacuum to afford the title compound (58.3 g, 88%) as a yellow solid. LCMS: [M+H]+ 341.20.

Step 7: 5-(1H-imidazol-1-yl)-2-(4-methoxybenzyl)-2H-pyrazolo[4,3-d]pyrimidine-7-carbonitrile Under an N$_2$ atmosphere, a solution of 7-chloro-5-(1H-imidazol-1-yl)-2-(4-methoxybenzyl)-2H-pyrazolo[4,3-d]pyrimidine (41.2 g, 120.90 mmol, 1 equiv), XantPhos (3.5 g, 6.04 mmol, 0.05 equiv), zinc cyanide (14.9 g, 126.72 mmol, 1.05 equiv), DMF (350 mL), and Pd$_2$(allyl)$_2$Cl$_2$ (2.2 g, 6.06 mmol, 0.05 equiv) was stirred for 2.0 h at 80° C. The resulting solution was diluted with 500 mL of H$_2$O. The solids were filtered out and the residue was applied onto a silica gel column with DCM/MeOH (97:3). This afforded the title compound (16.0 g) as a brown solid, which was carried forward without additional purification Step 8: 5-(1H-imidazol-1-yl)-1H-pyrazolo[4,3-d]pyrimidine-7-carboxylic acid A solution of 5-(1H-imidazol-1-yl)-2-(4-methoxybenzyl)-2H-pyrazolo[4,3-d]pyrimidine-7-carbonitrile (16.0 g, 48.2 mmol, 1 equiv) and HCl (37% w/w, 150 mL) was stirred for 12 h at 70° C. The resulting mixture was concentrated under vacuum and then diluted with 10 mL of H$_2$O. The pH value of the solution was adjusted to 5.0 with NaOH aqueous (2.0 M). The solids were filtered and slurried with CH$_3$CN (25 ml) and filtered to afford the title compound (4.0 g, 36%) as a brown solid. LCMS: [M+H]+ 231.00.

Int-B1: (1r,4r)-4-(2-Methoxyethoxy)cyclohexan-1-amine

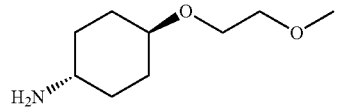

Step 1: (1r,4r)-4-(Dibenzylamino)cyclohexan-1-ol

A mixture of (1r,4r)-4-aminocyclohexan-1-ol (30.0 g, 260.5 mmol, 1.0 eq), benzyl bromide (133 g, 777.6 mmol, 3 eq), and $K_2CO_3$ (72.0 g, 520.9 mmol, 2 eq) in ACN (300 mL) was stirred for 2 h at 75° C. The reaction was quenched with water. The solids were collected by filtration to afford the title compound (65 g, 85%) as a white solid. LCMS: [M+H]$^+$ 296.2.

Step 2: (1r,4r)-N,N-Dibenzyl-4-(2-methoxyethoxy)cyclohexan-1-amine

A mixture of (1r,4r)-4-(dibenzylamino)cyclohexan-1-ol (59 g, 199.7 mmol, 1 eq), 1-bromo-2-methoxyethane (82.6 g, 594.3 mmol, 3 eq), and t-BuOK (33.6 g, 299.2 mmol, 1.5 eq) in DCM (1 L) was stirred for 4 h at RT. The reaction was quenched with water and extracted with 3×500 mL of DCM. The organic layers were combined, dried over sodium sulfate and concentrated. The crude product was applied onto a silica gel column eluting with EtOAc:petroleum ether (5:95) to afford the title compound (48 g, 68%) as red oil. LCMS: [M+H]$^+$ 354.2.

Step 3: (1r,4r)-4-(2-Methoxyethoxy)cyclohexan-1-amine

Under hydrogen, a mixture of (1r,4r)-N,N-dibenzyl-4-(2-methoxyethoxy)cyclohexan-1-amine (60.0 g, 169.7 mmol, 1 eq) and Pd(OH)$_2$ on carbon (10.0 g, 71.2 mmol, 0.42 eq) in EtOH (600 mL) was stirred for 14 h at RT. The solids were filtered out. The filtrate was concentrated under vacuum to afford the title compound (27 g, 92%) as a yellow oil. LCMS: [M+H]$^+$ 174.1.

Int-B2: (1r,4r)-4-(2-(2-(dimethylamino)ethoxy)ethoxy)cyclohexan-1-amine

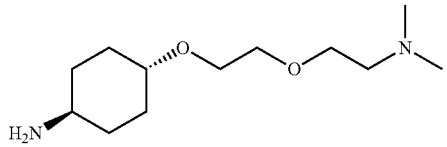 [SMILES: CN(C)CCOCCO[C@H]1CC[C@H](N)CC1]

Step 1: tert-butyl 2-(((1r,4r)-4-(dibenzylamino)cyclohexyl)oxy)acetate

A solution of (1r,4r)-4-(dibenzylamino)cyclohexan-1-ol (8.85 g, 30 mmol, 1 equiv), tert-butyl 2-bromoacetate (11.69 g, 60 mmol, 2 equiv), t-BuOK (6.72 g, 60 mmol, 2 equiv) in DCM (120 mL) was stirred at RT for 2 h. Then tert-butyl 2-bromoacetate (11.69 g, 60 mmol, 2 equiv) and t-BuOK (6.72 g, 60 mmol, 2 equiv) were added to the resulting solution. The mixture was stirred for another 2 h. The mixture was diluted with water (150 mL) and extracted with DCM (120 mL×3). The organic layers were combined, dried over $Na_2SO_4$ and concentrated. The crude product was purified by silica gel chomatography eluting with petroleum ether/EtOAc (10:1) to afford the title compound (5.6 g, 46%) as a white solid. LCMS: [M+H]$^+$ 410.30.

Step 2: 2-(((1r,4r)-4-(dibenzylamino)cyclohexyl)oxy)ethan-1-ol

LiAlH$_4$ (1.14 g, 30 mmol, 3 equiv) was added to a solution of tert-butyl 2-(((1r,4r)-4-(dibenzylamino)cyclohexyl)oxy)acetate (4.10 g, 10 mmol, 1 equiv) in THF (40 mL) at 0° C. The resulting solution was stirred for 2 h. After completion, the resulting solution was quenched by the addition of water (1.2 mL), 15% aqueous NaOH (1.2 mL) and water (3.6 mL) at 0° C. The resulting solution was diluted with 30 mL THF and stirred for 1 h at RT. The solids were filtered out and the filtrate was concentrated to afford 2.5 g of the title compound as a yellow oil. LCMS: [M+H]$^+$ 340.25.

Step 3: 2-(2-(((1r,4r)-4-(dibenzylamino)cyclohexyl)oxy)ethoxy)-N,N-dimethylacetamide To a solution of 2-(((1r,4r)-4-(dibenzylamino)cyclohexyl)oxy)ethan-1-ol (3.40 g, 10 mmol, 1 equiv) in DMF (50 mL) was added 60% NaH (1.20 g, 30 mmol, 3 equiv). The resulting solution was stirred for 10 min and 2-bromo-N,N-dimethylacetamide (5 g, 30 mmol, 3 equiv) was added. The resulting solution was stirred for another 12 h at RT. The mixture was diluted with water (200 mL) and extracted with EtOAc (120 mL×3). The organic layers were combined, dried over $Na_2SO_4$, and concentrated under reduced pressure. The residue was purified by silica gel chomatography (DCM/MeOH, 10:1) to afford the title compound (3.4 g, 75%) as a colorless oil. LCMS: [M+H]$^+$ 425.35.

Step 4: (1r,4r)-N,N-dibenzyl-4-(2-(2-(dimethylamino)ethoxy)ethoxy)cyclohexan-1-amine To a solution of 2-(2-(((1r,4r)-4-(dibenzylamino)cyclohexyl)oxy)ethoxy)-N,N-dimethylacetamide (3.10 g, 7.3 mmol, 1 equiv) in THF (35 mL) was added LiAlH$_4$ (0.83 g, 22 mmol, 3.00 equiv). The resulting solution was stirred for 2 h at 0° C. The reaction was quenched by the addition of water (1 mL), 15% aqueous NaOH (1 mL) and water (3 mL) at 0° C. The resulting solution was diluted with THF (30 mL) and stirred for 1 h at RT. The solids were filtered and the filtrate was concentrated under reduced pressure to afford 2.5 g of the title compound as a colorless oil. LCMS: [M+H]$^+$ 411.30.

Step 5: (1r,4r)-4-(2-(2-(dimethylamino)ethoxy)ethoxy)cyclohexan-1-amine

Under hydrogen, a mixture of (1r,4r)-N,N-dibenzyl-4-(2-(2-(dimethylamino)ethoxy)ethoxy)cyclohexan-1-amine (2.50 g, 6.1 mmol, 1 equiv) and Pd(OH)$_2$/C (1.2 g) in EtOH (30 mL) was stirred for 4 h at RT. The solids were filtered and the filtrate was concentrated under reduced pressure. The crude product was purified by reverse phase column eluting with MeCN/H$_2$O to afford the title compound (0.4 g, 25%) as a colorless oil. LCMS: [M+H]$^+$ 231.25.

Int-B3: 1-(4-aminopiperidin-1-yl)-2-morpholinoethan-1-one hydrogen chloride

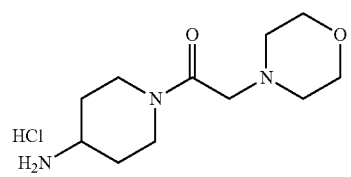 [SMILES: Cl ; NC1CCN(C(=O)CN2CCOCC2)CC1]

Step 1: tert-butyl (1-(2-morpholinoacetyl)piperidin-4-yl)carbamate

A solution of tert-butyl piperidin-4-ylcarbamate (1.68 g, 8.4 mmol, 1.2 equiv), 2-morpholinoacetic acid (1.02 g, 7 mmol, 1.00 equiv), HATU (3.99 g, 10.5 mmol, 1.5 equiv), and DIEA (3.62 g, 28 mmol, 4 equiv) in DMF (15 mL) was stirred for 1 h at RT. The reaction was quenched by water (50 mL) and extracted with EtOAc (30 mL×3). The organic layers were combined, dried over $Na_2SO_4$ and concentrated under reduced pressure. The crude product was slurried in MeOH (10 mL) and then filtered and rinsed with MeOH to afford the title compound (1 g, 43%) as a white solid. LCMS: $[M+H]^+$ 328.20.

Step 2: 1-(4-aminopiperidin-1-yl)-2-morpholinoethan-1-one hydrogen chloride

A solution of tert-butyl (1-(2-morpholinoacetyl)piperidin-4-yl)carbamate (0.95 g, 2.91 mmol, 1.00 equiv) in HCl/1,4-dioxane (4 M, 30.00 mL) was stirred for 1 h at RT. The reaction was concentrated under vacuum to afford 0.96 g of the title compound as a crude white solid. LCMS: $[M+H]^+$ 228.25.

Int-B4: 5-chloro-6-(2-morpholinoethoxy)pyridin-3-amine

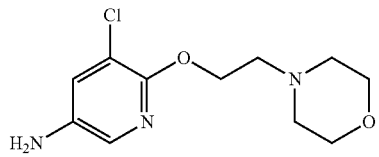 [SMILES: Nc1cnc(OCCN2CCOCC2)c(Cl)c1]

Step 1: 4-(2-((3-chloro-5-nitropyridin-2-yl)oxy)ethyl)morpholine

To a solution of 2-morpholinoethan-1-ol (1.60 g, 12.20 mmol, 1.23 equiv) in DMF (20 mL) was added NaH 60% (0.80 g, 20.002 mmol, 2.01 equiv) at 0° C. The resulting solution was stirred for 10 min. 2,3-dichloro-5-nitropyridine (1.92 g, 9.95 mmol, 1.00 equiv) was added and the resulting solution was stirred for 2 h at RT. The reaction was quenched with $H_2O$ and extracted with DCM (3×20 mL). The organic layers were combined, dried over anhydrous sodium sulfate and concentrated. The residue was applied onto a silica gel column eluting with EtOAc/petroleum ether (4/5) to afford the title compound (0.99 g, 35%) as a yellow oil. LCMS: $[M+H]^+$ 288.05.

Step 2: 5-chloro-6-(2-morpholinoethoxy)pyridin-3-amine

A solution of 4-(2-((3-chloro-5-nitropyridin-2-yl)oxy)ethyl)morpholine (0.90 g, 3.27 mmol, 1.00 equiv), zinc (1.35 g, 20.78 mmol, 6.60 equiv), and acetic acid (2.08 g, 34.62 mmol, 11.00 equiv) in EtOH (20 mL) was stirred for 36 h at 60° C. The reaction was quenched with water and extracted with EtOAc (40 mL×3). The combined organic layers were dried over $Na_2SO_4$ and concentrated under reduced pressure. The crude product was purified by reverse phase column eluting with $H_2O$/ACN (1/3) to afford the title compound (132 mg, 16%) as a brown oil. LCMS: $[M+H]^+$ 258.15.

Int-B5: 3-(2-methoxyethoxy)cyclohexan-1-amine Hydrogen Chloride

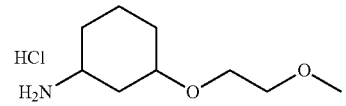

Step 1: tert-butyl (3-(2-methoxyethoxy)cyclohexyl)carbamate

To a solution of tert-butyl (3-hydroxycyclohexyl)carbamate (2.50 g, 11.612 mmol, 1.00 equiv) in DMF (15 mL) was added NaH (0.70 g, 17.418 mmol, 1.5 equiv, 60%) at 0° C. The resulting solution was stirred for 20 min. 1-Bromo-2-methoxyethane (3.23 g, 23.224 mmol, 2 equiv) was added and the mixture was stirred for 24 h at 25° C. The reaction was quenched by water/ice (15 mL). The resulting solution was extracted with DCM (80 mL×2.) The organic layers were combined, dried over anhydrous sodium sulfate, and concentrated under vacuum. The crude product was applied onto a silica gel column eluting with EtOAc/petroleum ether (20:80) to afford the title compound (1.12 g, 18%) as a yellow oil. LCMS: $[M+H]^+$ 274.00.

Step 2: 3-(2-methoxyethoxy)cyclohexan-1-amine hydrogen chloride

A solution of tert-butyl (3-(2-methoxyethoxy)cyclohexyl)carbamate (740 mg, 2.71 mmol, 1.00 equiv) in dioxane (5 mL) in HCl/1,4-dioxane (5 mL, 4M) was stirred for 1 h at 25° C. The resulting mixture was concentrated to afford the title compound (615 mg, 65.57%) as a yellow solid. LCMS: $[M+H]^+$ 174.00.

Int-B6: 6-(4-morpholinopiperidin-1-yl)pyridin-3-amine

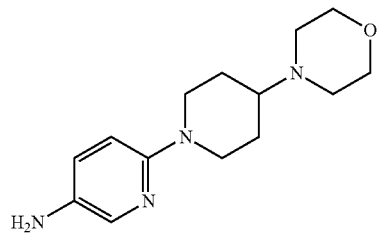 [SMILES: Nc1ccc(N2CCC(N3CCOCC3)CC2)nc1]

Step 1: 4-(1-(5-nitropyridin-2-yl)piperidin-4-yl)morpholine

To a solution of 4-(piperidin-4-yl)morpholine (851 mg, 5.00 mmol, 1.00 equiv), $K_2CO_3$ (1381 mg, 9.99 mmol, 2.00 equiv) in ACN (15 mL) was added 2-fluoro-5-nitropyridine (710 mg, 5.00 mmol, 1.00 equiv) and the mixture was stirred at 70° C. for 1 h. The resulting solution was quenched by water (50 mL). The solids were collected by filtration and washed with water to afford the title compound (1.15 g, 79%) as a yellow solid. LCMS: [M+H]⁺ 293.15.

Step 2: 6-(4-morpholinopiperidin-1-yl)pyridin-3-amine

Under H₂ atmosphere, a mixture of 4-(1-(5-nitropyridin-2-yl)piperidin-4-yl)morpholine (1110 mg, 3.80 mmol, 1.00 equiv) and Pd/C (2020 mg, 18.99 mmol, 5.00 equiv), DCM (5.00 mL), and EtOH (10 mL) was stirred at RT for 1 h. The solids were filtered and the filtrate was concentrated under vacuum to afford the title compound (985 mg, 99%) as a black solid. LCMS: [M+H]⁺ 263.20.

Int-B7: 1-methyl-N1-(2,2,2-trifluoroethyl)cyclohexane-1,4-diamine

Step 1: tert-butyl (4-(dibenzylamino)-1-methylcyclohexyl)carbamate

A solution of tert-butyl (4-amino-1-methylcyclohexyl)carbamate (630 mg, 2.76 mmol, 1 equiv), K₂CO₃ (952 mg, 6.89 mmol, 2.5 equiv), and (bromomethyl)benzene (1081 mg, 6.32 mmol, 2.29 equiv) in MeCN (5 mL) was stirred for 2 h at 80° C. The solids were filtered out. The filtrate was concentrated and applied onto a silica gel column with petroleum ether:EtOAc (13:87) to afford the title compound (80 mg, 71%) as a white solid. LCMS: [M+H]+ 409.30.

Step 2: N1,N1-dibenzyl-4-methylcyclohexane-1,4-diamine

A solution of tert-butyl (4-(dibenzylamino)-1-methylcyclohexyl)carbamate (3.3 g, 8.08 mmol, 1 equiv) in HCl in 1,4-dioxane (60 mL, 4 M) was stirred for 1 h at RT. The solids were collected by filtration to afford the title compound (2.1 g, 84%) as a white solid. LCMS: [M+H]⁺ 309.20.

Step 3: N4,N4-dibenzyl-1-methyl-N1-(2,2,2-trifluoroethyl)cyclohexane-1,4-diamine A solution of N1,N1-dibenzyl-4-methylcyclohexane-1,4-diamine (1 g, 3.24 mmol, 1 equiv), 2,2,2-trifluoroethyl trifluoromethanesulfonate (1.5 g, 6.46 mmol, 2 equiv), and K₂CO₃ (1.34 g, 9.73 mmol, 3 equiv) in ACN (50 mL) was stirred for 5 h at 80° C. The solids were filtered out. The filtrate was concentrated and applied onto a silica gel column with ethyl acetate/petroleum ether (20:80) to afford the title compound (850 mg, 67%) as yellow oil. LCMS: [M+H]⁺ 391.20.

Step 4: 1-methyl-N1-(2,2,2-trifluoroethyl)cyclohexane-1,4-diamine

Under hydrogen, a mixture of N4,N4-dibenzyl-1-methyl-N1-(2,2,2-trifluoroethyl)cyclohexane-1,4-diamine (820 mg, 2.1 mmol, 1 equiv), and Pd(OH)₂/C (29.5 mg, 0.21 mmol, 0.1 equiv) in EtOH (30 mL) was stirred for 2 h at RT. The solids were filtered out and the filtrate was concentrated under reduced pressure to afford the title compound (365 mg, 82%) as yellow oil. LCMS: [M+H]⁺ 211.10.

Int-B8: 4-(3,3,3-trifluoropropoxy)cyclohexan-1-amine

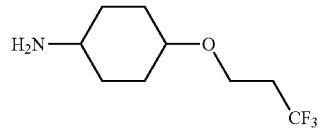

Step 1: 1-nitro-4-(3,3,3-trifluoropropoxy)benzene

To a solution of 3,3,3-trifluoropropan-1-ol (1348 mg, 11.82 mmol, 3.3 equiv) in THF (20 mL) was added into NaH (60% w/w) (170 mg, 7.09 mmol, 2 equiv) at 0° C. The mixture was stirred for 15 min. Then 1-fluoro-4-nitrobenzene (500 mg, 3.54 mmol, 1 equiv) was added to the solution at 0° C. The resulting solution was stirred for 1 h at RT. After completion, the reaction was quenched by the addition of water and extracted with 3×100 mL EtOAc. The organic layers were combined, washed with brine, dried over anhydrous sodium sulfate and concentrated under vacuum. The crude product was applied onto a silica gel column with ethyl acetate/petroleum ether (16:84) to afford the title compound (320 mg, 38%).

Step 2: 4-(3,3,3-trifluoropropoxy)cyclohexan-1-amine

In pressure tank reactor purged and maintained with an inert atmosphere of nitrogen, a solution of 1-nitro-4-(3,3,3-trifluoropropoxy)benzene (250 mg, 1.06 mmol, 1 equiv), isopropanol (20 mL), and Rh/Al₂O₃ (1.1 g, 10.52 mmol, 10 equiv) was stirred for 3 h at 80° C. After completion, the solids were filtered out. The resulting mixture was concentrated under vacuum to afford the title compound (183 mg, 82%) as a yellow oil. LCMS: [M+H]⁺ 212.30.

Int-B9: (1r,4r)-4-(((2,2,2-trifluoroethyl)amino)methyl)cyclohexan-1-amine hydrochloride

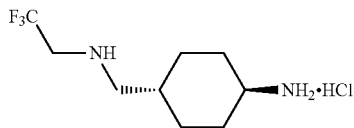

Step 1: tert-butyl ((1r,4r)-4-(((2,2,2-trifluoroethyl)amino)methyl)cyclohexyl)carbamate A solution of tert-butyl ((1r,4r)-4-formylcyclohexyl)carbamate (2 g, 8.79 mmol, 1 equiv), Ti(Oi-Pr)₄ (2.5 g, 8.79 mmol, 1 equiv), 2,2,2-trifluoroethylamine hydrochloride (1.43 g, 10.55 mmol, 1.2 equiv), and HOAc (527 mg, 8.79 mmol, 1 equiv) in EtOH (20 mL) was stirred for 1 h at RT. Then NaBH₃CN (828 mg, 13.19 mmol, 1.5 equiv) was added and stirred for 1 h at RT. The resulting solution was extracted with 3×100 mL of EtOAc. The organic layers were combined, dried over Na₂SO₄ and concentrated under reduced pressure. The crude product was applied onto a silica gel column eluting with ethyl acetate/petroleum ether (1:1) to afford the title compound (1 g, 37% yield) as an off-white oil. LCMS: [M+H]+ 311.10.

Step 2: (1r,4r)-4-(((2,2,2-trifluoroethyl)amino)methyl)cyclohexan-1-amine

A solution of tert-butyl ((1r,4r)-4-(((2,2,2-trifluoroethyl)amino)methyl)cyclohexyl)carbamate (1 g, 3.22 mmol, 1 equiv) in HCl (gas) in 1,4-dioxane (20 mL, 548.53 mmol, 204.3 equiv) was stirred for 1 h at RT. The resulting mixture was concentrated under vacuum to afford the title compound (505 mg, 75%) of as a white solid. LCMS: [M+H]+ 211.05.

Int-B10: 4-(2,2,2-trifluoroethoxy)cyclohexan-1-amine

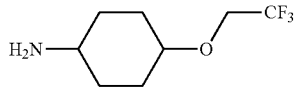 [SMILES: NC1CCC(OCC(F)(F)F)CC1]

Step 1: 1-nitro-4-(2,2,2-trifluoroethoxy)benzene

To a solution of 2,2,2-trifluoroethan-1-ol (1.7 g, 0.017 mmol, 1.2 equiv) in THF (20 mL) was added NaH (60% w/w) (0.85 g, 0.035 mmol, 2.5 equiv) in portions at 0° C. After stirring for 30 min, to this was added 1-fluoro-4-nitrobenzene (2 g, 14.17 mmol, 1 equiv) at 0° C. The resulting solution was stirred for 3 h at 25° C. The reaction was then quenched by the addition of water and extracted with 3×100 mL EtOAc. The organic layers were combined and washed with brine. The mixture was dried over anhydrous sodium sulfate and concentrated under vacuum. The crude product was applied onto a silica gel column with ethyl acetate/petroleum ether (1:9) to afford the title compound (1.2 g, 38%) as a yellow solid.

Step 2: 4-(2,2,2-trifluoroethoxy)cyclohexan-1-amine

Under hydrogen atmosphere, a solution of 1-nitro-4-(2,2,2-trifluoroethoxy)benzene (1.1 g, 4.97 mmol, 1 equiv) and Rh/Al₂O₃ (0.39 g, 3.83 mmol, 0.77 equiv) in i-PrOH (10 mL) was stirred for 3 h at 80° C. under 10 atm. After completion, the solids were filtered out. The resulting mixture was concentrated under vacuum to afford the title compound (450 mg, 46%) as colorless oil. LCMS: [M+H]+ 198.10.

Int-B11: N1-(1,1-difluoro-2-methylpropan-2-yl)cyclohexane-1,4-diamine hydrochloride

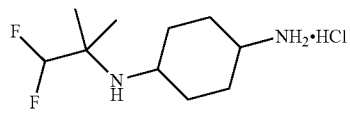

Step 1: tert-butyl(4-((1,1-difluoro-2-methylpropan-2-yl)amino)cyclohexyl)carbamate A solution of tert-butyl (4-oxocyclohexyl)carbamate (938.2 mg, 4.4 mmol, 1.2 equiv), 1,1-difluoro-2-methylpropan-2-amine (400 mg, 3.67 mmol, 1 equiv), Ti (Oi-Pr)₄ (1250 mg, 4.4 mmol, 1.2 equiv) in THF (20 mL) was stirred for 1 h at RT, then NH₃·BH₃ (136.4 mg, 4.4 mmol, 1.2 equiv) was added to the mixture and the solution was stirred for 1.5 h at RT. After completion, the reaction was then quenched by the addition of 30 mL of MeOH, and then concentrated. The crude product was purified by silica gel chromatography eluting with petroleum ether/ethyl acetate (3:1) to afford the title compound (350 mg, 31%) as a yellow solid. LCMS: [M+H]+ 307.10.

Step 2: N1-(1,1-difluoro-2-methylpropan-2-yl)cyclohexane-1,4-diamine hydrochloride A solution of tert-butyl (4-((1,1-difluoro-2-methylpropan-2-yl)amino)cyclohexyl)carbamate (300 mg, 0.98 mmol, 1 equiv) in HCl/dioxane (6.0 mL, 4 M) was stirred for 1 h at RT. After completion, the resulting mixture was concentrated to afford the title compound (329 mg) as a white solid. LCMS: [M+H]+ 207.10.

Int-B12: N¹-(1,1,1-trifluoro-2-methylpropan-2-yl)cyclohexane-1,4-diamine hydrochloride

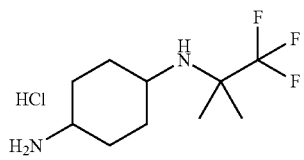

Step 1: tert-butyl (4-((1,1,1-trifluoro-2-methylpropan-2-yl)amino)cyclohexyl)carbamate A solution of 1,1,1-trifluoro-2-methylpropan-2-amine (2.7 g, 21.241 mmol, 1.0 eq), tert-butyl (4-oxocyclohexyl)carbamate (5.44 g, 0.025 mmol, 1.2 eq), and Ti(Oi-Pr)₄ (7.24 g, 0.025 mmol, 1.2 eq) in THF (100 mL) was stirred for 1 h at 25° C. then NH₃·BH₃ (0.79 g, 0.025 mmol, 1.20 eq) was added and the resulting solution was stirred for 3 h at 25° C. After completion, the reaction was then quenched by the addition of 200 mL of MeOH. The resulting mixture was concentrated under vacuum. The residue was applied onto a silica gel column with ethyl acetate/petroleum ether (1:4) to afford the title compound (1.7 g, 25% yield) as light yellow oil. LCMS: [M+H]+ 325.

Step 2: N¹-(1,1,1-trifluoro-2-methylpropan-2-yl)cyclohexane-1,4-diamine hydrochloride A solution of tert-butyl (4-((1,1,1-trifluoro-2-methylpropan-2-yl)amino)cyclohexyl)carbamate (300 mg, 0.93 mmol, 1 eq), and TFA (0.2 mL) in DCM (4 mL) was stirred for 1 h at 25° C. After completion, the resulting mixture was concentrated under vacuum to afford the title compound (180 mg, 87% yield) as colorless oil. LCMS: [M+H]+ 225.15.

Example 1: 5-(1H-Imidazol-1-yl)-N-((1r,4r)-4-(2-methoxyethoxy)cyclohexyl)-1H-benzo[d]imidazole-7-carboxamide

Example 2: N-(2-Fluoro-6-(trifluoromethyl)benzyl)-5-(1H-imidazol-1-yl)-1H-benzo[d]imidazole-7-carboxamide

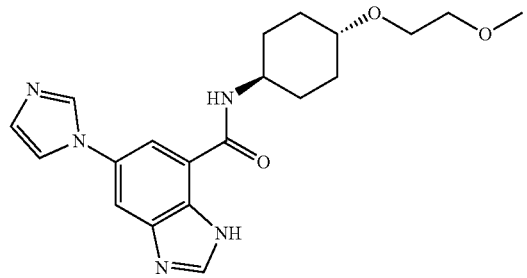 [SMILES: COCCO[C@H]1CC[C@H](NC(=O)c2cc(-n3ccnc3)cc3nc[nH]c23)CC1]

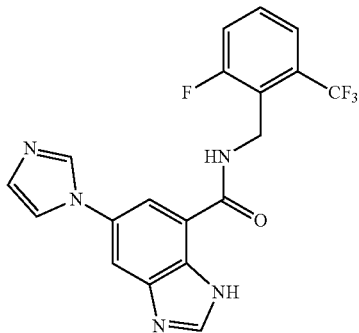 [SMILES: O=C(NCc1c(F)cccc1C(F)(F)F)c1cc(-n2ccnc2)cc2nc[nH]c12]

Step 1: 6-Imidazol-1-yl-3-(2-trimethylsilylethoxymethyl)benzimidazole-4-carboxylic acid A mixture of methyl 6-bromo-3-(2-trimethylsilylethoxymethyl)benzimidazole-4-carboxylate (700 mg, 1.82 mmol, 1 eq), imidazole (148 mg, 2.18 mmol, 1.2 eq), $Cs_2CO_3$ (888 mg, 2.72 mmol, 1.5 eq) and CuI (35 mg, 0.18 mmol, 0.1 eq) in NMP (10 mL) was heated at 150° C. overnight. After cooling to RT, the mixture was diluted with water (20 mL). The resulting precipitate was filtered. The filtrate was purified by reverse phase chromatography (5% ACN/water) to give the title compound (200 mg, 0.56 mmol, 31% yield) as a pale yellow solid. LCMS: [M+H]$^+$ 359.2.

Step 2: 5-(1H-Imidazol-1-yl)-N-((1r,4r)-4-(2-methoxyethoxy)cyclohexyl)-1-((2-(trimethylsilyl)ethoxy)methyl)-1H-benzo[d]imidazole-7-carboxamide A mixture of 6-imidazol-1-yl-3-(2-trimethylsilylethoxymethyl)benzimidazole-4-carboxylic acid (200 mg, 0.56 mmol, 1 eq), Int-B1 (97 mg, 0.56 mmol, 1 eq), HATU (318 mg, 0.84 mmol, 1.5 eq) and DIPEA (108 mg, 0.84 mmol, 1.5 eq) in DMF (5 mL) was stirred at RT for 3 h. After diluting with EtOAc (20 mL), the organic phase was washed with brine (5 mL×3). After concentration, the mixture was purified by silica gel chromatography (DCM:MeOH, 20:1) to give the title compound (75 mg, 0.15 mmol, 26% yield). LCMS: [M+H]$^+$ 514.4.

Step 3: 5-(1H-Imidazol-1-yl)-N-((1r,4r)-4-(2-methoxyethoxy)cyclohexyl)-1H-benzo[d]imidazole-7-carboxamide A mixture of 6-imidazol-1-yl-N-[4-(2-methoxyethoxy)cyclohexyl]-3-(2-trimethylsilylethoxymethyl)benzimidazole-4-carboxamide (75 mg, 0.15 mmol, 1.0 eq) in TFA (1 mL, 0.15 mmol, 1 eq) and DCM (2 mL) was stirred at RT for 4 h. After concentrating, the residue was purified by silica gel chromatography (DCM:MeOH, 20:1) to give the title compound (35 mg, 0.09 mmol, 63% yield) as a white solid. LCMS: [M+H]$^+$ 384.1, $^1$H NMR (400 MHz, DMSO-$d_6$) δ: 13.23 (s, 1H), 9.83 (d, J=6 Hz, 1H), 8.57 (s, 1H), 8.25 (s, 1H), 7.95 (d, J=8.8 Hz, 2H), 7.74 (s, 1H), 7.13 (s, 1H), 3.90 (m, 1H), 3.55-3.53 (m, 2H), 3.45-3.43 (m, 2H), m, 3.63-3.55 (m, 1H), 3.26 (s, 3H), 2.11-1.92 (m, 4H), 1.58-1.43 (m, 4H).

Step 1: 6-Bromo-N-[[2-fluoro-6-(trifluoromethyl)phenyl]methyl]-3-(2-trimethylsilylethoxymethyl)benzimidazole-4-carboxamide To a solution of Int-A1 (160 mg, 0.43 mmol, 1 eq) in DMF (10 mL) at RT under a $N_2$ atmosphere was added [2-fluoro-6-(trifluoromethyl)phenyl]methanamine (92 mg, 0.47 mmol, 1.1 eq), DIPEA (84 mg, 0.65 mmol, 1.5 eq) and HATU (197 mg, 0.52 mmol, 1.2 eq) and the mixture was stirred at RT overnight. The mixture was diluted with water (20 mL) and extracted with EtOAc (20 mL×3), the combined organic layers were washed with water (20 mL), dried over $Na_2SO_4$ and concentrated under reduced pressure. The residue was purified by prep-TLC (DCM: MeOH, 3:1) to afford the title compound (180 mg, 0.33 mmol, 76% yield). LCMS: [M+H]$^+$ 548.1.

Step 2: N-[[2-Fluoro-6-(trifluoromethyl)phenyl]methyl]-6-imidazol-1-yl-3-(2-trimethylsilylethoxymethyl)benzimidazole-4-carboxamide Following the procedure in Example 1, Step 1 using 6-bromo-N-[[2-fluoro-6-(trifluoromethyl)phenyl]methyl]-3-(2-trimethylsilylethoxymethyl)benzimidazole-4-carboxamide, the title compound (20 mg, 0.038 mmol, 11% yield) was isolated as a solid. LCMS: [M+H]$^+$ 534.4.

Step 3: N-(2-Fluoro-6-(trifluoromethyl)benzyl)-5-(1H-imidazol-1-yl)-1H-benzo[d]imidazole-7-carboxamide Following the procedure in Example 1, Step 3 using N-[[2-fluoro-6-(trifluoromethyl)phenyl]methyl]-6-imidazol-1-yl-3-(2-trimethylsilylethoxymethyl)benzimidazole-4-carboxamide, the title compound (8 mg, 0.019 mmol, 51% yield) was prepared as a solid. LCMS: [M+H]$^+$ 404.0, $^1$HNMR (400 MHz, DMSO-$d_6$) δ 13.3 (s, 1H), 10.2 (s, 1H), 8.52 (s, 1H), 8.27 (s, 1H), 7.98 (d, J=21.6 Hz, 2H), 7.79 (s, 1H), 7.66-7.64 (m, 3H), 7.13 (m, 1H), 4.88 (m, 2H).

Example 3: N-[[2-Fluoro-6-(trifluoromethyl)phenyl]methyl]-6-thiazol-5-yl-3H-benzimidazole-4-carboxamide

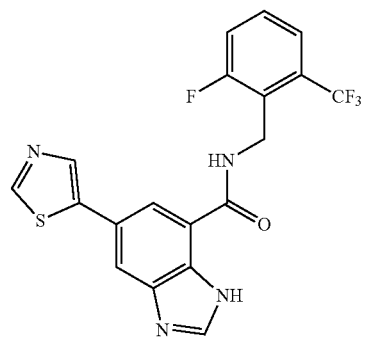 [SMILES: O=C(NCc1c(F)cccc1C(F)(F)F)c1cc(-c2cncs2)cc2nc[nH]c12]

Step 1: N-[[2-Fluoro-6-(trifluoromethyl)phenyl]methyl]-6-thiazol-5-yl-3-(2-trimethylsilylethoxymethyl)benzimidazole-4-carboxamide To a solution of 6-bromo-N-[[2-fluoro-6-(trifluoromethyl)phenyl]methyl]-3-(2-trimethylsilylethoxymethyl)benzimidazole-4-carboxamide, prepared in Example 1, Step 1, (120 mg, 0.22 mmol, 1 eq) in DMF (5 mL) was added PdCl$_2$(dppf)-CH$_2$Cl$_2$ (51 mg, 0.04 mmol, 0.2 eq), CuI (8 mg, 0.04 mmol, 0.2 eq) and K$_2$CO$_3$ (61 mg, 0.44 mmol, 2 eq). Tributyl(thiazol-5-yl)stannane (99 mg, 0.26 mmol, 1.2 eq) was added, and the mixture was heated to 100° C. overnight. The residue was diluted with water (20 mL) and extracted with EtOAc (30 mL×3). The combined organic layers were dried over Na$_2$SO$_4$ and concentrated under reduced pressure. The residue was purified by prep-TLC (DCM:MeOH, 30:1) to afford the title compound (50 mg, 0.09 mmol, 41% yield). LCMS: [M+H]$^+$ 551.2.

Step 2: N-[[2-Fluoro-6-(trifluoromethyl)phenyl]methyl]-6-thiazol-5-yl-3H-benzimidazole-4-carboxamide Following the procedure in Example 1, Step 3 using N-[[2-fluoro-6-(trifluoromethyl)phenyl]methyl]-6-thiazol-5-yl-3-(2-trimethylsilylethoxymethyl)benzimidazole-4-carboxamide, the title compound (30 mg, 0.069 mmol, 76% yield) was prepared as a solid. LCMS: [M+H]$^+$ 421.0; iHNMR (400 MHz, DMSO-d$_6$) δ 13.1 (s, 1H), 10.1 (s, 1H), 9.10 (s, 1H), 8.49 (s, 1H), 8.36 (s, 1H), 8.08 (d, J=28.0 Hz, 2H), 7.67-7.63 (m, 3H), 4.88 (s, 2H).

Example 4: N-((1r,4r)-4-(2-Methoxyethoxy)cyclohexyl)-5-(thiazol-5-yl)-1H-benzo[d]imidazole-7-carboxamide

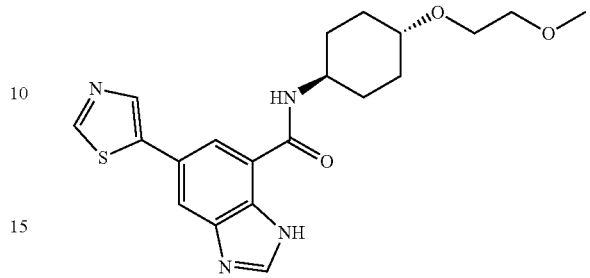

Step 1: 5-Bromo-N-((1r,4r)-4-(2-methoxyethoxy)cyclohexyl)-1-((2-(trimethylsilyl)ethoxy)methyl)-1H-benzo[d]imidazole-7-carboxamide To a solution of Int-A1 (100 mg, 0.27 mmol, 1 eq), HOBt (44 mg, 0.32 mmol, 1.2 eq), EDC (50 mg, 0.32 mmol, 1.2 eq) in DMF (2 mL) was added Int-B1 (51 mg, 0.30 mmol, 1.1 eq), and the mixture was stirred at 25° C. overnight. The mixture was diluted with water (25 mL) and extracted with EtOAc (20 mL×3). The combined organic layers were dried over Na$_2$SO$_4$ and concentrated under reduced pressure. The residue was purified by prep-TLC (petroleum ether:EtOAc, 1:1) to afford the title compound (50 mg, 0.095 mmol, 35% yield) as a brown oil. LCMS: [M+H]$^+$ 528.2.

Step 2: N-((1r,4r)-4-(2-Methoxyethoxy)cyclohexyl)-5-(thiazol-5-yl)-1-((2-(trimethylsilyl)ethoxy)methyl)-1H-benzo[d]imidazole-7-carboxamide Following the procedure in Example 3, Step 1 using 5-bromo-N-((1r,4r)-4-(2-methoxyethoxy)cyclohexyl)-1-((2-(trimethylsilyl)ethoxy)methyl)-1H-benzo[d]imidazole-7-carboxamide, the title compound was prepared as an oil (25 mg, 0.047 mmol, 50% yield). LCMS: [M+H]$^+$ 531.3.

Step 3: N-((1r,4r)-4-(2-Methoxyethoxy)cyclohexyl)-5-(thiazol-5-yl)-1H-benzo[d]imidazole-7-carboxamide Following the procedure in Example 1, Step 3 using N-((1r,4r)-4-(2-methoxyethoxy)cyclohexyl)-5-(thiazol-5-yl)-1-((2-(trimethylsilyl)ethoxy)methyl)-1H-benzo[d]imidazole-7-carboxamide, the title compound was isolated as a yellow solid (10 mg, 0.025 mmol, 53% yield). LCMS: [M+H]$^+$ 401.1; $^1$HNMR (400 MHz, DMSO-d$_6$) δ 13.10 (s, 1H), 9.79 (d, J=7.6 Hz, 1H), 9.09 (s, 1H), 8.53 (s, 1H), 8.35 (s, 1H), 8.08 (s, 1H), 8.03 (s, 1H), 3.90 (s, 1H), 3.53-3.56 (m, 2H), 3.43-3.45 (m, 2H), 3.29-3.35 (m, 1H), 3.26 (s, 3H), 1.98-2.02 (m, 4H), 1.29-1.44 (m, 4H).

Example 5: N-(2-Fluoro-6-(trifluoromethyl)benzyl)-5-(1H-imidazol-1-yl)-1H-indole-7-carboxamide

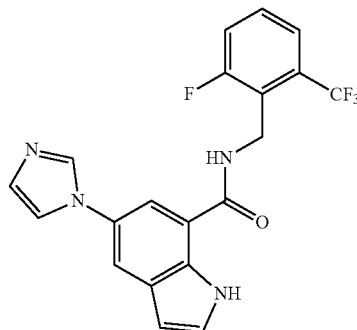

Step 1: Methyl 5-iodoindoline-7-carboxylate

To a stirred solution of 1-iodopyrrolidine-2,5-dione (21.2 g, 94.3 mmol, 3 eq) in ACN (100 mL), methyl indoline-7-carboxylate (5570 mg, 31.4 mmol, 1 eq) was added in portions at −20° C. After quenching with saturated $Na_2S_2O_3$ (20 mL), the aqueous phase was extracted with EtOAc (20 mL×3). The combined organic phases were dried over sodium sulfate and concentrated. The residue was purified by silica gel column chromatography (petroleum ether: EtOAc, 20:1, v/v) to give the title compound (1500 mg, 4.95 mmol, 16% yield) as a pale yellow solid. LCMS: $[M+H]^+$ 304.0.

Step 2: Methyl 5-iodo-1H-indole-7-carboxylate

To a solution of methyl 5-iodoindoline-7-carboxylate (910 mg, 3 mmol, 1 eq) in toluene (16 mL) was added $MnO_2$ (1357 mg, 15.61 mmol, 5.2 eq). The mixture was stirred at 75° C. for 16 h. The mixture was filtered, and the filtrate was concentrated under reduced pressure. The residue was purified by silica gel column chromatography (petroleum ether: EtOAc, 30:1, v/v) to afford the title compound (540 mg, 1.79 mmol, 60% yield) as a pale yellow solid. LCMS: $[M+H]^+$ 301.9.

Step 3: 5-Iodo-1H-indole-7-carboxylic acid

To a solution of methyl 5-iodo-1H-indole-7-carboxylate (540 mg, 1.79 mmol, 1 eq) in MeOH (3 mL) and THF (3 mL) was added NaOH (4.3 mL, 12.9 mmol, 7.2 eq), and the mixture was stirred at 25° C. for 1 h. The reaction mixture was concentrated and acidified with 1 M HCl solution. The resulting solids were collected by filtration to afford the title compound (467 mg, 1.63 mmol, 91% yield) as a white solid. LCMS: $[M+H]^+$ 285.9.

Step 4: N-(2-Fluoro-6-(trifluoromethyl)benzyl)-5-iodo-1H-indole-7-carboxamide A solution of 5-iodo-1H-indole-7-carboxylic acid (100 mg, 0.35 mmol, 1 eq), [2-fluoro-6-(trifluoromethyl)phenyl]methanamine (81 mg, 0.42 mmol, 1.2 eq), DIPEA (120 mg, 0.91 mmol, 2.6 eq), and HATU (160 mg, 0.42 mmol, 1.2 eq) in DMF (8 mL) was stirred at RT for 16 h. The mixture was concentrated under reduced pressure. The residue was diluted with water (30 mL) and extracted with EtOAc (30 mL×3). The combined organic layers were dried over $Na_2SO_4$ and concentrated under reduced pressure. The residue was purified by prep-TLC (petroleum ether:EtOAc, 3:1, v/v) to afford the title compound (150 mg, 0.33 mmol, 93% yield) as a gray solid. LCMS: $[M+H]^+$ 463.0.

Step 5: N-(2-Fluoro-6-(trifluoromethyl)benzyl)-5-(1H-imidazol-1-yl)-1H-indole-7-carboxamide A solution of N-(2-fluoro-6-(trifluoromethyl)benzyl)-5-iodo-1H-indole-7-carboxamide (150 mg, 0.32 mmol, 1 eq), imidazole (66 mg, 0.97 mmol, 3 eq), CuI (13 mg, 0.06 mmol, 0.2 eq), and $K_2CO_3$ (144 mg, 0.97 mmol, 3 eq) in DMF (10 mL) was stirred at RT for 16 h. The mixture was concentrated under reduced pressure. The residue was diluted with water (30 mL) and extracted with EtOAc (30 mL×3). The combined organic layers were dried over $Na_2SO_4$ and concentrated under reduced pressure. The residue was purified by prep-TLC (petroleum ether:EtOAc, 3:1, v/v) to afford the title compound (4.4 mg, 0.01 mmol, 3% yield) as a gray solid. LCMS: $[M+H]^+$ 403.0; $^1$HNMR (400 MHz, $CD_3OD$) δ 9.28 (br s, 1H), 8.09-8.06 (m, 1H), 9.09 (br s, 1H), 7.85-7.72 (m, 3H), 7.63-7.45 (m, 5H), 6.71 (d, J=2.8, 1H), 4.86 (s, 2H).

Example 6: N-((1r,4r)-4-(2-Methoxyethoxy)cyclohexyl)-5-(thiazol-5-yl)-1H-indole-7-carboxamide

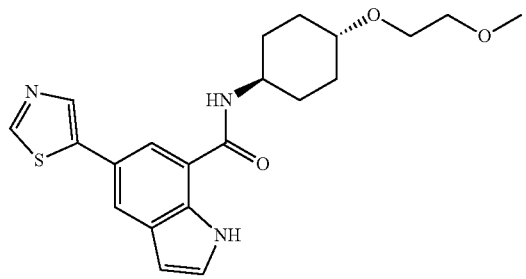 [SMILES: COCCO[C@H]1CC[C@H](NC(=O)c2cc(-c3cncs3)cc3nc[nH]c23)CC1]

Step 1: 5-Iodo-N-((1r,4r)-4-(2-methoxyethoxy)cyclohexyl)-1H-indole-7-carboxamide A solution of 5-iodo-1H-indole-7-carboxylic acid, prepared in Example 5, Step 2 (844 mg, 2.94 mmol, 1 eq), Int-B1 (611 mg, 3.53 mmol, 1.2 eq), DIPEA (1.33 mL, 7.64 mmol, 2.6 eq), HATU (1.34 g, 3.53 mmol, 1.2 eq) in DMF (15 mL) was stirred at RT for 6 h. The mixture was concentrated under reduced pressure. The residue was diluted with water (50 mL) and extracted with EtOAc (3×60 mL). The combined organic layers were dried over $Na_2SO_4$ and concentrated under reduced pressure. The residue was purified by column (petroleum ether:EtOAc, 3:1, v/v) to afford the title compound (740 mg, 1.67 mmol, 56% yield) as a gray solid. LCMS: $[M+H]^+$ 443.2.

Step 2: N-((1r,4r)-4-(2-Methoxyethoxy)cyclohexyl)-5-(thiazol-5-yl)-1H-indole-7-carboxamide To a mixture of 5-iodo-N-((1r,4r)-4-(2-methoxyethoxy)cyclohexyl)-1H-indole-7-carboxamide (50 mg, 0.11 mmol, 1 eq), $PdCl_2(dppf)_2$ (18.4 mg, 0.02 mmol, 0.2 eq), CuI (4.3 mg, 0.02 mmol, 0.2 eq) and $K_2CO_3$ (31.2 mg, 0.23 mmol, 2 eq) in DMF (4 mL) was added tributyl(thiazol-5-yl)stannane (63 mg, 0.17 mmol, 1.5 eq). The reaction mixture was stirred at 90° C. for 16 h under a nitrogen atmosphere. The mixture was filtered and diluted with water (100 mL) and extracted with EtOAc (3×50 mL). The combined organic layers were dried over $Na_2SO_4$ and concentrated under reduced pressure. The residue was purified by prep-HPLC (0.1% TFA in MeOH/$H_2O$) to give the title compound (2.3 mg, 0.006 mmol, 5.1% yield) as a yellow solid. LCMS: [M+H]$^+$ 400.1; HNMR (400 MHz, DMSO-$d_6$) δ 11.23 (s, 1H), 9.03 (s, 1H), 8.43 (d, J=7.6 Hz, 1H), 8.27 (s, 1H), 7.99-7.95 (m, 2H), 7.39 (s, 1H), 6.54 (s, 1H), 3.91-3.82 (m, 1H), 3.56-3.54 (m, 2H), 3.44-3.42 (m, 2H), 3.28-3.25 (m, 4H), 2.07-2.04 (m, 2H), 1.95-1.93 (m, 2H), 1.50-1.40 (m, 2H), 1.33-1.26 (m, 2H).

Example 7: 2-(1H-Imidazol-1-yl)-N-((1r,4r)-4-(2-methoxyethoxy)cyclohexyl)-5H-pyrrolo[3,2-d]pyrimidine-4-carboxamide

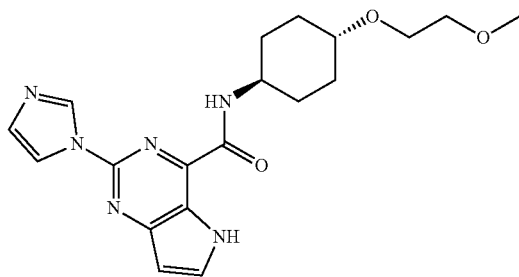

A solution of Int-A2 (23 g, 100 mmol, 1.0 eq), Int-B1 (19.1 g, 110 mmol, 1.1 eq), HATU (57.2 g, 150 mmol, 1.5 eq), and DIPEA (32.4 g, 250 mmol, 2.5 eq) in DMF (500 mL) was stirred at 35° C. for 2 h. The reaction was quenched with water and extracted with EtOAc. The organic layers were combined, dried over $Na_2SO_4$ and concentrated under reduced pressure. The crude product was purified by prep-HPLC eluting with ACN/$H_2O$ to afford the title compound (24.8 g, 64 mmol, 64% yield) as a white solid. LCMS: [M+H]$^+$ 385.15; $^1$H NMR (300 MHz, DMSO-$d_6$) δ 12.08 (s, 1H), 8.98 (s, 1H), 8.96-8.89 (m, 1H), 8.23 (s, 1H), 8.03 (t, J=4.0 Hz, 1H), 7.13 (s, 1H), 6.71 (d, J=3.1 Hz, 1H), 3.99-3.85 (m, 1H), 3.59-3.56 (m, 2H), 3.47-3.42 (m, 2H), 3.33-3.30 (m, 1H), 3.26 (s, 3H), 2.09-1.99 (m, 2H), 1.91-1.83 (m, 2H), 1.71-1.55 (m, 2H), 1.45-1.21 (m, 2H).

Example 8: 5-(1H-Imidazol-1-yl)-N-((1r,4r)-4-(2-methoxyethoxy)cyclohexyl)-1H-indazole-7-carboxamide

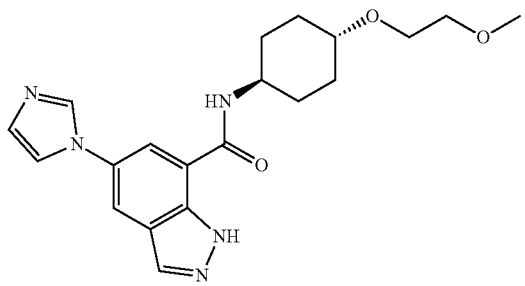 [SMILES: COCCO[C@H]1CC[C@H](NC(=O)c2cc(-n3ccnc3)cc3cn[nH]c23)CC1]

Step 1: Methyl 2-amino-5-iodo-3-methylbenzoate

To a solution of methyl 2-amino-3-methylbenzoate (1 g, 6.0 mmol, 1.0 eq) in ACN (50 mL) was added NIS (2.7 g, 12.0 mmol, 2.0 eq) and the mixture was stirred for 1 h at RT. The mixture was concentrated and purified by flash chromatography on silica gel eluting with EtOAc in petroleum ether (0-30%) to afford the title compound (1.2 g, 68.1% yield) as a yellow solid. LCMS: [M+H]$^+$ 292.10.

Step 2: Methyl 5-iodo-1H-indazole-7-carboxylate

To a solution of methyl 2-amino-5-iodo-3 methylbenzoate (1 g, 3.4 mmol, 1.0 eq) in CHCl$_3$ (40 mL) was added Ac$_2$O (807 mg, 7.9 mmol, 2.3 eq) at 0° C. and the mixture was stirred for 1 h at RT. Then tert-butyl nitrite (744 mg, 7.22 mmol, 2.1 eq) and KOAc (100 mg, 1.019 mmol, 0.30 eq) were successively added at 0° C. and the mixture was stirred overnight at reflux. The mixture was concentrated and purified by flash chromatography on silica gel eluting with DCM in petroleum ether (0-30%) to afford the title compound (0.8 g, 77.1% yield) as a yellow solid. LCMS: [M+H]$^+$ 303.00.

Step 3: 5-Iodo-1-((2-(trimethylsilyl)ethoxy)methyl)-1H-indazole-7-carboxylic acid To a solution of methyl 5-iodo-1H-indazole-7-carboxylate (600 mg, 1.99 mmol, 1.0 eq) in DMF (10 mL) was successively added NaH (79.4 mg, 1.99 mmol, 1.0 eq, 60%) and SEMCl (331.2 mg, 1.99 mmol, 1.0 eq) at 0° C. and the mixture was stirred for 1 h at RT. The reaction was quenched with water (10 mL). The aqueous layer was extracted with EtOAc (3×50 mL). The organic layers were combined, washed with brine (20 mL) and dried over $Na_2SO_4$. After concentration, the crude product was purified by flash chromatography on silica gel eluting with EtOAc in petroleum ether (0-100%) to afford the title compound (300 mg, 36.1% yield) as a yellow oil. LCMS: [M+H]$^+$ 419.02.

Step 4: 5-Iodo-N-((1r,4r)-4-(2-methoxyethoxy)cyclohexyl)-1((2-(trimethylsilyl)ethoxy)methyl)-1H-indazole-7-carboxamide A mixture of 5-iodo-1-((2-(trimethylsilyl)ethoxy)methyl)-1H-indazole-7-carboxylic acid, (280 mg, 0.67 mmol, 1.0 eq), Int-B1 (231.9 mg, 1.34 mmol, 2.0 eq), HATU (509.0 mg, 1.34 mmol, 2.0 eq), and DIPEA (259.5 mg, 2.01 mmol, 3.0 eq) in DMF (5 mL) was stirred overnight at RT. The mixture was concentrated and purified by flash chromatography on silica gel eluting with MeOH in DCM (0-10%) to afford the title compound (160 mg, 41.7% yield) as a yellow oil. LCMS: [M+H]$^+$ 574.15.

Step 5: 5-(1H-Imidazol-1-yl)-N-((1r,4r)-4-(2-methoxyethoxy)cyclohexyl)-1-((2-(trimethylsilyl)ethoxy)methyl)-1H-indazole-7-carboxamide Under nitrogen, a mixture of 5-iodo-N-((1r,4r)-4-(2-methoxyethoxycyclohexyl)-1((2-trimethylsilyl)ethoxy)methyl)-1H-indazole-7-carboxamide (140 mg, 0.25 mmol, 1.0 eq), Cs$_2$CO$_3$ (159.1 mg, 0.49 mmol, 2.0 eq), 1,10-phenanthroline (132 mg, 0.73 mmol, 3.0 eq), and 1H-imidazole (99.7 mg, 1.47 mmol, 6.0 eq) in dioxane (10 mL) was stirred overnight at 120° C. The mixture was concentrated and purified by flash chromatography on silica gel eluting with MeOH in DCM (0-10%) to afford the title compound (40 mg, 31.9% yield) as a yellow oil. LCMS: [M+H]+ 514.30.

Step 6: 5-(1H-imidazol-1-yl)-N-((1r,4r)-4-(2-methoxyethoxy)cyclohexyl)-1H-indazole-7-carboxamide To a solution of 5-(1H-imidazol-1-yl)-N-((1r,4r)-4-(2-methoxyethoxy)cyclohexyl)-1-((2-(trimethylsilyl)ethoxy)methyl)-1H-indazole-7-carboxamide (35 mg, 0.068 mmol, 1.0 eq) in DCM (1 mL) was added TFA (3 mL) and the mixture was stirred for 2 h at RT. The mixture was adjusted to pH 8-9 with 7M ammonia in methanol. The mixture was concentrated and purified by flash chromatography on silica gel eluting with MeOH in DCM (0-10%) to afford the title compound (15.3 mg, 57.4% yield) as an off-white solid. LCMS: [M+H]+ 384.20. $^1$H NMR (400 MHz, DMSO-d$_6$) δ 13.26 (s, 1H), 8.52 (d, J=7.6 Hz, 1H), 8.24 (t, J=1.1 Hz, 1H), 8.22 (s, 1H), 8.18 (d, J=1.9 Hz, 1H), 8.13 (d, J=2.0 Hz, 1H), 7.77 (t, J=1.3 Hz, 1H), 7.15 (t, J=1.1 Hz, 1H), 3.94-3.81 (m, 1H), 3.56 (dd, J=5.9, 3.8 Hz, 2H), 3.44 (dd, J=5.9, 3.8 Hz, 2H), 3.31-3.28 (m, 1H), 3.26 (s, 3H), 2.07 (d, J=12.1 Hz, 2H), 1.97 (d, J=12.6 Hz, 2H), 1.43 (q, J=11.8 Hz, 2H), 1.28 (q, J=11.2, 10.7 Hz, 2H).

Example 9: 5-(1H-Imidazol-1-yl)-N-((1r,4r)-4-(2-methoxyethoxy)cyclohexyl)-2-methyl-1H-indole-7-carboxamide

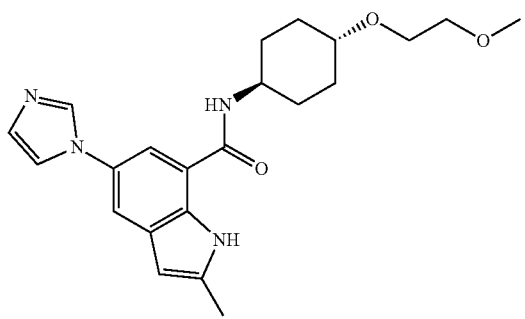

Step 1: 1-(3-Bromo-4-nitrophenyl)-1H-imidazole

A solution of 2-bromo-4-fluoro-1-nitrobenzene (1000 mg, 4.55 mmol, 1.0 eq), 1H-imidazole (340 mg, 5.00 mmol, 1.1 eq), and K$_2$CO$_3$ (949 mg, 6.82 mmol, 1.5 eq) in DMF (12 mL) was stirred for 2.5 h at 110° C. The reaction was quenched with water (20 mL). The resulting solution was extracted with 3×30 mL EtOAc. The organic layers were dried over anhydrous sodium sulfate and concentrated under vacuum. The residue was applied onto a silica gel column eluting with EtOAc/petroleum ether (3:2) to afford the title compound (990 mg, 81% yield) as a yellow solid. LCMS: [M+H]+ 268.00.

Step 2: 7-Bromo-5-(1H-imidazol-1-yl)-2-methyl-1H-indole

Under nitrogen, to a solution of 1-(3-bromo-4-nitrophenyl)-1H-imidazole (500 mg, 1.87 mmol, 1.0 eq) in THF (10 mL) was added 0.5 M prop-1-en-2-ylmagnesium bromide (15 mL, 7.46 mmol, 4.0 eq) at −40° C., The resulting solution was stirred for another 1 h at −40° C. The reaction was quenched with saturated aqueous NH$_4$Cl. The resulting solution was extracted with 3×30 mL of EtOAc and the organic layers were combined and dried over anhydrous sodium sulfate. After concentration, the residue was applied onto a silica gel column eluting with EtOAc/petroleum ether (1:4) to afford the title compound (220 mg, 42.7%) as a light yellow solid. LCMS: [M+H]+ 276.05.

Step 3: 5-(1H-Imidazol-1-yl)-N-((1r,4r)-4-(2-methoxyethoxy)cyclohexyl)-2-methyl-1H-indole-7-carboxamide A solution of 7-bromo-5-(1H-imidazol-1-yl)-2-methyl-1H-indole (200 mg, 0.72 mmol, 1.0 eq), Int-B1 (502 mg, 2.9 mmol, 4.0 eq), TEA (146.6 mg, 1.45 mmol, 2.0 eq), and Pd(dppf)Cl$_2$ (53 mg, 0.072 mmol, 0.1 eq) in DMSO (2 mL) was stirred for 6 h at 90° C. under CO (2 atm) atmosphere. The reaction was quenched with water. The resulting solution was extracted with 3×30 mL of EtOAc. The organic layers were dried over anhydrous sodium sulfate and concentrated under vacuum. The crude product (80 mg) was purified by Prep-HPLC eluting with ACN/H$_2$O to afford the title compound (20 mg, 7%) as a white solid. LCMS: [M+H]+ 397.20. $^1$H NMR (400 MHz, DMSO-d$_6$) δ 11.08 (s, 1H), 8.35 (d, J=7.7 Hz, 1H), 8.17 (s, 1H), 7.75 (d, J=10.7 Hz, 2H), 7.70 (s, 1H), 7.12 (s, 1H), 6.25 (s, 1H), 3.87 (dd, J=7.7, 4.0 Hz, 1H), 3.58-3.53 (m, 2H), 3.46-3.41 (m, 2H), 3.30-3.28 (m, 1H), 3.25 (s, 3H), 2.44 (s, 3H), 2.06 (d, J=12.2 Hz, 2H), 1.95 (d, J=12.6 Hz, 2H), 1.42 (q, J=11.8 Hz, 2H), 1.26 (q, J=11.8 Hz, 2H).

Example 10: 5-(1H-imidazol-1-yl)-N-((1r,4r)-4-(2-methoxyethoxy)cyclohexyl)-1H-pyrrolo[3,2-b]pyridine-7-carboxamide

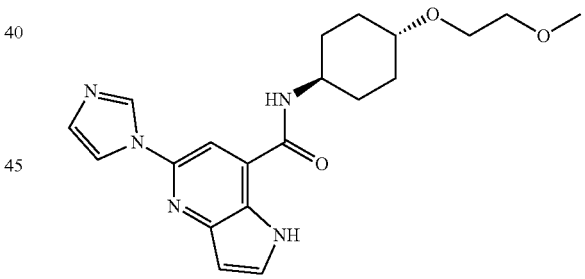

Step 1: 2-(1H-imidazol-yl)-5-nitropyridin-4-amine

A solution of 2-chloro-5-nitropyridin-4-amine (2.5 g, 14.4 mmol, 1 eq), 1H-imidazole (1.96 g, 28.81 mmol, 2 eq) and K$_2$CO$_3$ (3.98 g, 28.81 mmol, 2 eq) in DMF (10 mL) was stirred for 2 h at 100° C. The resulting solution was quenched with water, and the solids were collected by filtration to afford the title compound (3 g) as a yellow crude solid. LCMS (ESI, m/z): 206.18 [M+H]+.

Step 2: 4-Bromo-2-(1H-imidazol-1-yl)-5-nitropyridine

To a solution of 2-(1H-imidazol-1-yl)-5-nitropyridin-4-amine (3 g, 14.62 mmol, 1 eq) and CuBr$_2$ (4.9 g, 21.93 mmol, 1.5 eq) in CH$_3$CN (10 mL) was added isopentyl nitrite (2.57 g, 21.93 mmol, 1.5 eq). The resulting solution was stirred for 1 h at 65° C. The resulting mixture was concentrated and the crude product was purified by C18 reverse phase chromatography eluting with H₂O/CH₃CN to afford the title compound (1.6 g, 40.6%) as a yellow solid. LCMS (ESI, m/z): 269.06 [M+H]⁺.

Step 3: 7-Bromo-5-(1H-imidazol-1-yl)-1H-pyrrolo [3,2-b]pyridine

Under nitrogen, to a solution of 4-bromo-2-(1H-imidazol-1-yl)-5-nitropyridine (1.6 g, 5.95 mmol, 1.0 eq) in THF (10 mL) was added in 1 M vinylmagnesium bromide (23.8 mL, 23.79 mmol, 4.0 eq) at −78° C., and the resulting solution was stirred for 2 h at −78° C. The resulting solution was quenched with saturated aqueous NH₄Cl. After concentration, the crude product was applied onto a silica gel column eluting with EtOAc/petroleum ether (45:55) to afford the title compound (180 mg, 11.5%) as a yellow solid. LCMS (ESI, m/z): 263.10 [M+H]⁺.

Step 4: Methyl 5-(1H-imidazol-1-yl)-1H-pyrrolo[3,2-b]pyridine-7-carboxylate

Under carbon monoxide, a solution of 7-bromo-5-(1H-imidazol-1-yl)-1H-pyrrolo[3,2-b]pyridine (180 mg, 0.68 mmol, 1.0 eq), Pd(dppf)Cl₂ (100.1 mg, 0.14 mmol, 0.2 eq) and TEA (276.9 mg, 2.74 mmol, 4.0 eq) in MeOH (10 mL) was stirred for 2 h at 70° C. The resulting mixture was concentrated under vacuum and the crude product was purified by C18 reverse phase chromatography eluting with CH₃CN/H₂O to afford the title compound (50 mg, 30%) as a yellow solid. LCMS (ESI, m/z): 243.24 [M+H]⁺.

Step 5: 5-(1H-Imidazol-1-yl)-1H-pyrrolo[3,2-b]pyridine-7-carboxylic acid

To a solution of methyl 5-(1H-imidazol-1-yl)-1H-pyrrolo[3,2-b]pyridine-7-carboxylate (30 mg, 0.12 mmol, 1.0 eq) in MeOH/H₂O (1 mL/0.2 mL) was added NaOH (9.9 mg, 0.25 mmol, 2.0 eq), and the resulting solution was stirred for 1 h at RT. The resulting mixture was concentrated under vacuum and the crude product was purified by C18 reverse phase eluting with CH₃CN/H₂O to afford the title compound (10 mg, 35%) as a yellow solid. LCMS (ESI, m/z): 229.21 [M+H]⁺.

Step 6: 5-(1H-Imidazol-1-yl)-N-((1r,4r)-4-(2-methoxyethoxy)cyclohexyl)-1H-pyrrolo[3,2-b]pyridine-7-carboxamide A solution of 5-(1H-imidazol-1-yl)-1H-pyrrolo[3,2-b]pyridine-7-carboxylic acid (15 mg, 0.066 mmol, 1 eq), Int-B1 (11.4 mg, 0.066 mmol, 1 eq), HATU (25 mg, 0.066 mmol, 1.0 eq) and DIPEA (17 mg, 0.13 mmol, 2.0 eq) in DMF (1 mL) was stirred for 1 h at RT. The resulting mixture was purified by C18 reverse phase eluting with CH₃CN/H₂O to afford the title compound (5 mg, 20%) as a white solid. LCMS: 384.25 [M+H]⁺. ¹H NMR (400 MHz, CD3OD-d₄) δ 8.52 (d, J=1.3 Hz, 1H), 7.94 (d, J=1.4 Hz, 1H), 7.83 (s, 1H), 7.74 (d, J=3.3 Hz, 1H), 7.19 (t, J=1.2 Hz, 1H), 6.69 (d, J=3.3 Hz, 1H), 4.02-3.98 (m, 1H), 3.70-3.61 (m, 2H), 3.59-3.51 (m, 2H), 3.46-3.38 (m, 4H), 2.21-2.08 (m, 4H), 1.59-1.34 (m, 4H).

Example 11: N-(2-Fluoro-6-(trifluoromethyl)benzyl)-2-methyl-5-(thiazol-5-yl)-1H-indole-7-carboxamide

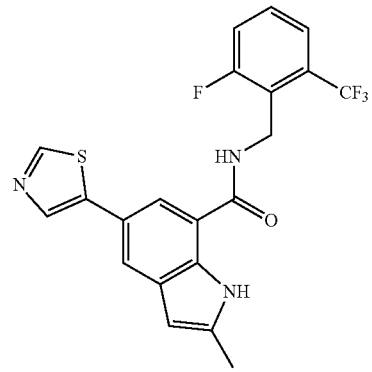 [SMILES: Cc1cc2cc(-c3cncs3)cc(C(=O)NCc3c(F)cccc3C(F)(F)F)c2[nH]1]

Step 1: Methyl 5-bromo-2-methyl-1H-indole-7-carboxylate

Under nitrogen, to a solution of methyl 5-bromo-2-nitrobenzoate (1 g, 3.85 mmol, 1 eq) in THF (15 mL) was added in prop-1-en-2-ylmagnesium bromide (2.23 g, 15.38 mmol, 4.0 eq), and the resulting solution was stirred for 2 h at −50° C. The solution was quenched with saturated aqueous NH₄Cl and extracted with 3×30 mL of EtOAc. The organic layers were combined, dried over anhydrous sodium sulfate and concentrated under vacuum. The crude product was applied onto a silica gel column eluting with EtOAc/petroleum ether to afford the title compound (160 mg, 15.1% yield) as a yellow solid. LCMS (ESI, m/z): 268.00 [M+H]⁺.

Step 2: Methyl 2-methyl-5-(thiazol-5-yl)-1H-indole-7-carboxylate

Under nitrogen, to a solution of methyl 5-bromo-2-methyl-1H-indole-7-carboxylate (70 mg, 0.26 mmol, 1.0 eq), Pd(dppf)Cl₂ (76 mg, 0.10 mmol, 0.4 eq), CuI (15 mg, 0.078 mmol, 0.3 eq) and Na₂CO₃ (55 mg, 0.52 mmol, 2.0 eq) in DMF (4 mL) was added in 5-(4,4,5,5-tetramethyl-1,3,2-dioxaborolan-2-yl) thiazole (110 mg, 0.52 mmol, 2.0 eq). The solution was stirred for 2 h at 80° C. The solution was quenched with H₂O. The solids were filtered out. The resulting mixture was extracted with 3×10 mL of EtOAc. The organic layers were combined, dried over anhydrous sodium sulfate and concentrated under vacuum. The crude product was purified by C18 reverse phase eluting with H₂O/CH₃CN to afford the title compound (30 mg, 42% yield) as a brown solid. LCMS (ESI, m/z): 273.32 [M+H]⁺.

Step 3: 2-Methyl-5-(thiazol-5-yl)-1H-indole-7-carboxylic acid

To a solution of methyl 2-methyl-5-(thiazol-5-yl)-1H-indole-7-carboxylate (30 mg, 0.11 mmol, 1 eq) in THF/H₂O (2 mL/0.4 mL) was added NaOH (9 mg, 0.22 mmol, 2.0 eq). The resulting solution was stirred for 6 h at RT. The pH value was adjusted to 4 with 2 M HCl. The solids were filtered out to afford the title compound (22 mg, 77% yield) as a brown solid. LCMS (ESI, m/z): 259.30 [M+H]⁺.

Step 4: N-(2-Fluoro-6-(trifluoromethyl)benzyl)-2-methyl-5-(thiazol-5-yl)-1H-indole-7-carboxamide A solution of 2-methyl-5-(thiazol-5-yl)-1H-indole-7-carboxylic acid (22 mg, 0.085 mmol, 1 eq), (2-fluoro-6-(trifluoromethyl)phenyl)methanamine (19.7 mg, 0.10 mmol, 2.0 eq), HATU (32.4 mg, 0.085 mmol, 1.0 eq) and DIPEA (22.0 mg, 0.17 mmol, 2.0 eq) in DMF (3 mL) was stirred for 40 min at RT. The resulting solution was quenched with $H_2O$ and extracted with 3×10 mL of EtOAc. The organic layers were combined, dried over anhydrous sodium sulfate and concentrated under vacuum. The crude product was purified by C18 reverse phase chromatography eluting with $H_2O$/$CH_3CN$ to afford the title compound (11.8 mg, 32% yield) as a white solid. LCMS (ESI, m/z): 434.00 [M+H]$^+$. $^1$H NMR (300 MHz, DMSO-d$_6$) δ 11.10 (s, 1H), 8.89 (d, J=0.8 Hz, 2H), 8.11 (d, J=0.8 Hz, 1H), 7.91-7.81 (m, 2H), 7.69-7.54 (m, 3H), 7.50 (t, J=9.0 Hz, 1H), 4.87 (m, 2H), 2.51 (s, 3H).

Example 12: 5-(1H-Imidazol-1-yl)-N-((1r,4r)-4-(2-methoxyethoxy)cyclohexyl)-1H-pyrrolo[2,3-c]pyridine-7-carboxamide

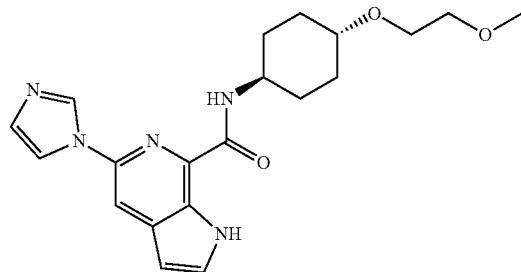

Step 1: 6-(1H-Imidazol-1-yl)-3-nitropyridin-2-amine

A solution of 6-chloro-3-nitropyridin-2-amine (10.0 g, 57.8 mmol, 1.0 eq), $K_2CO_3$ (16.0 g, 115.6 mmol, 2.0 eq) and 1H-imidazole (11.3 g, 173.4 mmol, 3.0 eq) in NMP (100 mL) was stirred for 5 h at 80° C. The reaction was diluted with 1000 mL of water, the solids were collected by filtration to afford the title compound (12 g) as a light brown crude solid. LCMS (ESI, m/z): 206.18 [M+H]$^+$.

Step 2: 2-Bromo-6-(1H-imidazol-1-yl)-3-nitropyridine

To a solution of 6-(1H-imidazol-1-yl)-3-nitropyridin-2-amine (8 g, 39.0 mmol, 1.0 eq) and $CuBr_2$ (13.1 g, 58.5 mmol, 1.5 eq) in $CH_3CN$ (100 mL) was added isopentyl nitrite (6.8 g, 58.5 mmol, 1.5 eq). The resulting solution was stirred for 12 h at 65° C. The resulting solution was quenched with water and the solids were collected by filtration. The crude product was further purified by C18 reverse phase eluting with $H_2O$/$CH_3CN$ to afford the title compound (2.4 g, 13.9%) as a light yellow solid. LCMS (ESI, m/z): 269.06 [M+H]$^+$.

Step 3: 7-Bromo-5-(1H-imidazol-1-yl)-1H-pyrrolo[2,3-c]pyridine

Under nitrogen, to a solution of 2-bromo-6-(1H-imidazol-1-yl)-3-nitropyridine (1.2 g, 4.46 mmol, 1 eq) in THF (50 mL) was added in bromo(ethenyl)magnesium (15.6 mL, 15.60 mmol, 3.5 eq) at −60° C., and the resulting solution was stirred for 3 h at this temperature. The resulting solution was quenched with saturated aqueous $NH_4Cl$ and extracted with 3×100 mL of EtOAc. The organic layers were combined and washed with 1×100 mL of brine, dried over anhydrous sodium sulfate and concentrated under vacuum. The crude product was purified by C18 reverse phase eluting with $H_2O$/$CH_3CN$ to afford the title compound (80 mg, 6%) as a brown solid. LCMS (ESI, m/z): 263.10 [M+H]$^+$.

Step 4: Methyl 5-(1H-imidazol-1-yl)-1H-pyrrolo[2,3-c]pyridine-7-carboxylate

Under carbon monoxide, a solution of 7-bromo-5-(1H-imidazol-1-yl)-1H-pyrrolo[2,3-c]pyridine (170 mg, 0.65 mmol, 1.0 eq), TEA (192 mg, 1.9 mmol, 2.9 eq) and Pd(dppf)Cl$_2$ (46 mg, 0.063 mmol, 0.10 eq) in $CH_3OH$ (10 mL) was stirred for 12 h at 70° C. The resulting mixture was concentrated under vacuum and the crude product was applied onto a silica gel column eluting with EtOAc/petroleum ether to afford the title compound (60 mg, 38%) as a brown solid. LCMS (ESI, m/z): 243.24 [M+H]$^+$.

Step 5: 5-(1H-Imidazol-1-yl)-1H-pyrrolo[2,3-c]pyridine-7-carboxylic acid

To a solution of methyl 5-(1H-imidazol-1-yl)-1H-pyrrolo[2,3-c]pyridine-7-carboxylate (60 mg, 0.25 mmol, 1.0 eq) in MeOH/$H_2O$ (5.0 mL/1 mL) was added NaOH (29.7 mg, 0.74 mmol, 3.0 eq). The resulting solution was stirred for 40 min at RT. The resulting solution was diluted with 3 mL of water. The pH value of the solution was adjusted to 4 with HCl (1 M). The solids were collected by filtration to afford the title compound (34 mg, 60%) as a light yellow solid. LCMS (ESI, m/z): 229.21 [M+H]$^+$.

Step 6: 5-(1H-Imidazol-1-yl)-N-((1r,4r)-4-(2-methoxyethoxy)cyclohexyl)-1H-pyrrolo[2,3-c]pyridine-7-carboxamide A solution of 5-(1H-imidazol-1-yl)-1H-pyrrolo[2,3-c]pyridine-7-carboxylic acid (35 mg, 0.15 mmol, 1.0 eq), Int-B1 (32 mg, 0.18 mmol, 1.2 eq), HATU (58 mg, 0.15 mmol, 1.0 eq) and DIPEA (39.6 mg, 0.31 mmol, 2.0 eq) in DMF (5 mL) was stirred for 40 min at RT. The resulting mixture was quenched with water and extracted with 3×10 mL EtOAc. The organic layers were combined, dried over anhydrous sodium sulfate and concentrated under vacuum. The crude product was purified with C18 reverse phase chromatography eluting with $H_2O$/$CH_3CN$ to afford the title compound (13 mg, 23%) as a white solid. LCMS (ESI, m/z): 384.20[M+H]$^+$. $^1$H NMR (300 MHz, Methanol-d$_4$) δ8.71 (d, J=1.4 Hz, 1H), 8.02-7.99 (m, 2H), 7.71 (dd, J=3.1, 1.2 Hz, 1H), 7.17 (d, J=1.5 Hz, 1H), 6.71 (dd, J=3.2, 1.2 Hz, 1H), 4.08-3.97 (m, 1H), 3.74-3.62 (m, 2H), 3.60-3.51 (m, 2H), 3.44-3.36 (m, 4H), 2.27-1.94 (m, 4H), 1.73-1.54 (m, 2H), 1.52-1.26 (m, 2H).

Example 13: N-((1r,4r)-4-(2-Methoxyethoxy)cyclohexyl)-2-methyl-5-(thiazol-5-yl)-1H-benzo[d]imidazole-7-carboxamide

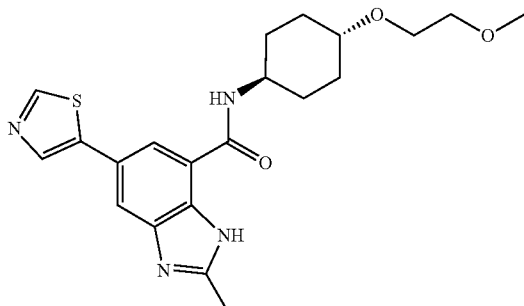

Step 1: Methyl 2-amino-5-iodo-3-nitrobenzoate

A solution of methyl 2-amino-3-nitrobenzoate (4.0 g, 20.39 mmol, 1.0 eq) and NIS (6.88 g, 30.59 mmol, 1.5 eq) in AcOH (60 mL) was stirred for 2 h at RT. The reaction was then quenched with saturated aqueous sodium sulfite. The pH value of the solution was adjusted to 8 with saturated aqueous sodium bicarbonate. The solids were collected by filtration to afford the title compound (6 g, 91%) as a yellow solid. LCMS (ESI, m/z): 323 [M+H]$^+$.

Step 2: Methyl 2,3-diamino-5-iodobenzoate

A solution of methyl 2-amino-5-iodo-3-nitrobenzoate (6.0 g, 18.63 mmol, 1.0 eq), Fe (1.6 g, 27.95 mmol, 1.50 eq), and $H_2O$ (50 mL) in EtOH (200 mL) was stirred for 25 min at 80° C. The insoluble solids were filtered out. The resulting mixture was concentrated, and the crude product was applied onto a silica gel column eluting with EtOAc/petroleum to afford the title compound (4.2 g, 77%) as a red solid. LCMS (ESI, m/z): 293.0 [M+H]$^+$.

Step 3: Methyl 5-iodo-2-methyl-1H-benzo[d]imidazole-7-carboxylate

A solution of methyl 2,3-diamino-5-iodobenzoate (4.2 g, 14.38 mmol, 1.0 eq), 1,1,1-triethoxyethane (7.0 g, 43.14 mmol, 3.0 eq), and $H_2SO_4$ (139.6 mg, 1.44 mmol, 0.10 eq) in MeOH (15 mL) was stirred for 2 h at RT. The resulting mixture was concentrated. The crude product was applied onto a silica gel column eluting with EtOAc/petroleum. The crude product was further purified by C18 reverse phase chromatography eluting with $H_2O/CH_3CN$ to afford the title compound (2.23 g, 49%) as a white solid. LCMS (ESI, m/z): 317.0 [M+H]$^+$.

Step 4: Methyl 2-methyl-5-(thiazol-5-yl)-1H-benzo[d]imidazole-7-carboxylate Under nitrogen, a solution of methyl 5-iodo-2-methyl-1H-benzo[d]imidazole-7-carboxylate (300.0 mg, 0.95 mmol, 1.0 eq), 5-(4,4,5,5-tetramethyl-1,3,2-dioxaborolan-2-yl)thiazole (321 mg, 1.52 mmol, 1.6 eq), Pd(dppf)Cl$_2$ (69 mg, 0.095 mmol, 0.10 eq), CuI (18.1 mg, 0.095 mmol, 0.10 eq), and CsF (288.3 mg, 1.90 mmol, 2.0 eq) in DMF (5 mL) was stirred for 2 h at 80° C. The insoluble solids were filtered out. The residue was purified by C18 reverse phase chromatography eluting with $H_2O/CH_3CN$ to afford the title compound (128 mg, 49%) as a white solid. LCMS (ESI, m/z): 274.2 [M+H]$^+$.

Step 5: 2-Methyl-5-(thiazol-5-yl)-1H-benzo[d]imidazole-7-carboxylic acid

A solution of methyl 2-methyl-5-(thiazol-5-yl)-1H-benzo[d]imidazole-7-carboxylate (128 mg, 0.47 mmol, 1.0 eq), NaOH (94 mg, 2.34 mmol, 5.0 eq), and $H_2O$ (1.5 mL) in MeOH (4.5 mL) was stirred for 3 h at RT. The pH value of the solution was adjusted to 6 with 1 M aqueous HCl. After concentration, the crude product was applied onto a silica gel column with dichloromethane/methanol to afford the title compound (110 mg, 90.6%) as a white solid. LCMS (ESI, m/z): 260.1 [M+H]$^+$.

Step 6: N-((1r,4r)-4-(2-Methoxyethoxy)cyclohexyl)-2-methyl-5-(thiazol-5-yl)-1H-benzo[d]imidazole-7-carboxamide A solution of 2-methyl-5-(thiazol-5-yl)-1H-benzo[d]imidazole-7-carboxylic acid (105 mg, 0.41 mmol, 1.0 eq), Int-B1 (84 mg, 0.47 mmol, 1.2 eq), DIPEA (157 mg, 1.22 mmol, 3.0 eq), and HATU (231 mg, 0.61 mmol, 1.5 eq) in DMF (3.5 mL) was stirred for 1 h at RT. The reaction was then quenched with the addition of 0.1 mL of ethanolamine. The crude product was purified by C18 reverse phase chromatography eluting with $H_2O/CH_3CN$ to afford the title compound (80 mg, 47%) as a white solid. LCMS: [M+H]$^+$ 415.20. $^1$HNMR (400 MHz, DMSO-d$_6$) δ: 12.69 (s, 1H), 9.75 (s, 1H), 9.08 (d, J=0.7 Hz, 1H), 8.34 (d, J=0.8 Hz, 1H), 8.00 (d, J=1.7 Hz, 1H), 7.92 (d, J=1.7 Hz, 1H), 3.89-3.85 (m, 1H), 3.59-3.51 (m, 2H), 3.50-3.40 (m, 2H), 3.36-3.30 (m, 1H), 3.26 (s, 3H), 2.59 (s, 3H), 2.01 (d, J=9.0 Hz, 4H), 1.47-1.27 (m, 4H).

Example 14: 2-(1H-Imidazol-1-yl)-N-((1r,4r)-4-(2-methoxyethoxy)cyclohexyl)-7H-purine-6-carboxamide

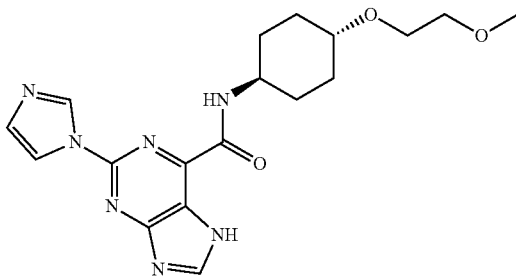

Step 1: 2-Chloro-6-(1-ethoxyvinyl)-7H-purine

Under nitrogen, a solution of 2,6-dichloro-7H-purine (3.78 g, 20.00 mmol, 1.0 eq), tributyl(1-ethoxyethenyl)stannane (8.67 g, 24.00 mmol, 1.2 eq), and Pd(PPh$_3$)$_2$Cl$_2$ (1.4 g, 2.00 mmol, 0.10 eq) in DMF (30 mL) was stirred at 80° C. for 18 h. The reaction was then quenched with saturated aqueous KF. The insoluble solids were filtered out. The resulting solution was extracted with EtOAc. The organic layers were combined, dried over sodium sulfate, and concentrated. The crude product was applied onto a silica gel column eluting with (DCM:MeOH 10:1) to afford the title compound (3 g, 67% yield). LCMS: [M+H]⁺ 225.1.

Step 2: Ethyl 2-chloro-7H-purine-6-carboxylate

A solution of 2-chloro-6-(1-ethoxyethenyl)-7H-purine (2.24 g, 9.97 mmol, 1.0 eq), KMnO$_4$ (315 mg, 1.99 mmol, 0.20 eq), NaIO$_4$ (10.7 g, 49.86 mmol, 5.0 eq), and H$_2$O (40 mL) in dioxane (40 mL) was stirred at RT for 18 h. The resulting solution was diluted with water (100 mL), and extracted with DCM. The organic layers were combined, dried over Na$_2$SO$_4$ and concentrated under reduced pressure to give the crude title compound (1 g, 44% yield). LCMS: [M+H]⁺ 227.1.

Step 3: Ethyl 2-chloro-7-((2-(trimethylsilyl)ethoxy)methyl)-7H-purine-6-carboxylate A solution of ethyl 2-chloro-7H-purine-6-carboxylate (460 mg, 2.03 mmol, 1.0 eq), [2-(chloromethoxy)ethyl]trimethylsilane (406 mg, 2.44 mmol, 1.20 eq), and NaH (60%, 160 mg, 4.06 mmol, 2.0 eq) in DMF (10 mL) was stirred at RT for 2 h. The reaction was then quenched with water. The resulting solution was extracted with EtOAc. The organic layers were dried over Na$_2$SO$_4$ and concentrated under reduced pressure. The crude product was purified by silica gel chromatography eluting with petroleum ether/EtOAc (1/1) to afford the title compound (400 mg, 56% yield) as a white solid. LCMS: [M+H]⁺ 357.1.

Step 4: Ethyl 2-(1H-imidazol-1-yl)-7-((2-(trimethylsilyl)ethoxy)methyl)-7H-purine-6-carboxylate Under nitrogen, a solution of ethyl 2-chloro-7-((2-(trimethylsilyl)ethoxy)methyl)-7H-purine-6-carboxylate (200 mg, 0.56 mmol, 1.0 eq), 1H-imidazole (191 mg, 2.80 mmol, 5.0 eq), Pd$_2$(dba)$_3$ (77 mg, 0.084 mmol, 0.15 eq), tBuXphos (60 mg, 0.14 mmol, 0.25 eq), and K$_3$PO$_4$ (238 mg, 1.12 mmol, 2.0 eq) in toluene (6 mL) was stirred at 110° C. for 3 h. The reaction was quenched with water. The resulting solution was extracted with EtOAc. The organic layers were dried over Na$_2$SO$_4$ and concentrated under reduced pressure. The crude product was purified by silica gel chromatography (DCM:MeOH 10:1) to afford the title compound (210 mg, 96% yield) as a white solid. LCMS: [M+H]⁺ 389.20.

Step 5: 2-(1H-Imidazol-1-yl)-7-((2-(trimethylsilyl)ethoxy)methyl)-7H-purine-6-carboxylic acid A solution of ethyl 2-(1H-imidazol-1-yl)-7-((2-(trimethylsilyl)ethoxy)methyl)-7H-purine-6-carboxylate (210 mg, 0.54 mmol, 1.0 eq) and NaOH (65 mg, 1.62 mmol, 3.0 eq) in H$_2$O (4 mL) and MeOH (4 mL) was stirred at RT for 4 h. The pH value of the solution was adjusted to 5 with 1 M HCl. The resulting solution was extracted with n-BuOH. The organic layers were concentrated to afford the crude title compound (160 mg, 82% yield) as a white solid. LCMS: [M+H]⁺ 361.15.

Step 6: 2-(1H-Imidazol-1-yl)-N-((1r,4r)-4-(2-methoxyethoxy)cyclohexyl)-7-((2-(trimethylsilyl)ethoxy)methyl)-7H-purine-6-carboxamide A solution of 2-(1H-imidazol-1-yl)-7-((2-(trimethylsilyl)ethoxy)methyl)-7H-purine-6-carboxylic acid (120 mg, 0.33 mmol, 1.0 eq), Int-B1 (69 mg, 0.40 mmol, 1.2 eq), HATU (165 mg, 0.43 mmol, 1.3 eq) and DIPEA (86 mg, 0.67 mmol, 2.0 eq) in DMF (2 mL) was stirred at RT for 1 h. After concentration, the crude product was purified by prep-HPLC to give the title compound (130 mg, 75% yield) as a white solid. LCMS: [M+H]⁺ 516.30.

Step 7: 2-(1H-Imidazol-1-yl)-N-((1r,4r)-4-(2-methoxyethoxy)cyclohexyl)-7H-purine-6-carboxamide A solution of 2-(1H-imidazol-1-yl)-N-((1r,4r)-4-(2-methoxyethoxy)cyclohexyl)-7-((2-(trimethylsilyl)ethoxy)methyl)-7H-purine-6-carboxamide (120 mg, 0.23 mmol, 1.0 eq) in DCM (10 mL) and TFA (2 mL) was stirred at RT for 1 h. After concentration, the crude product was purified by prep-HPLC to afford the title compound (47 mg, 52% yield) as a white solid. LCMS: [M+H]⁺ 386.25; ¹HNMR (300 MHz, DMSO-d$_6$) δ 13.56 (s, 1H), 9.01-8.91 (m, 2H), 8.79 (s, 1H), 8.24 (s, 1H), 7.15 (s, 1H), 3.91 (d, J=10.2 Hz, 1H), 3.56 (dd, J=5.9, 3.8 Hz, 2H), 3.43 (dd, J=5.9, 3.7 Hz, 2H), 3.28-3.23 (m, 4H), 2.07 (d, J=12.3 Hz, 2H), 1.89 (d, J=12.8 Hz, 2H), 1.66 (d, J=12.6 Hz, 1H), 1.58 (d, J=12.3 Hz, 1H), 1.32 (d, J=12.2 Hz, 1H), 1.24 (d, J=11.9 Hz, 1H).

Example 15: N-(2-Fluoro-6-(trifluoromethyl)benzyl)-5-(1H-imidazol-1-yl)-1H-pyrazolo[4,3-b]pyridine-7-carboxamide

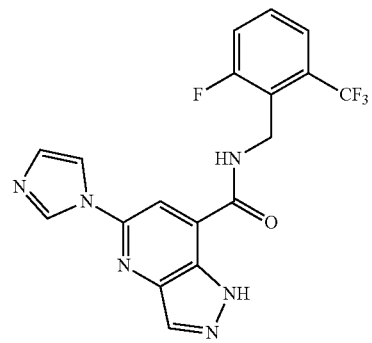

Step 1: 6-(1H-Imidazol-1-yl)-2-methyl-3-nitropyridine

A solution of 6-bromo-2-methyl-3-nitropyridine (3.0 g, 13.82 mmol, 1.0 eq), K$_2$CO$_3$ (3.8 g, 27.71 mmol, 2.0 eq) and 1H-imidazole (1.9 g, 27.62 mmol, 2.0 eq) in DMF (15 mL) was stirred for 2 h at 100° C. The resulting solution was quenched with water and extracted with 3×100 mL of EtOAc. The organic layers were combined and washed with 100 mL of brine, dried over anhydrous sodium sulfate and concentrated under vacuum, and then the residue was applied onto a silica gel column eluting with EtOAc/petroleum ether to afford the title compound (1.03 g, 37%) LCMS: 205.19 [M+H]⁺.

Step 2: 66-(1H-imidazol-1-yl)-2-methyl-3-nitropyridine

A solution of 6-(1H-imidazol-1-yl)-2-methyl-3-nitropyridine (1.03 g, 5.04 mmol, 1.0 eq) and Pd/C (100 mg, 0.94 mmol, 0.19 eq) in MeOH (20 mL) was stirred for 2 h at RT and the solids were filtered out. The resulting solution was concentrated under vacuum to afford the title compound (810 mg, 92%) as a brown solid. LCMS (ESI, m/z): 175.21 [M+H]$^+$.

Step 3: 4-Bromo-6-(1H-imidazol-1-yl)-2-methylpyridin-3-amine

A solution of 6-(1H-imidazol-1-yl)-2-methylpyridin-3-amine (520 mg, 2.99 mmol, 1.0 eq) and NBS (797 mg, 4.48 mmol, 1.5 eq) in TFA (10 mL) was stirred for 1.5 h at 0° C. The mixture was diluted with 30 mL of ice water, and the pH was adjusted to 8 with 20% NaOH. The resulting solution was extracted with 3×30 mL of EtOAc. The organic layers were combined, dried over anhydrous sodium sulfate and concentrated under vacuum. The residue was purified by C18 reverse phase chromatography eluting with H$_2$O/ACN to afford title compound (460 mg, 61%) as a yellow solid. LCMS (ESI, m/z): 253.10 [M+H]$^+$.

Step 4: 7-Bromo-5-(1H-imidazol-1-yl)-1H-pyrazolo[4,3-b]pyridine

A solution of 4-bromo-6-(1H-imidazol-1-yl)-2-methylpyridin-3-amine (460 mg, 1.82 mmol, 1.0 eq), acetic anhydride (930 mg, 9.11 mmol, 5.0 eq) and KOAc (54 mg, 0.55 mmol, 0.30 eq) in CHCl$_3$ (20 mL) was stirred for 2 h at 0° C. in a water/ice bath. Isopentyl nitrite (534 mg, 4.56 mmol, 2.5 eq) was then added and the resulting solution was stirred for 30 min at 0° C. and for another 3 h at 60° C. The resulting mixture was concentrated under vacuum and the residue was applied onto a silica gel column eluting with EtOAc to afford the title compound (350 mg 73%) as a brown solid. LCMS (ESI, m/z): 264.09 [M+H]$^+$.

Step 5: Methyl 5-(1H-imidazol-1-yl)-1H-pyrazolo[4,3-b]pyridine-7-carboxylate

Under an atmosphere of carbon monoxide, a solution of 7-bromo-5-(1H-imidazol-1-yl)-1H-pyrazolo[4,3-b]pyridine (220 mg, 0.83 mmol, 1.0 eq), TEA (250 mg, 2.47 mmol, 3.0 eq) and Pd(dppf)Cl$_2$ (61 mg, 0.084 mmol, 0.10 eq) in MeOH (10 mL) was stirred for 12 h at 70° C. The resulting solution was concentrated under vacuum and applied onto a silica gel column eluting with EtOAc to afford the title compound (73 mg, 36%) as a light yellow solid. LCMS (ESI, m/z): 244.23 [M+H]$^+$.

Step 6: 5-(1H-Imidazol-1-yl)-1H-pyrazolo[4,3-b]pyridine-7-carboxylic acid

To a solution of methyl 5-(1H-imidazol-1-yl)-1H-pyrazolo[4,3-b]pyridine-7-carboxylate (73 mg, 0.30 mmol, 1.0 eq) in MeOH (3.0 mL) was added NaOH (36 mg, 0.90 mmol, 3.0 eq) in H$_2$O (0.6 mL). The resulting solution was stirred for 40 min at RT, and then concentrated under vacuum and diluted with 1 mL of water. The pH was adjusted to 4 with 1 M HCl, and then the solids were collected by filtration to afford the title compound (40 mg, 58%) as a light yellow solid. LCMS (ESI, m/z): 230.20 [M+H]$^+$.

Step 7: N-(2-Fluoro-6-(trifluoromethyl)benzyl)-5-(1H-imidazol-1-yl)-1H-pyrazolo[4,3-b]pyridine-7-carboxamide A solution of 5-(1H-imidazol-1-yl)-1H-pyrazolo[4,3-b]pyridine-7-carboxylic acid (40 mg, 0.18 mmol, 1.0 eq), HATU (66 mg, 0.18 mmol, 1.0 eq), DIPEA (45 mg, 0.35 mmol, 2.0 eq) and (2-fluoro-6-(trifluoromethyl)phenyl)methanamine (34 mg, 0.18 mmol, 1.0 eq) in DMF (2.0 mL) was stirred for 40 min at RT. The reaction was quenched with water and extracted with 3×10 mL of EtOAc. The organic layers were combined, dried over sodium sulfate, and concentrated under vacuum, and then the residue was purified by C18 reverse phase eluting with H$_2$O/CH$_3$CN to afford the title compound (26 mg, 37%) as a white solid. LCMS (ESI, m/z): 405.05 [M+H]$^+$. $^1$H NMR (300 MHz, DMSO-d$_6$) δ13.81 (s, 1H), 9.41 (s, 1H), 8.55-8.36 (m, 2H), 8.13 (s, 1H), 7.95 (t, J=1.3 Hz, 1H), 7.68 (d, J=5.5 Hz, 3H), 7.15 (t, J=1.2 Hz, 1H), 4.81 (d, J=4.3 Hz, 2H).

Example 16: 5-(1H-Imidazol-1-yl)-N-((1r,4r)-4-(2-methoxyethoxy)cyclohexyl)-1H-pyrazolo[3,4-c]pyridine-7-carboxamide

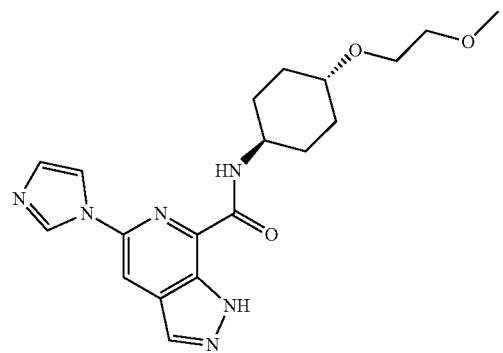 [SMILES: COCCO[C@H]1CC[C@H](NC(=O)c2nc(-n3ccnc3)cc3cn[nH]c23)CC1]

Step 1:
2-(1H-Imidazol-1-yl)-4-methyl-5-nitropyridine

A solution of 2-chloro-4-methyl-5-nitropyridine (5.0 g, 28.98 mmol, 1.0 eq), K$_2$CO$_3$ (8.0 g, 58.03 mmol, 2.0 eq) and 1H-imidazole (4.0 g, 58.02 mmol, 2.0 eq) in DMF (20 mL) was stirred for 2 h at 100° C. The resulting solution was quenched with water and extracted with 3×100 mL of EtOAc. The organic layers were combined, dried over sodium sulfate and washed with 100 mL brine, dried over anhydrous sodium sulfate and concentrated under vacuum. The crude product was applied onto a silica gel column eluting with EtOAc to afford the title compound (1.3 g, 22%) as a brown solid. LCMS (ESI, m/z): 205.19 [M+H]$^+$.

Step 2:
6-(1H-Imidazol-1-yl)-4-methylpyridin-3-amine

Under an atmosphere of hydrogen, a solution of 2-(1H-imidazol-1-yl)-4-methyl-5-nitropyridine (1.30 g, 6.37 mmol, 1.0 eq) and Pd/C (130 mg, 1.22 mmol, 0.19 eq) in MeOH (30 mL) was stirred for 4 h at RT. The solids were filtered out and then the resulting mixture was concentrated under vacuum to afford the title compound (1.17 g) as a crude brown solid. LCMS (ESI, m/z): 175.21 [M+H]$^+$.

Step 3: 2-Bromo-6-(1H-imidazol-1-yl)-4-methylpyridin-3-amine

A solution of 6-(1H-imidazol-1-yl)-4-methylpyridin-3-amine (550 mg, 3.16 mmol, 1.0 eq) and NBS (843 mg, 4.74 mmol, 1.5 eq) in TFA (6.0 mL) was stirred for 1.5 h at 0° C. The resulting solution was quenched with ice water. The pH value of the resulting solution was adjusted to 8 by NaOH (15% in water). The resulting solution was extracted with 3×30 mL of EtOAc. The organic layers were combined, dried over anhydrous sodium sulfate and concentrated under vacuum. The crude product was purified by C18 reverse phase eluting with H$_2$O/ACN to afford the title compound (360 mg, 45%) as a light yellow solid. LCMS (ESI, m/z): 253.10 [M+H]$^+$.

Step 4: 7-Bromo-5-(1H-imidazol-1-yl)-1H-pyrazolo[3,4-c]pyridine

A solution of 2-bromo-6-(1H-imidazol-1-yl)-4-methylpyridin-3-amine (360 mg, 1.42 mmol, 1.0 eq) and Ac$_2$O (728 mg, 7.13 mmol, 5.0 eq) in CHCl$_3$ (15 mL) was stirred for 2 h at 0° C. KOAc (42 mg, 0.43 mmol, 0.30 eq) and isopentyl nitrite (418.0 mg, 3.57 mmol, 2.5 eq) were added. The resulting solution was stirred for 30 min at 0° C. and for 3 h at 60° C. The resulting mixture was concentrated under vacuum and then the residue was applied onto a silica gel column eluting with EtOAc to afford the title compound (340 mg, 91%) as a brown solid. LCMS (ESI, m/z): 264.09 [M+H]$^+$.

Step 5: Methyl 5-(1H-imidazol-1-yl)-1H-pyrazolo[3,4-c]pyridine-7-carboxylate

Under an atmosphere of carbon monoxide, a solution of 7-bromo-5-(1H-imidazol-1-yl)-1H-pyrazolo[3,4-c]pyridine (230 mg, 0.87 mmol, 1.0 eq), TEA (265 mg, 2.62 mmol, 3.0 eq) and Pd(dppf)Cl$_2$ (64 mg, 0.087 mmol, 0.10 eq) in MeOH (10 mL) was stirred for 12 h at 70° C. The resulting mixture was concentrated under vacuum, and the crude mixture was applied onto a silica gel column eluting with EtOAc to afford the title compound (100 mg, 47%) as a light yellow solid. LCMS (ESI, m/z): 244.23 [M+H]$^+$.

Step 6: 5-(1H-Imidazol-1-yl)-1H-pyrazolo[3,4-c]pyridine-7-carboxylic acid

To a solution of methyl 5-(1H-imidazol-1-yl)-1H-pyrazolo[3,4-c]pyridine-7-carboxylate (100 mg, 0.41 mmol, 1.0 eq) in MeOH/H$_2$O (4.0 mL/0.8 mL) was added in NaOH (49 mg, 1.23 mmol, 3.0 eq), the resulting solution was stirred for 30 min at RT. The resulting solution was diluted with 3 mL water. The pH value was adjusted to 4 with 1 M HCl, and the solids were collected by filtration to afford the title compound (64 mg, 68%) as a yellow solid. LCMS (ESI, m/z): 230.20 [M+H]$^+$.

Step 7: 5-(1H-Imidazol-1-yl)-N-((1r,4r)-4-(2-methoxyethoxy)cyclohexyl)-1H-pyrazolo[3,4-c]pyridine-7-carboxamide To a solution of 5-(1H-imidazol-1-yl)-1H-pyrazolo[3,4-c]pyridine-7-carboxylic acid (65 mg, 0.28 mmol, 1.0 eq), HATU (108 mg, 0.28 mmol, 1.0 eq) and DIPEA (73 mg, 0.57 mmol, 2.0 eq) in DMF (5.0 mL) was added Int-B1 (49.1 mg, 0.28 mmol, 1.0 eq). The resulting solution was stirred for 40 min at RT. The resulting mixture was quenched with water and extracted with 3×20 mL of EtOAc. The organic layers were combined, dried over anhydrous sodium sulfate and concentrated under vacuum. The crude product was purified by C18 reverse phase eluting with H$_2$O/ACN to afford the title compound (46.9 mg, 43%) as a white solid. LCMS (ESI, m/z): 385.25 [M+H]$^+$. $^1$H NMR (300 MHz, DMSO-d$_6$) δ13.85 (s, 1H), 8.93 (d, J=1.3 Hz, 1H), 8.74 (d, J=8.7 Hz, 1H), 8.37 (dd, J=2.8, 1.0 Hz, 2H), 8.23 (s, 1H), 7.16 (s, 1H), 4.05-3.79 (m, 1H), 3.57 (dd, J=5.9, 3.7 Hz, 2H), 3.44 (dd, J=5.9, 3.7 Hz, 2H), 3.34-3.30 (m, 4H), 2.08 (d, J=12.3 Hz, 2H), 1.90 (d, J=11.9 Hz, 2H), 1.64 (m, 2H), 1.29 (m, 2H).

Example 17: N-((1r,4r)-4-(2-Methoxyethoxy)cyclohexyl)-5-(thiazol-5-yl)-1H-pyrazolo[4,3-b]pyridine-7-carboxamide

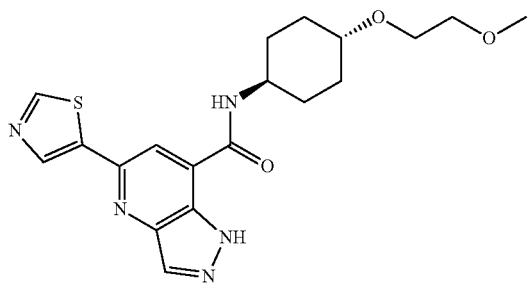 [SMILES: COCCO[C@H]1CC[C@H](NC(=O)c2cc(-c3cncs3)nc3cn[nH]c23)CC1]

Step 1: 5-Nitro-2-(thiazol-5-yl)isonicotinic acid

A solution of 2-chloro-5-nitroisonicotinic acid (1.00 g, 4.94 mmol, 1.0 eq), 5-(4,4,5,5-tetramethyl-1,3,2-dioxaborolan-2-yl)thiazole (1.58 g, 7.49 mmol, 1.5 eq), Pd(dppf)Cl$_2$ (362 mg, 0.50 mmol, 0.10 eq), CuI (190 mg, 1.0 mmol, 0.20 eq) and K$_2$CO$_3$ (1.4 g, 9.91 mmol, 2.0 eq) in DMF (20 mL) was stirred for 5 h at 80° C. After completion and allowing the reaction mixture to cool to RT, the solids were collected by filtration to afford the title compound (700 mg, 56%) as a gray solid. LCMS (ESI, m/z): 252.22 [M+H]$^+$.

Step 2: Methyl 5-nitro-2-(thiazol-5-yl)isonicotinate

A solution of 5-nitro-2-(thiazol-5-yl)isonicotinic acid and SOCl$_2$ (10 mL) in CH$_3$OH (30 mL) was stirred for 12 h at 70° C., The resulting solution was concentrated under vacuum, and the residue was applied onto a silica gel column eluting with EtOAc/petroleum ether to afford the title compound (343 mg, 68%) as a light yellow solid. LCMS (ESI, m/z): 266.24 [M+H]$^+$.

Step 3: Methyl 5-amino-2-(thiazol-5-yl)isonicotinate

Under a hydrogen atmosphere, a solution of methyl 5-nitro-2-(thiazol-5-yl)isonicotinate (360 mg, 1.36 mmol, 1.0 eq) and Pd/C (36 mg, 0.34 mmol, 0.25 eq) in CH$_3$OH (10 mL) was stirred for 10 h at RT. The solids were filtered out and the resulting solution was concentrated under vacuum to afford the title compound (300 mg, 94%) as a light brown solid. LCMS (ESI, m/z): 236.26 [M+H]$^+$.

Step 4: Methyl 3-amino-2-bromo-6-(thiazol-5-yl)isonicotinate

A solution of methyl 5-amino-2-(thiazol-5-yl)isonicotinate (300 mg, 1.28 mmol, 1.0 eq) and NBS (273 mg, 1.53 mmol, 1.2 eq) in TFA (5 mL) was stirred for 1.5 h at 0° C. The resulting solution was quenched with water, and the pH was adjusted to 8 by NaOH (15% in water). The resulting mixture was extracted with 3×20 mL EtOAc, and the organic layers were combined, dried over anhydrous sodium sulfate and concentrated under vacuum. The residue was purified by C18 reverse phase eluting with $H_2O$/ACN to afford the title compound (80 mg, 20%) as a light yellow solid. LCMS (ESI, m/z): 314.16 $[M+H]^+$.

Step 5: Methyl 3-amino-2-methyl-6-(thiazol-5-yl)isonicotinate

A solution of methyl 3-amino-2-bromo-6-(thiazol-5-yl) isonicotinate (86 mg, 0.27 mmol, 1.0 eq), $K_2CO_3$ (76 mg, 0.55 mmol, 2.0 eq), X-Phos (26 mg, 0.055 mmol, 0.20 eq), $Pd_2(dba)_3$ (25 mg, 0.027 mmol, 0.10 eq), 2,4,6-trimethyl-1,3,5,2,4,6-trioxatriborinane (207 mg, 1.65 mmol, 6.0 eq) and $H_2O$ (0.5 mL) in t-BuOH (6 mL) was stirred for 2 h at 80° C. The resulting solution was concentrated, and the residue was applied onto a silica gel column eluting with EtOAc/petroleum ether to afford the title compound (56 mg, 82%) as a light brown solid. LCMS (ESI, m/z): 250.29 $[M+H]^+$.

Step 6: Methyl 5-(thiazol-5-yl)-1H-pyrazolo[4,3-b]pyridine-7-carboxylate

A solution of methyl 3-amino-2-methyl-6-(thiazol-5-yl) isonicotinate (50 mg, 0.20 mmol, 1.0 eq), acetic anhydride (102 mg, 1.0 mmol, 5.0 eq) and KOAc (5.5 mg, 0.04 mmol, 0.2 eq) in $CHCl_3$ (5.0 mL) was stirred for 1.5 h at 0° C., and then isopentyl nitrite (58.0 mg, 0.50 mmol, 2.5 eq) was added dropwise. The resulting solution was stirred for 20 min at 0° C. and for another 2 h at 60° C. The resulting solution was concentrated under vacuum, and the residue was applied onto a silica gel column with EtOAc/petroleum ether to afford the title compound (60 mg) as light yellow solid. The crude solid was carried forward without additional purification. LCMS (ESI, m/z): 261.27 $[M+H]^+$.

Step 7: 5-(Thiazol-5-yl)-1H-pyrazolo[4,3-b]pyridine-7-carboxylic acid

To a solution of methyl 5-(thiazol-5-yl)-1H-pyrazolo[4,3-b]pyridine-7-carboxylate (60 mg, 0.23 mmol, 1.0 eq) in $CH_3OH/H_2O$ (3.0 mL/0.5 mL) was added NaOH (28 mg, 0.69 mmol, 3.0 eq). The resulting solution was stirred for 40 min at RT, and then the resulting solution was diluted with 2 mL of water. The pH of the resulting solution was adjusted to 4 with 1 M HCl, and the solid was collected by filtration to afford the title compound (25 mg, 44%) as a light yellow solid. LCMS (ESI, m/z): 247.24 $[M+H]^+$.

Step 8: N-((1r,4r)-4-(2-Methoxyethoxy)cyclohexyl)-5-(thiazol-5-yl)-1H-pyrazolo[4,3-b]pyridine-7-carboxamide A solution of 5-(thiazol-5-yl)-1H-pyrazolo[4,3-b]pyridine-7-carboxylic acid (20 mg, 0.08 mmol, 1.0 eq), Int-B1 (14 mg, 0.081 mmol, 1.0 eq), HATU (31 mg, 0.081 mmol, 1.0 eq) and DIPEA (32 mg, 0.24 mmol, 3.0 eq) in DMF (0.5 mL) was stirred for 40 min at RT, and the resulting solution was purified by C18 reverse phase eluting with $H_2O$/ACN to afford the title compound (8.4 mg, 26%) as a white solid. LCMS (ESI, m/z): 402.25 $[M+H]^+$. $^1H$ NMR (300 MHz, Methanol-$d_4$) δ 9.11 (d, J=9.1 Hz, 1H), 8.58 (s, 1H), 8.45 (d, J=9.1 Hz, 1H), 8.38 (d, J=4.5 Hz, 1H), 4.06-3.99 (m, 1H), 3.69-3.66 (m, 2H), 3.57-3.54 (m, 2H), 3.42-3.32 (m, 4H), 2.28-2.12 (m, 4H), 1.59-1.41 (m, 4H).

Example 18: 2-(1H-Imidazol-1-yl)-N-((1r,4r)-4-(2-methoxyethoxy)cyclohexyl)thieno[3,2-d]pyrimidine-4-carboxamide

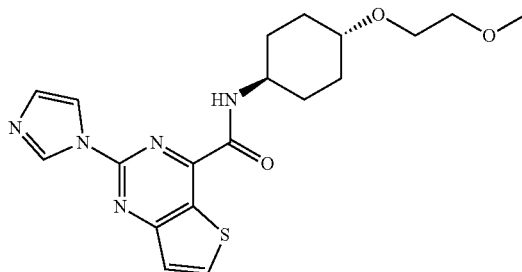

Step 1: 2-Chloro-4-(1-ethoxyvinyl)thieno[3,2-d]pyrimidine

Under a nitrogen atmosphere, a solution of 2,4-dichloro-thieno[3,2-d]pyrimidine (4.08 g, 19.9 mmol, 1.0 eq), tributyl (1-ethoxyethenyl)stannane (8.62 g, 23.88 mmol, 1.2 eq) and $Pd(PPh_3)_2Cl_2$ (1.40 g, 1.99 mmol, 0.10 eq) in DMF (40 mL) was stirred at 80° C. for 2 h. The resulting solution was cooled to RT and quenched with saturated aqueous KF. The insoluble solids were filtered out. The resulting solution was extracted with EtOAc. The organic layers were combined, dried over sodium sulfate, and concentrated. The residue was applied onto a silica gel column eluting with (DCM:MeOH 10:1) to afford the title compound (3.5 g, 73% yield). LCMS: $[M+H]^+$ 241.1.

Step 2: Ethyl 2-chlorothieno[3,2-d]pyrimidine-4-carboxylate

A solution of 2-chloro-4-(1-ethoxyethenyl)thieno[3,2-d] pyrimidine (2.40 g, 9.97 mmol, 1.0 eq), $KMnO_4$ (630.3 mg, 3.99 mmol, 0.40 eq), and $NaIO_4$ (10.66 g, 49.85 mmol, 5.0 eq) in $H_2O$ (50 mL) and dioxane (50 mL) was stirred at RT for 16 h. The resulting solution was quenched with water and extracted with EtOAc. The organic layers were combined, dried over $Na_2SO_4$ and concentrated under reduced pressure. The crude product was applied onto a silica gel column eluting with EtOAc:petroleum ether (2:3) to afford the title compound (500 mg, 21% yield). LCMS: $[M+H]^+$ 243.1.

Step 3: Ethyl 2-(1H-imidazol-1-yl)thieno[3,2-d]pyrimidine-4-carboxylate

Under nitrogen, a solution of ethyl 2-chlorothieno[3,2-d] pyrimidine-4-carboxylate (243 mg, 1.00 mmol, 1.0 eq), 1H-imidazole (340 mg, 5.00 mmol, 5.0 eq), $Pd_2(dba)_3$ (136 mg, 0.15 mmol, 0.15 eq), tBuXphos (85 mg, 0.20 mmol, 0.20 eq), $K_3PO_4$ (420 mg, 2.00 mmol, 2.0 eq) in toluene (10 mL) was stirred at 110° C. for 3 h. The reaction was quenched with water and extracted with EtOAc. The organic layers were dried over $Na_2SO_4$, filtered and concentrated under reduced pressure. The crude product was purified by silica gel chromatography eluting with (DCM:MeOH 10:1) to afford the title compound (220 mg, 81% yield) as a white solid. LCMS: $[M+H]^+$ 275.1.

Step 4: 2-(1H-Imidazol-1-yl)thieno[3,2-d]pyrimidine-4-carboxylic acid

A mixture of ethyl 2-(1H-imidazol-1-yl)thieno[3,2-d]pyrimidine-4-carboxylate (220 mg, 0.80 mmol, 1.0 eq), NaOH (96 mg, 2.41 mmol, 3.0 eq) in $H_2O$ (4 mL) and MeOH (4 mL) was stirred at RT for 2 h. The pH value of the solution was adjusted to 5 with 1 M HCl. The resulting solution was extracted with 10 mL of n-BuOH. The organic layers was concentrated to afford the crude title compound (200 mg) as a white solid. $[M+H]^+$ 247.1.

Step 5: 2-(1H-Imidazol-1-yl)-N-((1r,4r)-4-(2-methoxyethoxy)cyclohexyl)thieno[3,2-d]pyrimidine-4-carboxamide A solution of 2-(1H-imidazol-1-yl)thieno[3,2-d]pyrimidine-4-carboxylic acid (123 mg, 0.50 mmol, 1.0 eq), Int-B1 (87 mg, 0.50 mmol, 1.0 eq), HATU (228 mg, 0.60 mmol, 1.2 eq), and DIPEA (129 mg, 1.00 mmol, 2.0 eq) in DMF (2 mL) was stirred at RT for 1 h. The resulting solution was concentrated under vacuum. The crude product was purified by prep-HPLC eluting with $ACN/H_2O$ to afford the title compound (43.1 mg, 21% yield) as a white solid. LCMS: $[M+H]^+$ 402.05; iHNMR (300 MHz, DMSO-$d_6$) δ 9.21 (s, 1H), 9.14 (d, J=8.6 Hz, 1H), 8.74 (d, J=5.6 Hz, 1H), 8.35 (t, J=1.4 Hz, 1H), 7.70 (d, J=5.6 Hz, 1H), 7.28 (d, J=1.7 Hz, 1H), 4.10-3.99 (m, 1H), 3.58 (dd, J=6.0, 3.7 Hz, 2H), 3.46-3.32 (m, 6H), 2.10 (d, J=12.3 Hz, 2H), 1.91 (d, J=13.2 Hz, 2H), 1.69 (d, J=13.4 Hz, 1H), 1.60 (d, J=11.9 Hz, 1H), 1.39-1.25 (m, 2H).

Example 19: 2-(Aminomethyl)-5-(1H-imidazol-1-yl)-N-((1r,4r)-4-(2-methoxyethoxy)cyclohexyl)-1H-indole-7-carboxamide

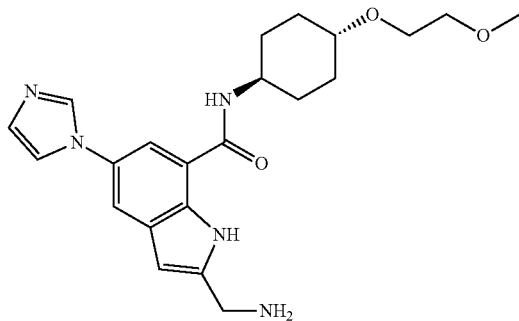 [SMILES: COCCO[C@H]1CC[C@H](NC(=O)c2cc(-n3ccnc3)cc3cc(CN)[nH]c23)CC1]

Step 1: 1-(3-Bromo-4-nitrophenyl)-1H-imidazole

A mixture of 2-bromo-4-fluoro-1-nitrobenzene (11.00 g, 50.00 mmol, 1.0 eq), 1H-imidazole (4.80 g, 70.51 mmol, 1.41 eq) and $K_2CO_3$ (6.90 g, 49.93 mmol, 1.0 eq) in DMF (50 mL) was stirred at 80° C. for 1 h. The reaction was quenched with water. The solids were collected by filtration to afford the title compound (12.9 g, 96% yield) as a pale yellow solid. LCMS: $[M+H]^+$ 268.00.

Step 2: 2-Bromo-4-(1H-imidazol-1-yl)aniline

A mixture of 1-(3-bromo-4-nitrophenyl)-1H-imidazole (1.60 g, 5.97 mmol, 1.0 eq), $NH_2NH_2 \cdot H_2O$ (5.0 mL, 99.90 mmol, 17.2 eq) and Raney Ni (0.50 g, 5.85 mmol, 0.98 eq) in EtOH (50 mL) was stirred at RT for 4 h. After filtration, the filtrate was concentrated and purified by silica gel chromatography eluting with EtOAc/petroleum ether (4/1) to afford the title compound (1.0 g, 70% yield) as a white solid. LCMS: $[M+H]^+$ 237.99.

Step 3: 2-Bromo-4-(1H-imidazol-1-yl)-6-iodoaniline

A solution of 2-bromo-4-(1H-imidazol-1-yl)aniline (11.00 g, 46.20 mmol, 1.0 eq) and NIS (10.4 g, 46.2 mmol, 1.0 eq) in TFA (100 mL) was stirred at RT for 2 days. The reaction was quenched with water and extracted with 3×200 mL of EtOAc. The organic layers were combined, dried over sodium sulfate and concentrated. The crude product was purified by silica gel chromatography eluting with EtOAc/petroleum ether (1/1) to afford the title compound (14.0 g, 83% yield) as a yellow oil. LCMS: $[M+H]^+$ 363.89.

Step 4: tert-Butyl (3-(2-amino-3-bromo-5-(1H-imidazol-1-yl)phenyl)prop-2-yn-1-yl)carbamate Under nitrogen, a mixture of 2-bromo-4-(1H-imidazol-1-yl)-6-iodoaniline (7.28 g, 20.00 mmol, 1.0 eq), tert-butyl prop-2-yn-1-ylcarbamate (3.11 g, 20.04 mmol, 1.0 eq), $Pd(PPh_3)_2Cl_2$ (1.40 g, 1.99 mmol, 0.10 eq), CuI (0.38 g, 2.00 mmol, 0.10 eq), and 1,1,3,3-tetramethylguanidine (10.0 mL) in DMF (100 mL) was stirred at 50° C. overnight. The reaction was quenched with water and extracted with 3×200 mL of EtOAc. The organic layers were combined, dried over sodium sulfate and concentrated. The crude product was purified by silica gel chromatography eluting with EtOAc/petroleum ether (1/1) to afford the title compound (4.5 g, 58% yield) as yellow oil. LCMS: $[M+H]^+$ 391.07.

Step 5: tert-Butyl ((7-bromo-5-(1H-imidazol-1-yl)-1H-indol-2-yl)methyl)carbamate A mixture of tert-butyl (3-(2-amino-3-bromo-5-(1H-imidazol-1-yl)phenyl)prop-2-yn-1-yl)carbamate (1.86 g, 4.75 mmol, 1.0 eq) and $NaAuCl_4 \cdot 2H_2O$ (80 mg, 0.20 mmol, 0.04 eq) in EtOH (30 mL) was stirred at 80° C. for 2 days. After concentration, the mixture was purified by silica gel chromatography eluting with EtOAc/petroleum ether (1/1) to afford the title compound (700 mg, 38% yield) as yellow solid. LCMS: $[M+H]^+$ 391.07.

Step 6: tert-butyl ((7-cyano-5-(1H-imidazol-1-yl)-1H-indol-2-yl)methyl)carbamate Under nitrogen, a mixture of tert-butyl ((7-bromo-5-(1H-imidazol-1-yl)-1H-indol-2-yl)methyl)carbamate (560 mg, 1.43 mmol, 1.0 eq), dicyanozinc (336 mg, 2.86 mmol, 2.0 eq) and $Pd(PPh_3)_4$ (165 mg, 0.14 mmol, 0.10 eq) in DMF (10 mL) was stirred at 90° C. for 2 h. The reaction was quenched with water and extracted with 3×50 mL EtOAc. The organic layers were combined, dried over sodium sulfate and concentrated. The crude product was purified by silica gel chromatography eluting with EtOAc/petroleum ether (1/1) to afford the title compound (360 mg, 75%) as a yellow solid. LCMS: $[M+H]^+$ 338.15.

Step 7: 2-((tert-Butoxycarbonylamino)methyl)-5-(1H-imidazol-1-yl)-1H-indole-7-carboxylic acid A mixture of tert-butyl ((7-cyano-5-(1H-imidazol-1-yl)-1H-indol-2-yl)methyl)carbamate (337 mg, 1 mmol, 1.0 eq), KOH (1.68 g, 29.94 mmol, 30 eq) and H₂O (4.0 mL, 0.006 mmol, 0.11 eq) in EtOH (40 mL) was stirred at 80° C. for 1 day. The pH value of the solution was adjusted to 4 with 2 M HCl and extracted with 3×50 mL EtOAc. The organic layers were combined, dried over sodium sulfate and concentrated. The crude product was purified by C18 reverse phase chromatography eluting with H₂O/CH₃CN to afford the title compound (100 mg, 28%) as a yellow solid. LCMS: [M+H]⁺ 357.15.

Step 8: tert-Butyl ((5-(1H-imidazol-1-yl)-7-(((1r,4r)-4-(2-methoxyethoxy)cyclohexyl)carbamoyl)-1H-indol-2-yl)methyl)carbamate A mixture of 2-((tert-butoxycarbonylamino)methyl)-5-(1H-imidazol-1-yl)-1H-indole-7-carboxylic acid (100 mg, 0.28 mmol, 1.0 eq), DIPEA (108 mg, 0.84 mmol, 3 eq), HATU (129 mg, 0.34 mmol, 1.2 eq) and Int-B1 (59 mg, 0.34 mmol, 1.2 eq) in DMF (1.0 mL) was stirred at RT for 1 h. The crude product was purified by C18 reverse phase chromatography eluting with H₂O/CH₃CN to afford the title compound (120 mg, 84%) as a white solid. LCMS: [M+H]⁺ 512.28.

Step 9: 2-(Aminomethyl)-5-(1H-imidazol-1-yl)-N-((1r,4r)-4-(2-methoxyethoxy)cyclohexyl)-1H-indole-7-carboxamide A mixture of tert-butyl ((5-(1H-imidazol-1-yl)-7-(((1r,4r)-4-(2-methoxyethoxy)cyclohexyl)carbamoyl)-1H-indol-2-yl)methyl)carbamate (120 mg, 0.24 mmol, 1.0 eq) and TFA (1.0 mL) in DCM (5.0 mL) was stirred at RT for 1 h. After concentration, the crude product was purified by C18 reverse phase chromatography eluting with H₂O/CH₃CN to afford the title compound (26.5 mg, 28%) as a white solid. LCMS: [M+H]⁺ 412.10. ¹H-NMR (400 MHz, Methanol-d₄) δ 8.12 (t, J=1.2 Hz, 1H), 7.87 (d, J=2.0 Hz, 1H), 7.79 (d, J=2.0 Hz, 1H), 7.60 (t, J=1.4 Hz, 1H), 7.18 (t, J=1.2 Hz, 1H), 6.61 (s, 1H), 4.15 (d, J=0.8 Hz, 2H), 4.04-3.93 (m, 1H), 3.70-3.64 (m, 2H), 3.59-3.52 (m, 2H), 3.39 (s, 3H), 3.44-3.33 (m, 1H), 2.17 (d, J=11.6 Hz, 2H), 2.09 (d, J=12.4 Hz, 2H), 1.54-1.45 (m, 4H).

Example 20: N-(2-Fluoro-6-(trifluoromethyl)benzyl)-2-(thiazol-5-yl)thieno[3,2-d]pyrimidine-4-carboxamide

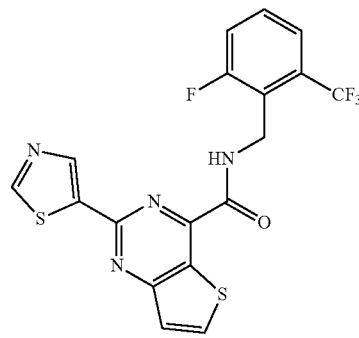 [SMILES: O=C(NCc1c(F)cccc1C(F)(F)F)c1nc(-c2cncs2)nc2ccsc12]

Step 1: 2-Chloro-4-(1-ethoxyvinyl)thieno[3,2-d]pyrimidine

Under nitrogen, a solution of 2,4-dichlorothieno[3,2-d]pyrimidine (10.0 g, 48.77 mmol, 1.0 eq), tributyl(1-ethoxyethenyl)stannane (21.1 g, 58.52 mmol, 1.2 eq), and Pd(PPh₃)₂Cl₂ (3.42 g, 4.88 mmol, 0.1 eq) in DMF (150 mL) was stirred for 1 h at 80° C. The solids were filtered out. The reaction was quenched with water, and the resulting solution was extracted with 2×100 mL of EtOAc and the organic layers combined and concentrated under vacuum. The resulting solids were washed with 2×10 mL of EtOH to afford the title compound (2.5 g, 21% yield) as a white solid. LCMS: [M+H]⁺ 241.01.

Step 2: 4-(1-Ethoxyvinyl)-2-(thiazol-5-yl)thieno[3,2-d]pyrimidine

A solution of 2-chloro-4-(1-ethoxyethenyl)thieno[3,2-d]pyrimidine (2.40 g, 9.97 mmol, 1.0 eq), 5-(tributylstannyl)-1,3-thiazole (5.60 g, 14.96 mmol, 1.5 eq), and Pd(PPh₃)₂Cl₂ (0.70 g, 0.99 mmol, 0.1 eq) in DMF (30 mL) was stirred for 1 h at 80° C. The reaction was quenched with water. The resulting solution was extracted with 2×30 mL of EtOAc, and the combined organic layers were dried over sodium sulfate and concentrated under vacuum. The residue was applied onto a silica gel column eluting with EtOAc/petroleum ether (1:3) to afford the title compound (900 mg, 31% yield) as a white solid. LCMS: [M+H]⁺ 290.03.

Step 3: Ethyl 2-(thiazol-5-yl)thieno[3,2-d]pyrimidine-4-carboxylate

A solution of 4-(1-ethoxyvinyl)-2-(thiazol-5-yl)thieno[3,2-d]pyrimidine (1.10 g, 3.80 mmol, 1.0 eq), KMnO₄ (0.24 g, 1.52 mmol, 0.4 eq), NaIO₄ (4.07 g, 19.01 mmol, 5 eq) in H₂O (12 mL) and dioxane (12 mL) was stirred 1 h at RT. The reaction was quenched with water. The resulting solution was extracted with 3×20 mL of EtOAc, and the organic layers were combined, dried over sodium sulfate and concentrated under vacuum. The resulting solids were washed with 2×10 mL of EtOH to afford the title compound (400 mg, 36.1% yield) as a white solid. LCMS: [M+H]⁺ 292.01.

Step 4: N-(2-Fluoro-6-(trifluoromethyl)benzyl)-2-(thiazol-5-yl)thieno[3,2-d]pyrimidine-4-carboxamide Under nitrogen, a solution of ethyl 2-(thiazol-5-yl)thieno[3,2-d]pyrimidine-4-carboxylate (150 mg, 0.52 mmol, 1.0 eq), 1-[2-fluoro-6-(trifluoromethyl)phenyl]methanamine (149 mg, 0.77 mmol, 1.5 eq), AlMe₃ (74 mg, 1.03 mmol, 2 eq) in toluene (2 mL) was stirred 1 h at 80° C. The resulting solution was extracted with 2×20 mL of EtOAc, and the organic layers were combined, dried over sodium sulfate and concentrated under vacuum. The crude product was purified by Prep-HPLC eluting with ACN/H₂O to afford the title compound (74 mg, 33% yield) as a white solid. LCMS: [M+H]⁺ 439.10. ¹H NMR (300 MHz, DMSO-d₆) δ 9.41 (t, J=5.5 Hz, 1H), 9.25 (d, J=0.8 Hz, 1H), 9.03 (d, J=0.8 Hz, 1H), 8.66 (d, J=5.6 Hz, 1H), 7.70-7.55 (m, 4H), 4.85 (d, J=5.4 Hz, 2H).

Example 21: N-((1r,4r)-4-(2-Methoxyethoxy)cyclohexyl)-5-(thiazol-5-yl)-1H-pyrazolo[3,4-c]pyridine-7-carboxamide

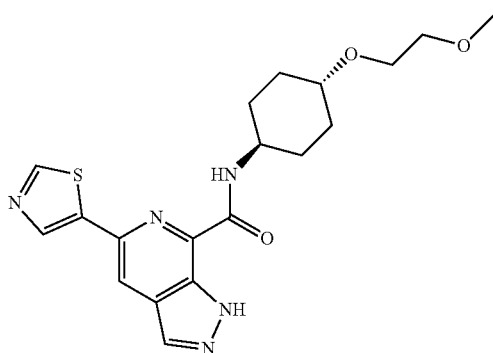 [SMILES: COCCO[C@H]1CC[C@H](NC(=O)c2nc(-c3cncs3)cc3cn[nH]c23)CC1]

Step 1: 5-(4-Methyl-5-nitropyridin-2-yl)thiazole

A solution of 2-chloro-4-methyl-5-nitropyridine (1.50 g, 8.69 mmol, 1.00 eq), 5-(4,4,5,5-tetramethyl-1,3,2-dioxaborolan-2-yl)thiazole (2.20 g, 10.43 mmol, 1.20 eq), Pd(dppf)Cl$_2$ (636 mg, 0.87 mmol, 0.1 eq), KF (2.52 g, 43.46 mmol, 5.00 eq) and CuI (331 mg, 1.74 mmol, 0.20 eq) in DMF (15 mL) was stirred for 1 h at 80° C. The resulting solution was quenched with water and extracted with 3×150 mL of EtOAc. The organic layers were combined, washed with 250 mL brine, dried over anhydrous sodium sulfate and concentrated under vacuum. The crude product was applied onto a silica gel column eluting with EtOAc/petroleum ether to afford the title compound (1.46 g, 60%) as a brown solid. LCMS (ESI, m/z): 222.23 [M+H]$^+$.

Step 2: 4-Methyl-6-(thiazol-5-yl)pyridin-3-amine

Under hydrogen, a solution of 5-(4-methyl-5-nitropyridin-2-yl)thiazole (1.08 g, 4.88 mmol, 1.00 eq) and Pd/C (104 mg, 0.98 mmol, 0.20 eq) in MeOH (30 mL) was stirred for 10 h at RT. The solids were filtered out and the filtrate was concentrated under vacuum. The crude product was purified by C18 reverse phase chromatography eluting with CH$_3$CN/H$_2$O to afford the title compound (697 mg, 75%) as a yellow solid. LCMS (ESI, m/z): 192.25[M+H]$^+$.

Step 3: 2-Bromo-4-methyl-6-(thiazol-5-yl)pyridin-3-amine

A solution of 4-methyl-6-(thiazol-5-yl)pyridin-3-amine (800 mg, 4.18 mmol, 1.00 eq) and NBS (893 mg, 5.020 mmol, 1.2 eq) in TFA (9 mL) was stirred for 2 h at 0° C. The resulting solution was diluted with 30 mL of DCM and concentrated under vacuum, and the crude product was purified by C18 reverse phase chromatography eluting with CH$_3$CN/H$_2$O to afford the title compound (655 mg, 58%) as a brown solid. LCMS (ESI, m/z): 270.15 [M+H]$^+$.

Step 4: 5-(7-Bromo-1H-pyrazolo[3,4-c]pyridin-5-yl)thiazole

A solution of 2-bromo-4-methyl-6-(thiazol-5-yl)pyridin-3-amine (481 mg, 1.88 mmol, 1.00 eq) and acetic anhydride (959 mg, 9.39 mmol, 5.00 eq) in CHCl$_3$ (10 mL) was stirred for 2 h at 0° C. KOAc (55 mg, 0.56 mmol, 0.30 eq) and isopentyl nitrite (550 mg, 4.70 mmol, 2.50 eq) were added. The resulting solution was stirred for 20 min at 0° C. and another 1.5 h at 60° C. The resulting mixture was concentrated under vacuum and the crude product was applied onto a silica gel column eluting with EtOAc/petroleum ether to afford the title compound (433 mg, 82%) as a yellow solid. LCMS (ESI, m/z): 281.13 [M+H]$^+$.

Step 5: tert-Butyl 7-bromo-5-(thiazol-5-yl)-1H-pyrazolo[3,4-c]pyridine-1-carboxylate A solution of 5-(7-bromo-1H-pyrazolo[3,4-c]pyridin-5-yl)thiazole (353 mg, 1.26 mmol, 1.00 eq), DMAP (31 mg, 0.25 mmol, 0.20 eq) and di-tert-butyldicarbonate (411 mg, 1.88 mmol, 1.50 eq) in DMF (4 mL) was stirred for 12 h at RT. The resulting solution was quenched with water and extracted with 3×40 mL EtOAc. The organic layers were combined, dried over anhydrous sodium sulfate and concentrated under vacuum to afford the title compound (338 mg, 71%) as a yellow solid. LCMS (ESI, m/z): 381.25 [M+H]$^+$.

Step 6: tert-Butyl 7-(1-ethoxyvinyl)-5-(thiazol-5-yl)-1H-pyrazolo[3,4-c]pyridine-1-carboxylate Under nitrogen, to a solution of tert-butyl 7-bromo-5-(thiazol-5-yl)-1H-pyrazolo[3,4-c]pyridine-1-carboxylate (300.00 mg, 0.79 mmol, 1.00 eq) and Pd(PPh$_3$)$_2$Cl$_2$ (55 mg, 0.079 mmol, 0.10 eq) in DMF (3.5 mL) was added tributyl (1-ethoxyethenyl)stannane (426 mg, 1.18 mmol, 1.50 eq). The resulting solution was stirred for 1 h at 80° C. The resulting solution was quenched with 40 mL of saturated aqueous KF and extracted with 3×40 mL EtOAc. The organic layers were combined and washed with 30 mL brine, dried over anhydrous sodium sulfate and concentrated under vacuum. The crude product was applied onto a silica gel column eluting with EtOAc/petroleum ether to afford the title compound (100 mg, 85%) as a yellow solid. LCMS (ESI, m/z): 373.44 [M+H]$^+$.

Step 7: Ethyl 5-(thiazol-5-yl)-1H-pyrazolo[3,4-c]pyridine-7-carboxylate

To a solution of tert-butyl 7-(1-ethoxyvinyl)-5-(thiazol-5-yl)-1H-pyrazolo[3,4-c]pyridine-1-carboxylate (100 mg, 0.37 mmol, 1.00 eq) in 1,4-dioxane (5 mL) was added NaIO$_4$ (236 mg, 1.10 mmol, 3.00 eq) in H$_2$O (2 mL). KMnO$_4$ (17.41 mg, 0.110 mmol, 0.30 eq) in H$_2$O (2 mL) was added dropwise. The resulting solution was stirred for 40 min at RT. The resulting solution was diluted with 20 mL H$_2$O and extracted with 3×30 mL of EtOAc. The organic portions were combined, dried over anhydrous sodium sulfate and concentrated under vacuum to afford the title compound (80 mg, 79%) as a yellow solid. LCMS (ESI, m/z): 275.30 [M+H]$^+$.

Step 8: 5-(Thiazol-5-yl)-1H-pyrazolo[3,4-c]pyridine-7-carboxylic acid

To a solution of ethyl 5-(thiazol-5-yl)-1H-pyrazolo[3,4-c]pyridine-7-carboxylate (70 mg, 0.26 mmol, 1.00 eq) in MeOH/H$_2$O (4 mL/0.8 mL) was added LiOH (15 mg, 0.64 mmol, 2.50 eq). The resulting solution was stirred for 1.5 h at RT. After completion the pH value was adjusted to 4 with 1 M HCl and the resulting solution was concentrated under vacuum. The crude product was purified by C18 reverse phase chromatography eluting with CH₃CN/H₂O to afford the title compound (14 mg, 90%) as a yellow solid. LCMS (ESI, m/z): 247.24 [M+H]⁺.

Step 9: N-((1r,4r)-4-(2-Methoxyethoxy)cyclohexyl)-5-(thiazol-5-yl)-1H-pyrazolo[3,4-c]pyridine-7-carboxamide To a solution of 5-(thiazol-5-yl)-1H-pyrazolo[3,4-c]pyridine-7-carboxylic acid (14 mg, 0.057 mmol, 1.00 eq), DIPEA (22 mg, 0.17 mmol, 3.00 eq) and HATU (22 mg, 0.057 mmol, 1.00 eq) in DMF (0.5 mL) was added in Int-B1 (11 mg, 0.063 mmol, 1.10 eq). The resulting solution was stirred for 40 min at RT. The reaction was quenched with H₂O and extracted with 3×10 mL EtOAc. The organic layers were combined, dried over anhydrous sodium sulfate and concentrated under vacuum. The crude product was purified by C18 reverse phase chromatography eluting with CH₃CN/H₂O to afford the title compound (6 mg, 25%) as a white solid. LCMS (ESI, m/z): 402.10 [M+H]⁺. ¹H NMR (400 MHz, CD₃OD-d₄) δ 9.03 (d, J=0.7 Hz, 1H), 8.56 (d, J=0.7 Hz, 1H), 8.46 (s, 1H), 8.30 (s, 1H), 4.03 (ddt, J=11.1, 7.4, 3.9 Hz, 1H), 3.71-3.64 (m, 2H), 3.60-3.53 (m, 2H), 3.49-3.34 (m, 1H), 3.40 (s, 3H), 2.21-2.10 (m, 4H), 1.68-1.55 (m, 2H), 1.52-1.39 (m, 2H).

Example 22: 2-(1H-Imidazol-1-yl)-N-((1r,4r)-4-(2-methoxyethoxy)cyclohexyl)-5-methyl-5H-pyrrolo[3,2-d]pyrimidine-4-carboxamide

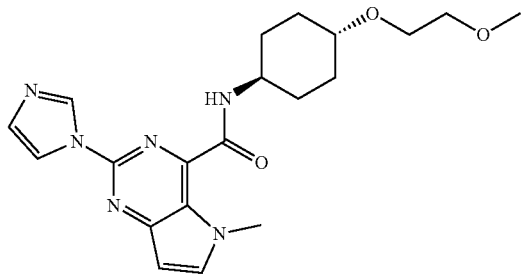 [SMILES: COCCO[C@H]1CC[C@H](NC(=O)c2nc(-n3ccnc3)nc3ccn(C)c23)CC1]

Step 1: 2-(1H-Imidazol-1-yl)-5-methyl-5H-pyrrolo[3,2-d]pyrimidine-4-carboxylic acid A solution of ethyl 2-(1H-imidazol-1-yl)-5H-pyrrolo[3,2-d]pyrimidine-4-carboxylate (257 mg, 1.0 mmol, 1.00 eq), 60% NaH (60 mg, 2.50 mmol, 2.50 eq), and MeI (213 mg, 1.50 mmol, 1.50 eq) in DMF (5 mL) was stirred for 2 h at 35° C. The resulting mixture was concentrated under vacuum. The crude product was purified by prep-HPLC to afford the title compound (100 mg, 41%) as a white solid. LCMS: [M+H]⁺ 244.08.

Step 2: 2-(1H-Imidazol-1-yl)-N-((1r,4r)-4-(2-methoxyethoxy)cyclohexyl)-5-methyl-5H-pyrrolo[3,2-d]pyrimidine-4-carboxamide A solution of 2-(1H-imidazol-1-yl)-5-methyl-5H-pyrrolo[3,2-d]pyrimidine-4-carboxylic acid (63 mg, 0.26 mmol, 1.00 eq), Int-B1 (54 mg, 0.31 mmol, 1.20 eq), HATU (148 mg, 0.39 mmol, 1.50 eq), and DIPEA (100 mg, 0.78 mmol, 3.00 eq) in DMF (1 mL) was stirred 1 h at RT. The crude product was purified by reverse phase column to afford the title compound (11 mg, 11% yield) as a white solid. LCMS: [M+H]⁺ 399.20. ¹H NMR (300 MHz, Methanol-d4) δ 8.77 (s, 1H), 8.10 (s, 1H), 7.86 (d, J=3.2 Hz, 1H), 7.14 (s, 1H), 6.69 (d, J=3.2 Hz, 1H), 4.04 (s, 3H), 4.03-3.90 (m, 1H), 3.65 (dd, J=5.9, 3.4 Hz, 2H), 3.54 (dd, J=5.8, 3.4 Hz, 2H), 3.40-3.38 (m, 1H), 3.37 (s, 3H), 2.21-2.06 (m, 4H), 1.60-1.20 (m, 4H).

Example 23: 5-(1H-Imidazol-1-yl)-N-((1r,4r)-4-(2-methoxyethoxy)cyclohexyl)-1H-pyrazolo[4,3-d]pyrimidine-7-carboxamide

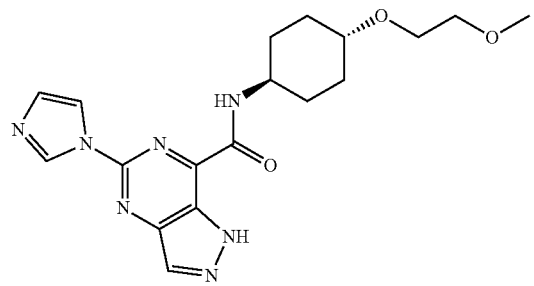 [SMILES: COCCO[C@H]1CC[C@H](NC(=O)c2nc(-n3ccnc3)nc3cn[nH]c23)CC1]

Step 1: 5-Chloro-7-(1-ethoxyvinyl)-1H-pyrazolo[4,3-d]pyrimidine

Under nitrogen, to a solution of 5,7-dichloro-1H-pyrazolo[4,3-d]pyrimidine (1.00 g, 5.29 mmol, 1.00 eq) in dioxane (4 mL) was added tributyl(1-ethoxyvinyl)stannane (2.29 g, 6.35 mmol, 1.2 eq) and Pd(PPh₃)₂Cl₂ (0.37 g, 0.53 mmol, 0.1 eq). The resulting solution was stirred for 1.5 h at 60° C. The reaction was quenched with saturated aqueous KF solution. The solids were filtered out. The filtrate was diluted with 150 mL EtOAc and washed with water. The organic layer was dried over anhydrous sodium sulfate and concentrated under vacuum. The crude product was applied onto a silica gel column eluting with EtOAc/petroleum ether (4/1) to afford the title compound (620 mg, 40% yield) as a yellow solid. LCMS: [M+H]⁺ 225.65.

Step 2: 7-(1-Ethoxyvinyl)-5-(1H-imidazol-1-yl)-1H-pyrazolo[4,3-d]pyrimidine

Under nitrogen, to a solution of 5-chloro-7-(1-ethoxyvinyl)-1H-pyrazolo[4,3-d]pyrimidine (520 mg, 1.74 mmol, 1.00 eq) in toluene (2 mL) was added 1H-imidazole (237 mg, 3.49 mmol, 2 eq), Pd₂(dba)₃ (160 mg, 0.17 mmol, 0.1 eq), K₃PO₄ (1.11 g, 5.23 mmol, 3.0 eq), and tBuXPhos (148 mg, 0.35 mmol, 0.2 eq) and the resulting mixture was stirred for 5 h at 80° C. The mixture was diluted with 150 mL EtOAc and washed with 3×50 mL H₂O. The organic layers were combined and dried over anhydrous sodium sulfate and concentrated under vacuum. The crude product was applied onto a silica gel column eluting with EtOAc/petroleum either (54/46) to afford the title compound (80 mg, 9% yield) as a yellow oil. LCMS: [M+H]⁺ 257.26.

Step 3: Ethyl 5-(1H-imidazol-1-yl)-1H-pyrazolo[4,3-d]pyrimidine-7-carboxylate

To a solution of 7-(1-ethoxyvinyl)-5-(1H-imidazol-1-yl)-1H-pyrazolo[4,3-d]pyrimidine (75 mg, 0.29 mmol, 1.00 eq) in dioxane (4 mL) and H₂O (4 mL) was added NaIO₄ (250 mg, 1.17 mmol, 4 eq), and KMnO₄ (9 mg, 0.059 mmol, 0.2 eq) and the mixture was stirred for 0.5 h at RT. The mixture was diluted with 30 mL EtOAc and washed with 2×10 mL of water. The organic layer was dried over anhydrous sodium sulfate and concentrated under vacuum. The crude product was applied onto a silica gel column eluting with EtOAc to afford the title compound (35 mg, 37% yield) as a white solid. LCMS: [M+H]⁺ 259.24.

Step 4: 5-(1H-Imidazol-1-yl)-N-((1r,4r)-4-(2-methoxyethoxy)cyclohexyl)-1H-pyrazolo[4,3-d]pyrimidine-7-carboxamide To a solution of ethyl 5-(1H-imidazol-1-yl)-1H-pyrazolo[4,3-d]pyrimidine-7-carboxylate (30 mg, 0.12 mmol, 1.00 eq) in toluene (4 mL) was added Int-B1 (20 mg, 0.12 mmol, 1 eq) and 1 M AlMe₃ in toluene solution (0.17 mL, 1.5 eq) and the mixture was stirred for 24 h at 100° C. The mixture was diluted with 30 mL of DCM and washed with 2×10 mL of water. The organic layers were combined and dried over anhydrous sodium sulfate and concentrated under vacuum. The crude product was purified by C18 reverse phase chromatography eluting with H₂O/CH₃CN (58:42) to afford the title compound (8.5 mg, 19% yield) as a white solid. LCMS: [M+H]⁺ 386.25. ¹H NMR (300 MHz, DMSO-d6) δ 9.13-9.00 (m, 2H), 8.52 (s, 1H), 8.25 (t, J=1.2 Hz, 1H), 7.17 (t, J=1.5 Hz, 1H), 4.01-3.90 (m, 1H), 3.58 (dd, J=5.2, 3.3 Hz, 2H), 3.45 (dd, J=5.9, 3.7 Hz, 2H), 3.25 (s, 3H), 3.24-3.20 (m, 1H), 2.09 (d, J=10.8 Hz, 2H), 1.92 (d, J=10.5 Hz, 2H), 1.70-1.58 (m, 2H), 1.36-1.24 (m, 2H).

Example 24: 5-(1H-Imidazol-1-yl)-N-((1r,4r)-4-(2-methoxyethoxy)cyclohexyl)thieno[3,2-b]pyridine-7-carboxamide

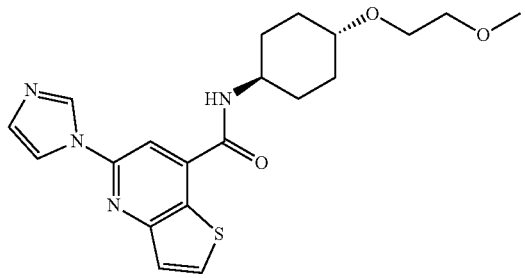 [SMILES: COCCO[C@H]1CC[C@H](NC(=O)c2cc(-n3ccnc3)nc3ccsc23)CC1]

Step 1: Methyl 3-(3-methoxy-3-oxopropanamido)thiophene-2-carboxylate

A solution of methyl 3-aminothiophene-2-carboxylate (7.85 g, 49.9 mmol, 1.00 eq), TEA (6.06 g, 59.88 mmol, 1.20 eq) and methyl 3-chloro-3-oxopropanoate (7.50 g, 54.93 mmol, 1.10 eq) in DCM (100 mL) was stirred at 25° C. for 2 h. The resulting mixture was washed with 3×30 mL of H₂O. The organic layer was concentrated under vacuum to afford the title compound (12 g, 89% yield) as yellow oil. LCMS: [M+H]⁺ 258.10.

Step 2: Methyl 5,7-dioxo-4,5,6,7-tetrahydrothieno[3,2-b]pyridine-6-carboxylate

A mixture of methyl 3-(3-ethoxy-3-oxopropanamido)thiophene-2-carboxylate (9.6 g) and t-BuOK (11.9 g) in t-BuOH (200 mL) was stirred at 70° C. for 1 h. After concentration, the resulting mixture was concentrated to afford the title compound (9.5 g, crude) as yellow solid. LCMS: [M+H]⁺ 226.10.

Step 3: 5,7-Dioxo-4,5,6,7-tetrahydrothieno[3,2-b]pyridine-6-carboxylic acid

A mixture of methyl 5,7-dioxo-4,5,6,7-tetrahydrothieno[3,2-b]pyridine-6-carboxylate (9.50 g, 42.18 mmol, 1.00 eq) and t-BuOK (11.90 g, 0.11 mmol) in H₂O (200 mL) was stirred at 60° C. overnight. After concentration, the resulting mixture was concentrated to afford the title compound (20 g, crude) as yellow solid. LCMS: [M+H]⁺ 212.10.

Step 4: Thieno[3,2-b]pyridine-5,7(4H,6H)-dione

A solution of 5,7-dioxo-4,5,6,7-tetrahydrothieno[3,2-b]pyridine-6-carboxylic acid (20.0 g, 94.70 mmol, 1.00 eq) in 6 M HCl (100 mL) was stirred at RT for 1 h. After concentration, the solids were collected by filtration to afford the title compound (4 g, 32% yield) as yellow solid. LCMS: [M+H]⁺167.95.

Step 5: 5,7-Dichlorothieno[3,2-b]pyridine

A solution of thieno[3,2-b]pyridine-5,7(4H,6H)-dione (4.00 g, 23.9 mmol, 1.00 eq) in phosphorus oxychloride (30 mL) was stirred at 100° C. overnight. After concentration, the solids were diluted with 200 mL of DCM and washed with 3×50 H₂O. The organic layers were combined and concentrated to afford the title compound (2.5 g, 51% yield) as a white solid. LCMS: [M+H]⁺ 203.95.

Step 6: 7-Chloro-5-(1H-imidazol-1-yl)thieno[3,2-b]pyridine

Under nitrogen, a mixture of 5,7-dichlorothieno[3,2-b]pyridine (1.72 g, 8.43 mmol, 1.00 eq), 1H-imidazole (0.74 g, 10.94 mmol, 1.30 eq), Pd₂(dba)₃·CHCl₃ (0.87 g, 0.84 mmol, 0.10 eq), tBuXPhos (0.35 g, 0.84 mmol, 0.10 eq) and K₃PO₄ (3.57 g, 16.82 mmol, 2.00 eq) in dioxane (15 mL) was stirred at 80° C. overnight. The insoluble solids were filtered. The filtrate was concentrated and purified by C18 reverse phase chromatography eluting with H₂O/CH₃CN to afford the title compound (150 mg, 28% yield) as a yellow solid. LCMS: [M+H]⁺ 236.05.

Step 7: 5-(1H-Imidazol-1-yl)-N-((1r,4r)-4-(2-methoxyethoxy)cyclohexyl)thieno[3,2-b]pyridine-7-carboxamide Under CO, a mixture of 7-chloro-5-(1H-imidazol-1-yl)thieno[3,2-b]pyridine (100 mg, 0.42 mmol, 1.00 eq), Int-B1 (246 mg, 1.42 mmol, 3.35 eq), Pd(dppf)Cl₂ (53 mg, 0.07 mmol, 0.17 eq), dppf (53 mg, 0.09 mmol, 0.23 eq) and TEA (0.50 mL) in NMP (3 mL) was stirred at 120° C. for 2.5 h. The resulting solution was concentrated. The crude product was purified by C18 reverse phase chromatography eluting with H₂O/CH₃CN to give the compound (36 mg, 21%) as a light green solid. LCMS: [M+H]⁺ 401.10; ¹H NMR (400 MHz, DMSO-d₆) δ 8.78 (d, J=7.6 Hz, 1H), 8.59 (d, J=1.2 Hz, 1H), 8.32 (d, J=5.6 Hz, 1H), 8.24 (s, 1H), 8.03 (t, J=1.4 Hz, 1H), 7.60 (d, J=5.6 Hz, 1H), 7.20 (t, J=1.2 Hz, 1H), 3.91-3.83 (m, 1H), 3.56 (dd, J=5.9, 3.9 Hz, 2H), 3.44 (dd, J=5.8, 3.9 Hz, 2H), 3.29 (d, J=4.2 Hz, 1H), 3.26 (s, 3H), 2.06 (d, J=12.3 Hz, 2H), 1.97 (d, J=12.5 Hz, 2H), 1.49-1.40 (m, 2H), 1.34-1.24 (m, 2H).

Example 25: 5-(1H-Imidazol-1-yl)-N-((1r,4r)-4-(2-methoxyethoxy)cyclohexyl)thiazolo[4,5-d]pyrimidine-7-carboxamide

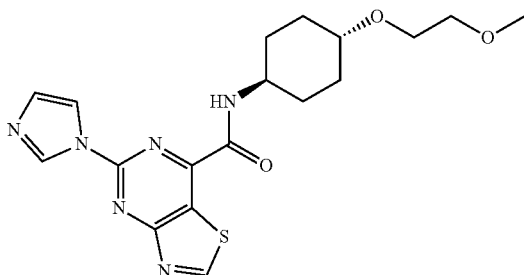

Step 1: 7-Chloro-5-(1H-imidazol-1-yl)thiazolo[4,5-d]pyrimidine

Under nitrogen, a solution of 5,7-dichlorothiazolo[4,5-d]pyrimidine (1.80 g, 8.74 mmol, 1.00 eq), 1H-imidazole (0.59 g, 8.67 mmol, 0.99 eq), $Pd_2(dba)_3$ (0.80 g, 0.87 mmol, 0.1 eq), tBuXPhos (0.93 g, 2.18 mmol, 0.25 eq), and $K_3PO_4$ (3.71 g, 17.47 mmol, 2 eq) in toluene (30 mL) was stirred 3 h at 60° C. The resulting mixture was concentrated and extracted with 3×150 mL of EtOAc. The organic layers were combined and concentrated. The crude product was applied onto a silica gel column eluting with EtOAc/petroleum ether (40:60) to afford the title compound (1.1 g, 53% yield) as a yellow solid. LCMS: [M+H]+ 237.99.

Step 2: 7-(1-Ethoxyvinyl)-5-(1H-imidazol-1-yl)thiazolo[4,5-d]pyrimidine

Under nitrogen, a solution of 7-chloro-5-(1H-imidazol-1-yl)thiazolo[4,5-d]pyrimidine (1.10 g, 4.63 mmol, 1.00 eq), tributyl(1-ethoxyethenyl)stannane (3.34 g, 9.26 mmol, 2 eq), $Pd(PPh_3)_2Cl_2$ (0.32 g, 0.46 mmol, 0.1 eq), and DMF (15 mL) was stirred 3 h at 60° C. The reaction was quenched with saturated aqueous KF. The insoluble solids were filtered out. The resulting solution was extracted with 3×50 mL of DCM. The organic layer was dried over sodium sulfate and concentrated. The crude product was purified by reverse phase column to afford the title compound (600 mg, 47% yield) as a yellow solid. LCMS: [M+H]+ 274.07.

Step 3: Ethyl 5-(1H-imidazol-1-yl)thiazolo[4,5-d]pyrimidine-7-carboxylate

A solution of 7-(1-ethoxyvinyl)-5-(1H-imidazol-1-yl)thiazolo[4,5-d]pyrimidine (600 mg, 2.20 mmol, 1.00 eq), $KMnO_4$ (139 mg, 0.88 mmol, 0.40 eq), $NaIO_4$ (1.88 g, 8.78 mmol, 4 eq) in $H_2O$ (10 mL) and dioxane (10 mL) was stirred 30 min at RT. The resulting solution was extracted with 3×10 mL DCM. The organic layers were combined, dried over sodium sulfate and concentrated. The crude product was purified by reverse phase column to afford the title compound (220 mg, 36% yield) as a white solid. LCMS: [M+H]+ 276.05.

Step 4: 5-(1H-Imidazol-1-yl)-N-((1r,4r)-4-(2-methoxyethoxy)cyclohexyl)thiazolo[4,5-d]pyrimidine-7-carboxamide Under nitrogen, a solution of ethyl 5-(1H-imidazol-1-yl) thiazolo[4,5-d] pyrimidine-7-carboxylate (200 mg, 0.78 mmol, 1.00 eq), Int-B1 (404 mg, 2.33 mmol, 3 eq), and 1 M $AlMe_3$ in toluene solution (3.1 mL, 4.0 eq) in toluene (10.0 mL) was stirred for 2 h at 75° C. The reaction was quenched with water and extracted with 3×150 mL of dichloromethane. The organic layers were combined, dried over sodium sulfate, and concentrated. The crude product was purified by reverse phase column to afford the title compound (14 mg, 5% yield) as a white solid. LCMS: [M+H]+ 403.15. $^1$H NMR (300 MHz, DMSO-d6) δ 9.85 (s, 1H), 9.34 (s, 1H), 8.85 (d, J=8.5 Hz, 1H), 8.68 (s, 1H), 7.30 (s, 1H), 4.00-3.77 (m, 1H), 3.56 (dd, J=5.9, 3.8 Hz, 2H), 3.44 (dd, J=5.9, 3.7 Hz, 2H), 3.28-3.22 (m, 4H), 2.05 (d, J=11.7 Hz, 2H), 1.87 (d, J=12.3 Hz, 2H), 1.65-1.52 (m, 2H), 1.34-1.22 (m, 2H).

Example 26: 6-(1H-Imidazol-1-yl)-N-((1r,4r)-4-(2-methoxyethoxy)cyclohexyl)-3H-imidazo[4,5-c]pyridine-4-carboxamide

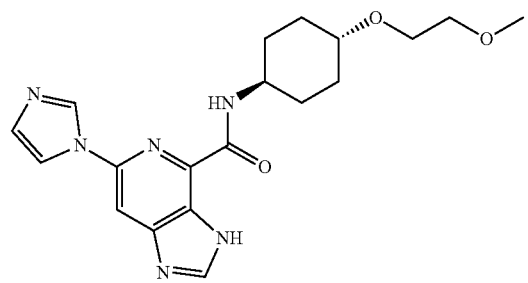 [SMILES: COCCO[C@H]1CC[C@H](NC(=O)c2nc(-n3ccnc3)cc3nc[nH]c23)CC1]

Step 1: 2,6-Dichloropyridine-3,4-diamine

Under nitrogen, a solution of 2,6-dichloro-3-nitropyridin-4-amine (7.50 g, 0.036 mmol, 1.00 eq), Fe (10.07 g, 0.180 mmol, 5 eq) in acetic acid (120 mL) was stirred for 1 h at 80° C. The resulting mixture was concentrated under vacuum. The residue was applied onto a silica gel column eluting with EtOAc/petroleum ether (3:1) to afford the title compound (5.5 g, 86% yield) as a yellow solid. LCMS: [M+H]+ 177.99.

Step 2: 4,6-Dichloro-3H-imidazo[4,5-c]pyridine

A solution of 2,6-dichloropyridine-3,4-diamine (5.50 g, 30.90 mmol, 1.00 eq), trimethyl orthoformate (19.67 g, 185.37 mmol, 6 eq) in acetic acid (100 mL) was stirred 1 h at 80° C. The resulting mixture was concentrated under vacuum. The residue was applied onto a silica gel column eluting with EtOAc/petroleum ether (1:4) to afford the title compound (5.5 g, 95% yield) as a yellow solid. LCMS: [M+H]+ 187.97.

Step 3: 6-Chloro-4-(1-ethoxyvinyl)-3H-imidazo[4,5-c]pyridine

Under nitrogen, a solution of 4,6-dichloro-3H-imidazo[4,5-c]pyridine (5.50 g, 29.25 mmol, 1.00 eq), tributyl(1-ethoxyethenyl)stannane (15.85 g, 43.88 mmol, 1.50 eq), and Pd(PPh$_3$)$_2$Cl$_2$ (2.05 g, 2.92 mmol, 0.1 eq) in DMF (93 mL) was stirred 1 h at 100° C. The reaction was quenched with water, the resulting solution was extracted with 2×100 mL of EtOAc and the organic layers were combined, dried over sodium sulfate and concentrated. The crude product (5 mL) was purified by Prep-HPLC eluting with a gradient of H$_2$O/ACN 5/95 increasing to H$_2$O/ACN 50/50 to afford the title compound after concentration (3 g, 45.85% yield) as white solid. LCMS: [M+H]$^+$ 224.05.

Step 4: 4-(1-Ethoxyvinyl)-6-(1H-imidazol-1-yl)-3H-imidazo[4,5-c]pyridine

Under nitrogen, a solution of 6-chloro-4-(1-ethoxyvinyl)-3H-imidazo[4,5-c]pyridine (2.50 g, 11.18 mmol, 1.00 eq), 1H-imidazole (15.22 g, 223.55 mmol, 20 eq), CuI (4.26 g, 22.36 mmol, 2 eq), and K$_2$CO$_3$ (3.09 g, 22.36 mmol, 2 eq) in NMP (35 mL) was stirred 1 h at 150° C. The reaction was quenched with water. The resulting solution was extracted with 3×100 mL of dichloromethane and the organic layers were combined, dried over sodium sulfate and concentrated. The crude product was purified by Prep-HPLC eluting with H$_2$O/ACN to afford the title compound after concentration (120 mg, 4% yield) as a white solid. LCMS: [M+H]$^+$ 256.11.

Step 5: Ethyl 6-(1H-imidazol-1-yl)-3H-imidazo[4,5-c]pyridine-4-carboxylate

A solution of 4-(1-ethoxyvinyl)-6-(1H-imidazol-1-yl)-3H-imidazo[4,5-c]pyridine (130 mg, 0.51 mmol, 1.00 eq), KMnO$_4$ (32 mg, 0.20 mmol, 0.4 eq), and NaIO$_4$ (436 mg, 2.04 mmol, 4 eq) in H$_2$O (3 mL) and dioxane (3 mL) was stirred for 1 h at RT. The reaction was quenched with water, and the resulting solution was extracted with 3×20 mL of EtOAc. The organic layers were combined, dried over sodium sulfate, and concentrated under vacuum to afford the title compound (60 mg, 46% yield) as a yellow solid. LCMS: [M+H]$^+$ 258.09.

Step 6: 6-(1H-Imidazol-1-yl)-N-((1r,4r)-4-(2-methoxyethoxy)cyclohexyl)-3H-imidazo[4,5-c]pyridine-4-carboxamide Under nitrogen, a solution of ethyl 6-(1H-imidazol-1-yl)-3H-imidazo[4,5-c]pyridine-4-carboxylate (50 mg, 0.19 mmol, 1.00 eq), Int-B1 (101 mg, 0.58 mmol, 3 eq), and 1M AlMe$_3$ in toluene solution (0.78 mL, 4 eq) in toluene (1 mL) was stirred 1 h at 80° C. The crude product (5 mL) was purified by Prep-HPLC to afford the title compound (14 mg, 19% yield) as a white solid. LCMS: [M+H]$^+$ 385.20. $^1$H NMR (400 MHz, DMSO-d6) δ 13.05 (s, 1H), 8.93 (s, 1H), 8.72 (s, 1H), 8.53 (s, 1H), 8.32-8.27 (m, 2H), 7.13 (t, J=1.2 Hz, 1H), 3.90 (m, 1H), 3.57 (dd, J=5.9, 3.8 Hz, 2H), 3.44 (dd, J=5.9, 3.8 Hz, 2H), 3.34-3.23 (m, 4H), 2.07 (d, J=12.0 Hz, 2H), 1.89 (d, J=12.2 Hz, 2H), 1.63 (q, J=12.7, 12.2 Hz, 2H), 1.31 (m, 2H).

Example 27: 2-(1H-Imidazol-1-yl)-N-(tetrahydro-2H-pyran-3-yl)-5H-pyrrolo[3,2-d]pyrimidine-4-carboxamide

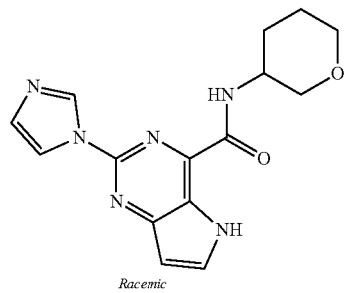 [SMILES: O=C(NC1CCCOC1)c1nc(-n2ccnc2)nc2cc[nH]c12]

Racemic

To a solution of Int-A2 (150 mg, 0.65 mmol, 1.00 eq) in DMF (2 mL) was added DIPEA (508 mg, 3.93 mmol, 6 eq), HATU (348 mg, 0.92 mmol, 1.4 eq), and tetrahydro-2H-pyran-3-amine hydrochloride (126 mg, 0.92 mmol, 1.4 eq) and the mixture was stirred for 0.5 h at RT. The mixture was purified by C18 reverse phase chromatography eluting with H$_2$O/CH$_3$CN (55:45) to afford the title compound (83 mg, 41% yield) as a white solid. LCMS: [M+H]$^+$ 313.10. $^1$H NMR (300 MHz, DMSO-d$_6$) δ 12.15 (s, 1H), 9.03 (s, 1H), 8.89 (d, J=8.4 Hz, 1H), 8.25 (t, J=1.2 Hz, 1H), 8.04 (t, J=3.0 Hz, 1H), 7.18 (s, 1H), 6.72-6.74 (m, 1H), 4.18-4.08 (m, 1H), 3.93-3.78 (m, 2H), 3.49-3.26 (m, 2H), 1.97-1.60 (m, 4H).

Examples 28a and 28b: (S)-2-(1H-Imidazol-1-yl)-N-(tetrahydro-2H-pyran-3-yl)-5H-pyrrolo[3,2-d]pyrimidine-4-carboxamide and (R)-2-(1H-imidazol-1-yl)-N-(tetrahydro-2H-pyran-3-yl)-5H-pyrrolo[3,2-d]pyrimidine-4-carboxamide

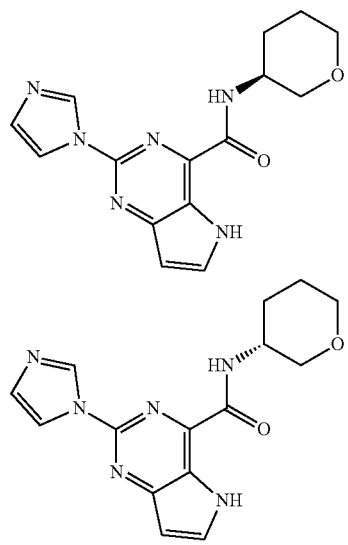

The compound of Example 27 (58 mg) was further purified by Chiral-HPLC with the following conditions (Column: CHIRALPAK IA, 2*25 cm, 5 um; Mobile Phase A: hexane:DCM=3:1 (10 M NH$_3$-MeOH), Mobile Phase B:EtOH; Flow rate: 16 mL/min; Gradient: maintaining 20% B for 13 min; 220/254 nm) to afford the title compounds with retention times of 2.39 minutes (Example 28a) and 2.87 minutes (Example 28b). The absolute stereochemistry of Examples 28a and 28b was not confirmed.

Example 28a

Isolated as a white solid (19.8 mg, 34% yield). LCMS: [M+H]$^+$ 313.20. $^1$H NMR (300 MHz, Methanol-d$_4$) δ 8.94 (t, J=1.2 Hz, 1H), 8.23 (t, J=1.2 Hz, 1H), 8.00 (d, J=3.3 Hz, 1H), 7.16 (t, J=1.2 Hz, 1H), 6.73 (d, J=3.0 Hz, 1H), 4.25-4.19 (m, 1H), 3.99 (dd, J=10.7, 4.0 Hz, 1H), 3.94-3.81 (m, 1H), 3.66-3.48 (m, 2H), 2.12-2.05 (m, 1H), 2.00-1.71 (m, 3H).

Example 28b

Isolated as a white solid (18.4 mg, 32% yield). LCMS: [M+H]$^+$ 313.20. $^1$H NMR (300 MHz, Methanol-d$_4$) δ 8.94 (t, J=1.1 Hz, 1H), 8.23 (t, J=1.4 Hz, 1H), 8.00 (d, J=3.1 Hz, 1H), 7.16 (t, J=1.3 Hz, 1H), 6.73 (d, J=3.2 Hz, 1H), 4.25-4.18 (m, 1H), 3.99 (dd, J=10.8, 3.7 Hz, 1H), 3.94-3.81 (m, 1H), 3.66-3.48 (m, 2H), 2.13-2.02 (m, 1H), 2.01-1.71 (m, 3H).

Example 29: 4-Fluoro-5-(1H-imidazol-1-yl)-N-((1r,4r)-4-(2-methoxyethoxy)cyclohexyl)-1H-indole-7-carboxamide

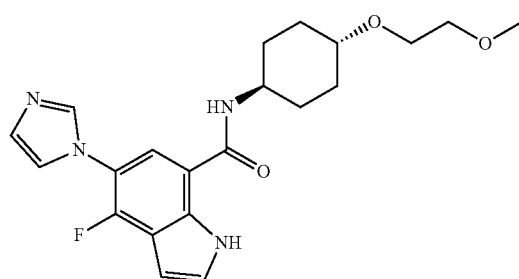

Step 1: 1-(5-Bromo-2-fluoro-4-nitrophenyl)-1H-imidazole

A mixture of 1-bromo-4,5-difluoro-2-nitrobenzene (3.30 g, 13.87 mmol, 1.00 eq), K$_2$CO$_3$ (2.87 g, 20.77 mmol, 1.50 eq) and 1H-imidazole (1.41 g, 20.71 mmol, 1.49 eq) in DMF (30 mL) was stirred overnight at 25° C. The reaction was quenched with water. The solids were collected by filtration to afford the title compound (3.6 g, 91%) as a yellow solid. LCMS: [M+H]$^+$ 285.95.

Step 2: 7-Bromo-4-fluoro-5-(imidazol-1-yl)-1H-indole

Under nitrogen, to a solution of 1-(5-bromo-2-fluoro-4-nitrophenyl)-1H-imidazole (3.3 g, 0.012 mol, 1.00 eq) in THF (100 mL) was added bromo(ethenyl)magnesium in THF (46.2 mL, 0.030 mol, 4 eq) dropwise at −45° C. The resulting solution was stirred for 2 h at −45° C. The reaction was quenched with NH$_4$Cl/H$_2$O and extracted with 3×100 mL of EtOAc. The organic layers were combined, dried over sodium sulfate and concentrated. The crude product was applied onto a silica gel column eluting with EtOAc/petro- leum ether (1/1) to give the title compound (550 mg, 17% yield) as a white solid. LCMS: [M+H]$^+$ 279.98.

Step 3: 4-Fluoro-5-(1H-imidazol-1-yl)-N-((1r,4r)-4-(2-methoxyethoxy)cyclohexyl)-1H-indole-7-carboxamide Under CO, a mixture of 7-bromo-4-fluoro-5-(imidazol-1-yl)-1H-indole (286 mg, 1.02 mmol, 1.00 eq), Int-B1 (346 mg, 2.0 mmol, 1.96 eq), Pd(dppf)Cl$_2$ (73 mg, 0.10 mmol, 0.10 eq) and TEA (1 mL) in DMSO (5 mL) was stirred at 80° C. overnight. The reaction was quenched with water and extracted with 3×50 mL of EtOAc. The organic layers were combined, dried over sodium sulfate, and concentrated. The crude product was purified by C18 reverse phase chromatography eluting with H$_2$O/CH$_3$CN to afford the title compound (71 mg, 17%) as a dark yellow solid. LCMS: [M+H]$^+$ 401.10. $^1$H NMR (400 MHz, DMSO-d$_6$) δ 11.62 (s, 1H), 8.37 (d, J=7.6 Hz, 1H), 8.00 (d, J=1.3 Hz, 1H), 7.90 (d, J=6.9 Hz, 1H), 7.55 (q, J=1.3 Hz, 1H), 7.48 (t, J=2.8 Hz, 1H), 7.14 (d, J=1.2 Hz, 1H), 6.66 (dd, J=3.2, 2.0 Hz, 1H), 3.88-3.78 (m, 1H), 3.54 (dd, J=5.9, 3.8 Hz, 2H), 3.42 (dd, J=5.8, 3.9 Hz, 2H), 3.27 (s, 3H), 3.26-3.21 (m, 1H), 2.04-1.95 (m, 2H), 1.91-1.82 (m, 2H), 1.42-1.31 (m, 2H), 1.30-1.25 (m, 2H).

Example 30: 5-(1H-imidazol-1-yl)-N-((1r,4r)-4-(2-methoxyethoxy)cyclohexyl)-2-methyl-1H-benzo[d]imidazole-7-carboxamide

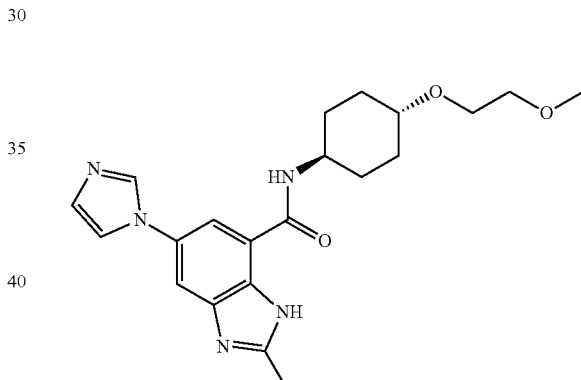

Step 1: Methyl 5-(1H-imidazol-1-yl)-2-nitrobenzoate

A mixture of methyl 5-fluoro-2-nitrobenzoate (5 g, 25.1 mmol, 1 eq), 1H-imidazole (1.88 g, 27.62 mmol, 1.10 eq), K$_2$CO$_3$ (5.21 g, 37.66 mmol, 1.5 eq) in DMF (80 mL) was stirred for 2 h at 120° C. The reaction was quenched water/ice and extracted with 3×100 mL of EtOAc. The organic layers were combined, dried over sodium sulfate, and concentrated. The crude product was applied onto a silica gel column eluting with EtOAc/petroleum ether (9/1) to afford the title compound (4.4 g, 71%) as a yellow solid. LCMS: [M+H]$^+$ 248.10.

Step 2: Methyl 2-amino-5-(1H-imidazol-1-yl)benzoate

Under hydrogen, a mixture of methyl 5-(1H-imidazol-1-yl)-2-nitrobenzoate (29.6 g, 119.74 mmol, 1 eq), Pd/C (2 g, 18.79 mmol, 0.16 eq) in MeOH (800 mL) was stirred for 24 h at RT. The insoluble solids were filtered out and rinsed with MeOH. The filtrate was concentrated to afford the title compound (22.77 g, 82%) as a yellow solid. LCMS: [M+H]+ 218.10.

Step 3: Methyl 2-amino-5-(1H-imidazol-1-yl)-3-nitrobenzoate

A mixture of methyl 2-amino-5-(1H-imidazol-1-yl)benzoate (1.00 g, 4.60 mmol, 1.00 eq), KNO$_3$ (931 mg, 9.21 mmol, 2.00 eq) in TFA (10 mL) was stirred for 2 h at 50° C. The resulting mixture was concentrated and dissolved in saturated NaHCO$_3$ (30 mL). The resulting solution was extracted with 3×30 mL of EtOAc. The organic layers were combined, dried over anhydrous sodium sulfate and concentrated to afford the title compound (960 mg) as a solid. LCMS: [M+H]+ 263.10.

Step 4: Methyl 2,3-diamino-5-(1H-imidazol-1-yl)benzoate

A mixture of methyl 2-amino-5-(1H-imidazol-1-yl)-3-nitrobenzoate (960 mg, 3.66 mmol, 1.00 eq), Pd/C (3.00 g) in MeOH (50 mL) was stirred for 0.5 h at RT. The insoluble solids were filtered and washed with MeOH. The filtrate was concentrated to afford the title compound (450 mg) as a solid. LCMS: [M+H]+ 233.10.

Step 5: Methyl 5-(1H-imidazol-1-yl)-2-methyl-1H-benzo[d]imidazole-7-carboxylate A solution of methyl 2,3-diamino-5-(1H-imidazol-1-yl) benzoate (200 mg, 0.86 mmol, 1.00 eq), 40% acetaldehyde (269 mg, 2.58 mmol, 3.00 eq), NaHSO$_3$ (134 mg, 1.29 mmol, 1.50 eq) in EtOH (2 mL) and H$_2$O (2 mL) was stirred for 2 h at 80° C. The reaction was quenched with aqueous NaOH. The resulting solution was extracted with 3×10 EtOAc. The organic layers were combined and concentrated. The crude product was applied onto a silica gel column eluting with EtOAc/petroleum ether (1/9) to afford the title compound (80 mg, 36%) as a solid. LCMS: [M+H]+ 257.10.

Step 6: 5-(1H-Imidazol-1-yl)-2-methyl-1H-benzo[d]imidazole-7-carboxylic acid A solution of methyl 5-(1H-imidazol-1-yl)-2-methyl-1H-benzo[d]imidazole-7-carboxylate (80 mg, 0.31 mmol, 1.00 eq), KOH (18 mg, 0.31 mmol, 1.00 eq) in MeOH (1.0 mL) and H$_2$O (0.20 mL) was stirred for 2 h at RT. The pH value was adjusted to 3 with 1 M HCl. The mixture was concentrated to afford the title compound (50 mg) as a crude solid, which was carried forward without additional purification. LCMS: [M+H]+ 243.10.

Step 7: 5-(1H-imidazol-1-yl)-N-((1r,4r)-4-(2-methoxyethoxy)cyclohexyl)-2-methyl-1H-benzo[d]imidazole-7-carboxamide A solution of 5-(1H-imidazol-1-yl)-2-methyl-1H-benzo[d]imidazole-7-carboxylic acid (50 mg, 0.21 mmol, 1.00 eq), Int-B2 (43 mg, 0.25 mmol, 1.20 eq), DIPEA (40 mg, 0.31 mmol, 1.50 eq), HATU (94 mg, 0.25 mmol, 1.20 eq) in DMF (2 mL) was stirred for 2 h at RT. The crude product was purified by reverse phase column eluting with ACN/H$_2$O to afford the title compound (18 mg, 22% yield) as a white solid. LCMS: [M+H]+ 398.20. $^1$H NMR (300 MHz, DMSO-d$_6$) δ 12.68 (d, J=168.4 Hz, 1H), 9.87 (d, J=7.5 Hz, 1H), 8.22 (s, 1H), 7.99-7.67 (m, 3H), 7.12 (s, 1H), 3.90-3.34 (m, 1H), 3.55 (dd, J=6.0, 3.7 Hz, 2H), 3.44 (t, J=4.8 Hz, 2H), 3.39-3.34 (m, 1H), 3.26 (s, 3H), 2.57 (d, J=20.2 Hz, 3H), 2.00 (d, J=9.8 Hz, 4H), 1.53-1.21 (m, 4H).

Example 31: N-(2-Fluoro-6-(trifluoromethyl)benzyl)-5-(thiazol-5-yl)-1H-indole-7-carboxamide

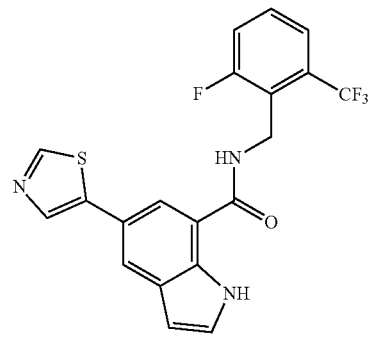 [SMILES: O=C(NCc1c(F)cccc1C(F)(F)F)c1cc(-c2cncs2)cc2cc[nH]c12]

Step 1: Methyl indoline-7-carboxylate

A mixture of methyl 1H-indole-7-carboxylate (95 g, 542 mmol, 1 eq), NaBH$_3$CN (170.4 g, 2.70 mol, 5 eq) in AcOH (1000 mL) was stirred for 2 h at RT. The reaction was quenched with water and extracted with 3×1000 mL EtOAc. The organic layers were combined and washed with 3×300 mL of H$_2$O. The organic layers were dried over sodium sulfate and concentrated. The crude product was applied onto a silica gel column eluting with EtOAc/petroleum ether (1:20) to afford the title compound (69 g, 72%) as a white solid. LCMS [M+H]+ 178.1.

Step 2: Methyl 5-iodoindoline-7-carboxylate

A solution of methyl indoline-7-carboxylate (67 g, 378.5 mmol, 1 eq) and NIS (89.3 g, 397 mmol, 1.05 eq) in AcOH (1200 mL) was stirred for 10 min at RT. The reaction was quenched with water. The precipitated solids were collected by filtration. The solids were washed with 500 mL water. This resulted in the title compound (100 g, 87.26%) as a white solid. LCMS [M+H]+ 304.05.

Step 3: Methyl 5-iodo-1H-indole-7-carboxylate

A mixture of methyl 5-iodoindoline-7-carboxylate (95 g, 313.43 mmol, 1 eq) and MnO$_2$ (408.7 g, 4.7 mol, 15 eq) in THF (800 mL) was stirred for 16 h at 75° C. The insoluble solids were filtered out. The filtrate was concentrated to afford the title compound (91 g, 96%) as a light yellow solid. LCMS [M+H]+ 302.10.

Step 4: Methyl 5-(thiazol-5-yl)-1H-indole-7-carboxylate

Under nitrogen, a mixture of methyl 5-iodo-1H-indole-7-carboxylate (500 mg, 1.661 mmol, 1 eq), 5-(4,4,5,5-tetramethyl-1,3,2-dioxaborolan-2-yl)-1,3-thiazole (351 mg, 1.66 mmol, 1.00 eq), K$_2$CO$_3$ (459 mg, 3.32 mmol, 2.0 eq), CuI (32 mg, 0.17 mmol, 0.1 eq), and Pd(dppf)Cl$_2$ (122 mg, 0.17 mmol, 0.10 eq) in EtOH (12 mL) and H$_2$O (3 mL) was stirred for 1 h at 60° C. in. The resulting solution was concentrated and applied onto a silica gel column eluting with EtOAc/petroleum ether (40/60) to afford the title compound (500 mg) as a white solid, which was carried forward without additional purification LCMS: [M+H]$^+$ 259.05.

Step 5: 5-(Thiazol-5-yl)-1H-indole-7-carboxylic acid

To a solution of methyl 5-(thiazol-5-yl)-1H-indole-7-carboxylate (500 mg, 1.94 mmol, 1 eq) in MeOH (20 mL) was added 2 mL of 5 M aqueous NaOH. The mixture was stirred for 6 h at RT. The pH value was adjusted to 6 with HCl (2 M). The resulting mixture was concentrated under vacuum and applied onto a silica gel column eluting with DCM/MeOH (10/1) to afford the title compound (250 mg, 26%) as a brown solid. LCMS: [M+H]$^+$ 245.03.

Step 6: N-(2-Fluoro-6-(trifluoromethyl)benzyl)-5-(thiazol-5-yl)-1H-indole-7-carboxamide A solution of 5-(thiazol-5-yl)-1H-indole-7-carboxylic acid (250 mg, 1.02 mmol, 1 eq), HATU (584 mg, 1.54 mmol, 1.50 eq), DIPEA (397 mg, 3.07 mmol, 3.0 eq), and 1-[2-fluoro-6-(trifluoromethyl)phenyl]methanamine (198 mg, 1.03 mmol, 1 eq) in DMF (8 mL) was stirred for 1 h at RT. The crude product was purified by reverse phase column and further purified by Prep-HPLC to afford the title compound (160 mg, 37%) as a white solid. LCMS: [M+H]$^+$ 420.10. $^1$H NMR (300 MHz, DMSO-d$_6$) δ 11.30 (s, 1H), 9.05 (s, 1H), 9.04-8.87 (m, 1H), 8.36 (s, 1H), 8.16-7.87 (m, 2H), 7.67-7.57 (m, 3H), 7.38 (s, 1H), 6.53 (d, J=2.7 Hz, 1H), 4.73 (s, 2H).

Example 32: N-((1r,4r)-4-(2-Methoxyethoxy)cyclohexyl)-2-(thiazol-5-yl)-5H-pyrrolo[3,2-d]pyrimidine-4-carboxamide

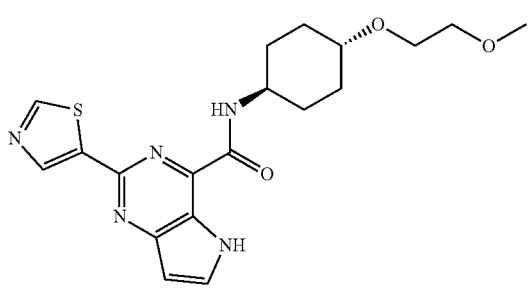

Step 1: Ethyl 2-(thiazol-5-yl)-5H-pyrrolo[3,2-d]pyrimidine-4-carboxylate

Under nitrogen, a mixture of ethyl 2-chloro-5H-pyrrolo[3,2-d]pyrimidine-4-carboxylate (655 mg, 2.90 mmol, 1 eq), 5-(4,4,5,5-tetramethyl-1,3,2-dioxaborolan-2-yl)thiazole (1.22 g, 5.8 mmol, 2 eq), Pd$_2$(dba)$_3$ (265 mg, 0.29 mmol, 0.10 eq), X-phos (277 mg, 0.58 mmol, 0.20 eq), potassium fluoride dihydrate (818 mg, 8.7 mmol, 3 eq) in toluene (8 mL) and H$_2$O (1 mL) was stirred for 10 h at 80° C. The reaction was quenched with water and extracted with 3×50 mL dichloromethane. The organic layers were combined, dried over anhydrous sodium sulfate and concentrated. This provided the title compound (690 mg, 74%) as a yellow solid. LCMS: [M+H]$^+$ 274.30.

Step 2: 2-(Thiazol-5-yl)-5H-pyrrolo[3,2-d]pyrimidine-4-carboxylic acid

A mixture of ethyl 2-(thiazol-5-yl)-5H-pyrrolo[3,2-d]pyrimidine-4-carboxylate (680 mg, 2.48 mmol, 1 eq) and 2 mL 2.5 M aqueous NaOH in MeOH (8 mL) was stirred for 2 h at RT. After completion, 50 mL of water was added to the resulting solution. The pH value was adjusted to 3 by addition of concentrated HCl. The resulting solution was washed with 3×10 mL EtOAc. The aqueous layers were concentrated under vacuum to afford the title compound (560 mg, 91%) as an off-white solid. LCMS: [M+H]$^+$ 246.24.

Step 3: N-((1r, 4r)-4-(2-Methoxyethoxy)cyclohexyl)-2-(thiazol-5-yl)-5H-pyrrolo[3,2-d]pyrimidine-4-carboxamide A mixture of 2-(thiazol-5-yl)-5H-pyrrolo[3,2-d]pyrimidine-4-carboxylic acid (300 mg, 1.22 mmol, 1.00 eq), Int-B1 (253 mg, 1.46 mmol, 1.20 eq), HATU (510 mg, 1.34 mmol, 1.10 eq), DIPEA (315 mg, 2.44 mmol, 2.00 eq) in DMF (5 mL) was stirred 1 h at RT. The crude product was purified by Prep-HPLC to afford the title compound (17 mg, 4% yield) as a white solid. LCMS: [M+H]$^+$ 402.15. $^1$H NMR (300 MHz, Methanol-d4) δ 9.06 (d, J=0.8 Hz, 1H), 8.84 (d, J=0.8 Hz, 1H), 7.94 (d, J=3.2 Hz, 1H), 6.73 (d, J=3.2 Hz, 1H), 4.10-3.90 (m, 1H), 3.68 (dd, J=5.8, 3.4 Hz, 2H), 3.56 (dd, J=5.8, 3.5 Hz, 2H), 3.50-3.41 (m, 1H), 3.39 (s, 3H), 2.21-2.01 (m, 4H), 1.80-1.60 (m, 2H), 1.59-1.31 (m, 2H).

Example 33: N-(2-Fluoro-6-(trifluoromethyl)benzyl)-6-(thiazol-5-yl)-3I-imidazo[4,5-c]pyridine-4-carboxamide

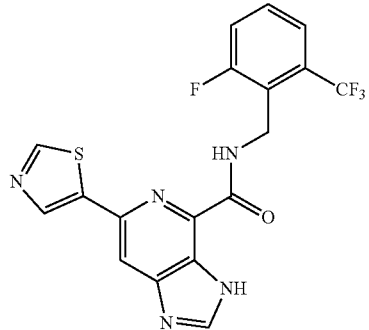 [SMILES: O=C(NCc1c(F)cccc1C(F)(F)F)c1nc(-c2cncs2)cc2nc[nH]c12]

Step 1: Ethyl 6-(thiazol-5-yl)-3H-imidazo[4,5-c]pyridine-4-carboxylate

Under nitrogen, a solution of ethyl 6-chloro-3H-imidazo[4,5-c]pyridine-4-carboxylate (945 mg, 4.19 mmol, 1.00 eq), 5-(4,4,5,5-tetramethyl-1,3,2-dioxaborolan-2-yl)thiazole (4.42 g, 20.941 mmol, 5.00 eq), Pd$_2$(dba)$_3$ (269 mg, 0.293 mmol, 0.07 eq), XPhos (280 mg, 0.59 mmol, 0.14 eq), and KF (1.22 g, 20.94 mmol, 5.00 eq) in dioxane (24 mL) and H$_2$O (6 mL) was stirred for 2.5 days at 100° C. The mixture was concentrated and purified by flash chromatography on silica gel eluting with EtOAc/MeOH (83/17) to afford the title compound (98 mg, 6% yield) as a brown solid. LCMS: [M+H]$^+$ 275.30.

Step 2: 6-(Thiazol-5-yl)-3H-imidazo[4,5-c]pyridine-4-carboxylic acid

To a solution of ethyl 6-(thiazol-5-yl)-3H-imidazo[4,5-c]pyridine-4-carboxylate (98 mg, 0.36 mmol, 1.00 eq) in MeOH (1.00 mL) and H$_2$O (1 mL) was added LiOH (23 mg, 0.54 mmol, 1.50 eq) and the mixture was stirred for 2 h at RT. The solids were filtered out. The filtrate was concentrated and purified by C18 reverse phase chromatography eluting with H$_2$O/CH$_3$CN (68/32) to afford the title compound (24 mg, 24.55% yield) as yellow oil. LCMS: [M+H]$^+$ 247.25.

Step 3: N-(2-Fluoro-6-(trifluoromethyl)benzyl)-6-(thiazol-5-yl)-3H-imidazo[4,5-c]pyridine-4-carboxamide A solution of 6-(thiazol-5-yl)-3H-imidazo[4,5-c]pyridine-4-carboxylic acid in DMF (0.50 mL), HATU (46 mg, 0.12 mmol, 1.50 eq), DIPEA (11 mg, 0.08 mmol, 1.00 eq), (2-fluoro-6-(trifluoromethyl)phenyl)methanamine (24 mg, 0.12 mmol, 1.50 eq) was stirred for 1 h at RT. The reaction was quenched with water and extracted with 2×30 mL of EtOAc. The organic layers were combined, dried over anhydrous sodium sulfate and concentrated under vacuum. The crude product was applied onto C18 reverse phase chromatography eluting with H$_2$O/CH$_3$CN (53/47) to afford the title compound (2.4 mg, 7% yield) as a white solid. LCMS: [M+H]+ 421.95. $^1$H NMR (400 MHz, Methanol-d4) δ 9.02 (s, 1H), 8.53 (d, J=10.0 Hz, 2H), 8.36 (s, 1H), 7.70-7.56 (m, 2H), 7.52 (t, J=8.4 Hz, 1H), 5.06 (s, 2H).

Example 34: N-((1r,4r)-4-(2-Methoxyethoxy)cyclohexyl)-2-(2-methyl-1H-imidazol-1-yl)-5H-pyrrolo[3,2-d]pyrimidine-4-carboxamide

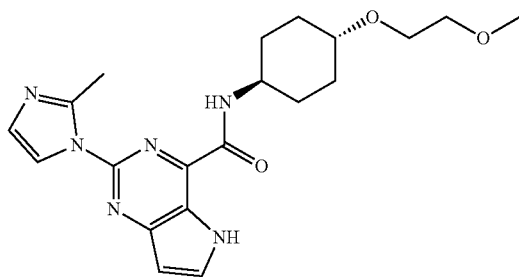 [SMILES: COCCO[C@H]1CC[C@H](NC(=O)c2nc(-n3ccnc3C)nc3cc[nH]c23)CC1]

Step 1: N-((1r,4r)-4-(2-Methoxyethoxy)cyclohexyl)-2-(5-methyl-1H-imidazol-1-yl)-5H-pyrrolo[3,2-d]pyrimidine-4-carboxamide Under nitrogen, a mixture of Int-A3 (200 mg, 0.57 mmol, 1.00 eq), 2-methyl-1H-imidazole (140 mg, 1.70 mmol, 3.00 eq), Pd$_2$(dba)$_3$ (52 mg, 0.057 mmol, 0.10 eq), tBuXPhos (24 mg, 0.057 mmol, 0.10 eq), K$_3$PO$_4$ (241 mg, 1.134 mmol, 2.00 eq) in toluene (5 mL) was stirred for 2 h at 100° C. The reaction was quenched with water and extracted with 3×50 mL EtOAc. The organic layers were combined, dried over anhydrous sodium sulfate and concentrated under vacuum. The crude product was purified by Flash-Prep-HPLC eluting with ACN/H$_2$O to afford the title compound (50 mg, 22%) as a white solid. LCMS: [M+H]$^+$ 399.35. $^1$H NMR (300 MHz, DMSO-d6) δ 12.08 (s, 1H), 8.74-8.72 (m, 2H), 8.02 (d, J=3.2 Hz, 1H), 6.82 (t, J=1.2 Hz, 1H), 6.71 (d, J=3.1 Hz, 1H), 3.92-3.81 (m, 1H), 3.54 (dd, J=5.9, 3.7 Hz, 2H), 3.43 (dd, J=5.9, 3.7 Hz, 2H), 3.31-3.19 (m, 4H), 2.58 (s, 3H), 2.12-1.98 (m, 2H), 2.95-1.81 (m, 2H), 1.68-1.51 (m, 2H), 1.36-1.19 (m, 2H).

Example 35: N-((1r,4r)-4-(2-Methoxyethoxy)cyclohexyl)-2-(2H-1,2,3-triazol-4-yl)-5H-pyrrolo[3,2-d]pyrimidine-4-carboxamide

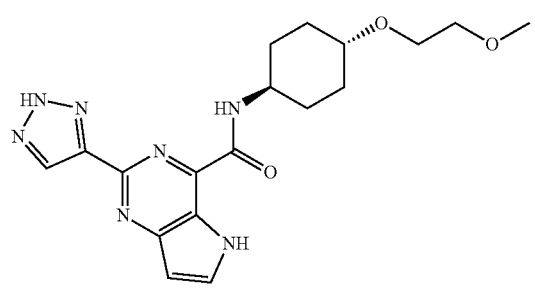 [SMILES: COCCO[C@H]1CC[C@H](NC(=O)c2nc(-c3cn[nH]n3)nc3cc[nH]c23)CC1]

Step 1: N-((1r,4r)-4-(2-Methoxyethoxy)cyclohexyl)-2-((trimethylsilyl)ethynyl)-5H-pyrrolo[3,2-d]pyrimidine-4-carboxamide Under nitrogen, a solution of Int-A3 (500 mg, 1.42 mmol, 1.00 eq), ethynyltrimethylsilane (2.09 g, 21.26 mmol, 15 eq), Pd(PPh$_3$)$_2$Cl$_2$ (100 mg, 0.14 mmol, 0.1 eq), CuI (27 mg, 0.14 mmol, 0.1 eq), and TEA (717 mg, 7.086 mmol, 5 eq) in DMSO (5 mL) was stirred for 1 h at 90° C. The resulting solution was quenched with water and extracted with 2×20 mL EtOAc. The organic layers were combined, dried over sodium sulfate, and concentrated under vacuum. The crude product was purified by Flash-Prep-HPLC eluting with H$_2$O/ACN to afford the title compound (300 mg, 51%) as a solid. LCMS: [M+H]$^+$ 415.20.

Step 2: N-((1r,4r)-4-(2-Methoxyethoxy)cyclohexyl)-2-(2H-1,2,3-triazol-4-yl)-5H-pyrrolo[3,2-d]pyrimidine-4-carboxamide Under nitrogen, a solution of N-((1r,4r)-4-(2-methoxyethoxy)cyclohexyl)-2-((trimethylsilyl)ethynyl)-5H-pyrrolo[3,2-d]pyrimidine-4-carboxamide (300 mg, 0.72 mmol, 1.00 eq), CuI (14 mg, 0.072 mmol, 0.1 eq), NaN$_3$ (14 mg, 2.171 mmol, 3 eq), and potassium fluoride dihydrate (204.06 mg, 2.171 mmol, 3 eq) in ACN (2.5 mL), THF (10 mL) and H$_2$O (2 mL) was stirred overnight at 60° C. The crude product was purified by Flash-Prep-HPLC eluting with H$_2$O/ACN to afford (29 mg, 10%) as a white solid. LCMS: [M+H]$^+$ 386.15. $^1$H-NMR (300 MHz, DMSO-d$_6$) δ12.02 (s, 1H), 8.84 (d, J=8.4 Hz, 1H), 8.48 (s, 1H), 7.98 (d, J=3.1 Hz, 1H), 6.74 (d, J=3.1 Hz, 1H), 3.94-3.90 (m, 1H), 3.57 (dd, J=5.9, 3.7 Hz, 2H), 3.45 (dd, J=5.9, 3.7 Hz, 2H), 3.38-3.28 (m, 1H), 3.27 (s, 3H), 2.13-2.08 (m, 2H), 20.07-1.95 (m, 2H), 1.79-1.59 (m, 2H), 1.41-1.25 (m, 2H).

Examples 36 and 37: N-((1r,4r)-4-(2-Methoxy-ethoxy)cyclohexyl)-2-(5-methyl-1H-imidazol-1-yl)-5H-pyrrolo[3,2-d]pyrimidine-4-carboxamide and N-((1r,4r)-4-(2-methoxyethoxy)cyclohexyl)-2-(4-methyl-1H-imidazol-1-yl)-5H-pyrrolo[3,2-d]pyrimidine-4-carboxamide

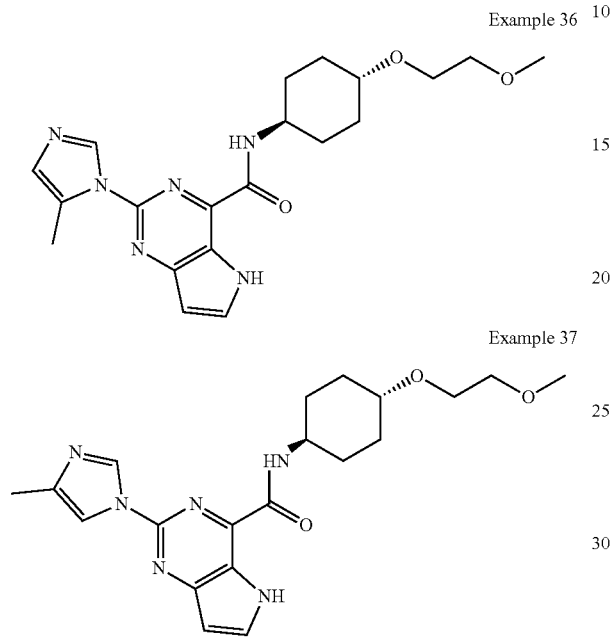

Example 36

Example 37

Step 1: N-((1r,4r)-4-(2-Methoxyethoxy)cyclohexyl)-2-(5-methyl-1H-imidazol-1-yl)-5H-pyrrolo[3,2-d]pyrimidine-4-carboxamide Under nitrogen, A mixture of Int-A3 (200 mg, 0.57 mmol, 1.00 eq), 4-methyl-1H-imidazole (93 mg, 1.13 mmol, 2.00 eq), Pd$_2$(dba)$_3$ (52 mg, 0.057 mmol, 0.10 eq), tBuXPhos (25 mg, 0.057 mmol, 0.10 eq) and K$_3$PO$_4$ (240 mg, 1.13 mmol, 2.00 eq) in toluene (5 mL) was stirred for 2 h at 100° C. The reaction was quenched water and extracted with 3×50 mL of EtOAc. The organic layers were combined, dried over anhydrous sodium sulfate and concentrated under vacuum. The crude product was purified by Flash-Prep-HPLC eluting with ACN/H$_2$O to afford Example 36 (8.8 mg, 3.88%) as a white solid. LCMS: [M+H]$^+$ 399.25. $^1$H NMR (300 MHz, DMSO-d6) δ 12.08 (s, 1H), 8.74-8.72 (m, 2H), 8.02 (d, J=3.2 Hz, 1H), 6.82 (t, J=1.2 Hz, 1H), 6.71 (d, J=3.1 Hz, 1H), 3.92-3.81 (m, 1H), 3.54 (dd, J=5.9, 3.7 Hz, 2H), 3.43 (dd, J=5.9, 3.7 Hz, 2H), 3.31-3.19 (m, 4H), 2.58 (s, 3H), 2.12-1.98 (m, 2H), 2.95-1.81 (m, 2H), 1.68-1.51 (m, 2H), 1.36-1.19 (m, 2H), and Example 37 (91.1 mg, 45.5%) as a white solid. LCMS: [M+H]$^+$ 399.25 $^1$H NMR (300 MHz, DMSO-d6) δ 12.04 (s, 1H), 9.04-8.82 (m, 2H), 8.07-7.91 (m, 2H), 6.68 (s, 1H), 4.04-3.82 (m, 1H), 3.61-3.53 (m, 2H), 3.48-3.41 (m, 2H), 3.29-3.19 (m, 4H), 2.22 (s, 3H), 2.17-1.98 (m, 2H), 1.98-1.81 (m, 2H), 1.74-1.51 (m, 2H), 1.38-1.18 (m, 2H). Regiochemistry was assigned by inference, with the minor isomer (Example 36) being the more sterically hindered nucleophile (Ueda, et al JACS, 2012, 134, 700-706).

Example 38: 2-(1H-Imidazol-4-yl)-N-((1r,4r)-4-(2-methoxyethoxy)cyclohexyl)-5H-pyrrolo[3,2-d]pyrimidine-4-carboxamide Step 1: N-((1r,4r)-4-(2-Methoxyethoxy)cyclohexyl)-2-(1-(triphenylmethyl)imidazol-4-yl)-5H-pyrrolo[3,2-d]pyrimidine-4-carboxamide Under nitrogen, a mixture of Int-A3 (353 mg, 1.00 mmol, 1.00 eq), 4-(tributylstannyl)-1-trityl-1H-imidazole (720 mg, 1.20 mmol, 1.20 eq), Pd(PPh$_3$)$_2$Cl$_2$ (70 mg, 0.10 mmol, 0.10 eq), K$_2$CO$_3$ (276 mg, 2.00 mmol, 2.00 eq) and H$_2$O (1 mL) in EtOH (10 mL) was stirred at 80° C. overnight. The reaction was quenched with water and extracted with 3×20 mL EtOAc. The organic layers were combined, dried over sodium sulfate, and concentrated. The crude product was applied onto a silica gel column and eluted with dichloromethane/methanol (5/1) to afford the title compound (380 mg, 61% yield) as a yellow solid. LCMS: [M+H]$^+$ 627.30.

Step 2: 2-(1H-Imidazol-4-yl)-N-((1r,4r)-4-(2-methoxyethoxy)cyclohexyl)-5H-pyrrolo[3,2-d]pyrimidine-4-carboxamide A mixture of N-[(1r,4r)-4-(2-methoxyethoxy)cyclohexyl]-2-[1-(triphenylmethyl)imidazol-4-yl]-5H-pyrrolo[3,2-d]pyrimidine-4-carboxamide (380 mg, 0.607 mmol, 1 eq) in TFA (5 mL) was stirred at 25° C. for 1 h. After concentration, the crude product was purified by C18 reverse phase chromatography eluting with H$_2$O/CH$_3$CN to give the compound (37 mg, 16% yield) as a light yellow solid. LCMS: [M+H]$^+$ 385.20.

H-NMR: (300 MHz, DMSO-d6) δ 13.03 (s, 1H), 11.81 (s, 1H), 8.86 (d, J=8.5 Hz, 1H), 7.96-7.85 (m, 2H), 7.77 (s, 1H), 6.64 (dd, J=3.1, 1.7 Hz, 1H), 4.00-3.80 (m, 1H), 3.55 (dd, J=5.9, 3.8 Hz, 2H), 3.43 (dd, J=5.9, 3.7 Hz, 2H), 3.30-3.28 (m, 1H), 3.25 (s, 3H), 2.15-2.07 (m, 2H), 1.95-1.85 (m, 2H), 1.70-1.50 (m, 2H), 1.45-1.20 (m, 2H).

Examples 39a and 39b: 2-(1H-Imidazol-1-yl)-N-((1s,4s)-4-(trifluoromethyl)cyclohexyl)-5H-pyrrolo[3,2-d]pyrimidine-4-carboxamide and 2-(1H-imidazol-1-yl)-N-((1r,4r)-4-(trifluoromethyl)cyclohexyl)-5H-pyrrolo[3,2-d]pyrimidine-4-carboxamide

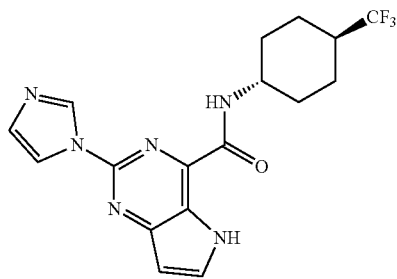

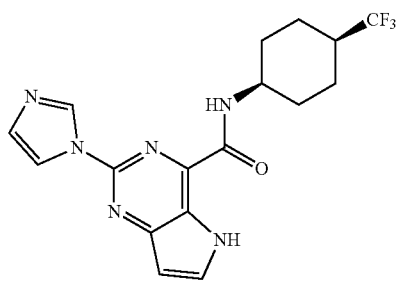

A mixture of Int-A2 (230 mg, 1.00 mmol, 1.00 eq), HATU (572 mg, 1.51 mmol, 1.5 eq), DIPEA (389 mg, 3.01 mmol, 3 eq), and 4-(trifluoromethyl)cyclohexan-1-amine (201 mg, 1.20 mmol, 1.2 eq) in DMF (5 mL) was stirred 1 h at RT. After concentration, the crude product was purified by C18 reverse phase chromatography eluting with H$_2$O/CH$_3$CN and further purified by chiral-HPLC with the following conditions: (Column: CHIRALPAK IC, 2*25 cm, 5 um; Mobile Phase A: hexane (8 M NH$_3$ in MeOH), Mobile Phase B: EtOH; flow rate: 20 mL/min; Gradient: 30% mobile phase B maintained for 12 min; 220/254 nm) to afford the title compounds with retention times of 1.13 minutes (Example 39a) and 1.51 minutes (Example 39b). The absolute stereochemistry of Examples 39a and 39b was not confirmed.

Example 39a: Isolated as a white solid (62 mg, 16%). LCMS: [M+H]+ 379.20. $^1$H NMR (300 MHz, DMSO-d6) δ 12.07 (s, 1H), 8.85 (dd, J=9.3, 25.5 Hz, 2H), 8.22 (d, J=1.4 Hz, 1H), 8.02 (d, J=3.1 Hz, 1H), 7.13 (d, J=1.2, 6.9 Hz, 1H), 6.71 (d, J=3.1 Hz, 1H), 4.00-3.80 (m, 1H), 2.40-2.20 (m, 1H), 2.01-1.89 (m, 4H), 1.77-1.63 (m, 2H), 1.59-1.41 (m, 2H).

Example 39b: Isolated as a white solid (116 mg, 31%). LCMS: [M+H]$^+$ 379.20. $^1$H NMR (300 MHz, DMSO-d6) δ 12.11 (s, 1H), 8.88 (s, 1H), 8.73 (d, J=7.0 Hz, 1H), 8.17 (d, J=1.2 Hz, 1H), 8.03 (d, J=3.1 Hz, 1H), 7.14 (d, J=1.2 Hz, 1H), 6.72 (d, J=3.1 Hz, 1H), 4.18-1.02 (m, 1H), 2.35-2.27 (m, 1H), 2.10-1.89 (m, 2H), 1.79-1.54 (m, 6H).

Example 41: 5-(1H-Imidazol-1-yl)-N-((1r,4r)-4-(2-methoxyethoxy)cyclohexyl)benzo[d]isothiazole-7-carboxamide

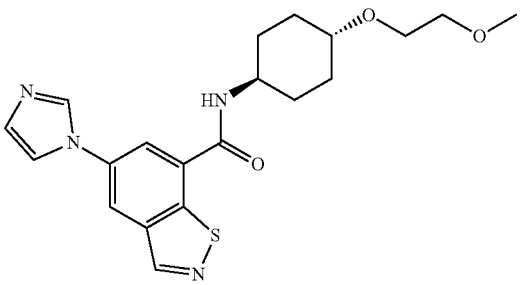 [SMILES: COCCO[C@H]1CC[C@H](NC(=O)c2cc(-n3ccnc3)cc3cnsc23)CC1]

Step 1:
5-Bromo-2-(tert-butylthio)-3-methylbenzaldehyde

A mixture of 5-bromo-2-fluoro-3-methylbenzaldehyde (10.8 g, 49.76 mmol, 1.00 eq), 2-methylpropane-2-thiol (5.38 g, 59.71 mmol, 1.20 eq), K$_2$CO$_3$ (11.7 g, 84.59 mmol, 1.70 eq) in DMF (120 mL) was stirred for 6 h at 60° C. The reaction was cooled to RT and quenched with water. The resulting solution was extracted with EtOAc. The organic layers were combined and concentrated. The crude product was applied onto a silica gel column eluting with (EtOAc: petroleum ether 1:10) to afford the title compound (10 g, 70% yield). LCMS: [M+H]$^+$ 287.1, 289.1.

Step 2: (E)-5-Bromo-2-(tert-butylthio)-3-methylbenzaldehyde oxime

A mixture of 5-bromo-2-(tert-butylthio)-3-methylbenzaldehyde (8.58 g, 29.87 mmol, 1.00 eq), NH$_2$OH·HCl (3.32 g, 47.796 mmol, 1.60 eq), and NaHCO$_3$ (10.79 g, 128.45 mmol, 4.30 eq) in EtOH (90 mL) was stirred at RT for 3 h. The resulting solution was diluting with water (100 mL) and extracted with EtOAc. The organic layers were combined, dried over Na$_2$SO$_4$ and concentrated. The crude product was purified by re-crystallization from petroleum ether. The solids were collected by filtration to afford the title compound (8 g, 89% yield). LCMS: [M+H]$^+$ 302.1, 304.1.

Step 3: 5-Bromo-7-methylbenzo[d]isothiazole

A mixture of (E)-5-bromo-2-(tert-butylthio)-3-methylbenzaldehyde oxime (7.50 g, 24.82 mmol, 1.00 eq) and 4-methylbenzenesulfonic acid (855 mg, 4.96 mmol, 0.20 eq) in toluene (100 mL) was stirred at 110° C. for 3 h. After cooling to RT, the reaction was quenched with the addition of aqueous NaHCO$_3$. The resulting solution was extracted with EtOAc. The organic layers were combined, dried over Na$_2$SO$_4$ and concentrated. The crude product was purified by re-crystallization from MeOH to afford the title compound (4.56 g, 72% yield) as a white solid. LCMS: [M+H]$^+$ 227.9, 229.9.

Step 4: 5-Bromobenzo[d]isothiazole-7-carboxylic acid

A mixture of 5-bromo-7-methylbenzo[d]isothiazole (4.56 g, 20 mmol, 1.00 eq), NBS (21.4 g, 120 mmol, 6.00 eq), BPO (970 mg, 0.20 eq) in CCl$_4$ (100 mL) was stirred for 18 h at 80° C. The resulting mixture was concentrated under vacuum, diluted with H$_2$O and extracted with EtOAc. The organic layers were combined, dried over anhydrous sodium sulfate and concentrated under vacuum. The crude product was dissolved in H$_2$O (40 mL) and dioxane (40 mL), and LiOH·H$_2$O (4.2 g, 100 mmol, 5.00 eq) was added. The resulting solution was stirred for 16 h at 100° C. The pH value of the solution was adjusted to 2 with HCl. The resulting solution was extracted with EtOAc and the organic layers combined. After concentration, a mixture of crude product, NaH$_2$PO$_4$ (7.56 g, 60 mmol, 3.00 eq), NaClO$_2$ (2.84 g, 30 mmol, 1.50 eq) and NH$_2$SO$_3$H (3.26 g, 32 mmol, 1.60 eq) in THF (42 mL), t-BuOH (14 mL) and H$_2$O (14 mL) was stirred at RT for 16 h. The reaction was diluted with H$_2$O. The solids were collected by filtration. The solids was further purified by triturating with (CH$_3$CN:H$_2$O=1:1) to afford the title compound (3 g, 58% yield) as a white solid. [M+H]$^+$ 257.9, 259.9.

Step 5: 5-Bromo-N-((1r,4r)-4-(2-methoxyethoxy)cyclohexyl)benzo[d]isothiazole-7-carboxamide A mixture of 5-bromobenzo[d]isothiazole-7-carboxylic acid (1.28 g, 4.96 mmol, 1.00 eq), Int-B1 (945 mg, 5.46 mmol, 1.10 eq), HATU (2.64 g, 6.94 mmol, 1.40 eq), DIPEA (2.56 g, 19.84 mmol, 4.00 eq) in DMF (15 mL) was stirred at RT for 1 h. The reaction was quenched with water and extracted with EtOAc. The organic layers were combined, dried over Na$_2$SO$_4$ and concentrated. The crude product was applied onto a silica gel column eluting with (EtOAc: petroleum ether, 1:1) to afford the title compound (1.8 g, 88% yield) as a white solid. LCMS: [M+H]$^+$ 413.1, 415.1.

Step 6: 5-(1H-Imidazol-1-yl)-N-((1r,4r)-4-(2-methoxyethoxy)cyclohexyl)benzo[d]isothiazole-7-carboxamide A mixture of 5-bromo-N-((1r,4r)-4-(2-methoxyethoxy)cyclohexyl)benzo[d]isothiazole-7-carboxamide (413 mg, 1.0 mmol, 1.0 eq), 1H-imidazole (816 mg, 11.99 mmol, 12 eq), CuI (381 mg, 2.0 mmol, 2.00 eq), K$_2$CO$_3$ (345 mg, 2.50 mmol, 2.50 eq) in NMP (10 mL) was stirred at 150° C. for 3 h. The reaction was quenched with MeOH. The insoluble solids were filtered out. The filtrate was concentrated, diluted with H$_2$O, and extracted with EtOAc. The organic layers were combined, dried over Na$_2$SO$_4$ and concentrated. The crude product was purified by prep-HPLC to give the title compound (69 mg, 18% yield) as a white solid. LCMS: [M+H]$^+$ 401.1; $^1$H NMR (400 MHz, DMSO-d6) δ 9.16 (s, 1H), 8.79 (d, J=7.6 Hz, 1H), 8.66 (d, J=1.8 Hz, 1H), 8.60 (d, J=1.9 Hz, 1H), 8.37 (t, J=1.1 Hz, 1H), 7.88 (t, J=1.4 Hz, 1H), 7.21 (t, J=1.1 Hz, 1H), 3.97-3.78 (m, 1H), 3.55 (dd, J=5.9, 3.9 Hz, 2H), 3.43 (dd, J=5.9, 3.8 Hz, 2H), 3.31-3.27 (m, 1H), 3.26 (s, 3H), 2.08-2.01 (m, 2H), 1.99-1.91 (m, 2H), 1.49-1.38 (m, 2H), 1.35-1.20 (in, 2H).

The following examples in Table 1 were prepared according to the methods described for the previous Examples.

TABLE 1

| Example # | Structure and Name | MS (M + H)$^+$ | Prepared according to Example # |
|---|---|---|---|
| 42 | 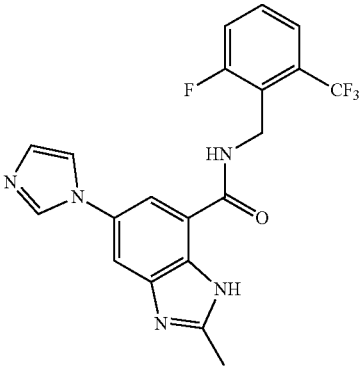 [SMILES: Cc1nc2cc(-n3ccnc3)cc(C(=O)NCc3c(F)cccc3C(F)(F)F)c2[nH]1]<br>N-(2-Fluoro-6-(trifluoromethyl)benzyl)-5-(1H-imidazol-1-yl)-2-methyl-1H-benzo[d]imidazole-7-carboxamide | 418.10 | 30 |
| 43 | 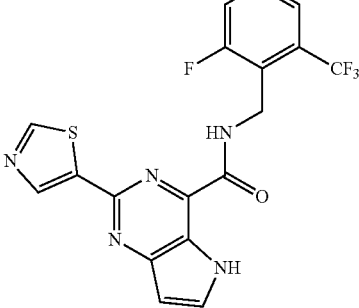 | 422.15 | 32 |

TABLE 1-continued

| Example # | Structure and Name | MS (M + H)+ | Prepared according to Example # |
|---|---|---|---|
| | N-(2-Fluoro-6-(trifluoromethyl)benzyl)-2-(thiazol-5-yl)-5H-pyrrolo[3,2-d]pyrimidine-4-carboxamide | | |
| 44 | N-(2-Fluoro-6-(trifluoromethyl)benzyl)-5-(1H-imidazol-1-yl)-1H-pyrrolo[3,2-b]pyridine-7-carboxamide | 404.10 | 10 |
| 45 | N-((1r,4r)-4-(2-Methoxyethoxy)cyclohexyl)-2-methyl-5-(thiazol-5-yl)-1H-indole-7-carboxamide | 414.25 | 11 |
| 46 | N-(2-Fluoro-6-(trifluoromethyl)benzyl)-2-(1H-imidazol-1-yl)-7H-purine-6-carboxamide | 406.15 | 14 |
| 47 | | 402.30 | 33 |

TABLE 1-continued

| Example # | Structure and Name | MS (M + H)+ | Prepared according to Example # |
|---|---|---|---|
| | N-((1r,4r)-4-(2-Methoxyethoxy)cyclohexyl)-6-(thiazol-5-yl)-3H-imidazo[4,5-c]pyridine-4-carboxamide | | |
| 48 | N-(2-Fluoro-6-(trifluoromethyl)benzyl)-5-(1H-imidazol-1-yl)-1H-pyrazolo[3,4-c]pyridine-7-carboxamide | 405.20 | 16 |
| 49 | N-(2-Fluoro-6-(trifluoromethyl)benzyl)-2-(1H-imidazol-1-yl)thieno[3,2-d]pyrimidine-4-carboxamide | 422.15 | 18 |
| 50 | N-((1r,4r)-4-(2-Methoxyethoxy)cyclohexyl)-2-(thiazol-5-yl)thieno[3,2-d]pyrimidine-4-carboxamide | 419.20 | 20 |

The examples in Table 2 were prepared by coupling Int-A2 to the appropriate amine according to the method described for Example 7 or Example 4, Step 1. Where noted, the appropriate Boc-protected amine was coupled to Int-A2 according to the procedure in either Example 7 or Example 4, Step 1. The Boc group was subsequently deprotected according to the procedure in Example 19, Step 9.

TABLE 2

| Example # | Structure | MS (M + H)+ | Prepared according to Example # |
|---|---|---|---|
| 51 | N-(2-Fluoro-6-(trifluoromethyl)benzyl)-2-(1H-imidazol-1-yl)-5H-pyrrolo[3,2-d]pyrimidine-4-carboxamide | 405.20 | 7 |
| 52 | 2-(1H-Imidazol-1-yl)-N-(1-(2,2,2-trifluoroethyl)piperidin-4-yl)-5H-pyrrolo[3,2-d]pyrimidine-4-carboxamide | 394.30 | 7 |
| 53 | 2-(1H-Imidazol-1-yl)-N-(1-(2-methoxyethyl)piperidin-4-yl)-5H-pyrrolo[3,2-d]pyrimidine-4-carboxamide | 370.10 | 7 |
| 54 | 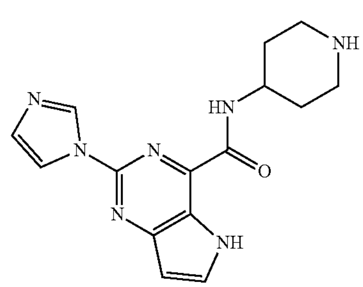 [SMILES: O=C(NC1CCNCC1)c1nc(-n2ccnc2)nc2cc[nH]c12] | 312.25 | 7 (Boc-protected amine) |

TABLE 2-continued

| Example # | Structure | MS (M + H)+ | Prepared according to Example # |
|---|---|---|---|
| | 2-(1H-Imidazol-1-yl)-N-(piperidin-4-yl)-5H-pyrrolo[3,2-d]pyrimidine-4-carboxamide | | |
| 55 | 2-(1H-Imidazol-1-yl)-N-(1-(3,3,3-trifluoropropyl)piperidin-4-yl)-5H-pyrrolo[3,2-d]pyrimidine-4-carboxamide | 408.25 | 4 |
| 56 | 2-(1H-Imidazol-1-yl)-N-((1r,4r)-4-((2-methoxyethyl)amino)cyclohexyl)-5H-pyrrolo[3,2-d]pyrimidine-4-carboxamide | 384.25 | 7 |
| 57 | 2-(1H-Imidazol-1-yl)-N-((1r,4r)-4-((2-methoxyethyl)(methyl)amino)cyclohexyl)-5H-pyrrolo[3,2-d]pyrimidine-4-carboxamide | 398.35 | 7 |
| 58 | 2-(1H-Imidazol-1-yl)-N-((1r,4r)-4-methoxycyclohexyl)-5H-pyrrolo[3,2-d]pyrimidine-4-carboxamide | 341.25 | 4 |

TABLE 2-continued

| Example # | Structure | MS (M + H)+ | Prepared according to Example # |
|---|---|---|---|
| 59 | 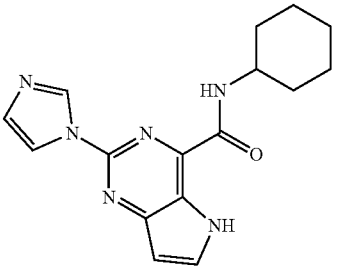 [SMILES: O=C(NC1CCCCC1)c1nc(-n2ccnc2)nc2cc[nH]c12]<br>N-cyclohexyl-2-(1H-Imidazol-1-yl)-5H-pyrrolo[3,2-d]pyrimidine-4-carboxamide | 311.10 | 7 |
| 60 | 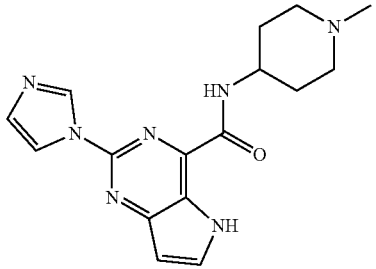 [SMILES: CN1CCC(NC(=O)c2nc(-n3ccnc3)nc3cc[nH]c23)CC1]<br>2-(1H-Imidazol-1-yl)-N-(1-methylpiperidin-4-yl)-5H-pyrrolo[3,2-d]pyrimidine-4-carboxamide | 326.10 | 4 |
| 61 | 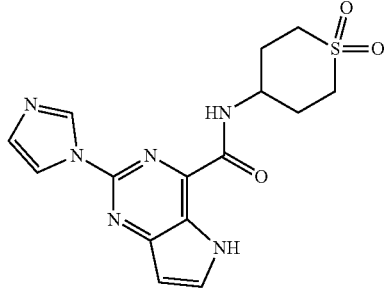 [SMILES: O=C(NC1CCS(=O)(=O)CC1)c1nc(-n2ccnc2)nc2cc[nH]c12]<br>N-(1,1-Dioxidotetrahydro-2H-thiopyran-4-yl)-2-(1H-imidazol-1-yl)-5H-pyrrolo[3,2-d]pyrimidine-4-carboxamide | 361.10 | 7 |
| 62 | 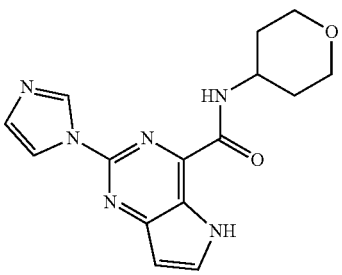 [SMILES: O=C(NC1CCOCC1)c1nc(-n2ccnc2)nc2cc[nH]c12]<br>2-(1H-Imidazol-1-yl)-N-(tetrahydro-2H-pyran-4-yl)-5H-pyrrolo[3,2-d]pyrimidine-4-carboxamide | 313.10 | 7 |

TABLE 2-continued

| Example # | Structure | MS (M + H)+ | Prepared according to Example # |
|---|---|---|---|
| 63 | 2-(1H-Imidazol-1-yl)-N-(4-(2-methoxyethoxy)phenyl)-5H-pyrrolo[3,2-d]pyrimidine-4-carboxamide | 379.15 | 7 |
| 64 | N-(1-Acetylpiperidin-4-yl)-2-(1H-imidazol-1-yl)-5H-pyrrolo[3,2-d]pyrimidine-4-carboxamide | 354.15 | 7 |
| 65 | 2-(1H-Imidazol-1-yl)-N-((1r,3r)-3-(2-methoxyethoxy)cyclobutyl)-5H-pyrrolo[3,2-d]pyrimidine-4-carboxamide | 357.10 | 7 |
| 66 | 2-(1H-Imidazol-1-yl)-N-((1r,3r)-3-methoxycyclobutyl)-5H-pyrrolo[3,2-d]pyrimidine-4-carboxamide | 313.05 | 7 |

TABLE 2-continued

| Example # | Structure | MS (M + H)+ | Prepared according to Example # |
|---|---|---|---|
| 67 | 2-(1H-Imidazol-1-yl)-N-(1-(3,3,3-trifluoropropyl)pyrrolidin-3-yl)-5H-pyrrolo[3,2-d]pyrimidine-4-carboxamide | 394.15 | 7 |
| 68 | 2-(1H-Imidazol-1-yl)-N-(1-(2,2,2-trifluoroethyl)pyrrolidin-3-yl)-5H-pyrrolo[3,2-d]pyrimidine-4-carboxamide | 380.15 | 7 |
| 69 | 2-(1H-Imidazol-1-yl)-N-((1s,4s)-4-(2-methoxyethoxy)cyclohexyl)-5H-pyrrolo[3,2-d]pyrimidine-4-carboxamide | 385.15 | 7 |
| 70 | 2-(1H-Imidazol-1-yl)-N-methyl-5H-pyrrolo[3,2-d]pyrimidine-4-carboxamide | 243.00 | 7 |

TABLE 2-continued

| Example # | Structure | MS (M + H)+ | Prepared according to Example # |
|---|---|---|---|
| 71 | 2-(1H-Imidazol-1-yl)-N-((1r,4r)-4-(2-(methylamino)ethoxy)cyclohexyl)-5H-pyrrolo[3,2-d]pyrimidine-4-carboxamide | 384.15 | 7 (Boc-protected amine) |
| 72 | N-((1r,4r)-4-(2-(Dimethylamino)ethoxy)cyclohexyl)-2-(1H-imidazol-1-yl)-5H-pyrrolo[3,2-d]pyrimidine-4-carboxamide | 398.30 | 7 |
| 73 | 2-(1H-Imidazol-1-yl)-N-(pyrrolidin-3-yl)-5H-pyrrolo[3,2-d]pyrimidine-4-carboxamide | 298.25 | 4 |
| 74 | 2-(1H-Imidazol-1-yl)-N-(1-methylpyrrolidin-3-yl)-5H-pyrrolo[3,2-d]pyrimidine-4-carboxamide | 312.05 | 7 |

TABLE 2-continued

| Example # | Structure | MS (M + H)+ | Prepared according to Example # |
|---|---|---|---|
| 75 | 2-(1H-Imidazol-1-yl)-N-(1-(methylsulfonyl)piperidin-4-yl)-5H-pyrrolo[3,2-d]pyrimidine-4-carboxamide | 390.05 | 7 |
| 76 | 2-(1H-Imidazol-1-yl)-N-(1-(oxetan-3-yl)piperidin-4-yl)-5H-pyrrolo[3,2-d]pyrimidine-4-carboxamide | 368.15 | 7 |
| 77 | N-Cyclobutyl-2-(1H-imidazol-1-yl)-5H-pyrrolo[3,2-d]pyrimidine-4-carboxamide | 283.10 | 7 |
| 78 | N-(Cyclohexylmethyl)-2-(1H-imidazol-1-yl)-5H-pyrrolo[3,2-d]pyrimidine-4-carboxamide | 325.10 | 7 |
| 79 | 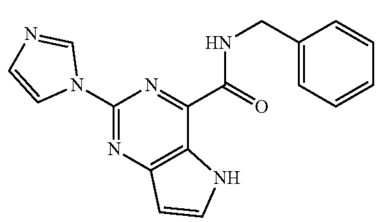 [SMILES: O=C(NCc1ccccc1)c1nc(-n2ccnc2)nc2cc[nH]c12] | 319.20 | 7 |

TABLE 2-continued

| Example # | Structure | MS (M + H)+ | Prepared according to Example # |
|---|---|---|---|
| | N-Benzyl-2-(1H-imidazol-1-yl)-5H-pyrrolo[3,2-d]pyrimidine-4-carboxamide | | |
| 80 | 2-(1H-Imidazol-1-yl)-N-((1r,4r)-4-(2-(methylamino)-2-oxoethoxy)cyclohexyl)-5H-pyrrolo[3,2-d]pyrimidine-4-carboxamide | 398.20 | 7 |
| 81 | 2-(1H-Imidazol-1-yl)-N-(pyridin-2-yl)-5H-pyrrolo[3,2-d]pyrimidine-4-carboxamide | 306.10 | 7 |
| 82 | 2-(1H-Imidazol-1-yl)-N-phenyl-5H-pyrrolo[3,2-d]pyrimidine-4-carboxamide | 305.05 | 7 |
| 83 | 2-(1H-Imidazol-1-yl)-N-(pyridin-3-yl)-5H-pyrrolo[3,2-d]pyrimidine-4-carboxamide | 306.10 | 7 |

TABLE 2-continued

| Example # | Structure | MS (M + H)+ | Prepared according to Example # |
|---|---|---|---|
| 84 | 2-(1H-Imidazol-1-yl)-N-(5-methoxypyridin-2-yl)-5H-pyrrolo[3,2-d]pyrimidine-4-carboxamide | 336.10 | 7 |
| 85 | 2-(1H-Imidazol-1-yl)-N-(6-methoxypyridin-3-yl)-5H-pyrrolo[3,2-d]pyrimidine-4-carboxamide | 336.10 | 7 |
| 86 | 2-(1H-Imidazol-1-yl)-N-(1H-pyrazol-3-yl)-5H-pyrrolo[3,2-d]pyrimidine-4-carboxamide | 295.10 | 7 |
| 87 | N-(4-Chlorophenyl)-2-(1H-imidazol-1-yl)-5H-pyrrolo[3,2-d]pyrimidine-4-carboxamide | 339.05 | 7 |

TABLE 2-continued

| Example # | Structure | MS (M + H)+ | Prepared according to Example # |
|---|---|---|---|
| 88 | N-(3-Chlorophenyl)-2-(1H-imidazol-1-yl)-5H-pyrrolo[3,2-d]pyrimidine-4-carboxamide | 339.10 | 7 |
| 89 | N-(2-Chlorophenyl)-2-(1H-imidazol-1-yl)-5H-pyrrolo[3,2-d]pyrimidine-4-carboxamide | 339.00 | 7 |
| 90 | N-Cyclopentyl-2-(1H-imidazol-1-yl)-5H-pyrrolo[3,2-d]pyrimidine-4-carboxamide | 297.10 | 7 |
| 91 | 2-(1H-Imidazol-1-yl)-N-(tetrahydrofuran-3-yl)-5H-pyrrolo[3,2-d]pyrimidine-4-carboxamide | 299.05 | 7 |

TABLE 2-continued

| Example # | Structure | MS (M + H)+ | Prepared according to Example # |
|---|---|---|---|
| 92 | N-Cycloheptyl-2-(1H-imidazol-1-yl)-5H-pyrrolo[3,2-d]pyrimidine-4-carboxamide | 325.10 | 7 |
| 93 | 2-(1H-Imidazol-1-yl)-N-isopropyl-5H-pyrrolo[3,2-d]pyrimidine-4-carboxamide | 271.10 | 7 |
| 94 | 2-(1H-Imidazol-1-yl)-N-(1-methyl-1H-pyrazol-3-yl)-5H-pyrrolo[3,2-d]pyrimidine-4-carboxamide | 309.05 | 7 |
| 95 | 2-(1H-Imidazol-1-yl)-N-(1-methyl-1H-imidazol-4-yl)-5H-pyrrolo[3,2-d]pyrimidine-4-carboxamide | 309.15 | 7 |

TABLE 2-continued

| Example # | Structure | MS (M + H)+ | Prepared according to Example # |
|---|---|---|---|
| 96 | N-(3-Chloro-4-fluorophenyl)-2-(1H-imidazol-1-yl)-5H-pyrrolo[3,2-d]pyrimidine-4-carboxamide | 357.05 | 7 |
| 97 | 2-(1H-Imidazol-1-yl)-N-((1r,4r)-4-(2-morpholinoethoxy)cyclohexyl)-5H-pyrrolo[3,2-d]pyrimidine-4-carboxamide | 440.25 | 7 |
| 98 | 2-(1H-Imidazol-1-yl)-N-(1H-pyrazol-4-yl)-5H-pyrrolo[3,2-d]pyrimidine-4-carboxamide | 295.10 | 7 |
| 99 | 2-(1H-Imidazol-1-yl)-N-(1-methyl-1H-pyrazol-4-yl)-5H-pyrrolo[3,2-d]pyrimidine-4-carboxamide | 309.05 | 7 |

TABLE 2-continued

| Example # | Structure | MS (M + H)+ | Prepared according to Example # |
|---|---|---|---|
| 100 | 2-(1H-Imidazol-1-yl)-N-(3-(2-methoxyethoxy)phenyl)-5H-pyrrolo[3,2-d]pyrimidine-4-carboxamide | 379.20 | 7 |

Example 101: 2-(1H-imidazol-1-yl)-N-((1r,4r)-4-((2,2,2-trifluoroethyl)amino)cyclohexyl)-5H-pyrrolo[3,2-d]pyrimidine-4-carboxamide

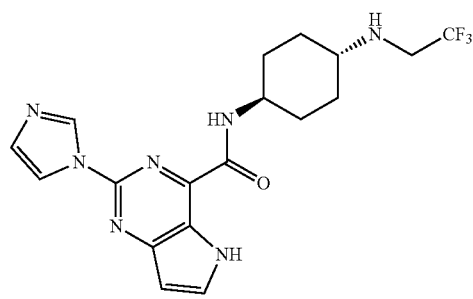 [SMILES: O=C(N[C@H]1CC[C@H](NCC(F)(F)F)CC1)c1nc(-n2ccnc2)nc2cc[nH]c12]

Step 1: tert-butyl((1r,4r)-4-(2-(1H-imidazol-1-yl)-5H-pyrrolo[3,2-d]pyrimidine-4-carboxamido)cyclohexyl)carbamate A solution of 2-(1H-imidazol-1-yl)-5H-pyrrolo[3,2-d]pyrimidine-4-carboxylic acid (687 mg, 3 mmol, 1 equiv), T3P (3.82 g, 50% in EtOAc, 12 mmol, 4 equiv), DIEA (348 mg, 12 mmol, 4 equiv), and tert-butyl ((1r,4r)-4-aminocyclohexyl)carbamate (642 mg, 3 mmol, 1.00 equiv) in DMF (10 mL) was stirred for 1 h at RT. The reaction was diluted with 20 mL of water. The solids were collected by filtration. The solids were further purified by slurrying in ACN followed by filtering, rinsing with ACN, and drying in the oven to afford the title compound (495 mg, 39%) as a brown solid. LCMS: [M+H]+ 426.25.

Step 2: N-((1r,4r)-4-aminocyclohexyl)-2-(1H-imidazol-1-yl)-5H-pyrrolo[3,2-d]pyrimidine-4-carboxamide A solution of tert-butyl((1r,4r)-4-(2-(1H-imidazol-1-yl)-5H-pyrrolo[3,2-d]pyrimidine-4-carboxamido)cyclohexyl) carbamate (475 mg, 1.12 mmol, 1.00 equiv) and TFA (1.5 mL) in DCM (7.5 mL) was stirred at RT for 1 h. The pH of the solution was adjusted to 8 with aqueous NaHCO$_3$. The resulting mixture was concentrated under vacuum. The crude product was purified by reverse phase column eluting with H$_2$O/ACN to afford the title compound (290 mg, 80%) as a light yellow solid. LCMS: [M+H]+ 326.20.

Step 3: 2-(1H-imidazol-1-yl)-N-((1r,4r)-4-((2,2,2-trifluoroethyl)amino)cyclohexyl)-5H-pyrrolo[3,2-d]pyrimidine-4-carboxamide A solution of N-((1r,4r)-4-aminocyclohexyl)-2-(1H-imidazol-1-yl)-5H-pyrrolo[3,2-d]pyrimidine-4-carboxamide (270 mg, 0.831 mmol, 1 equiv), 2,2,2-trifluoroacetaldehyde (244 mg, 2.49 mmol, 3.00 equiv), HOAc (49 mg, 0.83 mmol, 1.00 equiv), and Ti(Oi-Pr)$_4$ (235 mg, 0.83 mmol, 1.00 equiv) in EtOH (5 mL) was stirred for 4 h at 90° C. NaBH$_3$CN (103 mg, 1.66 mmol, 2 equiv) was added and the mixture was stirred for 1 h at 90° C. After cooling to RT the resulting mixture was concentrated under vacuum. The crude product was purified by reverse phase column eluting with H$_2$O/ACN. After concentration, the crude solids were further purified by slurrying in water, filtering and rinsing with water to afford the title compound (147 mg, 44%) as a white solid. LCMS: [M+H]+ 408.20. $^1$H NMR (400 MHz, DMSO-d6) δ 12.04 (s, 1H), 8.97 (s, 1H), 8.91 (d, J=8.8 Hz, 1H), 8.21 (s, 1H), 8.00 (d, J=2.8 Hz, 1H), 7.11 (s, 1H), 6.69 (d, J=1.6 Hz, 1H), 3.97-3.81 (m, 1H), 3.33-3.26 (m, 2H), 2.56-2.51 (m, 1H), 2.39-2.25 (br, 1H), 2.00-1.90 (m, 2H), 1.87-1.68 (m, 2H), 1.68-1.57 (m, 2H), 1.17-1.04 (m, 2H).

Example 101 can also be prepared according to the following procedure:

Example 101: 2-(1H-imidazol-1-yl)-N-((1r,4r)-4-((2,2,2-trifluoroethyl)amino)cyclohexyl)-5H-pyrrolo[3,2-d]pyrimidine-4-carboxamide and Example 102: 2-(1H-imidazol-1-yl)-N-((1s,4s)-4-((2,2,2-trifluoroethyl)amino)cyclohexyl)-5H-pyrrolo[3,2-d]pyrimidine-4-carboxamide

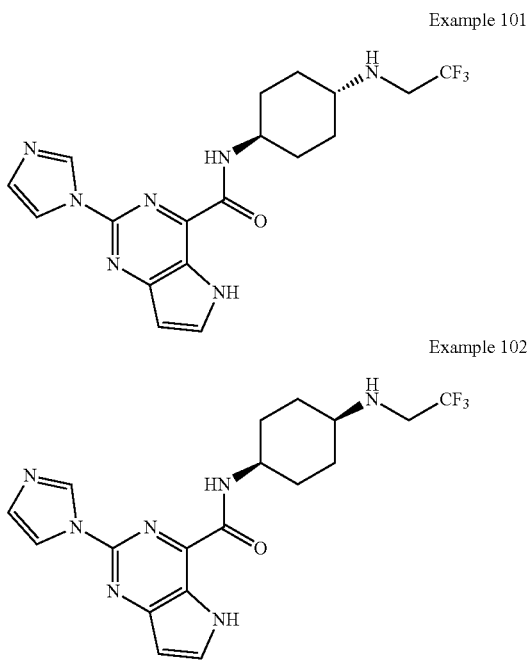

Example 101

Example 102

Step 1: 2-(1H-imidazol-1-yl)-N-(4-oxocyclohexyl)-5H-pyrrolo[3,2-d]pyrimidine-4-carboxamide A solution of 2-(1H-imidazol-1-yl)-5H-pyrrolo[3,2-d]pyrimidine-4-carboxylic acid (2 g, 8.7 mmol, 1 equiv), T3P (11.1 g, 50% in EtOAc, 34.8 mmol, 4 equiv), DIEA (4.5 g, 34.8 mmol, 4 equiv), and 4-aminocyclohexan-1-one (983 mg, 8.7 mmol, 1.00 equiv) in DMF (20 mL) was stirred at RT for 1 h. The resulting mixture was concentrated under vacuum. The crude product was purified by reverse phase column eluting with $H_2O$/ACN followed by concentration to afford the title compound (984 mg, 35%) as a brown solid. LCMS: [M+H]$^+$ 324.15.

Step 2: 2-(1H-imidazol-1-yl)-N-((1r,4r)-4-((2,2,2-trifluoroethyl)amino)cyclohexyl)-5H-pyrrolo[3,2-d]pyrimidine-4-carboxamide and 2-(1H-imidazol-1-yl)-N-((1s,4s)-4-((2,2,2-trifluoroethyl)amino)cyclohexyl)-5H-pyrrolo[3,2-d]pyrimidine-4-carboxamide A solution of 2-(1H-imidazol-1-yl)-N-(4-oxocyclohexyl)-5H-pyrrolo[3,2-d]pyrimidine-4-carboxamide (1.3 g, 4 mmol, 1 equiv), 2,2,2-trifluoroethan-1-amine (792 mg, 8 mmol, 2.00 equiv), HOAc (360 mg, 4 mmol, 1.00 equiv), and Ti(Oi-Pr)$_4$ (1.14 g, 4 mmol, 1.00 equiv) in EtOH (5 mL) was stirred for 2 h at RT. NaBH$_3$CN (496 mg, 8 mmol, 2 equiv) was added and the mixture was stirred for a another 1 h at RT. The resulting mixture was concentrated under vacuum. The crude product was purified by reverse phase column eluting with $H_2O$/ACN (60:40) and further purified by Prep-HPLC with the following condition (Column: XBridge Prep OBD C18 Column, 30×150 mm 5 μm; Mobile Phase A: Water (10 mM NH$_4$HCO$_3$), Mobile Phase B: ACN; Flow rate: 60 mL/min; Gradient: 33% B to 63% B in 7 min; 254 nm to afford the title compounds with retention times of 5.68 minutes (Example 101) and 6.33 minutes (Example 102).

Example 101: 2-(1H-imidazol-1-yl)-N-((1r,4r)-4-((2,2,2-trifluoroethyl)amino)cyclohexyl)-5H-pyrrolo[3,2-d]pyrimidine-4-carboxamide (320 mg, 26%) as a white solid. LCMS: [M+H]$^+$ 408.20. $^1$H NMR (400 MHz, DMSO-d6) δ 12.04 (s, 1H), 8.97 (s, 1H), 8.91 (d, J=8.8 Hz, 1H), 8.21 (s, 1H), 8.00 (d, J=2.8 Hz, 1H), 7.11 (s, 1H), 6.69 (d, J=1.6 Hz, 1H), 3.97-3.81 (m, 1H), 3.33-3.26 (m, 2H), 2.56-2.51 (m, 1H), 2.39-2.25 (br, 1H), 2.00-1.90 (m, 2H), 1.87-1.68 (m, 2H), 1.68-1.57 (m, 2H), 1.17-1.04 (m, 2H).

Example 102: 2-(1H-imidazol-1-yl)-N-((1s,4s)-4-((2,2,2-trifluoroethyl)amino)cyclohexyl)-5H-pyrrolo[3,2-d]pyrimidine-4-carboxamide (166 mg, 14%) as a white solid. LCMS: [M+H]$^+$ 408.20. $^1$H NMR (400 MHz, DMSO-d6) δ 12.06 (s, 1H), 8.94 (s, 1H), 8.88 (d, J=8.3 Hz, 1H), 8.22 (s, 1H), 8.02 (d, J=3.1 Hz, 1H), 7.12 (s, 1H), 6.71 (d, J=3.1 Hz, 1H), 4.05-3.90 (m, 1H), 3.33-3.24 (m, 2H), 2.80 (s, 1H), 2.33-2.20 (m, 1H), 1.98-1.87 (m, 2H), 1.85-1.73 (m, 2H), 1.61-1.57 (m, 4H).

Example 103: 2-(1H-imidazol-1-yl)-N-((1r,4r)-4-((3,3,3-trifluoropropyl)amino)cyclohexyl)-5H-pyrrolo[3,2-d]pyrimidine-4-carboxamide

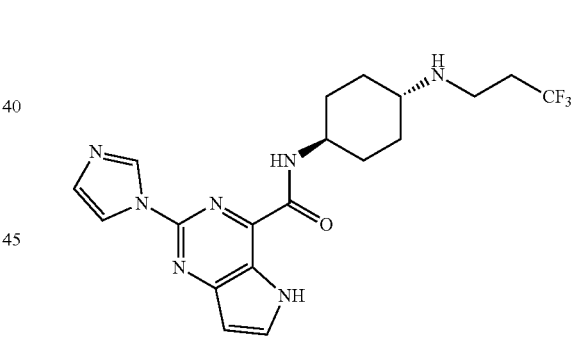

Step 1: tert-butyl ((1r,4r)-4-(2-(1H-imidazol-1-yl)-5H-pyrrolo[3,2-d]pyrimidine-4-carboxamido)cyclohexyl)carbamate A solution of ethyl 2-(1H-imidazol-1-yl)-5H-pyrrolo[3,2-d] pyrimidine-4-carboxylate (500 mg, 1.94 mmol, 1.00 equiv), tert-butyl ((1r,4r)-4-aminocyclohexyl)carbamate (833 mg, 3.89 mmol, 2.00 equiv), and AlMe$_3$ (1M in n-heptane, 5.9 mL, 5.832 mmol, 3 equiv) in toluene (10 mL) was stirred for 4 h at 80° C. After completion, the reaction was quenched by MeOH (150 mL). The solids were filtered off and the filtrate was concentrated under vacuum. The crude product was applied onto a silica gel column eluting with EtOAc/petroleum ether (2:1) to afford the title compound (263 mg, 32% yield) as a white solid. LCMS: [M+H]$^+$ 426.20.

Step 2: N-((1r,4r)-4-aminocyclohexyl)-2-(1H-imidazol-1-yl)-5H-pyrrolo[3,2-d]pyrimidine-4-carboxamide A solution of tert-butyl ((1r,4r)-4-(2-(1H-imidazol-1-yl)-5H-pyrrolo[3,2-d]pyrimidine-4-carboxamido)cyclohexyl)carbamate (263 mg, 0.618 mmol, 1.00 equiv) in HCl in 1,4-dioxane (4 M, 6 mL) was stirred for 6 h at RT. The resulting mixture was concentrated to afford the title compound (251 mg, 98% yield) as a light yellow solid. LCMS: [M+H]$^+$ 326.30.

Step 3: 2-(1H-imidazol-1-yl)-N-((1r,4r)-4-((3,3,3-trifluoropropyl)amino)cyclohexyl)-5H-pyrrolo[3,2-d]pyrimidine-4-carboxamide A mixture of N-((1r,4r)-4-aminocyclohexyl)-2-(1H-imidazol-1-yl)-5H-pyrrolo[3,2-d]pyrimidine-4-carboxamide (150 mg, 0.416 mmol, 1.00 equiv), 1,1,1-trifluoro-3-iodopropane (186 mg, 0.831 mmol, 2.00 equiv), and Cs$_2$CO$_3$ (406.15 mg, 1.247 mmol, 3.00 equiv) in ACN (6 mL) was stirred for 12 h at 70° C. in an oil bath. The solids were filtered, and the filtrate was concentrated under vacuum. The crude product was purified by reverse phase column with ACN/H$_2$O to afford the title compound (35 mg, 19%) as a white solid. LCMS: [M+H]$^+$ 422.15. $^1$H NMR (400 MHz, DMSO-d6) δ 12.08-12.04, (br, 1H), 8.97 (s, 1H), 8.88 (d, J=8.3 Hz, 1H), 8.23 (s, 1H), 8.02 (d, J=3.1 Hz, 1H), 7.12 (s, 1H), 6.70 (d, J=3.1 Hz, 1H), 3.95-3.82 (br, 1H), 3.32-3.30 (m, 1H), 2.77 (t, J=7.5 Hz, 2H), 2.45-2.31 (m, 3H), 1.97-1.91 (m, 2H), 1.88-1.80 (m, 2H), 1.69-1.58 (m, 2H), 1.16-1.10 (m, 2H).

Example 104: N-((1r,4r)-4-(cyanomethoxy)cyclohexyl)-2-(1H-imidazol-1-yl)-5H-pyrrolo[3,2-d]pyrimidine-4-carboxamide

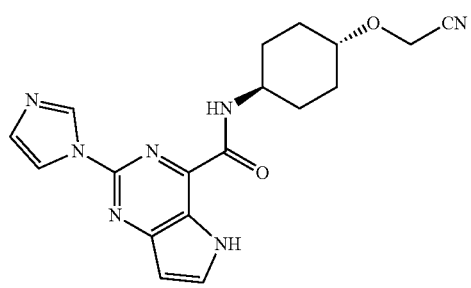

Step 1: 2-(((1r,4r)-4-(dibenzylamino)cyclohexyl)oxy)acetamide

A solution of 2-(((1r,4r)-4-(dibenzylamino)cyclohexyl)oxy)acetic acid (2.00 g, 5.14 mmol, 1.00 equiv), HATU (2.93 g, 7.71 mmol, 1.50 equiv), DIEA (2.66 g, 20.57 mmol, 4.00 equiv), and NH$_4$Cl (825 mg, 15.42 mmol, 3.00 equiv) in DMF (8 mL) was stirred for 1 h at 25° C. After concentrating under vacuum, the crude product was purified by C18 reverse phase chromatography eluting with H$_2$O/ACN to afford the title compound (1.27 g, 70%) as a white solid. LCMS: [M+H]$^+$ 353.15.

Step 2: 2-(((1r,4r)-4-aminocyclohexyl)oxy)acetamide

Under hydrogen, a mixture of 2-(((1r,4r)-4-(dibenzylamino)cyclohexyl)oxy)acetamide (1.23 g, 3.49 mmol, 1.00 equiv), Pd(OH)$_2$/C (400 mg, 2.63 mmol, 0.82 equiv), HOAc (1 mL) in EtOH (15 mL) was stirred for 1 h at 25° C. The solids were filtered and the filtrate was concentrated under vacuum to afford the title compound (600 mg, 67%) as a white solid. LCMS: [M+H]$^+$ 173.10.

Step 3: N-((1r,4r)-4-(2-amino-2-oxoethoxy)cyclohexyl)-2-(1H-imidazol-1-yl)-5H-pyrrolo[3,2-d]pyrimidine-4-carboxamide A solution of 2-(1H-imidazol-1-yl)-5H-pyrrolo[3,2-d]pyrimidine-4-carboxylic acid (100 mg, 0.44 mmol, 1.00 equiv), HATU (249 mg, 0.66 mmol, 1.50 equiv), DIEA (282 mg, 2.2 mmol, 5.00 equiv), and 2-(((1r,4r)-4-aminocyclohexyl)oxy)acetamide (76 mg, 0.44 mmol, 1.00 equiv) in DMF (5 mL) was stirred for 1 h at 25° C. The crude product was concentrated under vacuum and purified by reverse phase column eluting with H$_2$O/ACN to afford the title compound (52 mg, 31%) as a white solid. LCMS: [M+H]$^+$ 384.15.

Step 4: N-((1r,4r)-4-(cyanomethoxy)cyclohexyl)-2-(1H-imidazol-1-yl)-5H-pyrrolo[3,2-d]pyrimidine-4-carboxamide A solution of N-((1r,4r)-4-(2-amino-2-oxoethoxy)cyclohexyl)-2-(1H-imidazol-1-yl)-5H-pyrrolo[3,2-d]pyrimidine-4-carboxamide (42 mg, 0.11 mmol, 1.00 equiv), trifluoroacetic anhydride (115 mg, 0.55 mmol, 5.00 equiv), and pyridine (17 mg, 0.22 mmol, 2.00 equiv) in THF (15 mL) was stirred for 1 h at 0° C. The mixture was concentrated under vacuum and purified by reverse phase column eluting with H$_2$O/ACN to afford the title compound (5 mg, 13%) as a white solid. LCMS: [M+H]$^+$ 366.20. $^1$H NMR (300 MHz, DMSO-d$_6$) δ 12.08 (s, 1H), 8.97 (s, 1H), 8.92 (d, J=8.7 Hz, 1H), 8.22 (s, 1H), 8.02 (t, J=6.0 Hz, 1H), 7.13 (s, 1H), 6.70 (dd, J=1.8, 1.8 Hz, 1H), 4.54 (s, 2H), 4.10-3.81 (m, 1H), 3.61-3.52 (m, 1H), 2.23-2.09 (m, 2H), 2.01-1.83 (m, 2H), 1.78-1.68 (m, 2H), 1.52-1.28 (m, 2H).

Example 105: N-((1r,4r)-4-((2,2-difluoroethyl)amino)cyclohexyl)-2-(1H-imidazol-1-yl)-5H-pyrrolo[3,2-d]pyrimidine-4-carboxamide and

Example 106: N-((1s,4s)-4-((2,2-difluoroethyl)amino)cyclohexyl)-2-(1H-imidazol-1-yl)-5H-pyrrolo[3,2-d]pyrimidine-4-carboxamide Example 105

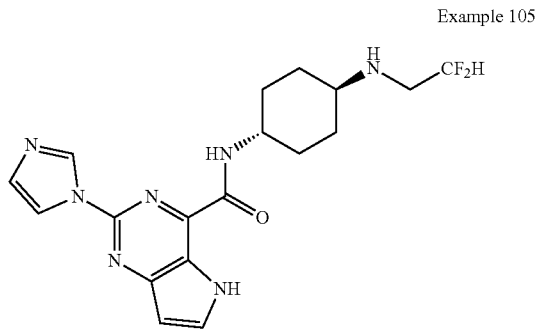

Example 106

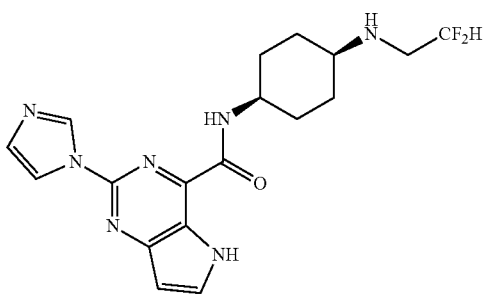

Step 1: N-((1r,4r)-4-((2,2-difluoroethyl)amino)cyclohexyl)-2-(1H-imidazol-1-yl)-5H-pyrrolo[3,2-d]pyrimidine-4-carboxamide and N-((1s,4s)-4-((2,2-difluoroethyl)amino)cyclohexyl)-2-(1H-imidazol-1-yl)-5H-pyrrolo[3,2-d]pyrimidine-4-carboxamide A solution of 2-(1H-imidazol-1-yl)-N-(4-oxocyclohexyl)-5H-pyrrolo[3,2-d]pyrimidine-4-carboxamide (Examples 101-102, Step 1; 194 mg, 0.599 mmol, 1.00 equiv), 2,2-difluoroethanamine (73 mg, 0.899 mmol, 1.50 equiv), HOAc (35.9 mg, 0.599 mmol, 1.00 equiv), and Ti(Oi-Pr)$_4$ (170 mg, 0.599 mmol, 1.00 equiv) in EtOH (7.00 mL) was stirred for 1 h at 25° C. NaBH$_3$CN (57 mg, 0.899 mmol, 1.50 equiv) was added, and the resulting solution was stirred for 1 h at 25° C. After concentration, the crude product was purified by reverse phase column eluting with H$_2$O/ACN (63:37) and further purified by Prep-HPLC with the following conditions (Column: Xselect CSH OBD Column 30*150 mm, 5 μm. Mobile Phase A: Water/10 mM NH$_4$HCO$_3$, Mobile Phase B: ACN. Flow rate: 60 mL/min; Gradient: 30% B to 40% B in 7 min; 254/220 nm) to afford title compounds with retention times of 6.28 minutes (Example 105) and 7.67 minutes (Example 106).

Example 105: N-((1r,4r)-4-((2,2-difluoroethyl)amino)cyclohexyl)-2-(1H-imidazol-1-yl)-5H-pyrrolo[3,2-d]pyrimidine-4-carboxamide (58 mg, 25% yield) as a light yellow solid. LCMS: [M+H]$^+$ 390.10 $^1$H-NMR (300 MHz, DMSO-d6) δ 12.06 (s, 1H), 8.97 (s, 1H), 8.91 (d, J=8.7 Hz, 1H), 8.23 (t, J=2.4 Hz, 1H), 8.02 (t, J=5.7 Hz, 1H), 7.13 (t, J=2.1 Hz, 1H), 6.70 (d, J=2.1 Hz, 1H), 6.20-5.70 (m, 1H), 4.01-3.80 (m, 1H), 3.31-3.28 (m, 1H), 2.99-2.87 (m, 2H), 2.50-2.40 (m, 1H), 2.10-1.96 (m, 2H), 1.95-1.86 (m, 2H), 1.64-1.55 (m, 2H), 1.28-1.12 (m, 2H)

Example 106: N-((1s,4s)-4-((2,2-difluoroethyl)amino)cyclohexyl)-2-(1H-imidazol-1-yl)-5H-pyrrolo[3,2-d]pyrimidine-4-carboxamide (38 mg, 16% yield) as a white solid. LCMS: [M+H]$^+$ 490.10. $^1$H-NMR (300 MHz, DMSO-d6) δ 12.07 (s, 1H), 8.95 (s, 1H), 8.87 (d, J=8.1 Hz, 1H), 8.22 (t, J=2.7 Hz, 1H), 8.02 (t, J=6.0 Hz, 1H), 7.13 (t, J=2.1 Hz, 1H), 6.70 (d, J=1.5 Hz, 1H), 6.22-5.80 (m, 1H), 4.10-3.90 (m, 1H), 3.31-3.28 (m, 1H), 2.90-2.80 (m, 2H), 2.77-2.70 (m, 1H), 2.08-1.95 (m, 2H), 1.80-1.70 (m, 2H), 1.62-1.52 (m, 4H).

Example 107: N-(4,4-difluorocyclohexyl)-5-(1H-imidazol-1-yl)-1H-pyrazolo[3,4-c]pyridine-7-carboxamide

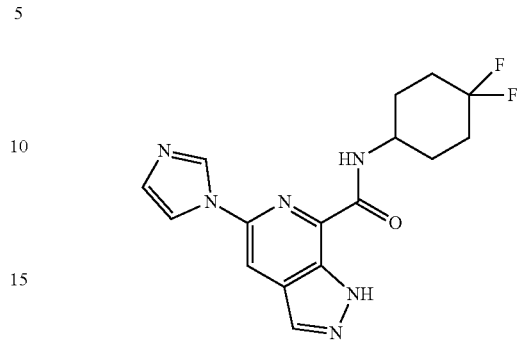

A solution of 5-(imidazol-1-yl)-1H-pyrazolo[3,4-c]pyridine-7-carboxylic acid (100.00 mg, 0.436 mmol, 1.00 equiv), DIEA (169 mg, 1.309 mmol, 3.00 equiv), HATU (199 mg, 0.524 mmol, 1.20 equiv) and 4,4-difluorocyclohexan-1-amine (59 mg, 0.436 mmol, 1.00 equiv) in DMF (3.00 mL) was stirred for 1 h at RT. The resulting solution was concentrated and the mixture was purified by a silica gel column with DCM/MeOH (93:7). The crude product was further purified by Prep-HPLC. Column: XBridge Prep OBD C18 Column, 30*150 mm, 5 μm. Mobile Phase: A: Water/10 mM NH$_4$HCO$_3$, B: ACN. Flow rate: 60 mL/min. Gradient: 23% B to 53% B in 10 min; 254 nm; to afford the title compound (65 mg 43% yield) with retention times of 8.52 minutes as a white solid. LCMS: [M+H]$^+$ 347.20. $^1$H NMR (400 MHz, DMSO-d$_6$) δ 13.85 (s, 1H), 8.94 (s, 1H), 8.84 (d, J=8.6 Hz, 1H), 8.38 (d, J=2.6 Hz, 2H), 8.23 (s, 1H), 7.15 (s, 1H), 4.22-4.08 (m, 1H), 2.15-1.86 (m, 8H).

Example 108: 2-(1H-imidazol-1-yl)-N-((1r,4r)-4-(2-methoxyethoxy)cyclohexyl)-6-methyl-5H-pyrrolo[3,2-d]pyrimidine-4-carboxamide

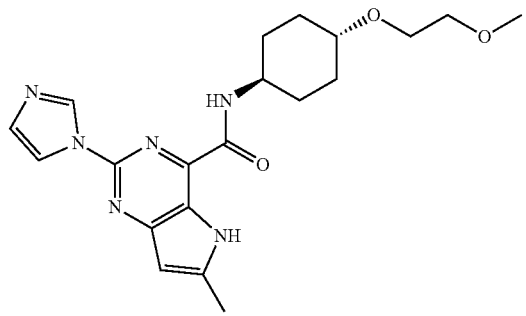

Step 1: 2-chloro-4-(1-ethoxyvinyl)-6-methyl-5H-pyrrolo[3,2-d]pyrimidine

Under nitrogen, a solution of 2,4-dichloro-6-methyl-5H-pyrrolo[3,2-d]pyrimidine (2.00 g, 9.899 mmol, 1.00 equiv), tributyl(1-ethoxyvinyl)stannane (3.93 g, 10.882 mmol, 1.10 equiv), and Pd(PPh$_3$)$_2$Cl$_2$ (0.21 g, 0.297 mmol, 0.03 equiv) in DMF (50 mL) was stirred for 1 h at 80° C. The solution was cooled to RT and quenched with saturated aqueous KF (100 mL). The insoluble solids were filtered. The filtrate was combined and extracted with EtOAc (100 mL×3). The organic layers were combined and concentrated. The crude product was applied onto a silica gel column eluting with EtOAc/petroleum ether (3/7) to afford (2.2 g, 94% yield) of the title compound as a white solid. LCMS: [M+H]+ 238.10.

Step 2. 4-(1-ethoxyvinyl)-2-(1H-imidazol-1-yl)-6-methyl-5H-pyrrolo[3,2-d]pyrimidine Under nitrogen, a mixture of 2-chloro-4-(1-ethoxyvinyl)-6-methyl-5H-pyrrolo[3,2-d]pyrimidine (2.70 g, 11.359 mmol, 1.00 equiv), 1H-imidazole (3.87 g, 56.846 mmol, 5.00 equiv), Pd$_2$(dba)$_3$CHCl$_3$ (1.18 g, 1.136 mmol, 0.10 equiv), t-BuXPhos (0.96 g, 2.272 mmol, 0.20 equiv), K$_3$PO$_4$ (4.82 g, 22.719 mmol, 2 equiv) in toluene (100 mL) was stirred at 110° C. for 3 h. The mixture was concentrated, diluted with water (200 mL), and extracted with EtOAc (100 mL×3). The organic layers were combined, dried over Na$_2$SO$_4$, and concentrated under reduced pressure. The crude product was applied onto a silica gel column eluting with EtOAc:petroleum ether (1:1) to afford (2.32 g, 76% yield) of the title compound as a white solid. LCMS: [M+H]+ 270.15.

Step 3: ethyl 2-(1H-imidazol-1-yl)-6-methyl-5H-pyrrolo[3,2-d]pyrimidine-4-carboxylate and 2-(1H-imidazol-1-yl)-6-methyl-5H-pyrrolo[3,2-d]pyrimidine-4-carboxylic acid A mixture of 4-(1-ethoxyvinyl)-2-(1H-imidazol-1-yl)-6-methyl-5H-pyrrolo[3,2-d]pyrimidine (2.30 g, 8.540 mmol, 1.00 equiv), KMnO$_4$ (1.08 g, 6.834 mmol, 0.80 equiv), and NaIO$_4$ (3.65 g, 17.081 mmol, 2 equiv) in dioxane (100 mL) and water (50 mL) was stirred at 0° C. for 1 h. The reaction mixture was diluted with water (50 mL) and extracted with EtOAc (100 mL×3). The organic layers were combined, dried over Na$_2$SO$_4$, and concentrated to afford 1.2 g of crude ester. LCMS: [M+H]+ 272.13. The aqueous portion was concentrated and purified by reverse phase column to afford 600 mg of the acid as a white solid. LCMS: [M+H]+ 244.10.

Step 4. 2-(1H-imidazol-1-yl)-N-((1r,4r)-4-(2-methoxyethoxy)cyclohexyl)-6-methyl-5H-pyrrolo[3,2-d]pyrimidine-4-carboxamide A solution of ethyl 2-(1H-imidazol-1-yl)-6-methyl-5H-pyrrolo[3,2-d]pyrimidine-4-carboxylate (100.00 mg, 0.369 mmol, 1.00 equiv), (1r,4r)-4-(2-methoxyethoxy)cyclohexan-1-amine (70.25 mg, 0.405 mmol, 1.10 equiv), and AlMe$_3$ (1M in n-heptane, 1.1 mL, 1.106 mmol, 3 equiv) in toluene (6 mL) was stirred at 80° C. for 1.5 h. The reaction was quenched with MeOH. The solids were filtered and the filtrate was concentrated. The crude product was purified by reverse phase column eluting with ACN/H$_2$O (2/3) followed by lyophilization to afford the title compound (66 mg, 45% yield) as a white solid. LCMS: [M+H]+ 399.3. $^1$H NMR (300 MHz, DMSO-d$_6$) δ11.94 (s, 1H), 8.93 (s, 1H), 8.85 (d, J=8.6 Hz, 1H), 8.20 (t, J=1.4 Hz, 1H), 7.11 (d, J=1.2 Hz, 1H), 6.45 (s, 1H), 4.01-3.82 (m, 1H), 3.57 (dd, J=5.9, 3.7 Hz, 2H), 3.44 (dd, J=5.9, 3.7 Hz, 2H), 3.30-3.28 (m, 1H), 3.26 (s, 3H), 2.56 (s, 3H), 2.11-2.02 (m, 2H), 1.90-1.81 (m, 2H), 1.76-1.55 (m, 2H), 1.35-1.25 (m, 2H).

Example 109: N-((1r,4r)-4-(2-hydroxypropan-2-yl)cyclohexyl)-5-(1H-imidazol-1-yl)-1H-pyrazolo[3,4-c]pyridine-7-carboxamide

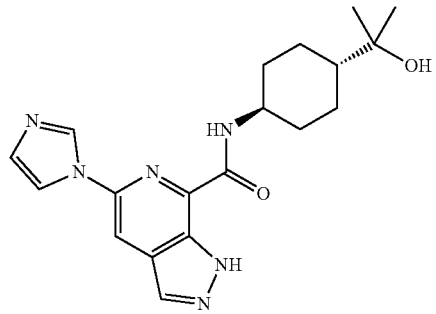 [SMILES: CC(C)(O)[C@H]1CC[C@H](NC(=O)c2nc(-n3ccnc3)cc3cn[nH]c23)CC1]

Step 1: ethyl (1r,4r)-4-(dibenzylamino)cyclohexane-1-carboxylate

A mixture of ethyl (1r,4r)-4-aminocyclohexane-1-carboxylate (3.00 g, 17.5 mmol, 1.00 equiv), benzyl bromide (6.30 g, 37.05 mmol, 2.1 equiv), and K$_2$CO$_3$ (7.20 g, 52.174 mmol, 3.00 equiv) in ACN (30 mL) was stirred for 2 h at 80° C. The reaction was quenched with water and filtered to afford the title compound (3.4 g, 55% yield) as a white solid. LCMS: [M+H]+ 352.15.

Step 2: 2-((1r,4r)-4-(dibenzylamino)cyclohexyl)propan-2-ol

Under nitrogen, to a solution of ethyl (1r,4r)-4-(dibenzylamino)cyclohexane-1-carboxylate (3.00 g, 8.547 mmol, 1.00 equiv) in THF (50.00 mL), was added CH$_3$MgBr (3 M, 8.5 mL, 25.424 mmol, 3.00 equiv) dropwise at −10° C. in an ice/salt bath, and the resulting solution was stirred for 3 h at 10° C. The reaction was then quenched by the addition of 50 mL H$_2$O and extracted with of EtOAc (3×50 mL.) The organic layers were combined, dried over anhydrous sodium sulfate, and concentrated under vacuum. The crude product was applied onto a silica gel column with EtOAc/petroleum ether (1:4) to afford the title compound (2.6 g, 93%) as a white solid. LCMS: [M+H]+ 338.15.

Step 3: 2-((1r,4r)-4-aminocyclohexyl)propan-2-ol

Under hydrogen, a mixture of 2-((1r,4r)-4-(dibenzylamino)cyclohexyl)propan-2-ol (2.6 g, 7.715 mmol, 1.00 equiv) and Pd(OH)$_2$/C (1.00 g, 7.142 mmol, 1.1 equiv) in EtOH (100 mL) was stirred for 2 h at RT. The solids were filtered and the filtrate was concentrated to afford the title compound (1.16 g, 97%) as a white solid. LCMS: [M+H]+ 158.20.

Step 4: N-((1r,4r)-4-(2-hydroxypropan-2-yl)cyclohexyl)-5-(1H-imidazol-1-yl)-1H-pyrazolo[3,4-c]pyridine-7-carboxamide A solution of 5-(1H-imidazol-1-yl)-1H-pyrazolo[3,4-c]pyridine-7-carboxylic acid (290 mg, 1.266 mmol, 1.00 equiv), 2-((1r,4r)-4-aminocyclohexyl)propan-2-ol (200.mg, 1.274 mmol, 1.00 equiv), DIEA (580.0 mg, 4.496 mmol, 3.00 equiv), and HATU (616 mg, 1.621 mmol, 1.20 equiv) in DMF (3 mL) was stirred at RT for 1.5 h. The resulting mixture was quenched with water and extracted with EtOAc (3×20 mL). The organic layers were combined, dried over anhydrous sodium sulfate and concentrated under vacuum. The crude product was purified by reverse phase column eluting with H$_2$O/ACN to afford the title compound (20 mg, 4%) as a white solid. LCMS: [M+H]$^+$ 369.20; $^1$H NMR (300 MHz, DMSO-d$_6$) δ 13.80 (s, 1H), 8.91 (s, 1H), 8.68 (d, J=8.7 Hz, 1H), 8.33 (d, J=4.8 Hz, 2H), 8.19 (t, J=1.2 Hz, 1H), 7.12 (t, J=1.2 Hz, 1H), 4.06 (s, 1H), 3.98-3.81 (m, 1H), 2.00-1.80 (m, 4H), 1.63-1.45 (m, 2H), 1.26-1.07 (m, 3H), 1.07-1.02 (m, 6H).

Example 110: 2-(1H-imidazol-1-yl)-N-((1r,4r)-4-(methyl(3,3,3-trifluoropropyl)amino)cyclohexyl)-5H-pyrrolo[3,2-d]pyrimidine-4-carboxamide and Example 111: 2-(1H-imidazol-1-yl)-N-((1s,4s)-4-(methyl(3,3,3-trifluoropropyl)amino)cyclohexyl)-5H-pyrrolo[3,2-d]pyrimidine-4-carboxamide

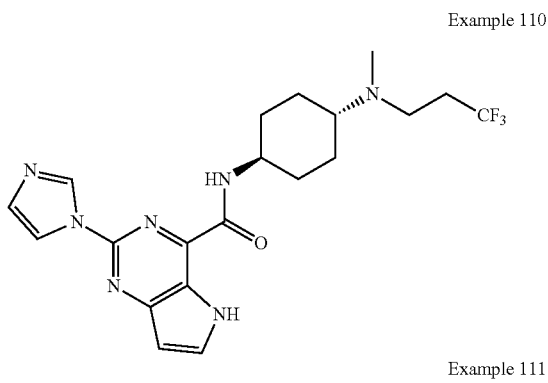

Example 110

Example 111

Step 1: 2-(1H-imidazol-1-yl)-N-((1r,4r)-4-(methyl(3,3,3-tri fluoropropyl)amino)cyclohexyl)-5H-pyrrolo[3,2-d]pyrimidine-4-carboxamide and 2-(1H-imidazol-1-yl)-N-((1s,4s)-4-(methyl(3,3,3-trifluoropropyl)amino)cyclohexyl)-5H-pyrrolo[3,2-d]pyrimidine-4-carboxamide A solution of 2-(1H-imidazol-1-yl)-N-(4-oxocyclohexyl)-5H-pyrrolo[3,2-d]pyrimidine-4-carboxamide (Examples 101-102, Step 1; 201 mg, 0.62 mmol, 1 equiv), 3,3,3-trifluoropropan-1-amine (105 mg, 0.93 mmol, 1.5 equiv), HOAc (37 mg, 0.62 mmol, 1.0 equiv), and Ti(Oi-Pr)$_4$ (176 mg, 0.62 mmol, 1.0 equiv) in EtOH (10 mL) was stirred for 1 h at 25° C. NaBH$_3$CN (58 mg, 0.93 mmol, 1.5 equiv) was added to the resulting solution and the mixture was stirred for 1 h at 25° C. Paraformaldehyde (55 mg, 1.86 mmol, 3 equiv) and NaBH$_3$CN (117 mg, 1.86 mmol, 3.00 equiv) was added and the mixture was stirred for another 2 h at 60° C. After completion, the resulting solution was concentrated. The crude product was purified by reverse phase column eluting with H$_2$O/ACN (65:35) and further purified by Prep-HPLC with the following condition (Column: XBridge Prep OBD C18 Column, 19*250 mm, 5 μm. Mobile Phase: A: Water (10 mM NH$_4$HCO$_3$+0.1% NH$_3$OH), B: ACN. Flow rate: 25 mL/min; Gradient: 37% B to 42% B in 10 min; 220 nm) to afford title compounds with retention times of 9.27 minutes (Example 110) and 10.00 minutes (Example 111).

Example 110: 2-(1H-imidazol-1-yl)-N-((1r,4r)-4-(methyl(3,3,3-trifluoropropyl)amino)cyclohexyl)-5H-pyrrolo[3,2-d]pyrimidine-4-carboxamide (22 mg, 11% yield) as a white solid. LCMS: [M+H]$^+$ 436.25. $^1$H NMR (300 MHz, DMSO-d6) δ 12.05 (s, 1H), 8.96 (s, 1H), 8.89 (d, J=8.4 Hz, 1H), 8.22 (d, J=1.8 Hz, 1H), 8.01 (t, J=6.0 Hz, 1H), 7.12 (s, 1H), 6.70 (d, J=1.5 Hz, 1H), 3.98-3.80 (br, 1H), 2.72-2.61 (m, 3H), 2.53-2.38 (m, 2H), 2.30-2.23 (m, 3H), 1.98-1.90 (m, 2H), 1.89-1.75 (m, 2H), 1.70-1.51 (m, 2H), 1.50-1.30 (m, 2H).

Example 111: 2-(1H-imidazol-1-yl)-N-((1s,4s)-4-(methyl(3,3,3-trifluoropropyl)amino)cyclohexyl)-5H-pyrrolo[3,2-d]pyrimidine-4-carboxamide (9 mg, 4% yield) as a white solid. LCMS: [M+H]$^+$ 436.25. $^1$H NMR (300 MHz, DMSO-d6) δ 12.07 (s, 1H), 8.91 (s, 1H), 8.80 (br, 1H), 8.19 (s, 1H), 8.01 (t, J=6.0 Hz, 1H), 7.12 (s, 1H), 6.70 (d, J=1.5 Hz, 1H), 4.18-3.99 (br, 1H), 3.66-3.50 (m, 1H), 2.90-2.70 (m, 2H), 2.50-2.33 (m, 2H), 2.30-2.20 (m, 3H), 2.02-1.80 (m, 4H), 1.77-1.40 (m, 4H).

Example 112: 2-(1H-imidazol-1-yl)-N-((1r,4r)-4-(methyl(2,2,2-trifluoroethyl)amino)cyclohexyl)-5H-pyrrolo[3,2-d]pyrimidine-4-carboxamide and Example 113: 2-(1H-imidazol-1-yl)-N-((1s,4s)-4-(methyl(2,2,2-trifluoroethyl)amino)cyclohexyl)-5H-pyrrolo[3,2-d]pyrimidine-4-carboxamide

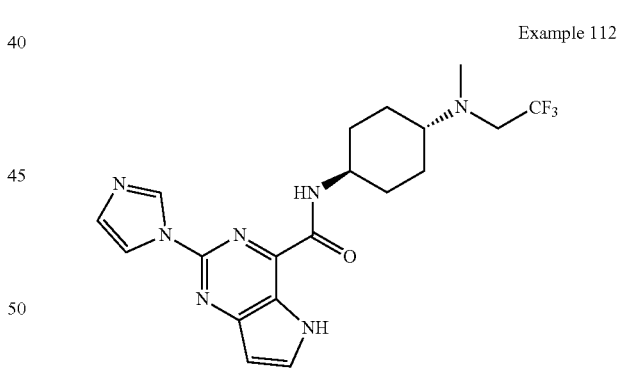

Example 112

Example 113

A solution of 2-(1H-imidazol-1-yl)-N-(4-oxocyclohexyl)-5H-pyrrolo[3,2-d]pyrimidine-4-carboxamide (Examples 101-102, Step 1; 150 mg, 0.462 mmol, 1.00 equiv), 2,2,2-trifluoroethan-1-amine (69 mg, 0.69 mmol, 1.50 equiv), HOAc (28 mg, 0.46 mmol, 1.00 equiv), and Ti(Oi-Pr)$_4$ (132 mg, 0.46 mmol, 1.00 equiv) in EtOH (10 mL) was stirred for 1 h at 25° C. NaBH$_3$CN (44 mg, 0.69 mmol, 1.50 equiv) was added to the resulting solution and the mixture was stirred for another 1 h at 25° C. Paraformaldehyde (100 mg, 1.105 mmol, 3.00 equiv) and NaBH$_3$CN (69 mg, 1.105 mmol, 3.00 equiv) was added and the mixture was stirred for another 1 h at 55° C. After completion, the resulting solution was concentrated. The crude product was purified by reverse phase column eluting with H$_2$O/ACN (50:50) and further purified by Prep-HPLC with the following conditions (Column: Xcelect CSH F-pheny OBD Column, 19*250 mm, 5 μm; Mobile Phase: A: Water/10 mM NH$_4$HCO$_3$, B: MeOH. Flow rate: 25 mL/min. Gradient: 67% B to 81% B in 7 min; 254 nm) to afford title compounds with retention times of 6.23 minutes (Example 112) and 7.00 minutes (Example 113).

Example 112: 2-(1H-imidazol-1-yl)-N-((1r,4r)-4-(methyl (2,2,2-trifluoroethyl)amino)cyclohexyl)-5H-pyrrolo[3,2-d]pyrimidine-4-carboxamide (24 mg 15% yield) as a white solid. LCMS: [M+H]$^+$ 422.20. $^1$H NMR (300 MHz, DMSO-d6) δ 12.09 (s, 1H), 8.89 (s, 1H), 8.79 (d, J=7.8 Hz, 1H), 8.18 (t, J=2.7 Hz, 1H), 8.02 (d, J=2.4 Hz, 1H), 7.12 (t, J=2.4 Hz, 1H), 6.71 (d, J=3.0 Hz, 1H), 4.10 (br, 1H), 3.28-3.19 (m, 2H), 2.73-2.50 (m, 1H), 2.40 (s, 3H), 2.01-1.89 (m, 2H), 1.88-1.70 (m, 2H), 1.62-1.54 (m, 4H).

Example 113: 2-(1H-imidazol-1-yl)-N-((1s,4s)-4-(methyl (2,2,2-trifluoroethyl)amino)cyclohexyl)-5H-pyrrolo[3,2-d]pyrimidine-4-carboxamide (5 mg 3%) as a white solid. LCMS: [M+H]$^+$ 422.20. 1H NMR (300 MHz, DMSO-d6) δ 12.05 (s, 1H), 8.96 (s, 1H), 8.89 (d, J=8.4 Hz, 1H), 8.22 (t, J=2.7 Hz, 1H), 8.02 (d, J=6.0 Hz 1H), 7.13 (t, J=2.4 Hz, 1H), 6.70 (t, J=3.0 Hz, 1H), 4.05 (br, 1H), 3.25-3.10 (m, 2H), 2.60-2.50 (m, 1H), 2.40 (s, 3H), 1.99-1.90 (m, 2H), 1.90-1.81 (m, 2H), 1.70-1.62 (m, 2H), 1.51-1.32 (m, 2H).

Example 114: N-((1r,4r)-4-(acetamidomethyl)cyclohexyl)-2-(1H-imidazol-1-yl)-5H-pyrrolo[3,2-d]pyrimidine-4-carboxamide

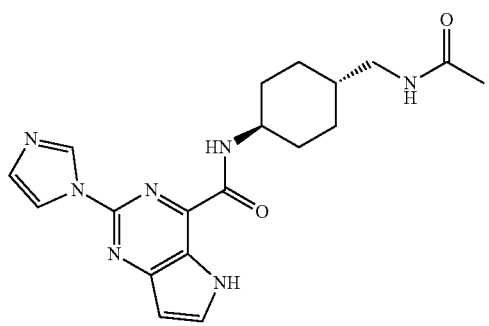 [SMILES: CC(=O)NC[C@H]1CC[C@H](NC(=O)c2nc(-n3ccnc3)nc3cc[nH]c23)CC1]

Step 1: tert-butyl (((1r,4r)-4-(2-(1H-imidazol-1-yl)-5H-pyrrolo[3,2-d]pyrimidine-4-carboxamido)cyclohexyl)methyl)carbamate A solution of 2-(1H-imidazol-1-yl)-5H-pyrrolo[3,2-d]pyrimidine-4-carboxylic acid (201 mg, 0.876 mmol, 1.00 equiv), tert-butyl (((1r,4r)-4-aminocyclohexyl)methyl)carbamate (200 mg, 0.876 mmol, 1.00 equiv), DIEA (340 mg, 2.628 mmol, 3.00 equiv), and HATU (500 mg, 1.314 mmol, 1.50 equiv) in DMF (4 mL) was stirred for 1 h at RT. The crude product was purified by reverse phase column to afford the title compound (170 mg, 44%) as a yellow solid. LCMS: [M+H]$^+$ 440.15.

Step 2: N-((1r,4r)-4-(aminomethyl)cyclohexyl)-2-(1H-imidazol-1-yl)-5H-pyrrolo[3,2-d]pyrimidine-4-carboxamide A solution of tert-butyl (((1r,4r)-4-(2-(1H-imidazol-1-yl)-5H-pyrrolo[3,2-d]pyrimidine-4-carboxamido)cyclohexyl) methyl)carbamate (160 mg, 0.364 mmol, 1.00 equiv) in HCl in 1,4-dioxane (4 M, 6 mL) was stirred for 1 h at RT. The resulting mixture was concentrated under vacuum to afford the title compound (110 mg, 89%) as a white solid. LCMS: [M+H]$^+$ 340.15.

Step 3: N-((1r,4r)-4-(acetamidomethyl)cyclohexyl)-2-(1H-imidazol-1-yl)-5H-pyrrolo[3,2-d]pyrimidine-4-carboxamide A solution of N-((1r,4r)-4-(aminomethyl)cyclohexyl)-2-(1H-imidazol-1-yl)-5H-pyrrolo[3,2-d]pyrimidine-4-carboxamide (100 mg, 0.295 mmol, 1.00 equiv), TEA (60 mg, 0.589 mmol, 2.00 equiv), acetic anhydride (60 mg, 0.589 mmol, 2.00 equiv) in DCM (4 mL) was stirred for 2 h at RT. The resulting mixture was concentrated under vacuum and purified by reverse phase column to afford the title compound (27 mg, 24%) as a white solid. LCMS: [M+H]$^+$ 382.20; $^1$H NMR (400 MHz, DMSO-d6) δ 12.06 (s, 1H), 8.98 (s, 1H), 8.92 (d, J=8.7 Hz, 1H), 8.24 (s, 1H), 8.02 (t, J=3.5, 2.6 Hz, 1H), 7.83 (t, J=5.7 Hz, 1H), 7.13 (s, 1H), 6.71 (dd, J=3.2 Hz, 1.2 Hz, 1H), 3.98-3.89 (m, 1H), 2.95 (t, J=6.2 Hz, 2H), 1.94-1.91 (m, 2H), 1.90 (s, 3H), 1.89-1.83 (m, 2H), 1.60-1.51 (m, 2H), 1.42-1.30 (m, 1H), 1.12-0.95 (m, 2H).

Example 115: 5-(1H-imidazol-1-yl)-N-((1r,4r)-4-((2,2,2-trifluoroethyl)amino)cyclohexyl)-1H-pyrazolo[3,4-c]pyridine-7-carboxamide and Example 116: 5-(1H-imidazol-1-yl)-N-((1s,4s)-4-((2,2,2-trifluoroethyl)amino)cyclohexyl)-1H-pyrazolo[3,4-c]pyridine-7-carboxamide Example 115

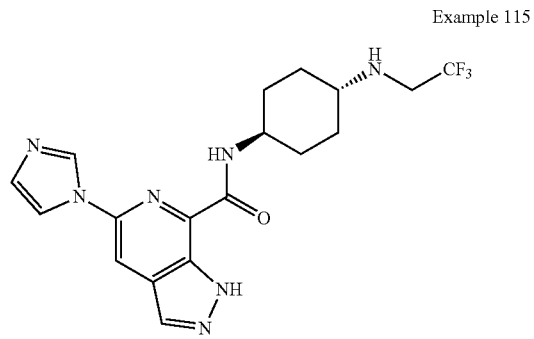

Example 116

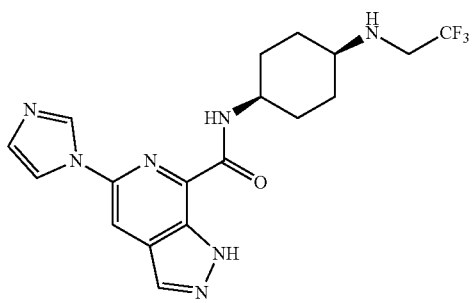

Step 1: 5-(1H-imidazol-1-yl)-N-(4-oxocyclohexyl)-1H-pyrazolo[3,4-c]pyridine-7-carboxamide A solution of 5-(1H-imidazol-1-yl)-1H-pyrazolo[3,4-c]pyridine-7-carboxylic acid (500 mg, 2.182 mmol, 1.00 equiv), DIEA (846 mg, 6.545 mmol, 3.00 equiv), 4-aminocyclohexan-1-one hydrochloride (494 mg, 4.363 mmol, 2.00 equiv) and HATU (995 mg, 2.618 mmol, 1.20 equiv) in DMF (1.5 mL) was stirred for 1 h at RT. The mixture was concentrated. The crude product was applied onto a silica gel column eluting with DCM/MeOH (92:8) to afford 1.5 g of the title compound as a crude brown solid. LCMS: [M+H]$^+$ 325.10.

Step 2: 5-(1H-imidazol-1-yl)-N-((1r,4r)-4-((2,2,2-trifluoroethyl)amino)cyclohexyl)-1H-pyrazolo[3,4-c]pyridine-7-carboxamide and 5-(1H-imidazo-1-yl)-N-((1s,4s)-4-((2,2,2-trifluoroethyl)amino)cyclohexyl)-1H-pyrazolo[3,4-c]pyridine-7-carboxamide A solution of 5-(1H-imidazol-1-yl)-N-(4-oxocyclohexyl)-1H-pyrazolo[3,4-c]pyridine-7-carboxamide (200 mg, 0.617 mmol, 1.00 equiv), Ti(Oi-Pr)$_4$ (175 mg, 0.617 mmol, 1.00 equiv), AcOH (37 mg, 0.617 mmol, 1.00 equiv) and 2,2,2-trifluoroethan-1-amine (122 mg, 1.233 mmol, 2.00 equiv) in EtOH (5 mL) was stirred for 1 h at RT. This was followed by the addition of NaBH$_3$CN (78 mg, 1.233 mmol, 2.00 equiv) at RT. The resulting solution was stirred for another 1 h at 70° C. in an oil bath. The resulting solution was concentrated. The crude product was applied on silica gel column eluting with DCM/MeOH (97:3). The crude product was purified by Prep-HPLC with the following condition (Column: Xselect CSH OBD Column 30*150 mm, 5 μm. Mobile Phase: A: Water/10 mM NH$_4$HCO$_3$, B: ACN. Flow rate: 60 mL/min. Gradient: 26% B to 48% B in 8 min; 254/220 nm) to afford title compounds to afford title compounds with retention times of 9.37 minutes (Example 115) and 10.27 minutes (Example 116).

Example 115: 5-(1H-imidazol-1-yl)-N-((1r,4r)-4-((2,2,2-trifluoroethyl)amino)cyclohexyl)-1H-pyrazolo[3,4-c]pyridine-7-carboxamide (54 mg, 21% yield) as a white solid. LCMS: [M+H]$^+$ 408.20. $^1$H NMR (300 MHz, DMSO-d$_6$) δ 13.79 (s, 1H), 8.88 (t, J=1.1 Hz, 1H), 8.69 (d, J=8.6 Hz, 1H), 8.33 (d, J=4.4 Hz, 2H), 8.19 (t, J=1.4 Hz, 1H), 7.12 (t, J=1.2 Hz, 1H), 3.97-3.81 (m, 1H), 3.24-3.11 (m, 2H), 2.45-2.39 (m, 1H), 2.30-2.17 (m, 1H), 2.01-1.90 (m, 2H), 1.90-1.82 (m, 2H), 1.70-1.50 (m, 2H), 1.21-1.01 (m, 2H).

Example 116: 5-(1H-imidazol-1-yl)-N-((1s,4s)-4-((2,2,2-trifluoroethyl)amino)cyclohexyl)-1H-pyrazolo[3,4-c]pyridine-7-carboxamide (16 mg, 6% yield) as a white solid. LCMS: [M+H]$^+$ 408.10. $^1$H NMR (300 MHz, DMSO-d$_6$) δ 13.81 (s, 1H), 8.85 (t, J=1.1 Hz, 1H), 8.65 (d, J=8.2 Hz, 1H), 8.34 (d, J=4.9 Hz, 2H), 8.18 (t, J=1.4 Hz, 1H), 7.13 (t, J=1.2 Hz, 1H), 4.01-3.81 (m, 1H), 3.24-3.11 (m, 2H), 2.75-2.70 (m, 1H), 2.25-2.19 (m, 1H), 1.99-1.82 (m, 2H), 1.70 (m, 2H), 1.64-1.58 (m, 4H).

Example 117: N-(4,4-difluorocyclohexyl)-2-(1H-imidazol-1-yl)-8-methyl-7H-purine-6-carboxamide

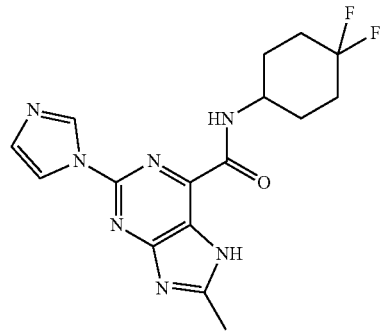 [SMILES: Cc1nc2nc(-n3ccnc3)nc(C(=O)NC3CCC(F)(F)CC3)c2[nH]1]

Step 1: 2-chloro-6-(1-ethoxyvinyl)-8-methyl-7H-purine

Under nitrogen, a mixture of 2,6-dichloro-8-methyl-7H-purine (1.00 g, 4.9 mmol, 1.0 eq), tributyl(1-ethoxyethenyl)stannane (1.95 g, 5.4 mmol, 1.1 eq), and Pd(PPh$_3$)$_2$Cl$_2$ (0.035 g, 0.05 mmol, 0.01 eq) in DMF (15 mL) was stirred at 85° C. for 16 h. The reaction was cooled to RT and diluted with 50 mL of EtOAc and 100 mL of saturated brine. The insoluble solids were filtered out. The layers were separated and the aqueous portion was extracted with EtOAc (2×50 mL). The organic layers were combined, washed with saturated brine (2×50 mL), dried over magnesium sulfate, and concentrated. The crude product was applied onto a silica gel column eluting with (20-100% EtOAc/hexanes) to afford the title compound (0.45 g, 38% yield). LCMS: [M+H]$^+$ 239.1.

Step 2: 6-(1-Ethoxyvinyl)-2-imidazol-1-yl-8-methyl-7H-purine

Under nitrogen, a mixture of 2-chloro-6-(1-ethoxyvinyl)-8-methyl-7H-purine (0.45 g, 1.88 mmol, 1.00 eq), 1H-imidazole (0.39 g, 5.65 mmol, 3 eq), CuI (0.11 g, 0.57 mmol, 0.3 eq), and Cs$_2$CO$_3$ (1.23 g, 3.77 mmol, 2 eq) in NMP (2 mL) was stirred 16 h at 150° C. The reaction was cooled to RT, diluted with 25 mL of EtOAc and 25 mL of saturated brine. The insoluble solids were filtered. The layers were separated and the aqueous layer was extracted with EtOAc (2×25 mL). The organic layers were combined, washed brine (2×50 mL), dried over magnesium sulfate, and concentrated. The crude product was applied onto a silica gel column eluting with (25-100% EtOAc/hexanes) to afford the title compound (0.7 g, 100% yield). LCMS: [M+H]$^+$ 271.1.

Step 3: Ethyl 2-imidazol-1-yl-8-methyl-7H-purine-6-carboxylate

To a solution of 6-(1-ethoxyvinyl)-2-imidazol-1-yl-8-methyl-7H-purine (0.4 g, 1.48 mmol, 1.0 eq) in dioxane (30 mL) was added a solution of NaIO$_4$ (0.95 g, 4.44 mmol, 3 eq) in H$_2$O (10 mL), followed by KMnO$_4$ (0.093 g, 0.59 mmol, 0.40 eq). The reaction was stirred at RT for 18 h. The resulting mixture was filtered and the solids were washed with EtOAc and water. The filtrate was concentrated then extracted with EtOAc. The organic layers were combined, dried over Na$_2$SO$_4$ and concentrated under reduced pressure to give the crude title compound (0.16 g, 39% yield). LCMS: [M+H]$^+$ 273.0.

Step 4: N-(4,4-difluorocyclohexyl)-2-imidazol-1-yl-8-methyl-7H-purine-6-carboxamide A solution of ethyl 2-imidazol-1-yl-8-methyl-7H-purine-6-carboxylate (105 mg, 0.38 mmol, 1.00 equiv), 4,4-difluorocyclohexanamine (73 mg, 0.54 mmol, 1.4 equiv), and DABAL-Me$_3$ (99 mg, 0.38 mmol, 1 equiv) in toluene (2 mL) was stirred at 90° C. for 16 h. After completion, the reaction was quenched with 5 mL of EtOAc and 2 mL of MeOH. After stirring for 30 min, 15 mL of saturated aqueous potassium sodium tartrate was added and the reaction mixture was stirred for an additional 30 min. The organic layer was separated, dried over magnesium sulfate, filtered, and concentrated. The resulting residue was taken up in DCM, sonicated, and the solids collected by suction filtration to afford the title compound (18 mg, 13% yield) as an off-white solid. LCMS: [M+H]$^+$ 362.2. H NMR (400 MHz, DMSO-d6) δ ppm 13.07-13.31 (m, 1H), 8.99 (br d, J=6.85 Hz, 1H), 8.93 (s, 1H), 8.20 (s, 1H), 7.11 (s, 1H), 4.05-4.17 (m, 1H), 2.64 (s, 3H), 1.85-2.16 (m, 8H).

Example 118: N-[4-(1-cyano-1-methyl-ethyl)phenyl]-2-imidazol-1-yl-5H-pyrrolo[3,2-d]pyrimidine-4-carboxamide

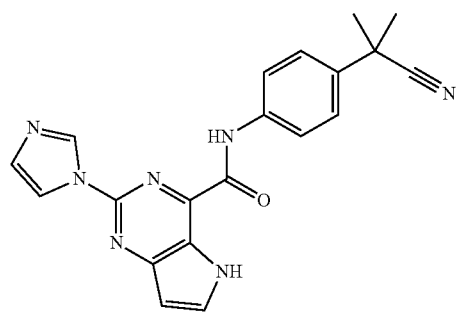 [SMILES: CC(C)(C#N)c1ccc(NC(=O)c2nc(-n3ccnc3)nc3cc[nH]c23)cc1]

A solution of methyl 2-imidazol-1-yl-5H-pyrrolo[3,2-d]pyrimidine-4-carboxylate (56 mg, 0.23 mmol, 1.00 equiv), 2-(4-aminophenyl)-2-methyl-propanenitrile (44 mg, 0.28 mmol, 1.2 equiv), DABAL-Me$_3$ (70 mg, 0.28 mmol, 1.2 equiv) in toluene (3 mL) was stirred at 110° C. for 16 h. After completion, the reaction was quenched with 5 mL of EtOAc and 2 mL of MeOH. After stirring for 30 min, 15 mL of saturated aqueous potassium sodium tartrate was added and the reaction mixture was stirred for an additional 30 min. The resulting solids were collected by suction filtration, rinsed with EtOAc and water, then dried under high vacuum to afford the title compound (45 mg, 52% yield) as a tan solid. LCMS: [M+H]$^+$ 372.2. $^1$H NMR (400 MHz, DMSO-d$_6$) δ ppm 12.26 (br s, 1H), 10.80 (br s, 1H), 9.03 (s, 1H), 8.29 (s, 1H), 8.06 (d, J=3.42 Hz, 1H), 8.00 (d, J=8.80 Hz, 2H), 7.59 (d, J=8.80 Hz, 2H), 7.14 (s, 1H), 6.75 (d, J=2.93 Hz, 1H), 1.71 (s, 6H).

Examples 119a and 119b: N-((1R,4r)-4-((R)-2-hydroxy-3-methylbutoxy)cyclohexyl)-2-(1H-imidazol-1-yl)-5H-pyrrolo[3,2-d]pyrimidine-4-carboxamide and N-((1S,4r)-4-((S)-2-hydroxy-3-methylbutoxy)cyclohexyl)-2-(1H-imidazol-1-yl)-5H-pyrrolo[3,2-d]pyrimidine-4-carboxamide

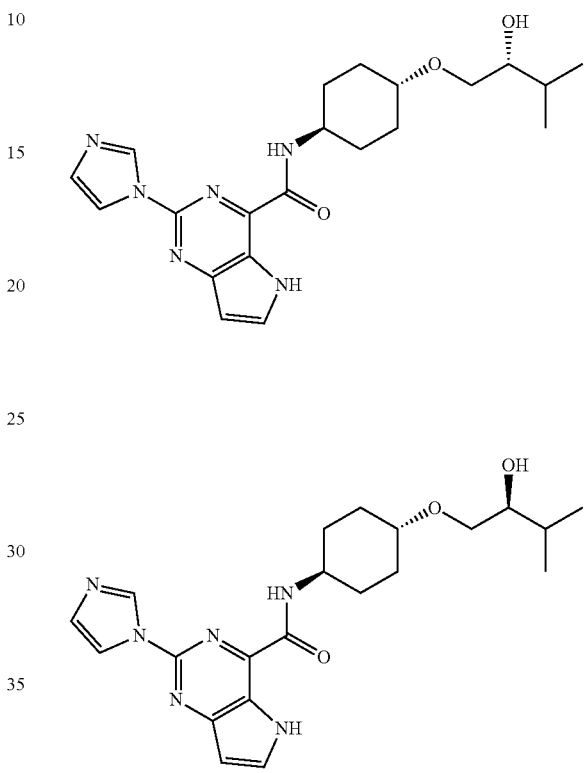

The racemic compound was prepared according to the amide coupling procedure described in Example 7. The racemic compound was further purified by Chiral-HPLC with the following conditions (Column: CHIRALPAK IA, 2*25 cm, 5 μm. Mobile Phase: A: Hexane/8 mM NH$_3$·MeOH, B: EtOH. Flow rate: 18 mL/min. Gradient: maintaining 50% B for 24 min; 254/220 nm) to afford the title compounds with retention times of 16.687 minutes (Example 119a) and 20.708 minutes (Example 119b). The absolute stereochemistry of Examples 119a and 119b was not confirmed.

Example 119a: Isolated as a white solid (4.8 mg, 2.34% yield) LCMS: [M+H]$^+$ 413.20. $^1$H NMR (400 MHz, DMSO-d6) δ 12.08 (s, 1H), 8.97 (s, 1H), 8.92 (d, J=8.5 Hz, 1H), 8.23 (s, 1H), 8.03 (t, J=3.0 Hz, 1H), 7.13 (s, 1H), 6.72 (s, 1H), 4.40 (d, J=4.3 Hz, 1H), 4.00-3.93 (m, 1H), 3.45-3.41 (m, 2H), 2.10-2.01 (m, 2H), 1.90-1.80 (m, 2H), 1.71-1.55 (m, 4H), 1.35-1.29 (m, 3H), 0.92-0.86 (m, 6H).

Example 119b: Isolated as a white solid (5.0 mg, 2.44% yield) LCMS: [M+H]$^+$ 413.20. $^1$H NMR (400 MHz, DMSO-d6) δ 12.06 (s, 1H), 8.97 (s, 1H), 8.91 (d, J=8.6 Hz, 1H), 8.23 (s, 1H), 8.03 (t, J=2.9 Hz, 1H), 7.13 (s, 1H), 6.71 (d, J=3.3, 1.3 Hz, 1H), 4.39 (d, J=4.6 Hz, 1H), 3.92-3.81 (m, 1H), 3.41-3.35 (m, 1H), 3.29-3.21 (m, 1H), 2.10-2.02 (m, 2H), 1.95-1.82 (m, 3H), 1.72-1.58 (m, 3H), 1.36-1.17 (m, 3H), 0.91-0.82 (m, 6H).

Examples 120a and 120b: N-((1s,4s)-4-hydroxy-4-(trifluoromethyl)cyclohexyl)-2-(1H-imidazol-1-yl)-5H-pyrrolo[3,2-d]pyrimidine-4-carboxamide and N-((1r,4r)-4-hydroxy-4-(trifluoromethyl)cyclohexyl)-2-(1H-imidazol-1-yl)-5H-pyrrolo[3,2-d]pyrimidine-4-carboxamide Example 121: 2-(1H-imidazol-1-yl)-N-((1r,4r)-4-(trifluoromethyl)cyclohexyl)thieno[3,2-d]pyrimidine-4-carboxamide and Example 122: 2-(1H-imidazol-1-yl)-N-((1s,4s)-4-(trifluoromethyl)cyclohexyl)thieno[3,2-d]pyrimidine-4-carboxamide

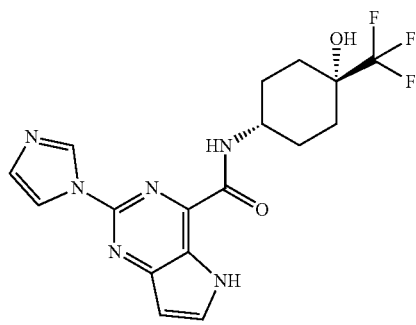

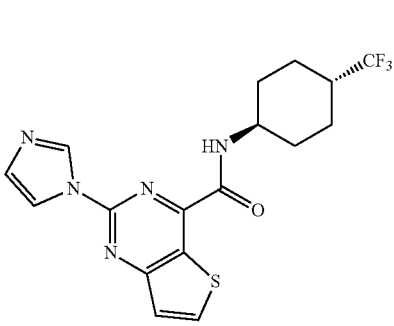

Example 121

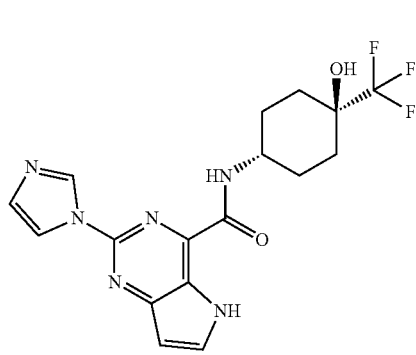

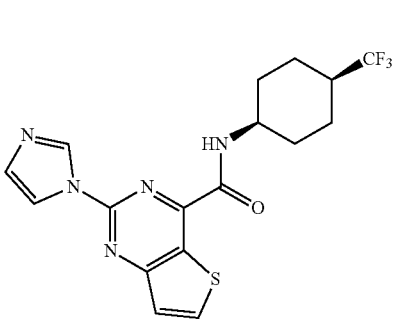

Example 122

The trans-/cis-compound was prepared according to the amide coupling procedure described in Example 23, Step 4. The trans-/cis-mixture was further purified by Prep-HPLC with the following conditions (Column: YMC-Actus Triart C18, 30*250 mm, 5 μm. Mobile Phase: A: Water/10 mM NH$_4$HCO$_3$, B: ACN. Flow rate: 60 mL/min. Gradient: 28% B to 58% B in 7 min; 254 nm) to afford the title compounds with retention times of 8.58 minutes (Example 120a) and 9.63 minutes (Example 120b). The absolute stereochemistry of Examples 120a and 120b was not confirmed.

Example 120a: Isolated as a white solid (15.7 mg, 10% yield) LCMS: [M+H]$^+$ 395.20. $^1$H NMR (300 MHz, DMSO-d$_6$) δ 8.86 (s, 1H), 8.70 (d, J=6.7 Hz, 1H), 8.15 (s, 1H), 8.03 (d, J=3.1 Hz, 1H), 7.14 (s, 1H), 6.71 (d, J=3.1 Hz, 1H), 5.87 (s, 1H), 4.14 (br, 1H), 1.97-1.88 (m, 6H), 1.62-1.59 (m, 2H).

Example 120b: Isolated as a white solid (4.9 mg, 3% yield) LCMS: [M+H]$^+$ 395.20. $^1$H NMR (300 MHz, DMSO-d$_6$) δ 12.05 (s, 1H), 9.08 (d, J=8.6 Hz, 1H), 9.00 (s, 1H), 8.25 (s, 1H), 8.01 (d, J=3.1 Hz, 1H), 7.12 (s, 1H), 6.70 (d, J=3.1 Hz, 1H), 5.89 (s, 1H), 4.03-3.93 (m, 1H), 2.07-1.61 (m, 8H).

The cis-/trans-mixture was prepared according to the amide coupling procedure described in Example 10. The trans-/cis-mixture was purified by Prep HPLC (Column: XBridge Prep OBD C18 Column, 30*150 mm, 5 μm. Mobile Phase: A: Water/10 mM NH$_4$HCO$_3$, B: ACN. Flow rate: 60 mL/min. Gradient: 35% B to 65% B in 7 min; 254 nm) to afford the title compounds with retention times of 9.03 minutes (Example 121) and 9.50 minutes (Example 122).

Example 121: Isolated as a white solid (19.6 mg. 8.14% yield). LCMS: [M+H]$^+$ 396.15. $^1$H NMR (300 MHz, DMSO-d$_6$) δ 9.19 (d, J=8.5 Hz, 1H), 9.07 (s, 1H), 8.70 (d, J=5.6 Hz, 1H), 8.29 (s, 1H), 7.66 (d, J=5.6 Hz, 1H), 7.17 (s, 1H), 3.99-3.91 (m, 1H), 2.35-2.20 (m, 1H), 2.02-1.97 (m, 2H), 1.95-1.91 (m, 2H), 1.73-1.55 (m, 2H), 1.50-1.33 (m, 2H).

Example 122: Isolated as a white solid (5.2 mg, 2.16% yield). LCMS: [M+H]$^+$ 396.15. $^1$H NMR (300 MHz, DMSO-d$_6$) δ 9.02 (d, J=1.1 Hz, 1H), 8.93 (d, J=7.0 Hz, 1H), 8.71 (d, J=5.6 Hz, 1H), 8.24 (d, J=1.4 Hz, 1H), 7.68 (d, J=5.6 Hz, 1H), 7.18 (d, J=1.2 Hz, 1H), 4.10-4.09 (m, 1H), 3.30-3.25 (m, 1H), 2.03-1.94 (m, 2H), 1.78-1.73 (m, 6H).

Examples 123a and 123b: N-((3S,4R)-3-fluoropiperidin-4-yl)-2-(1H-imidazol-1-yl)-5H-pyrrolo[3,2-d]pyrimidine-4-carboxamide and N-((3R,4R)-3-fluoropiperidin-4-yl)-2-(1H-imidazol-1-yl)-5H-pyrrolo[3,2-d]pyrimidine-4-carboxamide Examples 124a and 124b: 2-(1H-imidazol-1-yl)-N-((1S,3S)-3-(2-methoxyethoxy)cyclohexyl)-5H-pyrrolo[3,2-d]pyrimidine-4-carboxamide and 2-(1H-imidazol-1-yl)-N-((1S,3R)-3-(2-methoxyethoxy)cyclohexyl)-5H-pyrrolo[3,2-d]pyrimidine-4-carboxamide

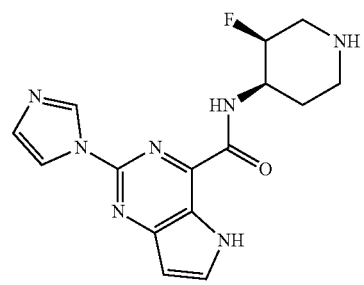

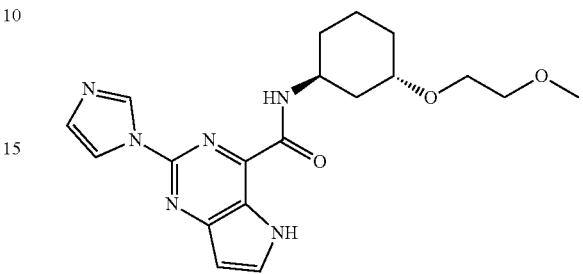

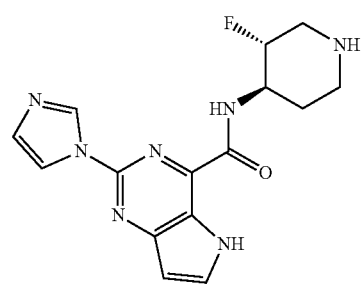

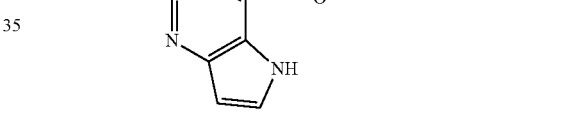

The cis-/trans-mixture was prepared according to the amide coupling procedure described in Example 101. The crude material was further purified by prep chromatography to give the cis- and trans-isomers separately as racemates. (Column: XBridge Prep OBD C18 Column, 30*150 mm, 5 μm. Mobile Phase: A: Water/10 mM NH₄HCO₃, B: ACN. Flow rate: 60 mL/min. Gradient: 3% B to 33% B in 10 min; 254 nm) to afford the title compounds with retention times of 9.13 minutes (Example 123a) and 9.62 minutes (Example 123b). The absolute stereochemistry of Examples 123a and 123b was not confirmed.

Example 123a: Isolated as a light yellow solid (21.0 mg, 17.1% yield). LCMS: [M+H]⁺ 330.10. ¹H NMR (400 MHz, DMSO-d₆) δ 12.10 (s, 1H), 8.96 (d, J=6.4 Hz, 1H), 8.95 (s, 1H), 8.22 (s, 1H), 8.04 (d, J=2.8 Hz, 1H), 7.13 (t, J=1.2 Hz, 1H), 6.73 (d, J=3.2 Hz, 1H), 4.75 (d, J=50.8 Hz, 1H), 4.31-4.15 (m, 1H), 3.33-3.20 (m, 1H), 3.10-3.01 (m, 1H), 2.89-2.76 (m, 1H), 2.71-2.59 (m, 1H), 2.51-2.43 (m, 1H), 2.07-1.95 (m, 1H), 1.72-1.59 (m, 1H).

Example 123b: Isolated as a white solid (12.5 mg, 10.2% yield). LCMS: [M+H]⁺ 330.20. ¹H NMR (400 MHz, DMSO-d₆) δ 12.09 (s, 1H), 9.22 (d, J=8.8 Hz, 1H), 8.99 (s, 1H), 8.24 (t, J=1.6 Hz, 1H), 8.03 (s, 1H), 7.14 (s, 1H), 6.72 (d, J=2.8 Hz, 1H), 4.80-4.64 (m, 1H), 4.20-4.05 (m, 1H), 3.33-3.21 (m, 2H), 2.98-2.85 (m, 1H), 2.61-2.49 (m, 2H), 1.95-1.82 (m, 1H), 1.79-1.65 (m, 1H).

The cis-/trans-mixture was prepared according to the amide coupling procedure described in Example 23, Step 4 and the crude material was further purified by prep chromatography to give the trans-/cis-isomers separately as racemates. (Column: CHIRALPAK IC, 2*25 cm, 5 μm; Mobile Phase: A: Hexane/8 M NH₃-MeOH, B: EtOH. Flow rate: 18 mL/min. Gradient: maintaining 50% B for 15 min; 220/254 nm) to afford the title compounds with retention times of 5.974 minutes (Example 124a) and 10.422 minutes (Example 124b). The absolute stereochemistry of Examples 124a and 124b was not confirmed.

Example 124a: Isolated as a white solid (18.6 mg, 2.65% yield). LCMS: [M+H]⁺ 385.20. ¹H NMR (300 MHz, DMSO-d₆) δ 12.09 (s, 1H), 9.01 (d, J=9.0 Hz, 1H), 8.98 (s, 1H), 8.23 (s, 1H), 8.01-7.90 (m, 1H), 7.14 (s, 1H), 6.81-6.62 (m, 1H), 4.10-3.90 (m, 1H), 3.73-3.55 (m, 2H), 3.48-3.30 (m, 3H), 3.24 (s, 3H), 2.19-2.30 (m, 1H), 2.01-1.90 (m, 1H), 1.88-1.70 (m, 2H), 1.61-1.42 (m, 2H), 1.43-1.21 (m, 1H), 1.19-1.04 (m, 1H).

Example 124b: Isolated as a white solid (20.9 mg, 3.10% yield). LCMS: [M+H]⁺ 385.20. ¹H NMR (300 MHz, DMSO-d₆) δ 12.09 (s, 1H), 9.02 (d, J=9.1 Hz, 1H), 8.96 (s, 1H), 8.23 (s, 1H), 8.06-8.02 (m, 1H), 7.14 (s, 1H), 6.71-6.74 (m, 1H), 4.18-3.90 (m, 1H), 3.61-3.55 (m, 2H), 3.45-3.39 (m, 3H), 3.25 (s, 3H), 2.31-2.10 (m, 1H), 2.10-1.92 (m, 1H), 1.89-1.75 (m, 2H), 1.65-1.10 (m, 4H).

Examples 125a and 125b: N-((1R,4r)-4-((R)-2-hydroxypropoxy)cyclohexyl)-2-(1H-imidazol-1-yl)-5H-pyrrolo[3,2-d]pyrimidine-4-carboxamide and N-((1R,4r)-4-((S)-2-hydroxypropoxy)cyclohexyl)-2-(1H-imidazol-1-yl)-5H-pyrrolo[3,2-d]pyrimidine-4-carboxamide Examples 126a and 126b: N-((1R,4r)-4-((R)-2-hydroxy-2,3-dimethylbutoxy)cyclohexyl)-2-(1H-imidazol-1-yl)-5H-pyrrolo[3,2-d]pyrimidine-4-carboxamide and N-((1R,4r)-4-((S)-2-hydroxy-2,3-dimethylbutoxy)cyclohexyl)-2-(1H-imidazol-1-yl)-5H-pyrrolo[3,2-d]pyrimidine-4-carboxamide

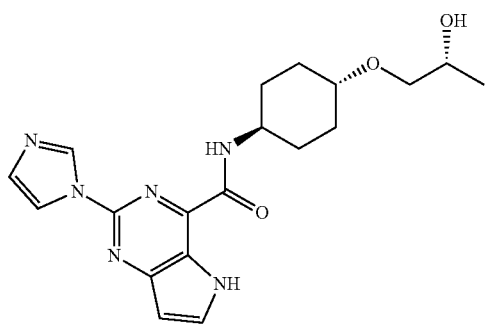

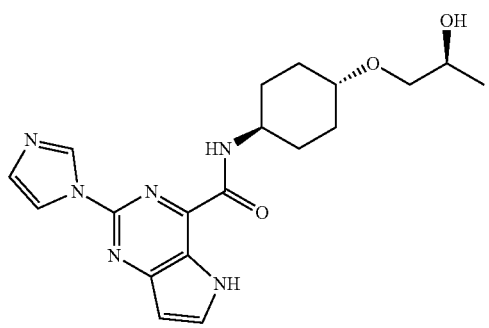

The racemic mixture was prepared according to the amide coupling procedure described in Example 7 and the crude material was purified by chiral chromatography (Column: CHIRALPAK IA, 2*25 cm, 5 μm. Mobile Phase: A: Hexane/8 mM NH₃·MeOH, B: EtOH. Flow rate: 17 mL/min. Gradient: 50% B to 50% B in 15 min; 254/220 nm) to afford the title compounds with retention times of 10.547 minutes (Example 125a) and 14.351 minutes (Example 125b). The absolute stereochemistry of Examples 125a and 125b was not confirmed.

Example 125a: Isolated as a white solid (14.2 mg, 9.2% yield). LCMS: [M+H]⁺ 385.25. ¹H NMR (300 MHz, DMSO-d₆) δ 12.03 (s, 1H), 9.03 (s, 1H), 8.95 (d, J=8.6 Hz, 1H), 8.30 (t, J=1.4 Hz, 1H), 8.05 (t, J=3.0 Hz, 1H), 7.17 (t, J=1.2 Hz, 1H), 6.75 (dd, J=3.1, 1.5 Hz, 1H), 4.55 (d, J=4.6 Hz, 1H), 4.08-3.90 (m, 1H), 3.78-3.68 (m, 1H), 3.40-3.20 (m, 3H), 2.20-2.06 (m, 2H), 2.00-1.88 (m, 2H), 1.75-1.60 (m, 2H), 1.38-1.18 (m, 2H), 1.02 (d, J=6.3 Hz, 3H).

Example 125b: Isolated as a white solid (14.9 mg, 9.7% yield). LCMS: [M+H]⁺ 385.25. ¹H NMR (300 MHz, DMSO-d₆) δ 12.03 (s, 1H), 8.94 (s, 1H), 8.87 (d, J=8.6 Hz, 1H), 8.20 (t, J=1.4 Hz, 1H), 8.00 (t, J=3.1 Hz, 1H), 7.11 (t, J=1.2 Hz, 1H), 6.69 (dd, J=3.1, 1.7 Hz, 1H), 4.48 (d, J=4.6 Hz, 1H), 4.01-3.80 (m, 1H), 3.74-3.61 (m, 1H), 3.35-3.16 (m, 3H), 2.06-1.99 (m, 2H), 1.88-1.79 (m, 2H, 2H), 1.70-1.50 (m, 2H), 1.37-1.17 (m, 2H), 1.02 (d, J=6.3 Hz, 3H).

The racemic mixture was prepared according to the amide coupling procedure described in Example 7 and the crude material was purified by chiral chromatography (Column: CHIRALPAK IA, 2*25 cm, 5 μm. Mobile Phase: A: MTBE/10 mM NH₃-MeOH, B: EtOH. Flow rate: 15 mL/min. Gradient: maintaining 50% B for 18 min; 220/254 nm) to afford the title compounds with retention times of 9.139 minutes (Example 126a) and 12.689 minutes (Example 126b). The absolute stereochemistry of Examples 126a and 126b was not confirmed.

Example 126a: Isolated as a white solid (9.7 mg, 4.90% yield). LCMS: [M+H]⁺ 427.20. ¹H NMR (300 MHz, DMSO-d₆) δ 12.05 (s, 1H), 8.95 (s, 1H), 8.88 (d, J=8.6 Hz, 1H), 8.22 (s, 1H), 8.01 (t, J=3.0 Hz, 1H), 7.12 (s, 1H), 6.70 (s, 1H), 3.93-3.91 (m, 2H), 3.31-3.21 (m, 2H), 2.51-2.49 (m, 1H), 2.15-2.01 (m, 2H), 1.96-1.81 (m, 2H), 1.79-1.58 (m, 3H), 1.39-1.19 (m, 2H), 0.99 (s, 3H), 0.91-0.85 (m, 6H).

Example 126b: Isolated as a white solid (8.1 mg, 4.09% yield). LCMS: [M+H]⁺ 427.20. ¹H NMR (300 MHz, DMSO-d₆) δ 12.05 (s, 1H), 8.95 (s, 1H), 8.88 (d, J=8.6 Hz, 1H), 8.22 (s, 1H), 8.01 (t, J=3.0 Hz, 1H), 7.12 (s, 1H), 6.70 (s, 1H), 3.93-3.81 (m, 2H), 3.30-3.23 (m, 2H), 2.52-2.45 (m, 1H), 2.12-2.01 (m, 2H), 1.91-1.81 (m, 2H), 1.80-1.54 (m, 3H), 1.38-1.20 (m, 2H), 0.99 (s, 3H), 0.90-0.85 (m, 6H).

Examples 127a and 127b: 2-(1H-imidazol-1-yl)-N-((1R,4r)-4-((R)-3,3,3-trifluoro-2-hydroxy-2-methylpropanamido)cyclohexyl)-5H-pyrrolo[3,2-d]pyrimidine-4-carboxamide and 2-(1H-imidazol-1-yl)-N-((1R,4r)-4-((S)-3,3,3-trifluoro-2-hydroxy-2-methylpropanamido)cyclohexyl)-5H-pyrrolo[3,2-d]pyrimidine-4-carboxamide Examples 128a and 128b: 2-(1H-imidazol-1-yl)-N-((1r,4r)-4-methoxy-4-methylcyclohexyl)-5H-pyrrolo[3,2-d]pyrimidine-4-carboxamide and 2-(1H-imidazol-1-yl)-N-((1s,4s)-4-methoxy-4-methylcyclohexyl)-5H-pyrrolo[3,2-d]pyrimidine-4-carboxamide

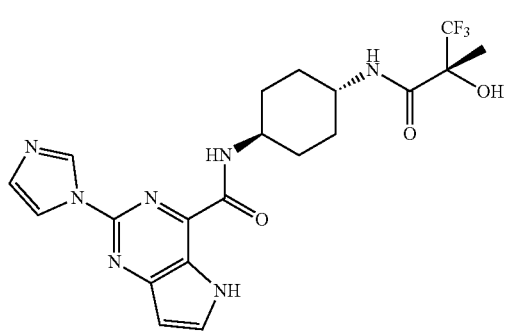

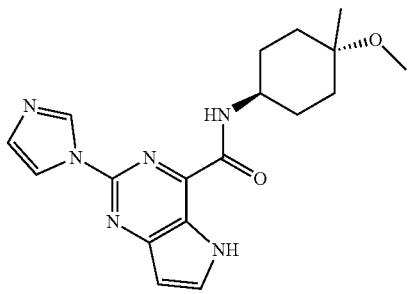

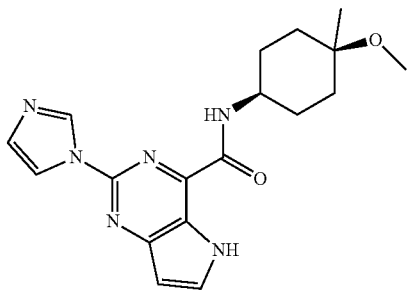

The racemic mixture was prepared according to the amide coupling procedure in described in Example 7 and the crude material was purified by chiral chromatography (Column: CHIRAL ART Cellulose-SB, 3*25 cm, 5 μm. Mobile Phase: A: Hexane/8 mM NH$_3$·MeOH, B: EtOH. Flow rate: 45 mL/min. Gradient: 20% B to 20% B in 12 min; 220/254 nm) to afford the title compounds with retention times of 7.90 minutes (Example 127a) and 10.80 minutes (Example 127b). The absolute stereochemistry of Examples 127a and 127b was not confirmed.

Example 127a: Isolated as a white solid (16.5 mg, 11% yield). LCMS: [M+H]$^+$ 466.20. $^1$H NMR (300 MHz, methanol-d$_4$) δ 8.95 (t, J=1.1 Hz, 1H), 8.23 (t, J=1.4 Hz, 1H), 7.97 (d, J=3.2 Hz, 1H), 7.13 (dd, J=1.6, 1.0 Hz, 1H), 6.71 (d, J=3.2 Hz, 1H), 4.11-3.97 (m, 1H), 3.84-3.71 (m, 1H), 2.12-1.94 (m, 4H), 1.81-1.63 (m, 2H), 1.58-1.49 (m, 5H).

Example 127b: Isolated as a white solid (15.3 mg, 10% yield). LCMS: [M+H]$^+$ 466.20. $^1$H NMR (300 MHz, methanol-d$_4$) δ 8.95 (t, J=1.1 Hz, 1H), 8.23 (t, J=1.4 Hz, 1H), 7.97 (d, J=3.2 Hz, 1H), 7.13 (dd, J=1.6, 1.0 Hz, 1H), 6.71 (d, J=3.2 Hz, 1H), 4.11-3.97 (m, 1H), 3.84-3.71 (m, 1H), 2.03-1.90 (m, 4H), 1.72-1.65 (m, 2H), 1.58-1.49 (m, 5H).

The cis/trans mixture was prepared according to the amide coupling procedure described in Example 7 and the crude material was purified by reversed phase chromatography (Column: RediSep Prep C18, 2*15 cm, 5 μm. Mobile Phase: A: water, B: ACN. Flow rate: 20 mL/min. Gradient: 20% B to 85% B for 20 min; 214/254 nm) to afford the title compounds with retention times of 9.4 minutes (Example 128a) and 10.0 minutes (Example 128b). The absolute stereochemistry of Examples 128a and 128b was not confirmed.

Example 128a: Isolated as a white solid (20 mg, 18% yield). LCMS: [M+H]$^+$ 355.2. $^1$H NMR (400 MHz, DMSO-d$_6$) δ 12.05 (br s, 1H), 8.91 (s, 1H), 8.81 (br d, J=8.31 Hz, 1H), 8.14-8.21 (m, 1H), 8.00 (br s, 1H), 7.11 (s, 1H), 6.69 (d, J=2.93 Hz, 1H), 3.88-4.00 (m, 1H), 3.13 (s, 3H), 1.65-1.86 (m, 6H), 1.42-1.59 (m, 2H), 1.22 (s, 3H).

Example 128b: Isolated as a white solid (24 mg, 22% yield). LCMS: [M+H]$^+$ 355.2. $^1$H NMR (400 MHz, DMSO-d$_6$) δ 12.00 (br s, 1H), 8.97 (s, 2H), 8.19-8.28 (m, 1H), 7.98 (br d, J=3.42 Hz, 1H), 7.09 (s, 1H), 6.67 (d, J=3.42 Hz, 1H), 3.84-3.98 (m, 1H), 3.05-3.19 (m, 3H), 1.76-1.92 (m, 4H), 1.58 (br dd, J=9.05, 4.16 Hz, 2H), 1.32-1.45 (m, 2H), 1.09 (s, 3H).

The following Examples in Table 3 were prepared according to the methods described for the previous Examples.

TABLE 3

| Example # | Structure and Name | MS (M + H)+ | Prepared according to Example # |
|---|---|---|---|
| 129 | 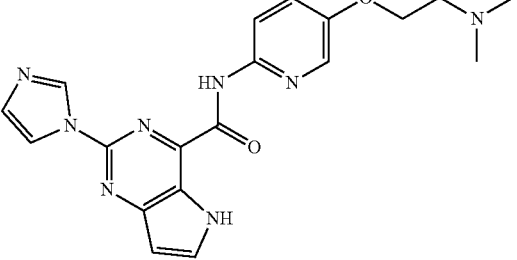<br>N-(5-(2-(dimethylamino)ethoxy)pyridin-2-yl)-2-(1H-imidazol-1-yl)-5H-pyrrolo[3,2-d]pyrimidie-4-carboxamide | 393.10 | 23, Step 4 |
| 130 | 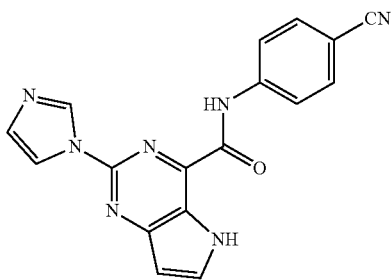<br>N-(4-cyanophenyl)-2-(1H-imidazol-1-yl)-5H-pyrrolo[3,2-d]pyrimidine-4-carboxamide | 330.10 | 7 |
| 131 | 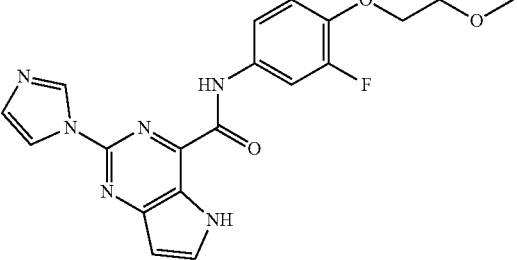<br>N-(3-fluoro-4-(2-methoxyethoxy)phenyl)-2-(1H-imidazol-1-yl)-5H-pyrrolo[3,2-d]pyrimidine-4-carboxamide | 397.10 | 7 |
| 132 | 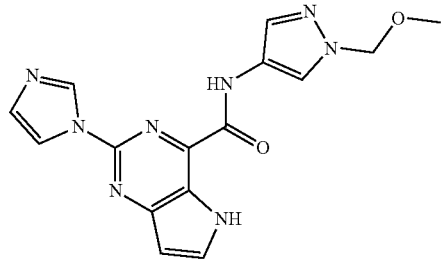<br>2-(1H-imidazol-1-yl)-N-(1-(methoxymethyl)-1H-pyrazol-4-yl)-5H-pyrrolo[3,2-d]pyrimidine-4-carboxamide | 339.20 | 7 |

TABLE 3-continued

| Example # | Structure and Name | MS (M + H)+ | Prepared according to Example # |
|---|---|---|---|
| 133 | 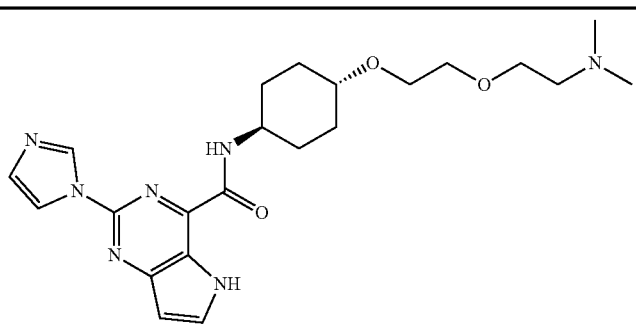<br>N-((1r,4r)-4-(2-(2-(dimethylamino)ethoxy)ethox)cyclohexyl)-2-(1H-imidazol-1-yl)-5H-pyrrolo[3,2-d]pyrimidine-4-carboxamide | 442.30 | 23, Step 4 |
| 134 | 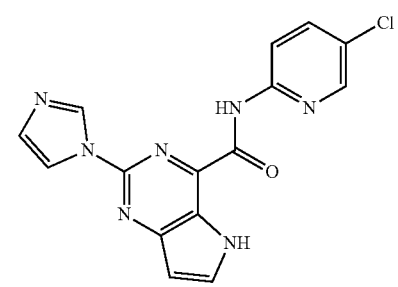<br>N-(5-chloropyridin-2-yl)-2-(1H-imidazol-1-yl)-5H-pyrrolo[3,2-d]pyrimidine-4-carboxamide | 340.00 | 23, Step 4 |
| 135 | 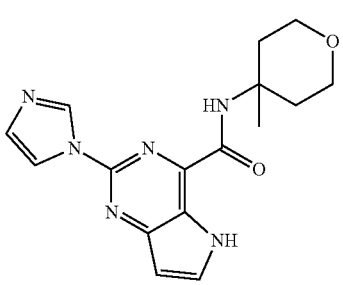<br>2-(1H-imidazol-1-yl)-N-(4-methyltetrahydro-2H-pyran-4-yl)-5H-pyrrolo[3,2-d]pyrimidine-4-carboxamide | 327.20 | 7 |
| 136 | 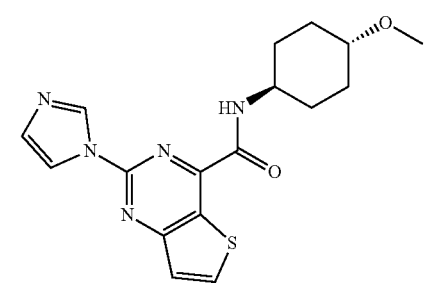<br>2-(1H-imidazol-1-yl)-N-((1r,4r)-4-methoxycyclohexyl)thieno[3,2-d]pyrimidine-4-carboxamide | 358.05 | 23, Step 4 |

TABLE 3-continued

| Example # | Structure and Name | MS (M + H)+ | Prepared according to Example # |
|---|---|---|---|
| 137 | N-(6-chloropyridin-3-yl)-2-(1H-imidazol-1-yl)-5H-pyrrolo[3,2-d]pyrimidine-4-carboxamide | 340.00 | 23, Step 4 |
| 138 | 2-(1H-imidazol-1-yl)-N-(pyridin-4-yl)-5H-pyrrolo[3,2-d]pyrimidine-4-carboxamide | 306.00 | 23, Step 4 |
| 139 | N-((1r,4r)-4-(2-hydroxypropan-2-yl)cyclohexyl)-2-(1H-imidazol-1-yl)-5H-pyrrolo[3,2-d]pyrimidine-4-carboxamide | 369.20 | 23, Step 4 |
| 140 | N-(2-chloropyridin-4-yl)-2-(1H-imidazol-1-yl)-5H-pyrrolo[3,2-d]pyrimidine-4-carboxamide | 340.00 | 23, Step 4 |

TABLE 3-continued

| Example # | Structure and Name | MS (M + H)+ | Prepared according to Example # |
|---|---|---|---|
| 141 | 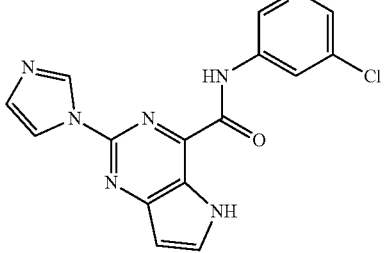N-(5-chloropyridin-3-yl)-2-(1H-imidazol-1-yl)-5H-pyrrolo[3,2-d]pyrimidine-4-carboxamide | 340.00 | 23, Step 4 |
| 142 | 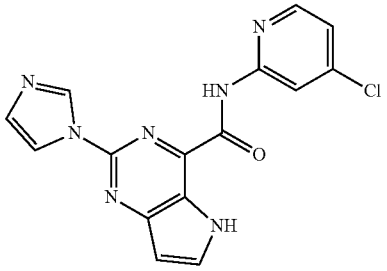N-(4-chloropyridin-2-yl)-2-(1H-imidazol-1-yl)-5H-pyrrolo[3,2-d]pyrimidine-4-carboxamide | 339.95 | 23, Step 4 |
| 143 | 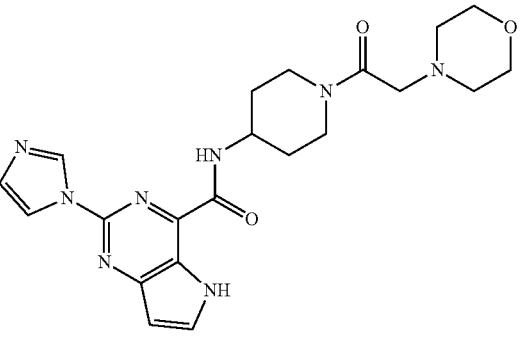2-(1H-imidazol-1-yl)-N-(1-(2-morpholinoacetyl)piperidin-4-yl)-5H-pyrrolo[3,2-d]pyrimidine-4-carboxamide | 439.20 | 23, Step 4 |
| 144 | 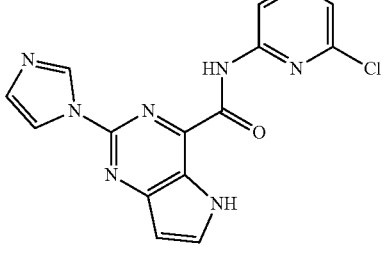N-(6-chloropyridin-2-yl)-2-(1H-imidazol-1-yl)-5H-pyrrolo[3,2-d]pyrimidine-4-carboxamide | 340.00 | 23, Step 4 |

TABLE 3-continued
| Example # | Structure and Name | MS (M + H)+ | Prepared according to Example # |
|---|---|---|---|
| 145 | 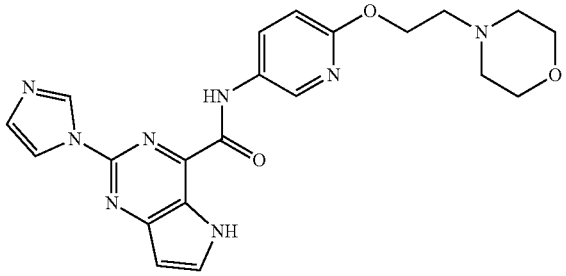  2-(1H-imidazol-1-yl)-N-(6-(2-morpholinoethoxy)pyridin-3-yl)-5H-pyrrolo[3,2-d]pyrimidine-4-carboxamide | 435.10 | 23, Step 4 |
| 146 | 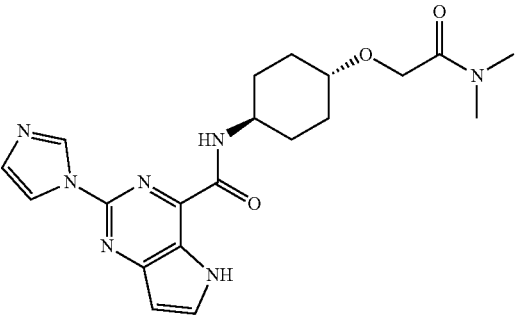  N-((1r,4r)-4-(2-(dimethylamino)-2-oxoethoxy)cyclohexyl)-2-(1H-imidazol-1-yl)-5H-pyrrolo[3,2-d]pyrimidine-4-carboxamide | 412.15 | 23, Step 4 |
| 147 | 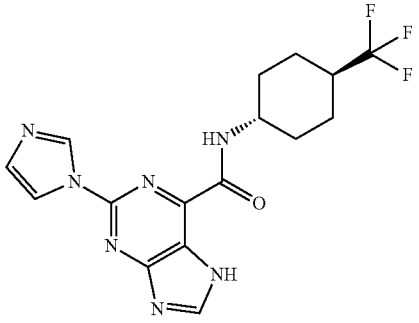  2-(1H-imidazol-1-yl)-N-((1r,4r)-4-(trifluoromethyl)cyclohexyl)-7H-purine-6-carboxamide | 380.4 | 7 |

TABLE 3-continued

| Example # | Structure and Name | MS (M + H)+ | Prepared according to Example # |
|---|---|---|---|
| 148 | 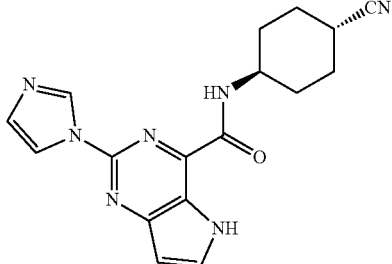<br>N-((1r,4r)-4-cyanocyclohexyl)-2-(1H-imidazol-1-yl)-5H-pyrrolo[3,2-d]pyrimidine-4-carboxamide | 336.15 | 23, Step 4 |
| 149 | 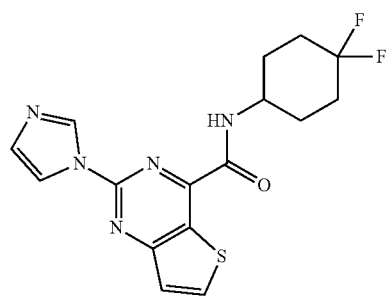<br>N-(4,4-difluorocyclohexyl)-2-(1H-imidazol-1-yl)thieno[3,2-d]pyrimidine-4-carboxamide | 364.10 | 7 |
| 150 | 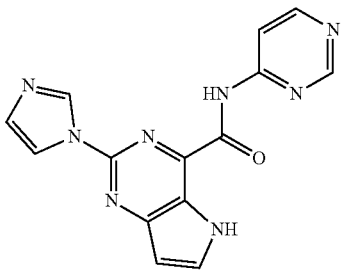<br>2-(1H-imidazol-1-yl)-N-(pyrimidin-4-yl)-5H-pyrrolo[3,2-d]pyrimidine-4-carboxamide | 307.05 | 23, Step 4 |
| 151 | 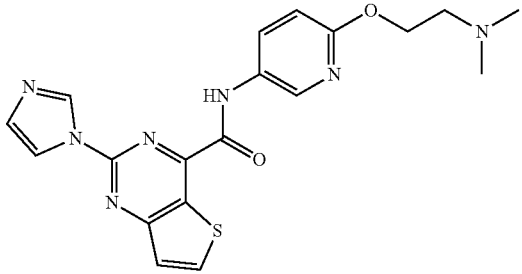<br>N-(6-(2-(dimethylamino)ethoxy)pyridin-3-yl)-2-(1H-imidazol-1-yl)thieno[3,2-d]pyrimidine-4-carboxamide | 410.20 | 23, Step 4 |

TABLE 3-continued

| Example # | Structure and Name | MS (M + H)+ | Prepared according to Example # |
|---|---|---|---|
| 152 | N-(4,4-difluorocyclohexyl)-2-(1H-imidazol-1-yl)-7H-purine-6-carboxamide | 348.4 | 7 |
| 153 | 2-(1H-imidazol-1-yl)-N-(pyrimidin-5-yl)-5H-pyrrolo[3,2-d]pyrimidine-4-carboxamide | 307.00 | 23, Step 4 |
| 154 | 2-(1H-imidazol-1-yl)-N-(6-(4-methylpiperazin-1-yl)pyridin-3-yl)-5H-pyrrolo[3,2-d]pyrimidine-4-carboxamide | 404.15 | 23, Step 4 |

TABLE 3-continued
| Example # | Structure and Name | MS (M + H)+ | Prepared according to Example # |
|---|---|---|---|
| 155 | 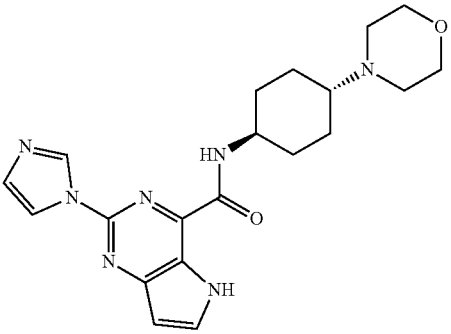<br>2-(1H-imidazol-1-yl)-N-((1r,4r)-4-morpholinocyclohexyl)-5H-pyrrolo[3,2-d]pyrimidine-4-carboxamide | 396.20 | 101 |
| 156 | 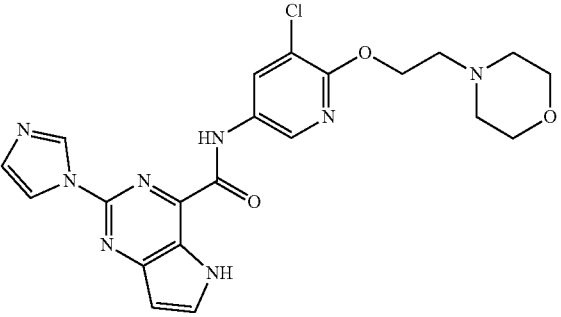<br>N-(5-chloro-6-(2-morpholinoethoxy)pyridin-3-yl)-2-(1H-imidazol-1-yl)-5H-pyrrolo[3,2-d]pyrimidine-4-carboxamide | 469.10 | 7 |
| 157 | 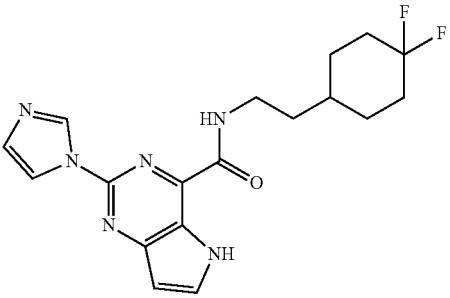<br>N-(2-(4,4-difluorocyclohexyl)ethyl)-2-(1H-imidazol-1-yl)-5H-pyrrolo[3,2-d]pyrimidine-4-carboxamide | 375.05 | 101, step 1 |

TABLE 3-continued
| Example # | Structure and Name | MS (M + H)+ | Prepared according to Example # |
|---|---|---|---|
| 158 | 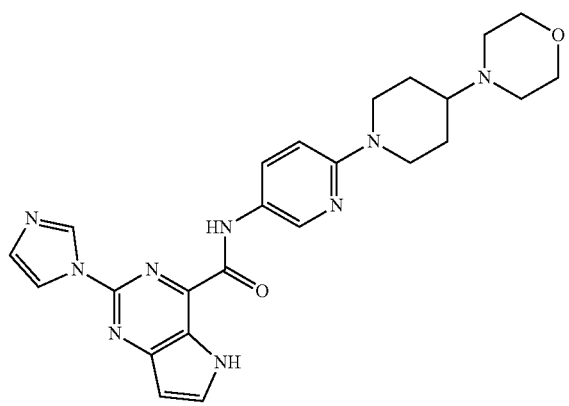<br>2-(1H-imidazol-1-yl)-N-(6-(4-morpholinopiperidin-1-yl)pyridin-3-yl)-5H-pyrrolo[3,2-d]pyrimidine-4-carboxamide | 474.20 | 23, Step 4 |
| 159 | 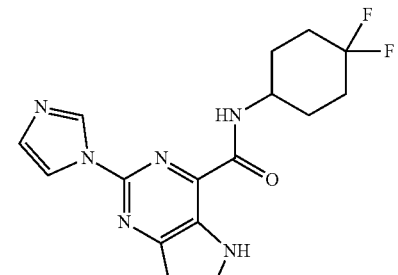<br>N-(4,4-difluorocyclohexyl)-5-(1H-imidazol-1-yl)-1H-pyrazolo[4,3-d]pyrimidine-7-carboxamide | 348.10 | 7 |
| 160 | 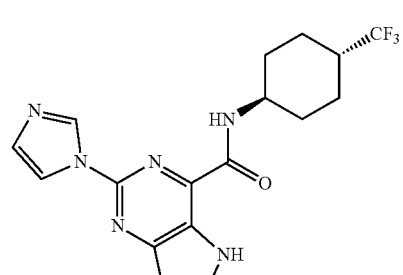<br>5-(1H-imidazol-1-yl)-N-((1r,4r)-4-(trifluoromethyl)cyclohexyl)-1H-pyrazolo[4,3-d]pyrimidine-7-carboxamide | 380.05 | 7 |

TABLE 3-continued

| Example # | Structure and Name | MS (M + H)+ | Prepared according to Example # |
|---|---|---|---|
| 161 | 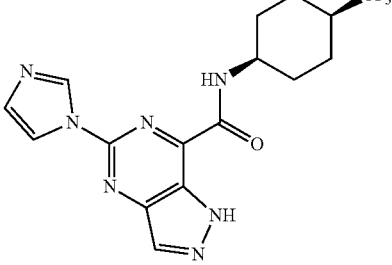<br>5-(1H-imidazol-1-yl)-N-((1s,4s)-4-(trifluoromethyl)cyclohexyl)-1H-pyrazolo[4,3-d]pyrimidine-7-carboxamide | 380.10 | 7 |
| 162 | 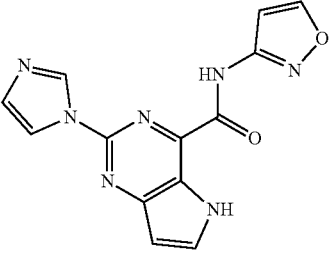<br>2-(1H-imidazol-1-yl)-N-(isoxazol-3-yl)-5H-pyrrolo[3,2-d]pyrimidine-4-carboxamide | 296.3 | 118 |
| 163 | 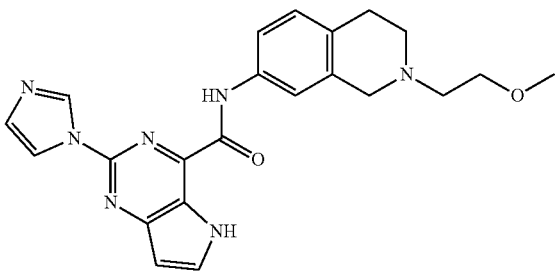<br>2-(1H-imidazol-1-yl)-N-(2-(2-methoxyethyl)-1,2,3,4-tetrahydroisoquinolin-7-yl)-5H-pyrrolo[3,2-d]pyrimidine-4-carboxamide | 418.20 | 7 |
| 164 | 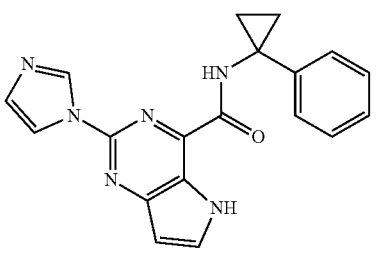<br>2-(1H-imidazol-1-yl)-N-(1-phenylcyclopropyl)-5H-pyrrolo[3,2-d]pyrimidine-4-carboxamide | 345.3 HATU | 7 |

TABLE 3-continued

| Example # | Structure and Name | MS (M + H)+ | Prepared according to Example # |
|---|---|---|---|
| 165 | 2-(1H-imidazol-1-yl)-N-(2-(2-methoxyethoxy)pyrimidin-5-yl)-5H-pyrrolo[3,2-d]pyrimidine-4-carboxamide | 381.15 | 118 |
| 166 | N-(((1r,4r)-4-cyanocyclohexyl)methyl)-2-(1H-imidazol-1-yl)-5H-pyrrolo[3,2-d]pyrimidine-4-carboxamide | 350.20 | 101, step 1 |
| 167 | 2-(1H-imidazol-1-yl)-N-((1r,4r)-4-(trifluoromethoxy)cyclohexyl)-5H-pyrrolo[3,2-d]pyrimidine-4-carboxamide | 395.3 | 7 |
| 168 | N-((1r,4r)-4-fluorocyclohexyl)-2-(1H-imidazol-1-yl)-5H-pyrrolo[3,2-d]pyrimidine-4-carboxamide | 329.2 | 7 |

TABLE 3-continued

| Example # | Structure and Name | MS (M + H)+ | Prepared according to Example # |
|---|---|---|---|
| 169 | 2-(1H-imidazol-1-yl)-N-((1s,4s)-4-morpholinocyclohexyl)-5H-pyrrolo[3,2-d]pyrimidine-4-carboxamide | 396.25 | 101 |
| 170 | 2-(1H-imidazl-1-yl)-N-((1r,4r)-4-(methylcarbamoyl)cyclohexyl)-5H-pyrrolo[3,2-d]pyrimidine-4-carboxamide | 368.20 | 7 |
| 171 | 5-(1H-imidazol-1-yl)-N-((1r,4r)-4-(trifluoromethyl)cyclohexyl)-1H-pyrazolo[3,4-c]pyridine-7-carboxamide | 379.20 | 7 |

TABLE 3-continued
| Example # | Structure and Name | MS (M + H)+ | Prepared according to Example # |
|---|---|---|---|
| 172 | 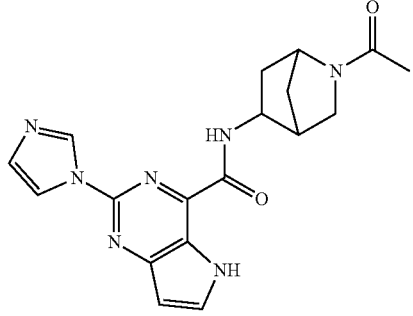<br>N-(2-acetyl-2-azabicyclo[2.2.1]heptan-5-yl)-2-(1H-imidazol-1-yl)-5H-pyrrolo[3,2-d]pyrimidine-4-carboxamide | 366.10 | 7 |
| 173 | 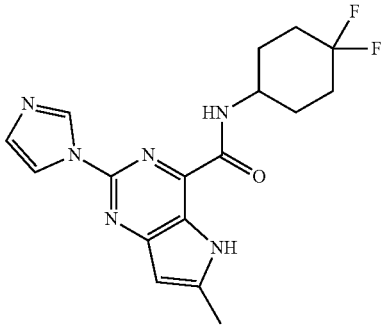<br>N-(4,4-difluorocyclohexyl)-2-(1H-imidazol-1-yl)-6-methyl-5H-pyrrolo[3,2-d]pyrimidine-4-carboxamide | 361.05 | 101, step 1 |
| 174 | 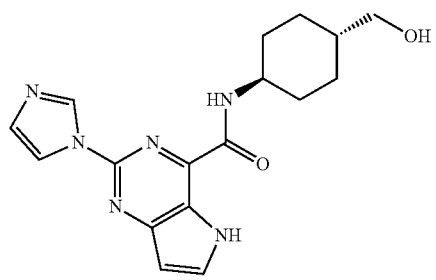<br>N-((1r,4r)-4-(hydroxymethyl)cyclohexyl)-2-(1H-imidazol-1-yl)-5H-pyrrolo[3,2-d]pyrimidine-4-carboxamide | 341.10 | 23, Step 4 |

TABLE 3-continued
| Example # | Structure and Name | MS (M + H)+ | Prepared according to Example # |
|---|---|---|---|
| 175 | 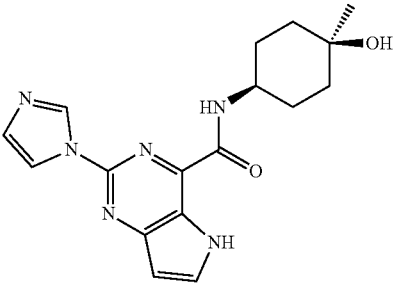<br>N-((1s,4s)-4-hydroxy-4-methylcyclohexyl)-2-(1H-imidazol-1-yl)-5H-pyrrolo[3,2-d]pyrimidine-4-carboxamide | 341.3 | 7 |
| 176 | 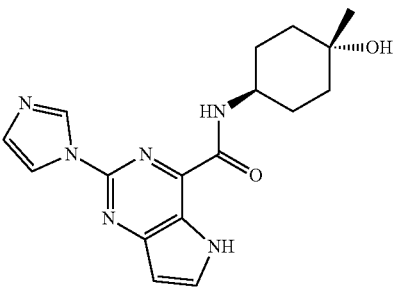<br>N-((1r,4r)-4-hydroxy-4-methylcyclohexyl)-2-(1H-imidazol-1-yl)-5H-pyrrolo[3,2-d]pyrimidine-4-carboxamide | 341.3 | 7 |
| 177 | 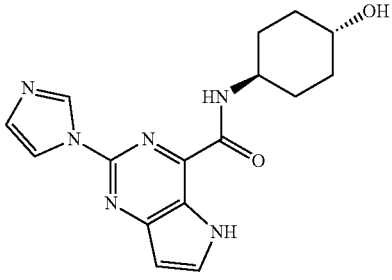<br>N-((1r,4r)-4-hydroxycyclohexyl)-2-(1H-imidazol-1-yl)-5H-pyrrolo[3,2-d]pyrimidine-4-carboxamide | 327.2 | 7 |

TABLE 3-continued

| Example # | Structure and Name | MS (M + H)+ | Prepared according to Example # |
|---|---|---|---|
| 178 | 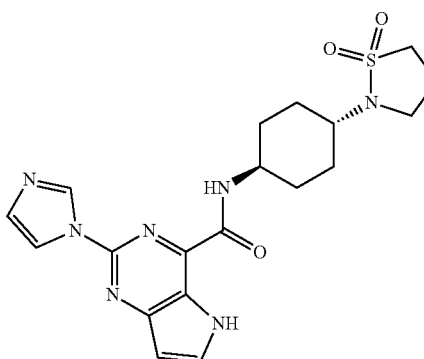<br>N-((1r,4r)-4-(1,1-dioxidoisothiazolidin-2-yl)cyclohexyl)-2-(1H-imidazol-1-yl)-5H-pyrrolo[3,2-d]pyrimidine-4-carboxamide | 430.3 | 7 |
| 179 | 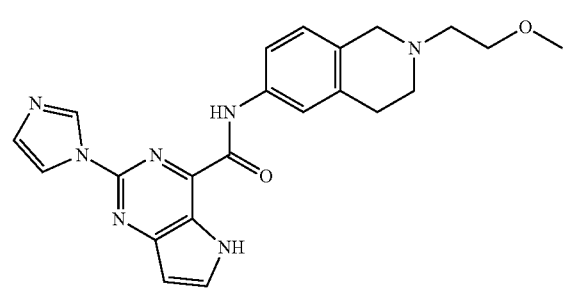<br>2-(1H-imidazol-1-yl)-N-(2-(2-methoxyethyl)-1,2,3,4-tetrahydroisoquinolin-6-yl)-5H-pyrrolo[3,2-d]pyrimidine-4-carboxamide | 418.15 | 7 |
| 180 | 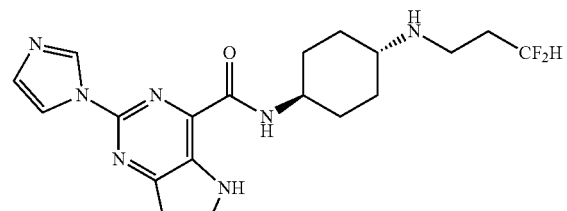<br>N-((1r,4r)-4-((3,3-difluoropropyl)amino)cyclohexyl)-2-(1H-imidazol-1-yl)-5H-pyrrolo[3,2-d]pyrimidine-4-carboxamide | 404.25 | 101 |

TABLE 3-continued
| Example # | Structure and Name | MS (M + H)+ | Prepared according to Example # |
|---|---|---|---|
| 181 | 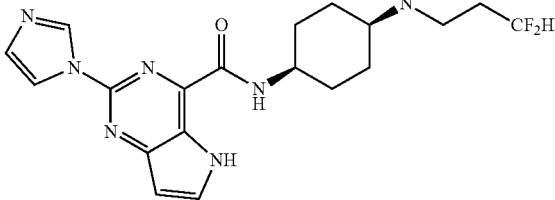<br>N-((1s,4s)-4-((3,3-difluoropropyl)amino)cyclohexyl)-2-(1H-imidazol-1-yl)-5H-pyrrolo[3,2-d]pyrimidine-4-carboxamide | 404.25 | 101 |
| 182 | 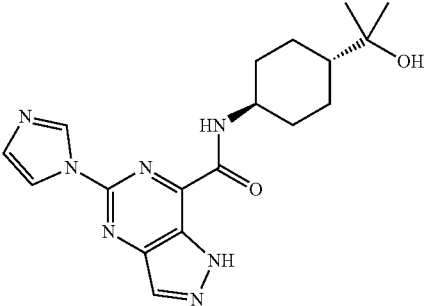 [SMILES: CC(C)(O)[C@H]1CC[C@H](NC(=O)c2nc(-n3ccnc3)nc3cn[nH]c23)CC1]<br>N-((1r,4r)-4-(2-hydroxypropan-2-yl)cyclohexyl)-5-(1H-imidazol-1-yl)-1H-pyrazolo[4,3-d]pyrimidine-7-carboxamide | 370.20 | 118 |
| 183 | 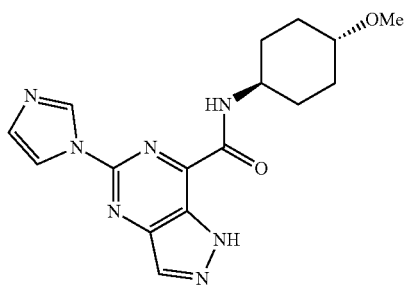<br>5-(1H-imidazol-1-yl)-N-((1r,4r)-4-methoxycyclohexyl)-1H-pyrazolo[4,3-d]pyrimidine-7-carboxamide | 342.05 | 118 |

TABLE 3-continued

| Example # | Structure and Name | MS (M + H)+ | Prepared according to Example # |
|---|---|---|---|
| 184 | N-((1r,4r)-4-(2-hydroxypropan-2-yl)cyclohexyl)-2-(1H-imidazol-1-yl)-6-methyl-5H-pyrrolo[3,2-d]pyrimidine-4-carboxamide | 383.20 | 101, step 1 |
| 185 | N-((1r,4r)-4-(cyanomethyl)cyclohexyl)-2-(1H-imidazol-1-yl)-5H-pyrrolo[3,2-d]pyrimidine-4-carboxamide | 350.20 | 7 |
| 186 | N-((1s,4s)-4-hydroxycyclohexyl)-2-(1H-imidazol-1-yl)-5H-pyrrolo[3,2-d]pyrimidine-4-carboxamide | 327.2 | 7 |

TABLE 3-continued
| Example # | Structure and Name | MS (M + H)+ | Prepared according to Example # |
|---|---|---|---|
| 187 | 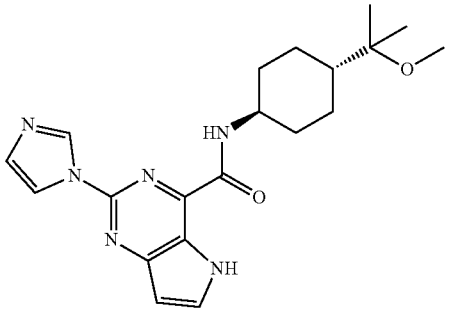<br>2-(1H-imidazol-1-yl)-N-((1r,4r)-4-(2-methoxypropan-2-yl)cyclohexyl)-5H-pyrrolo[3,2-d]pyrimidine-4-carboxamide | 383.2 | 7 |
| 188 | 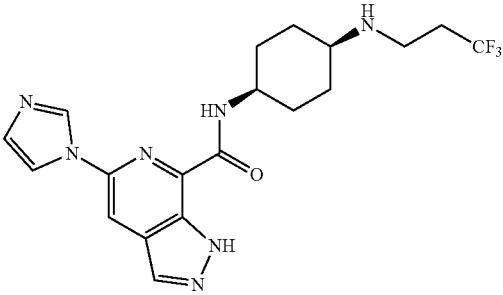<br>5-(1H-imidazol-1-yl)-N-((1s,4s)-4-((3,3,3-trifluoropropyl)amino)cyclohexyl)-1H-pyrazolo[3,4-c]pyridine-7-carboxamide | 422.20 | 115 |
| 189 | 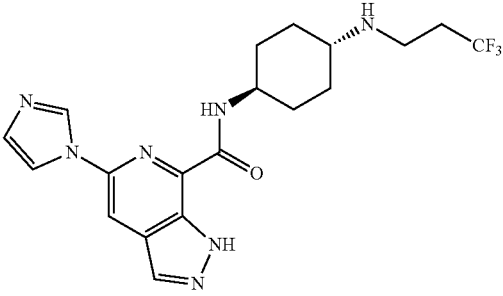<br>5-(1H-imidazol-1-yl)-N-((1r,4r)-4-((3,3,3-trifluoropropyl)amino)cyclohexyl)-1H-pyrazolo[3,4-c]pyridine-7-carboxamide | 422.20 | 115 |

Detailed Synthesis of Example 182: N-((1r,4r)-4-(2-hydroxypropan-2-yl)cyclohexyl)-5-(1H-imidazol-1-yl)-1H-pyrazolo[4,3-d]pyrimidine-7-carboxamide

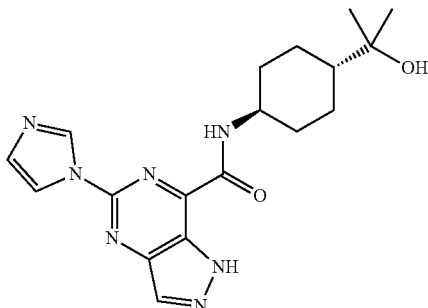

A solution of 5-(1H-imidazol-1-yl)-1H-pyrazolo[4,3-d]pyrimidine-7-carboxylic acid (Int-A4, 350 mg, 1.52 mmol, 1 equiv), 2-((1r,4r)-4-aminocyclohexyl)propan-2-ol (263 mg, 1.67 mmol, 1.1 equiv), HATU (693.8 mg, 1.83 mmol, 1.2 equiv), DIEA (589.5 mg, 4.56 mmol, 3 equiv) in DMF (6 mL) was stirred for 1 h at RT. After concentrating under vacuum, the crude product was purified by C18 silica gel with $H_2O/CH_3CN$ to afford the title compound (105.4 mg, 19%) as a white solid. LCMS: $[M+H]^+$ 370.15. $^1$H NMR (400 MHz, DMSO-d6) δ 14.25 (s, 1H), 9.08 (s, 1H), 9.06 (s, 1H), 8.52 (s, 1H), 8.26 (s, 1H), 7.17 (s, 1H), 4.11 (s, 1H), 3.95-3.79 (m, 1H), 1.95-1.81 (m, 4H), 1.64-1.50 (m, 2H), 1.30-1.11 (m, 3H), 1.08 (s, 6H).

Detailed Synthesis of Example 188: 5-(1H-imidazol-1-yl)-N-((1s,4s)-4-((3,3,3-trifluoropropyl)amino)cyclohexyl)-1H-pyrazolo[3,4-c]pyridine-7-carboxamide and Example 189: 5-(1H-imidazol-1-yl)-N-((1r,4r)-4-((3,3,3-trifluoropropyl)amino)cyclohexyl)-1H-pyrazolo[3,4-c]pyridine-7-carboxamide Example 188

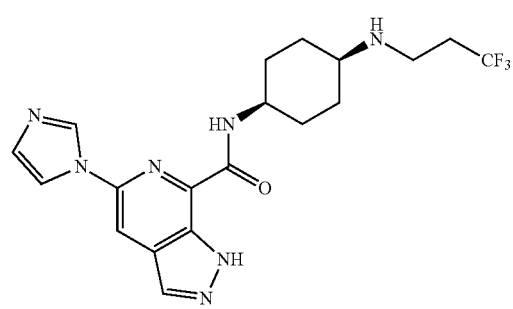

Example 189

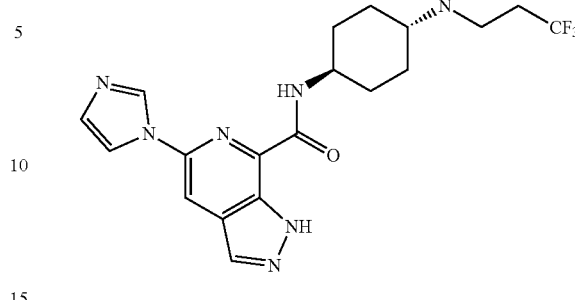

Step 1: 5-(1H-imidazol-1-yl)-N-(4-oxocyclohexyl)-1H-pyrazolo[3,4-c]pyridine-7-carboxamide A solution of 5-(1H-imidazol-1-yl)-1H-pyrazolo[3,4-c]pyridine-7-carboxylic acid (500 mg, 2.18 mmol, 1 eq), DIEA (845.8 mg, 6.55 mmol, 3 eq), 4-aminocyclohexan-1-one hydrochloride (493.7 mg, 4.36 mmol, 2 eq) and HATU (995.3 mg, 2.62 mmol, 1.2 eq) in DMF (1.5 mL) was stirred for 1 h at RT. The mixture was concentrated. The crude product was applied onto a silica gel column eluting with dichloromethane/methanol (92:8) to afford 1.5 g of the title compound as a crude brown solid. LCMS: $[M+H]^+$ 325.10.

Step 2: 5-(1H-imidazol-1-yl)-N-((1s,4s)-4-((3,3,3-trifluoropropyl)amino)cyclohexyl)-1H-pyrazolo[3,4-c]pyridine-7-carboxamide and 5-(1H-imidazo-1-yl)-N-((1r,4r)-4-((3,3,3-trifluoropropyl)amino)cyclohexyl)-1H-pyrazolo[3,4-c]pyridine-7-carboxamide A solution of 5-(1H-imidazol-1-yl)-N-(4-oxocyclohexyl)-1H-pyrazolo[3,4-c]pyridine-7-carboxamide (200 mg, 0.62 mmol, 1 eq), Ti(Oi-Pr)$_4$ (175.3 mg, 0.62 mmol, 1 eq), $CH_3COOH$ (37.0 mg, 0.62 mmol, 1 eq) and 3,3,3-trifluoropropan-1-amine (139.5 mg, 1.23 mmol, 2 eq) in EtOH (5 mL) was stirred for 1 h at RT. This was followed by the addition of NaBH$_3$CN (77.5 mg, 1.23 mmol, 2 eq) at RT. The resulting solution was stirred for 1 h at 70° C. in an oil bath. After completion, the resulting solution was concentrated. The crude product was applied on silica gel column eluting with dichloromethane/methanol (19:1). The crude product was purified by Chiral-Prep-HPLC (Column: CHIRALPAK IA, 2*25 cm, 5 μm. Mobile Phase A: Hexane (8 mM NH$_3$·MeOH), Mobile Phase B: EtOH. Flow rate: 16 mL/min. Gradient: 50% B for 15 min; 254/220 nm) to afford title compounds with retention times of 1.480 minutes (Example 188) and 2.068 minutes (Example 189).

Example 188: 5-(1H-imidazol-1-yl)-N-((1s,4s)-4-((3,3,3-trifluoropropyl)amino)cyclohexyl)-1H-pyrazolo[3,4-c]pyridine-7-carboxamide (17.0 mg, 6.5% yield) was isolated as a white solid. LCMS: $[M+H]^+$ 422.10. $^1$H NMR (300 MHz, DMSO-d6) δ 13.81 (s, 1H), 8.85 (t, J=3 Hz, 1H), 8.64 (d, J=8.1 Hz, 1H), 8.34 (d, J=4.9 Hz, 2H), 8.18 (t, J=1.4 Hz, 1H), 7.12 (t, J=1.2 Hz, 1H), 4.10-3.96 (m, 1H), 2.80-2.69 (m, 3H), 2.46-2.34 (m, 2H), 1.99-1.83 (m, 3H), 1.70-1.53 (m, 6H).

Example 189: 5-(1H-imidazol-1-yl)-N-((1r,4r)-4-((3,3,3-trifluoropropyl)amino)cyclohexyl)-1H-pyrazolo[3,4-c]pyridine-7-carboxamide (37.0 mg, 14.2% yield) was isolated as a white solid. LCMS: $[M+H]^+$ 422.10. $^1$H NMR (300 MHz, DMSO-d6) δ 13.79 (s, 1H), 8.88 (t, J=3.0 Hz, 1H), 8.70 (d, J=8.6 Hz, 1H), 8.33 (d, J=4.5 Hz, 2H), 8.19 (t, J=1.4 Hz, 1H), 7.12 (t, J=1.2 Hz, 1H), 4.01-3.87 (m, 1H), 2.81-2.70 (m, 2H), 2.48-2.25 (m, 3H), 2.01-1.81 (m, 4H), 1.70-1.52 (m, 2H), 1.24-1.06 (m, 2H).

Example 190: N-(6-(3-(dimethylamino)prop-1-yn-1-yl)pyridin-3-yl)-2-(1H-imidazol-1-yl)-5H-pyrrolo[3,2-d]pyrimidine-4-carboxamide

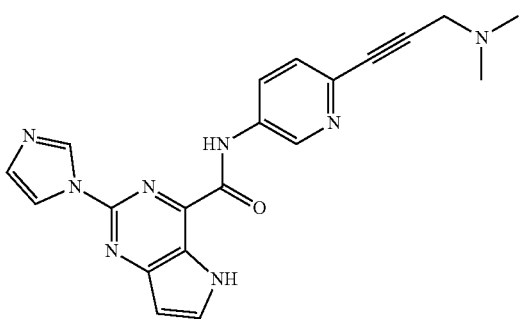 [SMILES: CN(C)CC#Cc1ccc(NC(=O)c2nc(-n3ccnc3)nc3cc[nH]c23)cn1]

Step 1: N-(6-bromopyridin-3-yl)-2-(1H-imidazol-1-yl)-5H-pyrrolo[3,2-d]pyrimidine-4-carboxamide A solution of 2-(1H-imidazol-1-yl)-5H-pyrrolo[3,2-d]pyrimidine-4-carboxylic acid (200 mg, 0.87 mmol, 1 equiv), $T_3P$ (971.8 mg, 3.05 mmol, 3.5 equiv), DIEA (338.3 mg, 2.62 mmol, 3 equiv) and 6-bromopyridin-3-amine (151 mg, 0.87 mmol, 1 equiv) in DCM (2 mL) was stirred at for 1 h at RT. After completion, the resulting mixture was concentrated under vacuum. The crude product was applied onto a silica gel column eluting with DCM/MeOH (85:15) to afford the title compound (134 mg, 40% yield) as a white solid. LCMS: [M+H]$^+$ 384.10.

Step 2: N-(6-(3-(dimethylamino)prop-1-yn-1-yl)pyridin-3-yl)-2-(1H-imidazol-1-yl)-5H-pyrrolo[3,2-d]pyrimidine-4-carboxamide Under nitrogen atmosphere, a solution of N-(6-bromopyridin-3-yl)-2-(1H-imidazol-1-yl)-5H-pyrrolo[3,2-d]pyrimidine-4-carboxamide (100 mg, 0.26 mmol, 1 equiv), TEA (0.4 mL, 0.36 mmol, 1 equiv), CuI (4.9 mg, 0.026 mmol, 0.1 equiv), Pd(PPh$_3$)$_2$Cl$_2$ (18.3 mg, 0.026 mmol, 0.1 equiv) and N,N-dimethylprop-2-yn-1-amine (64.9 mg, 0.78 mmol, 3 equiv) in DMSO (2 mL) was stirred for 1 h at 80° C. The resulting mixture was concentrated under vacuum. The crude product was applied onto a silica gel column eluting with DCM/MeOH (72:28) and further purified by Prep-HPLC to afford the title compound (12.8 mg, 13% yield) as a white solid. LCMS: [M+H]$^+$ 387.20. 1H NMR (300 MHz, DMSO-d6) δ 12.33 (s, 1H), 11.00 (s, 1H), 9.14 (s, 1H), 9.07 (s, 1H), 8.33 (dd, J=8.6, 2.6 Hz, 2H), 8.09 (d, J=3.1 Hz, 1H), 7.62 (d, J=8.5 Hz, 1H), 7.16 (br, 1H), 6.77 (d, J=3.1 Hz, 1H), 3.49 (s, 2H), 2.26 (s, 6H).

Example 191: 5-(1H-imidazol-1-yl)-N-((1r,4r)-4-((2,2,2-trifluoroethyl)amino)cyclohexyl)-1H-pyrazolo[4,3-d]pyrimidine-7-carboxamide

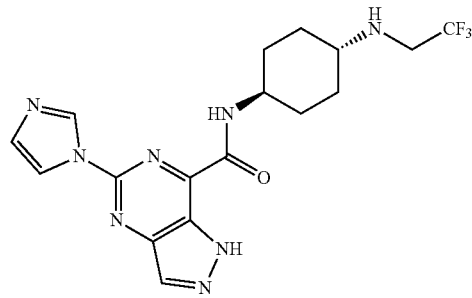 [SMILES: O=C(N[C@H]1CC[C@H](NCC(F)(F)F)CC1)c1nc(-n2ccnc2)nc2cn[nH]c12]

Step 1: tert-butyl ((1r,4r)-4-((2,2,2-trifluoroethyl)amino)cyclohexyl)carbamate

A solution of tert-butyl ((1r,4r)-4-aminocyclohexyl)carbamate (45 g, 210 mmol, 1 equiv), 2,2,2-trifluoroethyl trifluoromethanesulfonate (58.4 g, 252 mmol, 1.2 equiv), and DIEA (81.4 g, 629.93 mmol, 3 equiv) in CH$_3$CN (400 mL) was stirred for 2 h at 70° C. The resulting mixture was concentrated under vacuum. The residue was applied onto a silica gel column with ethyl acetate/petroleum ether (23%: 77%) to afford the title compound (62.2 g, 99.9%) as white solid. LCMS: [M+H]$^+$ 296.17

Step 2: (1r,4r)-N1-(2,2,2-trifluoroethyl)cyclohexane-1,4-diamine dihydrochloride A solution of tert-butyl ((1r,4r)-4-((2,2,2-trifluoroethyl)amino)cyclohexyl)carbamate (62.2 g, 209.9 mmol, 1 equiv) in HCl in 1,4-dioxane (1.0 L, 4 M) was stirred overnight at 70° C. After completion, the resulting mixture was concentrated under vacuum. The crude product was washed with 500 mL of EtOAc. The solids were collected by filtration to afford title compound (55.1 g) as white solid, which was carried forward without additional purification LCMS: [M+H]$^+$ 197.1.

Step 3: 5-(1H-imidazol-1-yl)-N-((1r,4r)-4-((2,2,2-trifluoroethyl)amino)cyclohexyl)-1H-pyrazolo[4,3-d]pyrimidine-7-carboxamide A solution of 5-(1H-imidazol-1-yl)-1H-pyrazolo[4,3-d]pyrimidine-7-carboxylic acid (1.0 g, 4.34 mmol, 1 equiv), T$_3$P (5.53 g, 50% in ethyl acetate, 17.38 mmol, 4 equiv), DIEA (2.25 g, 17.38 mmol, 4 equiv), and (1r,4r)-N1-(2,2,2-trifluoroethyl)cyclohexane-1,4-diamine dihydrochloride (1.403 g, 5.21 mmol, 1.2 equiv) in DMF (10 mL) was stirred for 1 h at RT. After completion, the reaction mixture was concentrated under vacuum. The reaction mixture purified by C18 reverse phase chromatography eluting with H$_2$O/CH$_3$CN (62/38). The collected fractions were concentrated under vacuum to remove most of the MeCN. The solids were collected by filtration to afford the title compound (1.104 g, 62%) as a light yellow solid. LCMS: [M+H]$^+$ 409.10. $^1$H NMR (400 MHz, DMSO-d6) δ 14.23 (s, 1H), 9.07 (s, 1H), 9.03 (d, J=6.4 Hz, 1H), 8.50 (s, 1H), 8.23 (d, J=1.4 Hz, 1H), 7.16 (t, J=1.2 Hz, 1H), 3.95-3.87 (m, 1H), 3.30-3.25 (m, 2H), 2.53-2.41 (m, 1H), 2.32-2.19 (m, 1H), 2.06-1.97 (m, 2H), 1.93-1.85 (m, 2H), 1.65-1.51 (m, 2H), 1.22-1.08 (m, 2H).

Example 192a and 192b: N-((1S,4r)-4-((S)-1-hydroxyethyl)cyclohexyl)-5-(1H-imidazol-1-yl)-1H-pyrazolo[3,4-c]pyridine-7-carboxamide and N-((1R,4r)-4-((R)-1-hydroxyethyl)cyclohexyl)-5-(1H-imidazol-1-yl)-1H-pyrazolo[3,4-c]pyridine-7-carboxamide

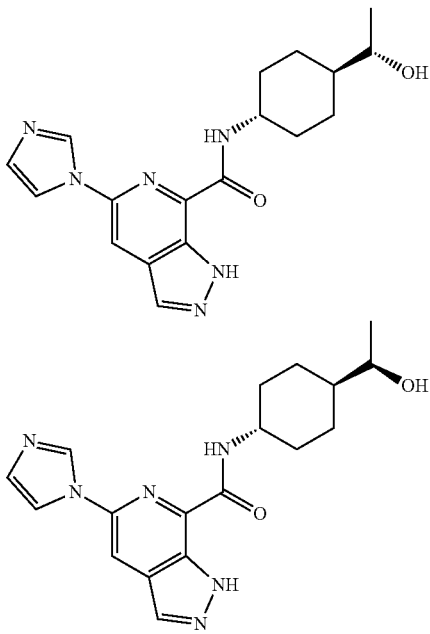

Step 1: ethyl (1r,4r)-4-(dibenzylamino)cyclohexane-1-carboxylate

A solution of ethyl (1r,4r)-4-aminocyclohexane-1-carboxylate (1.75 g, 10.22 mmol, 1 equiv), (bromomethyl)benzene (3.67 g, 21.46 mmol, 2.1 equiv), and K$_2$CO$_3$ (4.24 g, 30.66 mmol, 3 equiv) in MeCN (50 mL) was stirred for 1 h at 80° C. After completion, the reaction was quenched by the addition of 100 mL of water. The resulting solution was extracted with 3×100 mL of DCM. The organic layers were combined, washed with brine, dried over anhydrous sodium sulfate and concentrated under vacuum to afford the title compound (3.43 g, 95%) as a yellow oil. LCMS: [M+H]$^+$ 352.15.

Step 2: (1r,4r)-4-(dibenzylamino)cyclohexane-1-carboxylic acid

A solution of ethyl (1r,4r)-4-(dibenzylamino)cyclohexane-1-carboxylate (3.60 g, 10.24 mmol, 1 equiv), NaOH (0.82 g, 20.5 mmol, 2 equiv), H$_2$O (15 mL) in MeOH (60 mL) was stirred for 1 h at RT. The pH value of the solution was adjusted to 6 with HCl (0.1 M). Then solids were collected by filtration and dried to afford the title compound (2.7 g, 81.5%) as a white solid. LCMS: [M+H]$^+$ 324.15.

Step 3: (1r,4r)-4-(dibenzylamino)-N-methoxy-N-methylcyclohexane-1-carboxamide

A solution of (1r,4r)-4-(dibenzylamino)cyclohexane-1-carboxylic acid (1.8 g, 5.57 mmol, 1 equiv), N,O-dimethylhydroxylamine hydrochloride (0.54 g, 5.57 mmol, 1 equiv), DIEA (2.16 g, 16.7 mmol, 3 equiv), and HATU (2.54 g, 6.68 mmol, 1.2 equiv) in DMF (50 mL) was stirred for 1 h at RT. After completion, the resulting solution was diluted with 30 mL of H$_2$O. The resulting solution was extracted with 3×30 mL of EtOAc. The organic layers were combined, washed with brine, dried over anhydrous sodium sulfate and concentrated under vacuum. The crude product was purified by silica gel column to afford the title compound (1.22 g, 60%) as a white solid. LCMS: [M+H]$^+$ 367.15.

Step 4: 1-((1r,4r)-4-(dibenzyiamino)cyclohexyl)ethan-1-one

To a solution of (1r,4r)-4-(dibenzylamino)-N-methoxy-N-methylcyclohexane-1-carboxamide (1.22 g, 3.33 mmol, 1 equiv) in THF (20 mL) was added a solution of bromo(methyl)magnesium in THF (1.1 mL, 1.01 equiv, 3 M) at 0° C. The resulting solution was stirred for 1 h at RT. The reaction was quenched by the addition of 50 mL of NH$_4$Cl (aq). The resulting solution was extracted with 3×50 mL of EtOAc. The organic layers were combined, dried over anhydrous sodium sulfate and concentrated under vacuum to afford the title compound (823 mg, 76%) as a light yellow solid. LCMS: [M+H]$^+$ 322.15.

Step 5: (S)-1-((1r,4S)-4-(dibenzylamino)cyclohexyl)ethan-1-ol and (R)-1-((1r,4R)-4-(dibenzylamino)cyclohexyl)ethan-1-ol A solution of 1-((1r,4r)-4-(dibenzylamino)cyclohexyl)ethan-1-one (800 mg, 2.49 mmol, 1 equiv), NaBH$_4$ (282.5 mg, 7.47 mmol, 3 equiv) in MeOH (2 mL) was stirred for 1 h at RT. The reaction was quenched by the addition of 30 mL of water. The resulting solution was concentrated under vacuum. The residue was purified by a silica gel column (ethyl acetate/petroleum ether, 30:70) to afford the mixture of title compounds (735 mg, 91%) as a white solid. LCMS: [M+H]$^+$ 324.15.

Step 6: (S)-1-((1r,4S)-4-aminocyclohexyl)ethan-ol and (R)-1-((1r,4R)-4-aminocyclohexyl)ethan-1-ol Maintained under an atmosphere of hydrogen, a solution of (S)-1-((1r,4S)-4-(dibenzylamino)cyclohexyl)ethan-1-ol and (R)-1-((1r,4R)-4-(dibenzylamino)cyclohexyl)ethan-1-ol (700 mg, 2.16 mmol, 1 equiv), and Pd(OH)$_2$/C (911.7 mg, 6.49 mmol, 3 equiv) in EtOH (20 mL) was stirred for 1 h at RT. After completion, the solids were filtered out. The filtrate was concentrated under vacuum to afford the crude mixture of title compounds (246 mg, 79%) as a light yellow solid. LCMS: [M+H]$^+$ 144.15.

Step 7: N-((1S,4r)-4-((S)-1-hydroxyethyl)cyclohexyl)-5-(1H-imidazol-1-yl)-1H-pyrazolo[3,4-c]pyridine-7-carboxamide and N-((1R,4r)-4-((R)-1-hydroxyethyl)cyclohexyl)-5-(1H-imidazol-1-yl)-1H-pyrazolo[3,4-c]pyridine-7-carboxamide A solution of (S)-1-((1r,4S)-4-aminocyclohexyl)ethan-1-ol and (R)-1-((1r,4R)-4-aminocyclohexyl)ethan-1-ol (100 mg, 0.69 mmol, 1 equiv), 5-(1H-imidazol-1-yl)-1H-pyrazolo[3,4-c]pyridine-7-carboxylic acid (160 mg, 0.69 mmol, 1 equiv), DIEA (270.7 mg, 2.1 mmol, 3 equiv), and HATU (318.6 mg, 0.84 mmol, 1.2 equiv) in DMF (2.0 mL) was stirred for 1 h at RT. After completion, the resulting solution was concentrated. The crude product was purified by reverse phase column with $H_2O/CH_3CN$ (33:67) and further purified by Prep-HPLC with the following conditions (Column: CHIRALPAK IG, 2*25 cm, 5 um; Mobile Phase A:Hexane:DCM=3:1 (0.5% 2M $NH_3$-MeOH), Mobile Phase B:EtOH; Flow rate:16 mL/min; Gradient: maintaining 50% B for 24 min; 220/254 nm) Retention times: 15.427 min (Example 192a) and 19.166 min (Example 192b). Chiral HPLC: CHIRALPAK IG-3, 4.6*50 mm, 3 um. (Hexane:DCM=3:1)(0.1% DEA):EtOH=50:50. Flow=1.0 mL/min. Retention times: 2.902 minutes (Example 192a) and 3.537 min (Example 192b). The absolute stereochemistry of Example 192a and Example 192b was not confirmed.

Example 192a: (44.1 mg, 18% yield) as a white solid. LCMS: [M+H]$^+$ 355.05. $^1$H NMR (300 MHz, DMSO-d6) δ 13.83 (s, 1H), 8.93 (s, 1H), 8.71 (d, J=9.0 Hz, 1H), 8.36 (d, J=1.2 Hz, 1H), 8.35 (s, 1H), 8.22 (t, J=1.4 Hz, 1H), 7.15 (t, J=1.2 Hz, 1H), 4.33 (d, J=4.8 Hz, 1H), 3.98-3.85 (m, 1H), 3.39 (d, J=6.3 Hz, 1H), 1.94-1.85 (m, 3H), 1.73-1.68 (m, 1H), 1.60-1.52 (m, 2H), 1.18-1.03 (m, 6H).

Example 192b: (48.3 mg, 20% yield) as a white solid. LCMS: [M+H]$^+$ 355.05. $^1$H NMR (300 MHz, DMSO-d6) δ 13.83 (s, 1H), 8.92 (s, 1H), 8.71 (d, J=8.6 Hz, 1H), 8.36 (d, J=1.2 Hz, 1H), 8.35 (s, 1H), 8.22 (t, J=1.4 Hz, 1H), 7.15 (t, J=1.2 Hz, 1H), 4.34 (d, J=5.1 Hz, 1H), 3.98-3.81 (m, 1H), 3.39 (d, J=6.3 Hz, 1H), 1.95-1.90 (m, 3H), 1.73-1.69 (m, 1H), 1.60-1.50 (m, 2H), 1.25-1.07 (m, 6H).

Example 193: N-((1r,4r)-4-((2,2-difluoropropyl)amino)cyclohexyl)-5-(1H-imidazol-1-yl)-1H-pyrazolo[3,4-c]pyridine-7-carboxamide and Example 194: N-((1s,4s)-4-((2,2-difluoropropyl)amino)cyclohexyl)-5-(1H-imidazol-1-yl)-1H-pyrazolo[3,4-c]pyridine-7-carboxamide

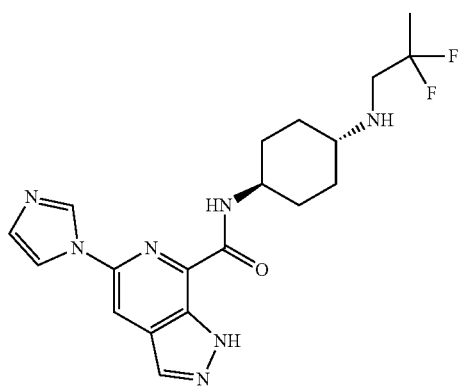

Example 193

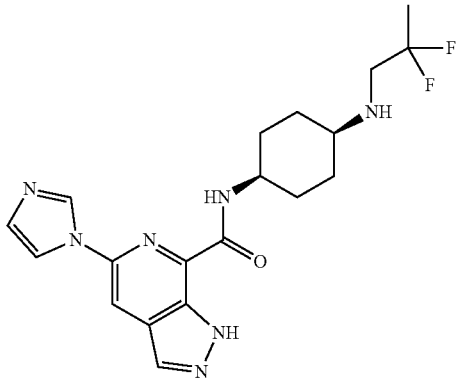

Example 194

Step 1: tert-butyl (4-((2,2-difluoropropyl)amino)cyclohexyl)carbamate

A solution of tert-butyl (4-oxocyclohexyl)carbamate (3.0 g, 14.07 mmol, 1 equiv), 2,2-difluoropropan-1-amine hydrochloride (2.0 g, 15.47 mmol, 1.1 equiv), HOAc (845 mg, 14.07 mmol, 1 equiv), and Ti(Oi-Pr)$_4$ (4 g, 14.07 mmol, 1 equiv) in EtOH (20 mL) was stirred for 1.5 h at 25° C. Then NaBH$_3$CN (1.33 g, 21.1 mmol, 1.5 equiv) was added and the mixture was stirred for 1 h at 25° C. After completion, the solution was concentrated. The crude product was purified by a silica gel column with EtOAc to afford the title compound (4 g, 97%) as a white solid. LCMS: [M+H]$^+$ 293.20.

Step 2: N1-(2,2-difluoropropyl)cyclohexane-1,4-diamine hydrochloride

A solution of tert-butyl (4-((2,2-difluoropropyl)amino)cyclohexyl)carbamate (4 g, 13.68 mmol, 1 equiv) in HCl in 1,4-dioxane (50 mL, 4 M) was stirred for 1 h at RT. The resulting mixture was concentrated under vacuum to afford the title compound (3 g, 83%) as a white solid. LCMS: [M+H]$^+$ 193.20.

Step 3: N-((1r,4r)-4-((2,2-difluoropropyl)amino)cyclohexyl)-5-(1H-imidazol-1-yl)-1H-pyrazolo[3,4-c]pyridine-7-carboxamide and N-((1s,4s)-4-((2,2-difluoropropyl)amino)cyclohexyl)-5-(1H-imidazol-1-yl)-1H-pyrazolo[3,4-c]pyridine-7-carboxamide A solution of N1-(2,2-difluoropropyl)cyclohexane-1,4-diamine (673 mg, 2.54 mmol, 1.1 equiv), 5-(1H-imidazol-1-yl)-1H-pyrazolo[3,4-c]pyridine-7-carboxylic acid (529 mg, 2.31 mmol, 1 equiv), T$_3$P (2.2 g, 50% in ethyl acetate, 6.92 mmol, 3 equiv), DIEA (1.79 g, 13.85 mmol, 6 equiv) in DMF (5 mL) was stirred for 1 h at RT. The mixture was purified by reverse phase column eluting with $H_2O/CH_3CN$ (50:50) and further purified by Prep-HPLC using the following conditions (Column: XBridge Prep OBD C18 Column, 30×150 mm Sum; Mobile Phase A: Water (10 mM NH$_4$HCO$_3$), Mobile Phase B:ACN; Flow rate:60 mL/min; Gradient: 18% B to 48% B in 10 min; 254 nm) to afford the title compounds with retention times: 8.40 minutes (Example 193) and 9.27 minutes (Example 194).

Example 193: N-((1r,4r)-4-((2,2-difluoropropyl)amino) cyclohexyl)-5-(1H-imidazol-1-yl)-1H-pyrazolo[3,4-c]pyridine-7-carboxamide (118.6 mg, 12.8%) as a light yellow solid. LCMS: [M+H]$^+$ 404.25. $^1$H NMR (300 MHz, DMSO-d6) δ 13.81 (s, 1H), 8.90 (s, 1H), 8.70 (d, J=8.7 Hz, 1H), 8.35 (d, J=4.2 Hz, 2H), 8.20 (s, 1H), 7.14 (s, 1H), 4.00-3.80 (m, 1H), 2.91 (t, J=14.1 Hz 2H), 2.42-2.38 (m, 1H), 2.12-1.89 (m, 2H), 1.88-1.80 (m, 3H), 1.70-1.50 (m, 5H), 1.22-1.10 (m, 2H).

Example 194: N-((1s,4s)-4-((2,2-difluoropropyl)amino) cyclohexyl)-5-(1H-imidazol-1-yl)-1H-pyrazolo[3,4-c]pyridine-7-carboxamide (80.9 mg, 8.8%) as a light yellow solid. LCMS: [M+H]$^+$ 404.25. $^1$H NMR (300 MHz, DMSO-d6) δ 13.84 (s, 1H), 8.86 (s, 1H), 8.68 (d, J=8.4 Hz, 1H), 8.35 (d, J=4.8 Hz, 2H), 8.18 (s, 1H), 7.14 (s, 1H), 4.10-3.92 (m, 1H), 3.00-2.83 (m, 2H), 2.80-2.70 (m, 1H), 2.00-1.72 (m, 2H), 1.67-1.50 (m, 9H).

Example 195: N-((1r,4r)-4-((2,2-difluoroethyl) amino)cyclohexyl)-5-(1H-imidazol-1-yl)-1H-pyrazolo[3,4-c]pyridine-7-carboxamide

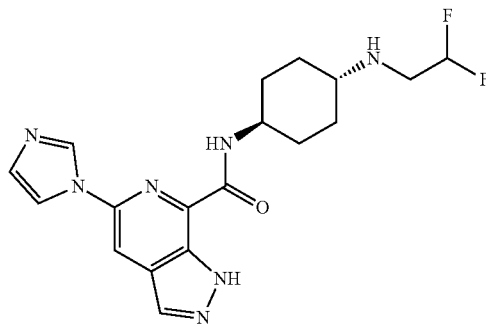

Step 1: tert-butyl ((1r,4r)-4-((2,2-difluoroethyl) amino)cyclohexyl)carbamate

A solution of tert-butyl ((1r,4r)-4-aminocyclohexyl)carbamate (41.5 g, 193.65 mmol, 1 equiv), 1,1-difluoro-2-iodoethane (37.2 g, 193.65 mmol, 1 equiv), and K$_2$CO$_3$ (53.53 g, 387.29 mmol, 2 equiv) in acetonitrile (40 mL) was stirred for 16 h at 80° C. After completion, the solids were filtered out, and the filtrate was concentrated. The crude product was purified by silica gel chromatography eluting with petroleum ethyl acetate/petroleum ether (1:1) to afford the title compound (22.89 g, 43%) as a white solid. LCMS: [M+H]$^+$ 279.05.

Step 2: (1r,4r)-N1-(2,2-difluoroethyl)cyclohexane-1, 4-diamine dihydrochloride

A solution of tert-butyl ((1r,4r)-4-((2,2-difluoroethyl) amino)cyclohexyl) carbamate (28.9 g, 103.83 mmol, 1 equiv) in HCl/Dioxane (40 mL, 4 M) was stirred for 20 h at RT. After completion, the solids were collected by filtration and slurried in 20 mL ethyl acetate. Then solids were collected by filtration and dried to afford the crude title compound (23.9 g, yield) as a white solid. LCMS: [M+H]$^+$ 179.10.

Step 3: N-((1r,4r)-4-((2,2-difluoroethyl)amino)cyclohexyl)-5-(1H-imidazol-1-yl)-1H-pyrazolo[3,4-c] pyridine-7-carboxamide A solution of 5-(1H-imidazol-1-yl)-1H-pyrazolo[3,4-c] pyridine-7-carboxylic acid (12 g, 52.36 mmol, 1 equiv), HATU (19.9 g, 52.36 mmol, 1 equiv), DIEA (27.07 g, 209.43 mmol, 4 equiv), and (1r,4r)-N1-(2,2-difluoroethyl) cyclohexane-1,4-diamine (10.26 g, 57.59 mmol, 1.1 equiv) in DMF (120 mL) was stirred for 50 min at RT. After completion, the reaction mixture was added into 600 mL of NaHCO$_3$ aqueous. The solids were collected by filtration and slurried in 50 mL acetonitrile. Then solids were collected by filtration and dried under oven to afford the title compound (10.47 g, 51%) as a white solid. LCMS: [M+H]$^+$ 390.15. $^1$H NMR (300 MHz, DMSO-d$_6$) δ 13.83 (s, 1H), 8.90 (s, 1H), 8.72 (d, J=8.7 Hz, 1H), 8.34 (d, J=3.8 Hz, 2H), 8.20 (t, J=1.4 Hz, 1H), 7.13 (s, 1H), 5.96 (t, J=45.1 Hz, 1H), 3.90-3.82 (m, 1H), 2.97-2.86 (m, 2H), 2.49-2.39 (m, 1H), 1.98-1.84 (m, 5H), 1.65-1.53 (m, 2H), 1.24-1.04 (m, 2H).

Example 196: 5-(1H-imidazol-1-yl)-N-((1r,4r)-4-(2-methoxyethoxy)cyclohexyl)-2-methyl-2H-pyrazolo [3,4-c]pyridine-7-carboxamide and Example 197: 5-(1H-imidazol-1-yl)-N-((1r,4r)-4-(2-methoxyethoxy)cyclohexyl)-1-methyl-1H-pyrazolo [3,4-c]pyridine-7-carboxamide

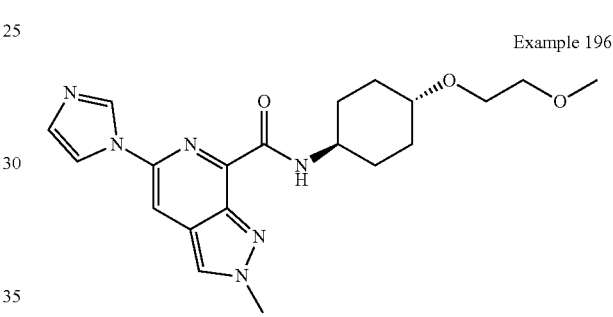

Example 196

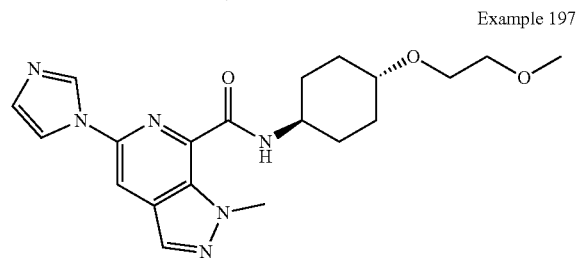

Example 197

Step 1: 5-(1H-imidazol-1-yl)-2-methyl-2H-pyrazolo [3,4-c]pyridine-7-carboxylic acid and 5-(1H-imidazol-1-yl)-1-methyl-1H-pyrazolo[3,4-c]pyridine-7-carboxylic acid To a solution of ethyl 5-(1H-imidazol-1-yl)-1H-pyrazolo [3,4-c]pyridine-7-carboxylate (643 mg, 2.5 mmol, 1 equiv) in DMF (5 mL) was added NaH (60% w/w) (150 mg, 3.75 mmol, 1.5 equiv) at 0° C. The resulting solution was stirred for 20 min. Then iodomethane (355 mg, 2.50 mmol, 1 equiv) was added and the mixture was stirred for 1 h at 0° C. Then a solution of NaOH (120 mg, 3.00 mmol, 1.2 equiv) in 2 mL of water was added into the mixture. The mixture was stirred for 30 min. Then pH of the solution was adjusted to 5 with HCl (2 M). The resulting solution was diluted with 30 ml THF. The solids were filtered out and the filtrate was concentrated. The product was purified by reverse phase column eluting with H$_2$O/MeCN (30:70) to afford a mixture of the title compounds (320 mg, 53%) as a brown solid. LCMS: [M+H]$^+$ 243.05.

Step 2: 5-(1H-imidazol-1-yl)-N-((1r,4r)-4-(2-methoxyethoxy)cyclohexyl)-2-methyl-2H-pyrazolo[3,4-c]pyridine-7-carboxamide and 5-(1H-imidazol-1-yl)-N-((1r,4r)-4-(2-methoxyethoxy)cyclohexyl)-1-methyl-1H-pyrazolo[3,4-c]pyridine-7-carboxamide A solution of the acid mixture from Step 1 (290 mg, 1.19 mmol, 1 equiv), (1r,4r)-4-(2-Methoxyethoxy)cyclohexan-1-amine (Int-B1, 248 mg, 1.43 mmol, 1.2 equiv), DIEA (460.0 mg, 3.56 mmol, 3 equiv), and $T_3P$ (2.34 g, 3.58 mmol, 3 equiv, 50% in EA) in DMF (2 ml) was stirred at RT for 1.5 h. The crude product was purified by reverse phase column eluting with $H_2O/CH_3CN$ (70:30) and further purified by Prep-HPLC with the following conditions (Column: XBridge Prep OBD C18 Column, 30×150 mm 5um; Mobile Phase A:Water (10 mM $NH_4HCO_3$), Mobile Phase B:ACN; Flow rate: 60 mL/min; Gradient: 12% B to 33% B in 7 min; 254 nm) retention times: 7.90 minutes (Example 197) and 9.15 minutes (Example 196).

Example 196: 5-(1H-imidazol-1-yl)-N-((1r,4r)-4-(2-methoxyethoxy)cyclohexyl)-2-methyl-2H-pyrazolo[3,4-c]pyridine-7-carboxamide (60.5 mg, 12.7%) as a light yellow solid. LCMS: $[M+H]^+$ 399.20. $^1H$ NMR (300 MHz, DMSO-d6) δ 8.80 (d, J=8.1 Hz, 1H), 8.62 (t, J=1.1 Hz, 1H), 8.34 (s, 1H), 8.24 (s, 1H), 8.03 (s, 1H), 7.12 (t, J=1.2 Hz, 1H), 4.23 (s, 3H), 3.92-3.78 (m, 1H), 3.53 (dd, J=5.9, 3.7 Hz, 2H), 3.41 (dd, J=5.9, 3.7 Hz, 2H), 3.27-3.20 (m, 4H), 2.12-1.89 (m, 4H), 1.60-1.41 (m, 2H), 1.36-1.18 (m, 2H).

Example 197: 5-(1H-imidazol-1-yl)-N-((1r,4r)-4-(2-methoxyethoxy)cyclohexyl)-1-methyl-1H-pyrazolo[3,4-c]pyridine-7-carboxamide (38.8 mg, 8.2%) as a light yellow solid. LCMS: $[M+H]^+$ 399.20. $^1H$ NMR (300 MHz, DMSO-d6) δ 8.70 (s, 1H), 8.63 (s, 1H), 8.59 (d, J=9.0 Hz, 1H) 8.19 (s, 1H), 8.01 (t, J=1.4 Hz, 1H), 7.11 (t, J=1.2 Hz, 1H), 4.30 (s, 3H), 3.92-3.73 (m, 1H), 3.53 (dd, J=5.9, 3.7 Hz, 2H), 3.42 (dd, J=5.9, 3.7 Hz, 2H), 3.27-3.21 (m, 4H), 2.09-1.85 (m, 4H), 1.58-1.40 (m, 2H), 1.37-1.19 (m, 2H).

Example 198: 5-(1H-imidazol-1-yl)-N-((1r,4r)-4-(2-methoxyethoxy)cyclohexyl)thieno[2,3-c]pyridine-7-carboxamide

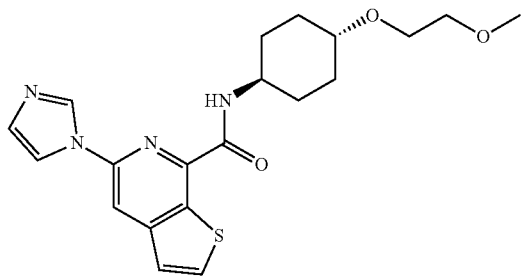 [SMILES: COCCO[C@H]1CC[C@H](NC(=O)c2nc(-n3ccnc3)cc3ccsc23)CC1]

Step 1: 3-(cyanomethyl)thiophene-2-carboxylic acid

A solution of 3-bromothiophene-2-carboxylic acid (38.0 g, 183.54 mmol, 1 equiv), 3-oxo-3-phenylpropanenitrile (37.3 g, 256.96 mmol, 1.4 equiv), EtONa (31.22 g, 458.85 mmol, 2.5 equiv), and $Cu(OAc)_2$ (6.67 g, 36.71 mmol, 0.2 equiv) in EtOH (800 mL) was stirred for 14 h at 80° C. After completion, the solids were filtered out. The resulting mixture was concentrated and dissolved in 500 mL of $H_2O$. The pH of the solution was adjusted to 5 with HCl (3 M). The solids were filtered out. The filtrate was concentrated and applied onto a silica gel column with dichloromethane/methanol (4:1) to afford the title compound (17 g, 55%) as a yellow solid. LCMS: $[M+H]^+$ 168.00.

Step 2: 5,7-dibromothieno[2,3-c]pyridine

A solution of $PBr_3$ (37.1 mL) was added into DMF (3.50 mL) slowly with stirring at 0° C. To this was added 3-(cyanomethyl)thiophene-2-carboxylic acid (5.6 g, 33.5 mmol, 1 equiv) in several batches at 0° C. The resulting solution was stirred for 3 h at 120° C. The reaction mixture was cooled to room temperature with a water/ice bath. The reaction mixture was then poured into ice water. The solids were collected by filtration. The solid was dried to afford the title compound (4.2 g, 43%) as a yellow solid. LCMS: $[M+H]^+$ 291.80, 293.80, 295.80.

Step 3: 5-bromo-7-(1-ethoxyvinyl)thieno[2,3-c]pyridine

A solution of 5,7-dibromothieno[2,3-c]pyridine (4.86 g, 16.59 mmol, 1 equiv), $Pd(PPh_3)_2Cl_2$ (116.4 mg, 0.17 mmol, 0.01 equiv), and tributyl(1-ethoxyethenyl)stannane (5991 mg, 16.59 mmol, 1 equiv) in DMF (60 mL) was stirred for 2 h at 75° C. under $N_2$. The reaction was then quenched by the addition of saturated aqueous KF. The solids were filtered out. The resulting solution was extracted with 3×200 mL of ethyl acetate dried over anhydrous sodium sulfate and concentrated. The residue was applied onto a silica gel column eluting with ethyl acetate/petroleum ether (2:98) to afford the title compound (3.1 g, 66%) as a yellow solid. LCMS: $[M+H]^+$ 283.90, 285.85.

Step 4: 7-(1-ethoxyvinyl)-5-(1H-imidazol-1-yl)thieno[2,3-c]pyridine

A solution of 5-bromo-7-(1-ethoxyethenyl)thieno[2,3-c]pyridine (3.10 g, 10.91 mmol, 1 equiv), imidazole (2228 mg, 32.73 mmol, 3 equiv), $Pd_2(dba)_3 \cdot CHCl_3$ (1129 mg, 1.09 mmol, 0.1 equiv), tBuXPhos (463.6 mg, 1.09 mmol, 0.1 equiv), and $K_3PO_4$ (4631.2 mg, 21.82 mmol, 2 equiv) in toluene (80 mL) was stirred for 3 h at 110° C. under $N_2$ atmosphere. The solids were filtered out. The resulting mixture was concentrated. The residue was applied onto a silica gel column eluting with ethyl acetate/petroleum ether (4:1) to afford the title compound (1.8 g, 61%) as a yellow solid. LCMS: $[M+H]^+$ 272.08.

Step 5: ethyl 5-(1H-imidazol-1-yl)thieno[2,3-c]pyridine-7-carboxylate

To solution of 7-(1-ethoxyvinyl)-5-(1H-imidazol-1-yl)thieno[2,3-c]pyridine (1.8 g, 6.63 mmol, 1 equiv) in dioxane (100 mL) and $H_2O$ (100 mL) was added $NaIO_4$ (2837.8 mg, 13.27 mmol, 2 equiv) in several batches at 10° C. To this was added $KMnO_4$ (524.2 mg, 3.32 mmol, 0.5 equiv) in several batches at 10° C. The resulting solution was stirred for 1 h at 10° C. in a water/ice bath. The solids were filtered out. The resulting solution was extracted with 3×100 mL of ethyl acetate; the organic layers were combined, dried over anhydrous sodium sulfate and concentrated. The residue was applied onto a silica gel column with DCM/MeOH (95:5) to afford the title compound (650 mg, 36%) as a yellow solid. LCMS: $[M+H]^+$ 274.06.

Step 6: 5-(1H-imidazol-1-yl)thieno[2,3-c]pyridine-7-carboxylic acid

To a solution of ethyl 5-(1H imidazol-1-yl)thieno[2,3-c]pyridine-7-carboxylate (650 mg, 2.38 mmol, 1 equiv) in MeOH (30 mL) and H$_2$O (6.0 mL) was added NaOH (475.6 mg, 11.89 mmol, 5 equiv) and the reaction was stirred for 1 h at RT. The resulting mixture was concentrated. The pH of the solution was adjusted to 5 with HCl (12 M). The solids were collected by filtration. The solid was dried to afford the title compound (275 mg, 47%) as a yellow solid. LCMS: [M+H]$^+$ 246.03

Step 7: 5-(1H-imidazol-1-yl)-N-((1r,4r)-4-(2-methoxyethoxy)cyclohexyl)thieno[2,3-c]pyridine-7-carboxamide A solution of 5-(1H-imidazol-1-yl)thieno[2,3-c]pyridine-7-carboxylic acid (100 mg, 0.41 mmol, 1 equiv), (1r,4r)-4-(2-methoxyethoxy)cyclohexan-1-amine (70.6 mg, 0.41 mmol, 1 equiv), DIEA (158.1 mg, 1.22 mmol, 3 equiv), and HATU (186.04 mg, 0.49 mmol, 1.2 equiv) in DMF (3.0 mL) was stirred for 1.5 h at RT. The crude product was purified by reverse phase column eluting with MeCN/H$_2$O (38/62) to afford the title compound (99.7 mg, 60%). LCMS: [M+H]$^+$ 401.20. $^1$H NMR (300 MHz, DMSO-d6) δ: δ 8.98 (s, 1H), 8.80 (d, J=8.7 Hz, 1H), 8.45 (d, s, 1H), 8.27 (dd, J=9.3, 3.5 Hz, 2H), 7.57 (d, J=5.5 Hz, 1H), 7.16 (s, 1H), 3.90-3.88 (m, 1H), 3.60-3.51 (m, 2H), 3.48-3.39 (m, 2H), 3.31-3.26 (m, 4H), 2.12-2.06 (m, 2H), 1.92-1.81 (m, 2H) 1.75-1.52 (m, 2H), 1.35-1.1 (m, 2H).

Example 199: 5-(1H-imidazol-1-yl)-N-((1r,4r)-4-(2-(methylamino)-2-oxoethyl)cyclohexyl)-1H-pyrazolo[3,4-c]pyridine-7-carboxamide

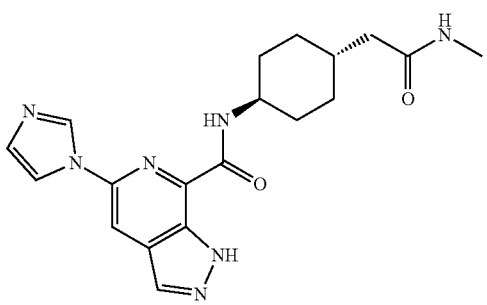 [SMILES: CNC(=O)C[C@H]1CC[C@H](NC(=O)c2nc(-n3ccnc3)cc3cn[nH]c23)CC1]

Step 1: ethyl 2-((1r,4r)-4-(5-(1H-imidazol-1-yl)-1H-pyrazolo[3,4-c]pyridine-7-carboxamido)cyclohexyl)acetate A solution of 5-(imidazol-1-yl)-1H-pyrazolo[3,4-c]pyridine-7-carboxylic acid (229 mg, 1 mmol, 1 equiv), HATU (569.9 mg, 1.5 mmol, 1.5 equiv), DIEA (387.4 mg, 3 mmol, 3 equiv), and ethyl 2-[(1r,4r)-4-aminocyclohexyl]acetate hydrochloride (243.7 mg, 1.1 mmol, 1.1 equiv) in DMF (3.0 mL) was stirred for 2 h at RT. The resulting solution was diluted with 50 mL H$_2$O. The resulting solution was extracted with 3×50 mL EtOAc, dried over anhydrous sodium sulfate and concentrated under vacuum to afford the title compound (240 mg, 61%) as a yellow solid. LCMS: [M+H]$^+$ 397.19.

Step 2: 2-((1r, 4r)-4-(5-(1H-imidazol-1-yl)-1H-pyrazolo[3,4-c]pyridine-7-carboxamido)cyclohexyl)acetic acid A solution of ethyl 2-((1r,4r)-4-(5-(1H-imidazol-1-yl)-1H-pyrazolo[3,4-c]pyridine-7-carboxamido)cyclohexyl)acetate (240 mg, 0.61 mmol, 1 equiv), NaOH (72.6 mg, 1.82 mmol, 3 equiv), H$_2$O (2.0 mL, 111.02 mmol, 183.4 equiv) in THF (2.0 mL) was stirred for 2 h at RT. The resulting mixture was concentrated under vacuum. The mixture was diluted with 5 mL of water. The pH of the solution was adjusted to 5 with HCl (2 M). The solids were collected by filtration to afford the title compound (231 mg) as a light yellow solid that was carried forward without additional purification. LCMS: [M+H]$^+$ 369.16.

Step 3: 5-(1H-imidazol-1-yl)-N-((1r,4r)-4-(2-(methylamino)-2-oxoethyl)cyclohexyl)-1H-pyrazolo[3,4-c]pyridine-7-carboxamide A solution of 2-((1r,4r)-4-(5-(1H-imidazol-1-yl)-1H-pyrazolo[3,4-c]pyridine-7-carboxamido)cyclohexyl)acetic acid (100 mg, 0.27 mmol, 1 equiv), HATU (154.8 mg, 0.41 mmol, 1.5 equiv), DIEA (140.3 mg, 1.09 mmol, 4 equiv), and methanamine hydrochloride (20.16 mg, 0.3 mmol, 1.1 equiv) in DMF (3 mL) was stirred for 1.5 h at RT. The resulting mixture was concentrated under vacuum. The residue was applied onto a reverse phase column with H$_2$O/ACN (65:35). The crude product was further purified by Prep-HPLC using the following condition (Column: XSelect CSH Prep C18 OBD Column, 19×150 mm 5 μm; Mobile Phase A:Water (10 mM NH$_4$HCO$_3$), Mobile Phase B:ACN; Flow rate: 60 mL/min; Gradient: 18% B to 48% B in 10 mi; 254 nm) to afford the title compound (25.3 mg, 24%) as a white solid. LCMS: [M+H]$^+$ 382.20. 1H NMR (400 MHz, DMSO-d6) δ 13.83 (s, 1H), 8.93 (s, 1H), 8.74 (d, J=6.6 Hz, 1H), 8.36 (d, J=3.6 Hz, 2H), 8.22 (s, 1H), 7.74 (d, J=3.3 Hz, 1H), 7.15 (s, 1H), 3.98-3.82 (m, 1H), 2.58 (s, 3H), 2.00 (d, J=5.1 Hz, 2H), 1.88-1.80 (m, 2H), 1.80-1.66 (m, 3H), 1.64-1.52 (m, 2H), 1.18-0.98 (in, 2H).

The following Examples in Table 4 were prepared according to the methods described for the previous Examples.

TABLE 4

| Example # | Structure and name | Prepared according to example # | LCMS (M + H)+ |
|---|---|---|---|
| 200 | N-((1r,4r)-4-(2-hydroxyethyl)cyclohexyl)-2-(1H-imidazol-1-yl)-5H-pyrrolo[3,2-d]pyrimidine-4-carboxamide | 7 | 355.05 |
| 201 | N-((1r,4r)-4-(2-(dimethylamino)-2-oxoethoxy)cyclohexyl)-5-(1H-imidazol-1-yl)-1H-pyrazolo[4,3-d]pyrimidine-7-carboxamide | 23 Step 4 | 413.10 |
| 202 | N-((1r,4r)-4-(2-(dimethylamino)-2-oxoethoxy)cyclohexyl)-5-(1H-imidazol-1-yl)-1H-pyrazolo[3,4-c]pyridine-7-carboxamide | 23 Step 4 | 412.15 |
| 203 | 5-(1H-imidazol-1-yl)-N-(6-(2-(pyrrolidin-1-yl)ethoxy)pyridin-3-yl)-1H-pyrazolo[3,4-c]pyridine-7-carboxamide | 7 | 419.10 |

TABLE 4-continued

| Example # | Structure and name | Prepared according to example # | LCMS (M + H)+ |
|---|---|---|---|
| 204 | N-((1r,4r)-4-(3,3-difluoroazetidin-1-yl)cyclohexyl)-2-(1H-imidazol-1-yl)-5H-pyrrolo[3,2-d]pyrimidine-4-carboxamide | 101 | 402.10 |
| 205 | N-(4-cyanophenyl)-5-(1H-imidazol-1-yl)-1H-pyrazolo[3,4-c]pyridine-7-carboxamide | 7 | 330.05 |
| 206 | N-((1r,4r)-4-(2,2-difluoroethylamino)cyclohexyl)-5-(1H-imidazol-1-yl)-1H-pyrazolo[4,3-d]pyrimidine-7-carboxamide | 101 | 391.20 |
| 207[a] | N-((1S,4r)-4-((S)-2-hydroxypropoxy)cyclohexyl)-5-(1H-imidazol-1-yl)-1H-pyrazolo[3,4-c]pyridine-7-carboxamide | 118 | 385.25 |

TABLE 4-continued

| Example # | Structure and name | Prepared according to example # | LCMS (M + H)+ |
|---|---|---|---|
| 208[a] | N-((1R,4r)-4-((R)-2-hydroxypropoxy)cyclohexyl)-5-(1H-imidazol-1-yl)-1H-pyrazolo[3,4-c]pyridine-7-carboxamide | 118 | 385.25 |
| 209 | N-((1r,4r)-4-(acetamidomethyl)cyclohexyl)-5-(1H-imidazol-1-yl)-1H-pyrazolo[3,4-c]pyridine-7-carboxamide | 114 | 382.25 |
| 210 | N-((1r,4r)-4-(2-hydroxypropan-2-yl)cyclohexyl)-2-(1H-imidazol-1-yl)thieno[3,2-d]pyrimidine-4-carboxamide | 101 step 1 | 386.15 |
| 211 | 2-(1H-imidazol-1-yl)-N-(isoindolin-5-yl)-5H-pyrrolo[3,2-d]pyrimidine-4-carboxamide | 7 | 346.10 |

TABLE 4-continued

| Example # | Structure and name | Prepared according to example # | LCMS (M + H)+ |
|---|---|---|---|
| 212 | 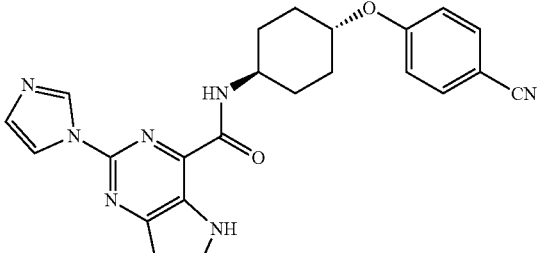<br>N-((1r,4r)-4-(4-cyanophenoxy)cyclohexyl)-2-(1H-imidazol-1-yl)-5H-pyrrolo[3,2-d]pyrimidine-4-carboxamide | 7 | 428.10 |
| 213 | 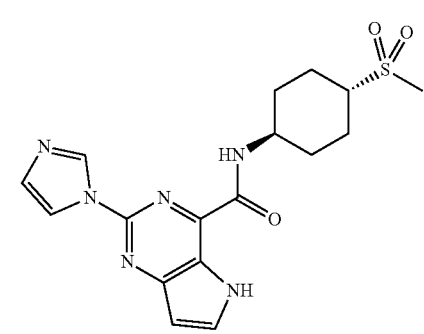 [SMILES: CS(=O)(=O)[C@H]1CC[C@H](NC(=O)c2nc(-n3ccnc3)nc3cc[nH]c23)CC1]<br>2-(1H-imidazol-1-yl)-N-((1r,4r)-4-(methylsulfonyl)cyclohexyl)-5H-pyrrolo[3,2-d]pyrimidine-4-carboxamide | 7 | 389.05 |
| 214 | 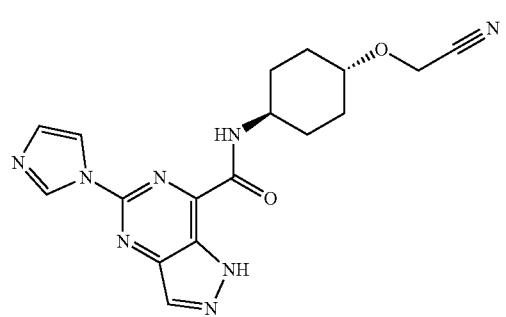 [SMILES: N#CCO[C@H]1CC[C@H](NC(=O)c2nc(-n3ccnc3)nc3cn[nH]c23)CC1]<br>N-((1r,4r)-4-(cyanomethoxy)cyclohexyl)-5-(1H-imidazol-1-yl)-1H-pyrazolo[4,3-d]pyrimidine-7-carboxamide | 104 | 367.10 |
| 215 | 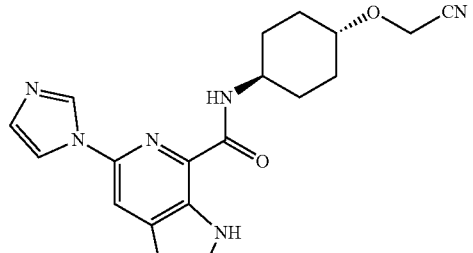<br>N-((1r,4r)-4-(cyanomethoxy)cyclohexyl)-5-(1H-imidazol-1-yl)-1H-pyrazolo[3,4-c]pyridine-7-carboxamide | 104 | 366.10 |

TABLE 4-continued

| Example # | Structure and name | Prepared according to example # | LCMS (M + H)+ |
|---|---|---|---|
| 216 | 2-(1H-imidazol-1-yl)-N-((1r,4r)-4-(oxetan-3-ylamino)cyclohexyl)-5H-pyrrolo[3,2-d]pyrimidine-4-carboxamide | 115 | 382.20 |
| 217 | 5-(1H-imidazol-1-yl)-N-((1r,4r)-4-(methylcarbamoyl)cyclohexyl)-1H-pyrazolo[3,4-c]pyridine-7-carboxamide | 7 | 368.20 |
| 218 | 5-(1H-imidazol-1-yl)-N-((1r,4r)-4-(methyl(2,2,2-trifluoroethyl)amino)cyclohexyl)-1H-pyrazolo[3,4-c]pyridine-7-carboxamide | 101 | 422.20 |
| 219 | N-((1r,4r)-4-(cyanomethyl)cyclohexyl)-5-(1H-imidazol-1-yl)-1H-pyrazolo[3,4-c]pyridine-7-carboxamide | 7 | 350.20 |

TABLE 4-continued

| Example # | Structure and name | Prepared according to example # | LCMS (M + H)+ |
|---|---|---|---|
| 220 | 2-(1H-imidazol-1-yl)-N-((1r,4r)-4-(2,2,2-trifluoroethylamino)cyclohexyl)thieno[3,2-d]pyrimidine-4-carboxamide | 101 | 425.15 |
| 221 | N-((1r,4r)-4-(2,2-difluoroethylamino)cyclohexyl)-2-(1H-imidazol-1-yl)thieno[3,2-d]pyrimidine-4-carboxamide | 101 | 407.15 |
| 222 | 2-(1H-imidazol-1-yl)-N-((1r,4r)-4-((3,3,3-trifluoropropyl)amino)cyclohexyl)thieno[3,2-d]pyrimidine-4-carboxamidee | 101 | 439.10 |
| 223 | N-(6-(2-(dimethylamino)ethoxy)pyridin-3-yl)-5-(1H-imidazol-1-yl)-1H-pyrazolo[3,4-c]pyridine-7-carboxamide | 23 Step 4 | 393.20 |

TABLE 4-continued

| Example # | Structure and name | Prepared according to example # | LCMS (M + H)+ |
|---|---|---|---|
| 224 | 5-(1H-imidazol-1-yl)-N-(6-(piperazin-1-yl)pyridin-3-yl)-1H-pyrazolo[3,4-c]pyridine-7-carboxamide | 7 | 390.20 |
| 225 | N-((1r,4r)-4-(hydroxymethyl)cyclohexyl)-5-(1H-imidazol-1-yl)-1H-pyrazolo[3,4-c]pyridine-7-carboxamide | 118 | 341.20 |
| 226 | N-((1s,4s)-4-hydroxy-4-methylcyclohexyl)-5-(1H-imidazol-1-yl)-1H-pyrazolo[3,4-c]pyridine-7-carboxamide | 118 | 341.20 |
| 227 | N-((1r,4r)-4-(3,3-difluoroazetidin-1-yl)cyclohexyl)-5-(1H-imidazol-1-yl)-1H-pyrazolo[3,4-c]pyridine-7-carboxamide | 115 | 402.20 |

TABLE 4-continued

| Example # | Structure and name | Prepared according to example # | LCMS (M + H)+ |
|---|---|---|---|
| 228 | 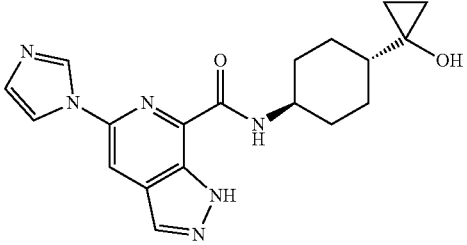 [SMILES: O=C(N[C@H]1CC[C@H](C2(O)CC2)CC1)c1nc(-n2ccnc2)cc2cn[nH]c12]<br>N-((1r,4r)-4-(1-hydroxycyclopropyl)cyclohexyl)-5-(1H-imidazol-1-yl)-1H-pyrazolo[3,4-c]pyridine-7-carboxamide | 7 | 367.2 |
| 229 | 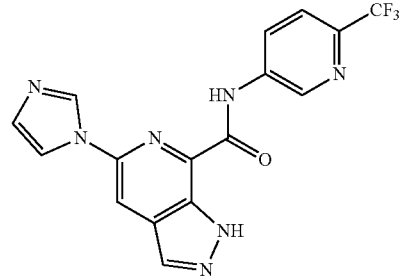 [SMILES: O=C(Nc1ccc(C(F)(F)F)nc1)c1nc(-n2ccnc2)cc2cn[nH]c12]<br>5-(1H-imidazol-1-yl)-N-(6-(trifluoromethyl)pyridin-3-yl)-1H-pyrazolo[3,4-c]pyridine-7-carboxamide | 7 | 374.05 |
| 230 | 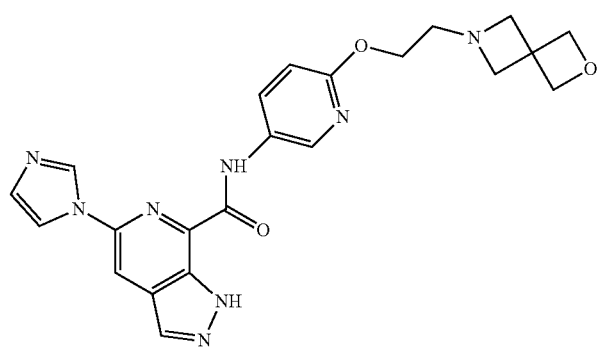 [SMILES: O=C(Nc1ccc(OCCN2CC3(COC3)C2)nc1)c1nc(-n2ccnc2)cc2cn[nH]c12]<br>N-(6-(2-(2-oxa-6-azaspiro[3.3]heptan-6-yl)ethoxy)pyridin-3-yl)-5-(1H-imidazol-1-yl)-1H-pyrazolo[3,4-c]pyridine-7-carboxamide | 7 | 447.10 |
| 231 | 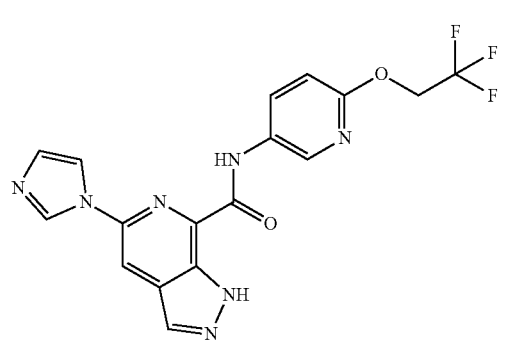 [SMILES: O=C(Nc1ccc(OCC(F)(F)F)nc1)c1nc(-n2ccnc2)cc2cn[nH]c12]<br>5-(1H-imidazol-1-yl)-N-(6-(2,2,2-trifluoroethoxy)pyridin-3-yl)-1H-pyrazolo[3,4-c]pyridine-7-carboxamide | 118 | 404.15 |

TABLE 4-continued
| Example # | Structure and name | Prepared according to example # | LCMS (M + H)+ |
|---|---|---|---|
| 232 | 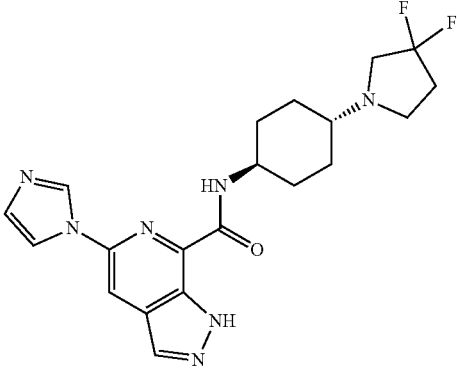 [SMILES: O=C(N[C@H]1CC[C@H](N2CCC(F)(F)C2)CC1)c1nc(-n2ccnc2)cc2cn[nH]c12]<br>N-((1r,4r)-4-(3,3-difluoropyrrolidin-1-yl)cyclohexyl)-5-(1H-imidazol-1-yl)-1H-pyrazolo[3,4-c]pyridine-7-carboxamide | 115 | 416.25 |
| 233 | 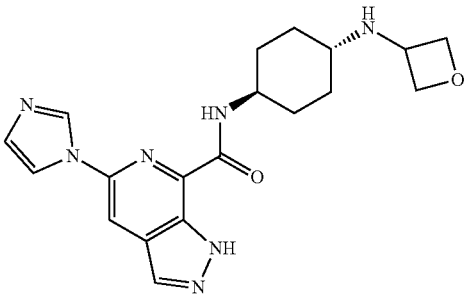 [SMILES: O=C(N[C@H]1CC[C@H](NC2COC2)CC1)c1nc(-n2ccnc2)cc2cn[nH]c12]<br>5-(1H-imidazol-1-yl)-N-((1r,4r)-4-(oxetan-3-ylamino)cyclohexyl)-1H-pyrazolo[3,4-c]pyridine-7-carboxamide | 7 | 382.15 |
| 234 | 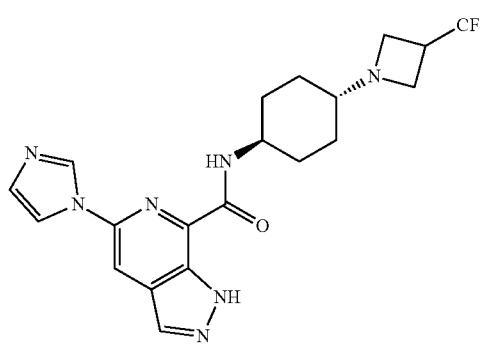<br>5-(1H-imidazol-1-yl)-N-((1r,4r)-4-(3-(trifluoromethyl)azetidin-1-yl)cyclohexyl)-1H-pyrazolo[3,4-c]pyridine-7-carboxamide | 115 | 434.20 |

TABLE 4-continued
| Example # | Structure and name | Prepared according to example # | LCMS (M + H)+ |
|---|---|---|---|
| 235 | 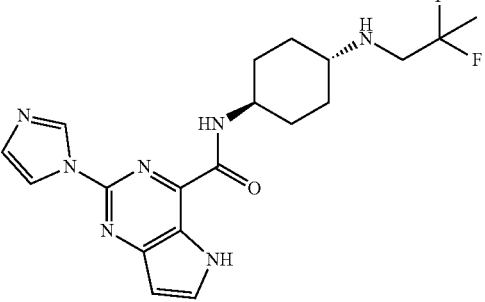<br>N-((1r,4r)-4-((2,2-difluoropropyl)amino)cyclohexyl)-2-(1H-imidazol-1-yl)-5H-pyrrolo[3,2-d]pyrimidine-4-carboxamide | 101 | 404.15 |
| 236 | 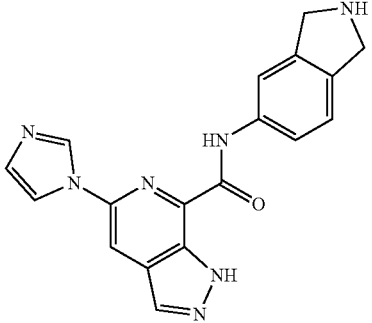 [SMILES: O=C(Nc1ccc2c(c1)CNC2)c1nc(-n2ccnc2)cc2cn[nH]c12]<br>5-(1H-imidazol-1-yl)-N-(isoindolin-5-yl)-1H-pyrazolo[3,4-c]pyridine-7-carboxamide | 7 | 346.20 |
| 237 | 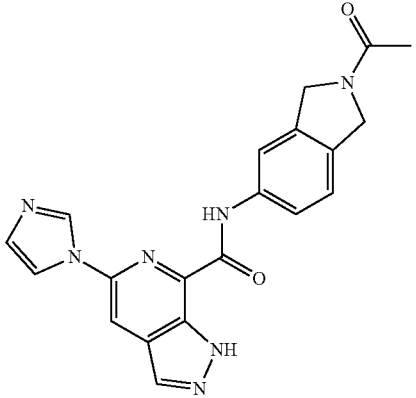 [SMILES: CC(=O)N1Cc2ccc(NC(=O)c3nc(-n4ccnc4)cc4cn[nH]c34)cc2C1]<br>N-(2-acetylisoindolin-5-yl)-5-(1H-imidazol-1-yl)-1H-pyrazolo[3,4-c]pyridine-7-carboxamide | 7 | 388.05 |

TABLE 4-continued

| Example # | Structure and name | Prepared according to example # | LCMS (M + H)+ |
|---|---|---|---|
| 238 | N-((1r,4r)-4-(1-hydroxycyclopropyl)cyclohexyl)-5-(1H-imidazol-1-yl)-1H-pyrazolo[4,3-d]pyrimidine-7-carboxamide | 7 | 368.15 |
| 239 | 5-(1H-imidazol-1-yl)-N-((1s,4s)-4-methyl-4-((2,2,2-trifluoroethyl)amino)cyclohexyl)-1H-pyrazolo[3,4-c]pyridine-7-carboxamide | 101 step 1 | 422.20 |
| 240 | 5-(1H-imidazol-1-yl)-N-((1r,4r)-4-methyl-4-((2,2,2-trifluoroethyl)amino)cyclohexyl)-1H-pyrazolo[3,4-c]pyridine-7-carboxamide | 101 step 1 | 422.20 |
| 241 | 5-(1H-imidazol-1-yl)-N-((1r,4r)-4-(3-(trifluoromethyl)azetidin-1-yl)cyclohexyl)-1H-pyrazolo[4,3-d]pyrimidine-7-carboxamide | 7 | 435.20 |

TABLE 4-continued

| Example # | Structure and name | Prepared according to example # | LCMS (M + H)+ |
|---|---|---|---|
| 242 | 5-(1H-imidazol-1-yl)-N-((1r,4r)-4-(methylcarbamoyl)cyclohexyl)-1H-pyrazolo[4,3-d]pyrimidine-7-carboxamide | 101 step 1 | 369.25 |
| 243 | N-((1r,4r)-4-(acetamidomethyl)cyclohexyl)-5-(1H-imidazol-1-yl)-1H-pyrazolo[4,3-d]pyrimidine-7-carboxamide | 114 | 383.10 |
| 244 | N-((1r,4r)-4-((2,2-difluoropropyl)amino)cyclohexyl)-5-(1H-imidazol-1-yl)-1H-pyrazolo[4,3-d]pyrimidine-7-carboxamide | 101 step 1 | 405.10 |
| 245 | N-(3,3-difluoropropyl)-5-(1H-imidazol-1-yl)-1H-pyrazolo[3,4-c]pyridine-7-carboxamide | 7 | 307.00 |

TABLE 4-continued

| Example # | Structure and name | Prepared according to example # | LCMS (M + H)+ |
|---|---|---|---|
| 246 | N-((1r,4r)-4-((2,2-difluoropropyl)amino)cyclohexyl)-2-(1H-imidazol-1-yl)thieno[3,2-d]pyrimidine-4-carboxamide | 7 | 421.10 |
| 247 | 5-(1H-imidazol-1-yl)-N-((1s,4s)-4-methyl-4-((2,2,2-trifluoroethyl)amino)cyclohexyl)-1H-pyrazolo[3,4-c]pyridine-7-carboxamide | 101 step 1 | 422.20 |
| 248 | 5-(1H-imidazol-1-yl)-N-((1r,4r)-4-(methyl(2,2,2-trifluoroethyl)amino)cyclohexyl)-1H-pyrazolo[4,3-d]pyrimidine-7-carboxamide | 101 | 423.20 |
| 249 | 5-(1H-imidazol-1-yl)-N-((1r,4r)-4-(3,3,3-trifluoropropoxy)cyclohexyl)-1H-pyrazolo[3,4-c]pyridine-7-carboxamide | 7 | 423.10 |

TABLE 4-continued

| Example # | Structure and name | Prepared according to example # | LCMS (M + H)+ |
|---|---|---|---|
| 250 | 5-(1H-imidazol-1-yl)-N-((1r,4r)-4-(((2,2,2-trifluoroethyl)amino)methyl)cyclohexyl)-1H-pyrazolo[3,4-c]pyridine-7-carboxamide | 101 step 1 | 422.25 |
| 251 | 5-(1H-imidazol-1-yl)-N-((1s,4s)-4-(2,2,2-trifluoroethoxy)cyclohexyl)-1H-pyrazolo[3,4-c]pyridine-7-carboxamide | 101 step 1 | 409.20 |
| 252 | 5-(1H-imidazol-1-yl)-N-((1r,4r)-4-(2,2,2-trifluoroethoxy)cyclohexyl)-1H-pyrazolo[3,4-c]pyridine-7-carboxamide | 101 step 1 | 409.20 |
| 253 | N-((1r,4r)-4-((1,1-difluoro-2-methylpropan-2-yl)amino)cyclohexyl)-5-(1H-imidazol-1-yl)-1H-pyrazolo[3,4-c]pyridine-7-carboxamide | 7 | 418.15 |

TABLE 4-continued

| Example # | Structure and name | Prepared according to example # | LCMS (M + H)+ |
|---|---|---|---|
| 254 | 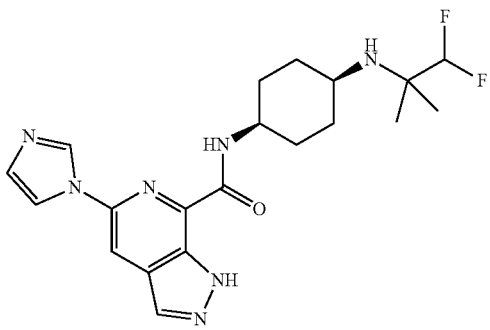 [SMILES: CC(C)(N[C@H]1CC[C@@H](NC(=O)c2nc(-n3ccnc3)cc3cn[nH]c23)CC1)C(F)F]<br>N-((1s,4s)-4-((1,1-difluoro-2-methylpropan-2-yl)amino)cyclohexyl)-5-(1H-imidazol-1-yl)-1H-pyrazolo[3,4-c]pyridine-7-carboxamide | 7 | 418.20 |

<sup>a</sup>Details on chiral purification.
Column: CHIRALPAK ID, 2 * 25 cm, 5 um.
Mobile Phase A: Hexane:DCM = 3:1(10 mM NH₃—MeOH),
Mobile Phase B: EtOH;
Flow rate: 20 mL/min. Gradient: 40% B to 40% B for 24 min; 254/220 nm.
Retention times: 11.805 min (Example 207) and 19.743 min (Example 208).
The absolute stereochemistry of Example 207 and Example 208 was not confirmed.

Detailed Synthesis of Example 210: N-((1r,4r)-4-(2-hydroxypropan-2-yl)cyclohexyl)-2-(1H-imidazol-1-yl)thieno[3,2-d]pyrimidine-4-carboxamide

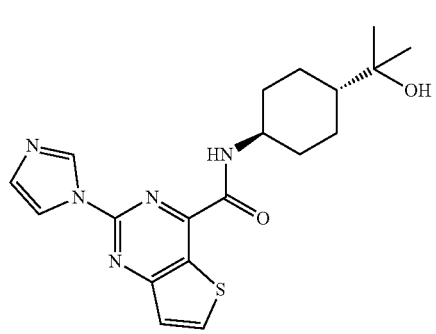 [SMILES: CC(C)(O)[C@H]1CC[C@H](NC(=O)c2nc(-n3ccnc3)nc3ccsc23)CC1]

A solution of 2-(1H-imidazol-1-yl)thieno[3,2-d]pyrimidine-4-carboxylic acid (98 mg, 0.39 mmol, 1 eq), DIEA (205.7 mg, 1.59 mmol, 4 eq), T3P (506.5 mg, 1.59 mmol, 4 eq), and 2-((1r,4r)-4-aminocyclohexyl)propan-2-ol (93.9 mg, 0.59 mmol, 1.5 eq) in DMF (5 mL) was stirred for 1 h at RT. After concentrating under vacuum, the crude product was purified by C18 reverse phase eluting with H₂O/CH₃CN (9:11) to afford the title compound (89.5 mg, 58.3% yield) as off-white solid. LCMS: [M+H]⁺ 386.15. ¹H NMR (400 MHz, DMSO-d6) δ 9.12 (d, J=10.8 Hz, 1H), 9.09 (s, 1H), 8.71 (d, J=5.6 Hz, 1H), 8.29 (s, 1H), 7.67 (d, J=5.6 Hz, 1H), 7.19 (s, 1H), 4.08 (s, 1H), 3.95-3.80 (m, 1H), 1.98-1.85 (m, 4H), 1.71-1.50 (m, 2H), 1.30-1.18 (m, 3H), 1.16 (s, 6H).

Detailed Synthesis of Example 221: N-((1r,4r)-4-(2,2-difluoroethylamino)cyclohexyl)-2-(1H-imidazol-1-yl)thieno[3,2-d]pyrimidine-4-carboxamide

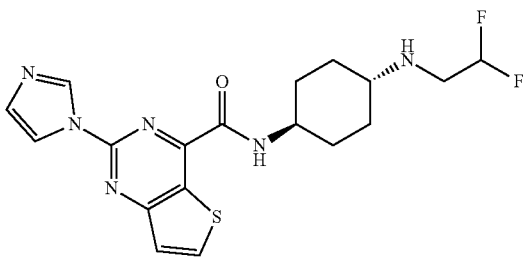 [SMILES: O=C(N[C@H]1CC[C@H](NCC(F)F)CC1)c1nc(-n2ccnc2)nc2ccsc12]

Step 1: 2-(1H-imidazol-1-yl)-N-(4-oxocyclohexyl)thieno[3,2-d]pyrimidine-4-carboxamide A solution of 2-(1H-imidazol-1-yl)thieno[3,2-d]pyrimidine-4-carboxylic acid (246 mg, 0.99 mmol, 1 eq), DIEA (387 mg, 2.99 mmol, 3 eq), T₃P (1.90 g, 3.00 mmol, 3 eq, 50% w/w in EtOAc), 4-aminocyclohexanone hydrochloride (179.0 mg, 1.19 mmol, 1.2 eq), and DMF (4 mL) was stirred for 1.5 h at RT. The resulting solution was quenched by 50 mL of water and extracted with ethyl acetate (3×50 mL). The organic layers were combined, dried over Na₂SO₄ and concentrated under reduced pressure. The crude product was purified by reverse phase column eluting with H₂O/CH₃CN (62:38) to afford title compound (222 mg, 65.1% yield) of as a brown solid. LCMS: [M+H]⁺ 342.09.

Step 2: N-((1r,4r)-4-(2,2-difluoroethylamino)cyclohexyl)-2-(1H-imidazol-1-yl)thieno[3,2-d]pyrimidine-4-carboxamide A solution of 2-(1H-imidazol-1-yl)-N-(4-oxocyclohexyl)thieno[3,2-d]pyrimidine-4-carboxamide (85.0 mg, 0.25 mmol, 1 eq), Ti(O^iPr)_4 (71.0 mg, 0.25 mmol, 1 eq), HOAc (7.50 mg, 0.13 mmol, 0.5 eq), 2,2-difluoroethanamine (60.6 mg, 0.75 mmol, 3 eq), and EtOH (3 mL) was stirred for 1.0 h at RT. This was followed by the addition of NaBH$_3$CN (31.5 mg, 0.50 mmol, 2 eq) at RT. After completion, the resulting solution was concentrated. The crude product was purified by reverse phase column eluting with H$_2$O/CH$_3$CN (60:40) and further purified by Prep-HPLC with the following conditions: (Column: XBridge Prep OBD C18 Column, 30×150 mm, 5 μm. Mobile Phase A: Water (10 mM NH$_4$HCO$_3$), Mobile Phase B: ACN. Flow rate: 60 mL/min. Gradient: 32% B to 62% B in 10 min; 254 nm; retention time of 9.40 min) to afford title compound (15.3 mg, 15.2% yield) as a white solid. LCMS: [M+H]$^+$ 407.15. $^1$H NMR (300 MHz, Methanol-d4) δ 9.05 (t, J=1.1 Hz, 1H), 8.54 (d, J=5.6 Hz, 1H), 8.29 (t, J=1.5 Hz, 1H), 7.60 (d, J=5.6 Hz, 1H), 7.18 (dd, J=1.6, 1.0 Hz, 1H), 5.90 (t, J=57.0 Hz 1H), 4.07-3.90 (m, 1H), 3.00 (td, J=15.5, 4.3 Hz, 2H), 2.62-2.50 (m, 1H), 2.14-2.01 (m, 4H), 1.72-1.58 (m, 2H), 1.38-1.20 (m, 2H).

Detailed Synthesis of Example 222: 2-(1H-imidazol-1-yl)-N-((1r,4r)-4-((3,3,3-trifluoropropyl)amino)cyclohexyl)thieno[3,2-d]pyrimidine-4-carboxamide

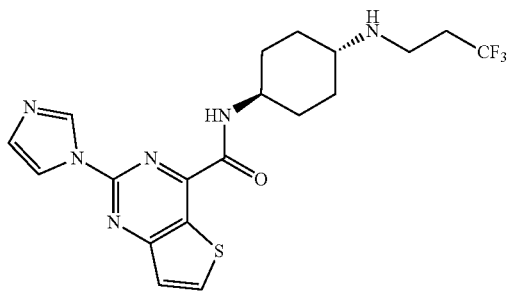 [SMILES: O=C(N[C@H]1CC[C@H](NCCC(F)(F)F)CC1)c1nc(-n2ccnc2)nc2ccsc12]

Step 1: 2-(1H-imidazol-1-yl)-N-(4-oxocyclohexyl)thieno[3,2-d]pyrimidine-4-carboxamide A solution of 2-(1H-imidazol-1-yl)thieno[3,2-d]pyrimidine-4-carboxylic acid (267 mg, 1.08 mmol, 1 eq), 4-aminocyclohexan-1-one hydrochloride (194.7 mg, 1.30 mmol, 1.2 eq), T3P (2.07 g, 50% in ethyl acetate, 6.51 mmol, 6 eq), and DIEA (420.4 mg, 3.25 mmol, 3 eq) in DMF (5 mL) was stirred for 1 h at RT. The resulting solution was concentrated. The crude product was purified by reverse phase column eluting with H$_2$O/CH$_3$CN (70:30) to afford title compound (160 mg, 43.2% yield) as a light yellow solid. LCMS: [M+H]$^+$ 342.10.

Step 2: 2-(1H-imidazol-1-yl)-N-((1r,4r)-4-((3,3,3-trifluoropropyl)amino)cyclohexyl)thieno[3,2-d]pyrimidine-4-carboxamide A solution of 2-(1H-imidazol-1-yl)-N-(4-oxocyclohexyl)thieno[3,2-d]pyrimidine-4-carboxamide (120 mg, 0.35 mmol, 1 eq), 3,3,3-trifluoropropan-1-amine (119.3 mg, 1.06 mmol, 3 eq), HOAc (21.1 mg, 0.35 mmol, 1 eq), and Ti(Oi-Pr)$_4$ (99.9 mg, 0.35 mmol, 1 eq) in EtOH (7 mL) was stirred for 1 h at RT. This was followed by the addition of NaBH$_3$CN (33.1 mg, 0.53 mmol, 1.5 eq) and the resulting solution was stirred for a 1 h at RT. After completion, the resulting solution was concentrated. The crude product was purified by reverse phase column eluting with H$_2$O/CH$_3$CN (48:52) and further purified by Prep-HPLC with the following condition: (Column: YMC-Actus Triart C18 30*250 mm, 5 μm. Mobile Phase A:Water (10 mM NH$_4$HCO$_3$), Mobile Phase B: ACN; Flow rate: 60 mL/min; Gradient: 42% B to 58% B in 8 min; 254/220 nm; retention time=5.88 min) to afford title compound (40.8 mg, 26.5% yield) as a white solid. LCMS: [M+H]$^+$ 439.10. $^1$H NMR (300 MHz, DMSO-d6) δ 9.13 (d, J=9.0 Hz, 1H), 9.09 (s, 1H), 8.71 (d, J=5.4 Hz, 1H), 8.29 (t, J=2.7 Hz, 1H), 7.67 (d, J=5.7 Hz, 1H), 7.18 (t, J=0.9 Hz, 1H), 4.02-3.80 (m, 1H), 2.80-2.70 (m, 2H), 2.48-2.23 (m, 3H), 2.02-1.96 (m, 2H), 1.95-1.81 (m, 2H), 1.70-1.50 (m, 2H), 1.22-1.05 (m, 2H).

Detailed Synthesis of Example 235: N-((1r,4r)-4-((2,2-difluoropropyl)amino)cyclohexyl)-2-(1H-imidazol-1-yl)-5H-pyrrolo[3,2-d]pyrimidine-4-carboxamide

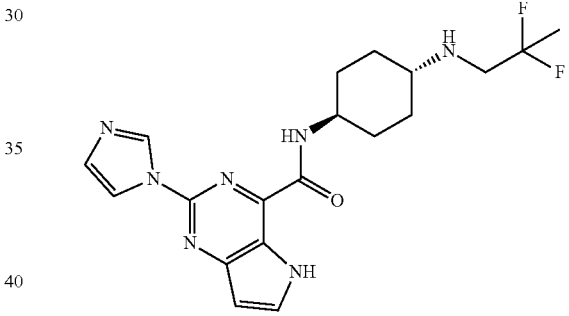

A solution of 2-(1H-imidazol-1-yl)-N-(4-oxocyclohexyl)-5H-pyrrolo[3,2-d]pyrimidine-4-carboxamide (129.6 mg, 0.40 mmol, 1 eq), 2,2-difluoropropan-1-amine hydrochloride (78.9 mg, 0.59 mmol, 1.5 eq), HOAc (24.0 mg, 0.40 mmol, 1 eq), and Ti(Oi-Pr)$_4$ (113.6 mg, 0.40 mmol, 1 eq) in EtOH (6 mL) was stirred for 2 h at RT. Then NaBH$_3$CN (50.2 mg, 0.79 mmol, 2 eq) was added and stirred for 1 h at RT. After concentrated under vacuum, the crude product was purified by C18 reverse phase eluting with H$_2$O/CH$_3$CN (27:23) and further purified by Prep-HPLC with the following condition: (Column: YMC-Actus Triart C18, 20*250 mm, 5 μm. Mobile Phase A: Water (10 mM NH$_4$HCO$_3$), Mobile Phase B: ACN; Flow rate: 60 mL/min; Gradient: 30% B to 60% B in 10 min; 254 nm) to afford the title compound with retention time of 9.20 minutes (38.9 mg, 24.1% yield) as a white solid. LCMS: [M+H]$^+$ 404.15. $^1$H NMR (400 MHz, DMSO-d6) δ 8.97 (s, 1H), 8.92 (d, J=8.8 Hz, 1H), 8.23 (t, J=1.4 Hz, 1H), 8.02 (d, J=2.8 Hz, 1H), 7.12 (s, 1H), 6.70 (d, J=3.2 Hz, 1H), 3.98-3.85 (m, 1H), 3.34 (d, J=9.2 Hz, 1H), 2.90 (t, J=14 Hz, 2H), 2.48-2.40 (m, 1H), 2.02-1.93 (m, 2H), 1.92-1.82 (m, 2H), 1.68-1.58 (m, 4H), 1.55 (s, 1H), 1.21-1.09 (m, 2H).

Detailed Synthesis of Example 244: N-((1r,4r)-4-((2,2-difluoropropyl)amino)cyclohexyl)-5-(1H-imidazol-1-yl)-1H-pyrazolo[4,3-d]pyrimidine-7-carboxamide

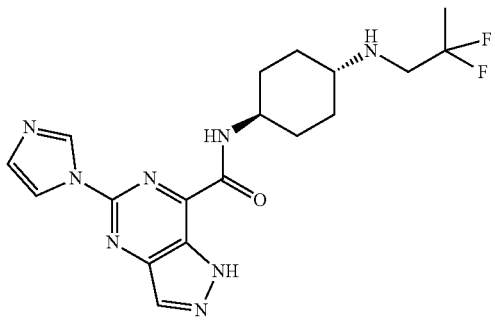 [SMILES: CC(F)(F)CN[C@H]1CC[C@H](NC(=O)c2nc(-n3ccnc3)nc3cn[nH]c23)CC1]

A solution of 5-(1H-imidazol-1-yl)-1H-pyrazolo[4,3-d]pyrimidine-7-carboxylic acid (700 mg, 3.04 mmol, 1 eq), DIEA (1179.1 mg, 9.12 mmol, 3 eq), N1-(2,2-difluoropropyl)cyclohexane-1,4-diamine HCl (802.8 mg, 3.04 mmol, 1 eq), and HATU (1387.5 mg, 3.65 mmol, 1.2 eq) in DMF (5 mL). The resulting solution was stirred for 2 h at 25° C. The reaction was quenched by 20 mL of water. The solids were collected by filtration. The crude product was purified by reverse phase column eluting with H$_2$O/CH$_3$CN (6/4) to afford the title compound (70.2 mg, 6.4% yield) as a white solid. LCMS: [M+H]$^+$ 405.20. $^1$H NMR (300 MHz, DMSO-d$_6$) δ 14.25 (s, 1H) 9.15-9.01 (m, 2H), 8.52 (s, 1H), 8.26 (t, J=1.4 Hz, 1H), 7.17 (s, 1H), 4.01-3.83 (m, 1H), 2.92 (t, J=14.1 Hz, 2H), 2.48-2.39 (m, 1H), 2.06-1.85 (m, 4H), 1.71-1.51 (m, 5H), 1.29-1.06 (m, 2H).

Example 255: N-((1r,4r)-4-(3,3-difluoroazetidin-1-yl)cyclohexyl)-5-(1H-imidazol-1-yl)-1H-pyrazolo[4,3-d]pyrimidine-7-carboxamide

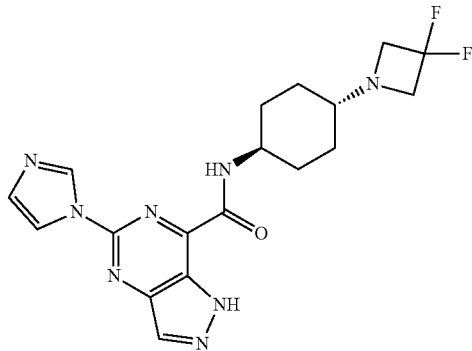 [SMILES: O=C(N[C@H]1CC[C@H](N2CC(F)(F)C2)CC1)c1nc(-n2ccnc2)nc2cn[nH]c12]

A solution of 5-(1H-imidazol-1-yl)-N-(4-oxocyclohexyl)-1H-pyrazolo[4,3-d]pyrimidine-7-carboxamide (101 mg, 0.31 mmol, 1 eq), 3,3-difluoroazetidine (48.3 mg, 0.37 mmol, 1.2 eq), HOAc (18.6 mg, 0.31 mmol, 1 eq), and Ti(Oi-Pr)$_4$ (88.0 mg, 0.31 mmol, 1 eq) in EtOH (5 mL) was stirred for 2 h at 25° C. This was followed by the addition of NaBH$_3$CN (29.3 mg, 0.47 mmol, 1.5 eq) and the resulting solution was stirred for 1 h at 25° C. After completion, the resulting solution was concentrated. The crude product was purified by reverse phase column eluting with H$_2$O/CH$_3$CN (50:50) and further purified by Prep-HPLC with the following conditions: (Column: YMC-Actus Triart C18, 20*250 mm, 5 µm; Mobile Phase A: Water (10 mM NH$_4$HCO$_3$), Mobile Phase B: ACN; Flow rate: 60 mL/min; Gradient: 26% B to 56% B in 10 min; 254 nm; retention time of 9.5 min) to afford title compound (5.6 mg, 4.5% yield) as a white solid. LCMS: [M+H]$^+$ 403.20. $^1$H NMR (300 MHz, DMSO-d6) δ 14.22 (s, 1H), 9.10 (d, J=8.4 Hz, 1H), 9.05 (s, 1H), 8.51 (s, 1H), 8.24 (t, J=2.7 Hz, 1H), 7.17 (t, J=2.1 Hz, 1H), 4.02-3.90 (m, 1H), 3.50-3.60 (m, 4H), 2.20-2.08 (m, 1H), 1.90-1.78 (m, 4H), 1.70-1.50 (m, 2H), 1.28-1.02 (m, 2H).

Example 256: N-((1s,4s)-4-(3-fluoro-3-methylazetidin-1-yl)cyclohexyl)-5-(1H-imidazol-1-yl)-1H-pyrazolo[4,3-d]pyrimidine-7-carboxamide and Example 257: N-((1r,4r)-4-(3-fluoro-3-methylazetidin-1-yl)cyclohexyl)-5-(1H-imidazol-1-yl)-1H-pyrazolo[4,3-d]pyrimidine-7-carboxamide Example 256

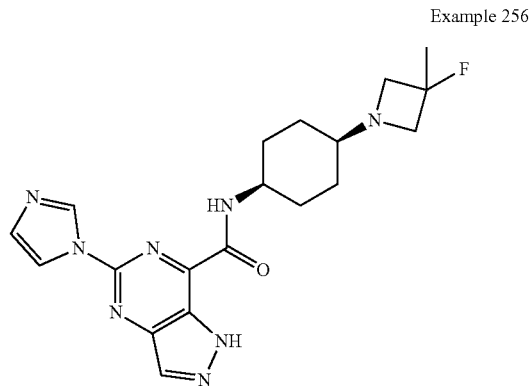

Example 257

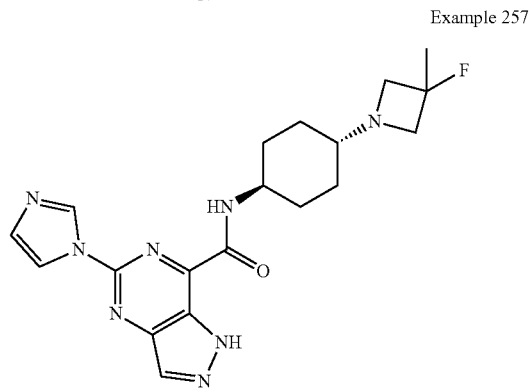

Step 1: tert-butyl (4-(3-fluoro-3-methylazetidin-1-yl)cyclohexyl)carbamate

A solution of tert-butyl (4-oxocyclohexyl) carbamate (300 mg, 1.41 mmol, 1 eq), 3-fluoro-3-methylazetidine (125 mg, 1.41 mmol, 1 eq), HOAc (84 mg, 1.41 mmol, 1 eq), NaBH$_3$CN (133 mg, 2.11 mmol, 1.5 eq), and Ti(Oi-Pr)$_4$ (399 mg, 1.41 mmol, 1 eq) in EtOH (5 mL) was stirred for 2 h at RT. After completion, the resulting mixture was concentrated under vacuum. The crude product was applied onto a silica gel column eluding with ethyl acetate/petroleum ether (9/1) to afford the title compound (400 mg, 99.3% yield) as a white solid. LCMS: [M+H]$^+$ 287.25.

Step 2: 4-(3-fluoro-3-methylazetidin-1-yl)cyclohexan-1-amine

A solution of tert-butyl (4-(3-fluoro-3-methylazetidin-1-yl)cyclohexyl)carbamate (200 mg, 1.1 mmol, 1 eq) in HCl in dioxane (4 M, 6.00 mL) was stirred at RT for 1 h. After completion, the resulting mixture was concentrated under vacuum to afford title compound (150 mg, 77% yield) as a white solid. LCMS: [M+H]$^+$ 187.15.

Step 3: N-((1s,4s)-4-(3-fluoro-3-methylazetidin-1-yl)cyclohexyl)-5-(1H-imidazol-1-yl)-1H-pyrazolo[4,3-d]pyrimidine-7-carboxamide and N-((1r,4r)-4-(3-fluoro-3-methylazetidin-1-yl)cyclohexyl)-5-(1H-imidazol-1-yl)-1H-pyrazolo[4,3-d]pyrimidine-7-carboxamide A solution of 5-(1H-imidazol-1-yl)-1H-pyrazolo[4,3-d]pyrimidine-7-carboxylic acid (150 mg, 0.65 mmol, 1 eq), 4-(3-fluoro-3-methylazetidin-1-yl)cyclohexan-1-amine, DIEA (252 mg, 1.96 mmol, 3 eq), and HATU (372 mg, 0.98 mmol, 1.5 eq) in DMF (2 mL) was stirred for 1 h at RT. The resulting mixture was concentrated under vacuum. The crude product was purified on a silica gel column with MeOH/DCM (7/93). The product was further purified by Chiral-Prep-HPLC with the following conditions (Column: CHIRALPAK IA, 2*25 cm, 5 μm. Mobile Phase A: Hexane (2M NH$_3$·MeOH), Mobile Phase B: EtOH. Flow rate: 15 mL/min. Gradient: maintaining 50% B for 14 min; 254/220 nm) to afford the title compounds with retention times of 8.399 minutes (Example 256) and 10.595 minutes (Example 257).

Example 256 N-((1s,4s)-4-(3-fluoro-3-methylazetidin-1-yl)cyclohexyl)-5-(1H-imidazol-1-yl)-1H-pyrazolo[4,3-d]pyrimidine-7-carboxamide (25.8 mg, 9.9% yield) was isolated as a white solid. LCMS: [M+H]$^+$ 399.20. $^1$H NMR (400 MHz, DMSO-d6) δ 14.22 (s, 1H), 9.20 (d, J=8.3 Hz, 1H), 9.08 (s, 1H), 8.51 (s, 1H), 8.28 (s, 1H), 7.16 (s, 1H), 4.05-3.95 (m, 1H), 3.30-3.25 (m, 2H), 3.19 (d, J=8.4 Hz, 1H), 3.13 (d, J=8.5 Hz, 1H), 2.36-2.29 (m, 1H), 1.99-1.81 (m, 2H), 1.75-1.62 (m, 2H), 1.61-1.39 (m, 7H).

Example 257 N-((1r,4r)-4-(3-fluoro-3-methylazetidin-1-yl)cyclohexyl)-5-(1H-imidazol-1-yl)-1H-pyrazolo[4,3-d]pyrimidine-7-carboxamide (31.5 mg, 12.1% yield) was isolated as a white solid. LCMS: [M+H]$^+$ 399.20. $^1$H NMR (400 MHz, DMSO-d6) δ 14.25 (s, 1H), 9.10 (d, J=8.7 Hz, 1H), 9.06 (s, 1H), 8.52 (s, 1H), 8.25 (s, 1H), 7.17 (s, 1H), 3.95-3.80 (m, 1H), 3.27-3.21 (m, 2H), 3.16 (d, J=8.0 Hz, 1H), 3.11 (d, J=8.0 Hz, 1H), 2.08-1.99 (m, 1H), 1.93-1.84 (m, 4H), 1.67-1.60 (m, 2H), 1.60-1.47 (m, 3H), 1.11-1.05 (m, 2H).

Example 258: N-((1r,4r)-4-(3-cyano-3-methylazetidin-1-yl)cyclohexyl)-5-(1H-imidazol-1-yl)-1H-pyrazolo[3,4-c]pyridine-7-carboxamide and Example 259: N-((1s,4s)-4-(3-cyano-3-methylazetidin-1-yl)cyclohexyl)-5-(1H-imidazol-1-yl)-1H-pyrazolo[3,4-c]pyridine-7-carboxamide

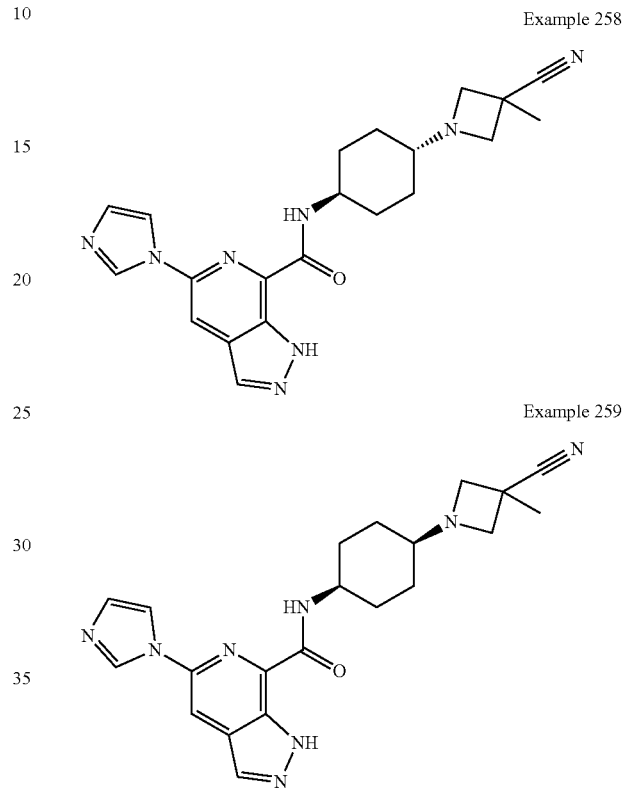

Example 258

Example 259

A solution of 5-(1H-imidazol-1-yl)-N-(4-oxocyclohexyl)-1H-pyrazolo[3,4-c]pyridine-7-carboxamide (200 mg, 0.62 mmol, 1 eq), 3-methylazetidine-3-carbonitrile (65.2 mg, 0.68 mmol, 1.1 eq), HOAc (37.0 mg, 0.62 mmol, 1 eq), and Ti(Oi-Pr)$_4$ (175.2 mg, 0.62 mmol, 1 eq) in EtOH (2 mL) was stirred for 1 h at RT. NaBH$_3$CN (38.8 mg, 0.62 mmol, 1 eq) was added and the resulting solution was stirred for 1 h at RT. After completion, the resulting mixture was concentrated under vacuum. The crude product was purified by reverse phase column eluting with H$_2$O/MeCN (45:55). The crude product was further purified by the following conditions (Column: XBridge Prep OBD C18 Column 19*250 mm, 5 μm. Mobile Phase A: Water (10 mM NH$_4$HCO$_3$), Mobile Phase B: MeOH. Flow rate: 25 mL/min. Gradient: 46% B to 54% B in 10 min; 254 nm) to afford title compounds with retention times of 7.6 minutes (Example 258) and 9.9 minutes (Example 259).

Example 258: N-((1r,4r)-4-(3-cyano-3-methylazetidin-1-yl)cyclohexyl)-5-(1H-imidazol-1-yl)-1H-pyrazolo[3,4-c]pyridine-7-carboxamide (21.7 mg, 8.7% yield) was isolated as a white solid. LCMS: [M+H]$^+$ 405.20. $^1$H NMR (400 MHz, DMSO-d6) δ 13.83 (s, 1H), 8.92 (s, 1H), 8.76 (d, J=8.6 Hz, 1H), 8.36 (d, J=4.8 Hz, 2H), 8.22 (s, 1H), 7.15 (s, 1H), 3.92-3.85 (m, 1H), 3.47 (d, J=6.9 Hz, 2H), 3.13 (d, J=7.0 Hz, 2H), 2.11-2.05 (m, 1H), 1.87-1.72 (m, 4H), 1.65-1.54 (m, 5H), 1.08-1.02 (m, 2H).

Example 259: N-((1s,4s)-4-(3-cyano-3-methylazetidin-1-yl)cyclohexyl)-5-(1H-imidazol-1-yl)-1H-pyrazolo[3,4-c]pyridine-7-carboxamide (27.8 mg, 11.2% yield) was isolated as a white solid. LCMS: [M+H]⁺ 405.20. ¹H NMR (400 MHz, DMSO-d6) δ 13.83 (s, 1H), 8.98 (s, 1H), 8.84 (s, 1H), 8.41 (s, 2H), 8.26 (s, 1H), 7.17 (s, 1H), 3.95-3.83 (m, 1H), 3.56-3.49 (m, 3H), 3.15-3.01 (m, 1H), 2.39-2.26 (m, 1H), 1.89 (d, J=12.7 Hz, 2H), 1.61-1.47 (m, 9H).

Example 260: N-((1r,4r)-4-(2-hydroxypropan-2-yl)cyclohexyl)-5-(1H-imidazol-1-yl)thieno[2,3-c]pyridine-7-carboxamide

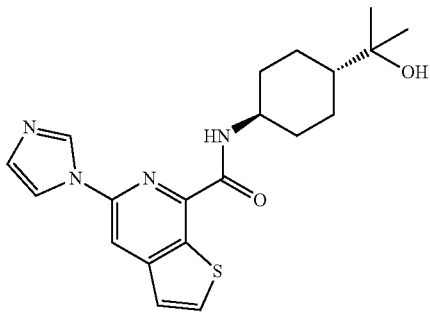 [SMILES: CC(C)(O)[C@H]1CC[C@H](NC(=O)c2nc(-n3ccnc3)cc3ccsc23)CC1]

A solution of 5-(1H-imidazol-1-yl)thieno[2,3-c]pyridine-7-carboxylic acid (72 mg, 0.29 mmol, 1 eq), 2-((1r,4r)-4-aminocyclohexyl)propan-2-ol (46.2 mg, 0.29 mmol, 1 eq), HATU (133.9 mg, 0.35 mmol, 1.2 eq), and DIEA (113 mg, 0.88 mmol, 3 eq) in DMF (2 mL) was stirred for 1 h at RT. After completion, the resulting solution was concentrated. The crude product was purified by reverse phase column eluting with H₂O/CH₃CN (40:60) to afford the title compound (26.3 mg, 23.3% yield) as a light yellow solid. LCMS: [M+H]⁺ 385.15. ¹H NMR (300 MHz, DMSO-d6) δ 9.01 (s, 1H), 8.82 (d, J=8.7 Hz, 1H), 8.46 (s, 1H), 8.28 (d, J=1.8 Hz, 1H), 8.27 (d, J=1.8 Hz, 1H), 7.58 (d, J=5.4 Hz, 1H), 7.17 (d, J=0.9 Hz, 1H), 4.09 (s, 1H), 3.88-3.78. (m, 1H), 2.00-1.82 (m, 4H), 1.70-1.50 (m, 2H), 1.32-1.07 (m, 9H).

Example 261: N-((1r,4r)-4-((2,2-difluoroethyl)amino)cyclohexyl)-5-(1H-imidazol-1-yl)thieno[2,3-c]pyridine-7-carboxamide

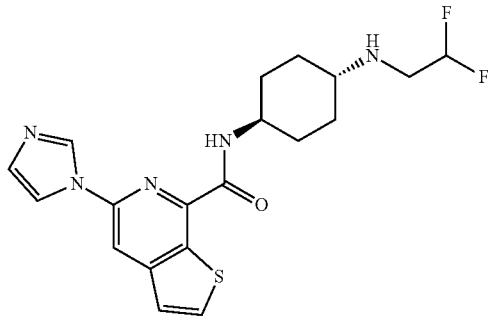 [SMILES: O=C(N[C@H]1CC[C@H](NCC(F)F)CC1)c1nc(-n2ccnc2)cc2ccsc12]

A solution of 5-(1H-imidazol-1-yl)thieno[2,3-c]pyridine-7-carboxylic acid (52 mg, 0.21 mmol, 1 eq), (1r,4r)-N1-(2,2-difluoroethyl)cyclohexane-1,4-diamine dihydrochloride (63.9 mg, 0.25 mmol, 1.2 eq), DIEA (109.6 mg, 0.85 mmol, 4 eq), and HATU (96.7 mg, 0.25 mmol, 1.2 eq) in DMF (2 mL) was stirred for 1 h at RT. After concentration, the crude product was purified by C18 reverse phase eluting with H₂O/CH₃CN (1:1) and further purified by Prep-HPLC with the following conditions (Column: YMC-Actus Triart C18 30*250 mm, 5 μm. Mobile Phase A: Water (10 mM NH₄HCO₃), Mobile Phase B: ACN. Flow rate: 60 mL/min. Gradient: 37% B to 46% B in 8 min; 254/220 nm) to afford the title compound with retention time of 7.72 minutes (27.6 mg, 32.1% yield) as a white solid. LCMS: [M+H]⁺ 406.15. ¹H NMR (400 MHz, DMSO-d6) δ 9.01 (s, 1H), 8.84 (d, J=8.7 Hz, 1H), 8.46 (s, 1H), 8.29 (d, J=5.6 Hz, 2H), 7.58 (d, J=5.5 Hz, 1H), 7.18 (s, 1H), 5.96 (t, J=4.3 Hz, 1H), 4.01-3.81 (m, 1H), 3.07-3.85 (m, 2H), 2.49-2.39 (m, 1H), 2.02-1.80 (m, 5H), 1.68-1.55 (m, 2H), 1.21-1.03 (m, 2H).

Example 262: N-((1r,4r)-4-((2,2-difluoropropyl)amino)cyclohexyl)-5-(1H-imidazol-1-yl)thieno[2,3-c]pyridine-7-carboxamide

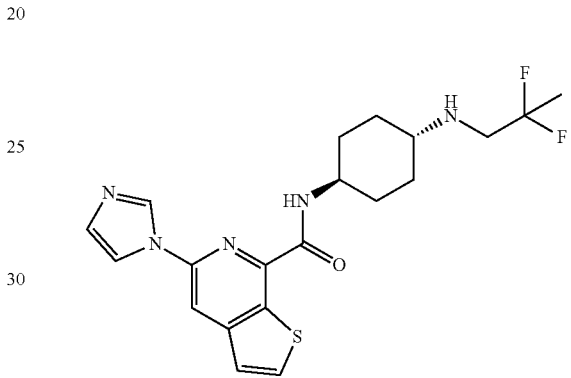

A solution of 5-(imidazol-1-yl)thieno[2,3-c]pyridine-7-carboxylic acid (60 mg, 0.25 mmol, 1 eq), (1r,4r)-N1-(2,2-difluoropropyl)cyclohexane-1,4-diamine (47.0 mg, 0.25 mmol, 1 eq), DIEA (94.9 mg, 0.73 mmol, 3 eq), and HATU (139.5 mg, 0.37 mmol, 1.5 eq) in DMF (1 mL) was stirred for 1 h at RT. The residue was applied onto reverse phase column eluting with H₂O/ACN (42/58) to afford the title compound (13.7 mg, 13.4% yield) as a white solid. LCMS: [M+H]⁺ 420.15. ¹H NMR (300 MHz, DMSO-d₆) δ 8.99 (t, J=1.1 Hz, 1H), 8.81 (d, J=8.7 Hz, 1H), 8.44 (s, 1H), 8.32-8.23 (m, 2H), 7.56 (d, J=5.5 Hz, 1H), 7.15 (s, 1H), 3.95-3.76 (m, 1H), 2.98-2.81 (m, 2H), 2.48-2.41 (m, 1H), 2.05-1.75 (m, 4H), 1.71-1.48 (m, 5H), 1.25-1.13 (m, 2H).

Example 263: N-((1r,4r)-4-(1-hydroxycyclopropyl)cyclohexyl)-5-(1H-imidazol-1-yl)thieno[2,3-c]pyridine-7-carboxamide

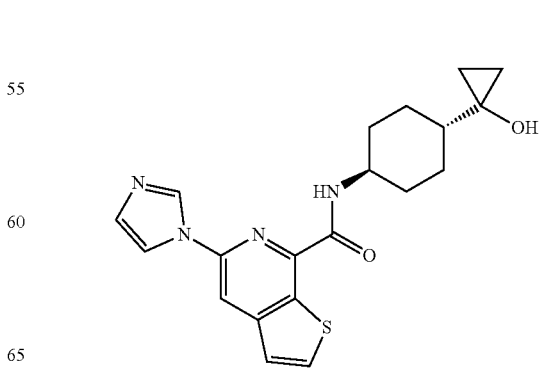

Step 1: methyl (1r,4r)-4-(dibenzylamino)cyclohexane-1-carboxylate

A solution of methyl (1r,4r)-4-aminocyclohexane-1-carboxylate hydrochloride (5 g, 25.82 mmol, 1 eq), benzyl bromide (9.27 g, 54.2 mmol, 2.1 eq), and $K_2CO_3$ (10.7 g, 77.5 mmol, 3 eq) in $CH_3CN$ (30 mL) was stirred for 2 h at 80° C. in an oil bath. After completion, the reaction was quenched by the addition of 200 mL of water. The solids were collected by filtration and concentrated under vacuum to afford the title compound (6 g, 68.9% yield) as white solid. LCMS: $[M+H]^+$ 338.2.

Step 2: 1-((1r,4r)-4-(dibenzylamino)cyclohexyl)cyclopropan-1-ol

A solution of methyl (1r,4r)-4-(dibenzylamino)cyclohexane-1-carboxylate (500 mg, 1.48 mmol, 1 eq), $Ti(Oi-Pr)_4$ (631.7 mg, 2.22 mmol, 1.5 eq), and EtMgBr (1.5 mL, 4.47 mmol, 3.0 eq) in THF (15 mL) was stirred for 14 h at RT. After completion, the reaction was then quenched by the addition of 50 mL of water. The solids were filtered out, the filtrate was extracted with 3×50 mL ethyl acetate and the organic layers combined. The organic layers were washed with 3×50 mL saturated aqueous sodium chloride. The combined organics was concentrated under vacuum. The crude product was applied onto a silica gel column eluting with ethyl acetate/petroleum ether (20:80) to afford the title compound (410 mg, 82.3% yield) as white solid. LCMS: $[M+H]^+$ 336.3.

Step 3: 1-((1r,4r)-4-aminocyclohexyl)cyclopropan-1-ol

Under an atmosphere of hydrogen, a solution of 1-[(1r,4r)-4-(dibenzylamino)cyclohexyl]cyclopropan-1-ol (500 mg, 1.49 mmol, 1 eq), and $Pd(OH)_2/C$ (300 mg, 2.14 mmol, 1.4 eq) in EtOH (15 mL) was stirred for 1 h at RT. After completion, the solids were filtered out. The filtrate was concentrated under vacuum to afford the crude title compound (250 mg) as light green oil. LCMS: $[M+H]^+$ 156.

Step 4: N-((1r,4r)-4-(I-hydroxycyclopropyl)cyclohexyl)-5-(1H-imidazol-1-yl)thieno[2,3-c]pyridine-7-carboxamide A solution of 5-(imidazol-1-yl)thieno[2,3-c]pyridine-7-carboxylic acid (100 mg, 0.41 mmol, 1 eq), DIEA (158 mg, 1.22 mmol, 3 eq), 1-[(1r,4r)-4-aminocyclohexyl]cyclopropan-1-ol (63.3 mg, 0.41 mmol, 1 eq), and HATU (232.6 mg, 0.61 mmol, 1.5 eq) in DMF (1 mL) was stirred for 1 h at RT. The residue was applied onto reverse phase column eluting with $H_2O$/ACN (4/6) to afford the title compound (43.9 mg, 28.2% yield) as a light yellow solid. LCMS: $[M+H]^+$ 383.20. $^1$H NMR (300 MHz, DMSO-$d_6$) δ 8.99 (d, J=1.2 Hz, 1H), 8.81 (d, J=8.8 Hz, 1H), 8.45 (s, 1H), 8.39-8.23 (m, 2H), 7.58 (d, J=5.5 Hz, 1H), 7.17 (s, 1H), 4.91 (s, 1H), 3.94-3.76 (m, 1H), 1.95-1.85 (m, 2H), 1.82-1.71 (m, 2H), 1.66-1.48 (m, 2H), 1.47-1.28 (m, 1H), 1.03-0.89 (m, 1H), 0.56-0.42 (m, 2H), 0.41-0.26 (m, 2H).

Example 264a and 264b: N-((1R,4r)-4-((R)-1-hydroxyethyl)cyclohexyl)-5-(1H-imidazol-1-yl)thieno[2,3-c]pyridine-7-carboxamide and

N-((1S,4r)-4-((S)-1-hydroxyethyl)cyclohexyl)-5-(1H-imidazol-1-yl)thieno[2,3-c]pyridine-7-carboxamide

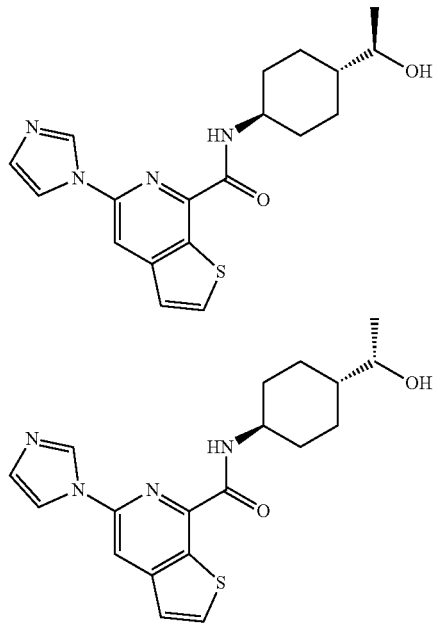

A solution of 5-(imidazol-1-yl)thieno[2,3-c]pyridine-7-carboxylic acid (100 mg, 0.41 mmol, 1 eq), DIEA (158.1 mg, 1.22 mmol, 3 eq), 1-(4-aminocyclohexyl)ethanol (58.4 mg, 0.41 mmol, 1 eq), and HATU (186.0 mg, 0.49 mmol, 1.2 eq) in DMF (4 mL) was stirred for 2 h at RT. The residue was applied onto a C18 column eluting with $H_2O/CH_3CN$ (60/40) and further purified by Prep Chiral HPLC with the following condition (Column: CHIRALPAK IG, 2*25 cm, 5 μm. Mobile Phase A: Hexane:DCM=3:1 (0.5% 2 M $NH_3$-MeOH), Mobile Phase B: EtOH. Flow rate: 18 mL/min. Gradient: maintaining 50% B for 18 min; 220/254 nm) to afford title compounds with retention times of 10.18 minutes (Example 264a) and 13.24 minutes (Example 264b). The absolute stereochemistry of Examples 264a and 264b was not confirmed.

Example 264a Isolated as a white solid (19.7 mg, 13.0%). LCMS: $[M+H]^+$ 371.15. $^1$H NMR (400 MHz, DMSO-d6) δ 9.01 (s, 1H), 8.84 (d, J=8.8 Hz, 1H), 8.46 (s, 1H), 8.30 (d, J=5.5 Hz, 1H), 8.28 (s, 1H), 7.58 (d, J=5.5 Hz, 1H), 7.18 (s, 1H), 4.36 (d, J=4.9 Hz, 1H), 3.89-3.79 (m, 1H), 3.45-3.38 (m, 1H), 1.94-1.82 (m, 3H), 1.75-1.71 (m, 1H), 1.60-1.53 (m, 2H), 1.26-1.15 (m, 2H), 1.18-1.03 (m, 4H). Column: CHIRALPAK IG-3, 4.6*50 mm, 3 μm; Mobile Phase A: Hexane:DCM=3:1 (0.1% DEA), Mobile Phase B: EtOH; Flow rate: 1.0 mL/min; Gradient: 50% B to 50% B for 4 min; 254 nm; RT: 2.223 min.

Example 264b: Isolated as a white solid (13.1 mg, 8.7%). LCMS: $[M+H]^+$ 371.15. $^1$H NMR (400 MHz, DMSO-d6) δ 9.01 (s, 1H), 8.83 (d, J=8.7 Hz, 1H), 8.46 (s, 1H), 8.30 (d, J=5.5 Hz, 1H), 8.28 (s, 1H), 7.58 (d, J=5.5 Hz, 1H), 7.18 (s, 1H), 4.36 (d, J=4.9 Hz, 1H), 3.89-3.79 (m, 1H), 3.45-3.38 (m, 1H), 1.94-1.82 (m, 3H), 1.74-1.69 (m, 1H), 1.60-1.53

(m, 2H), 1.26-1.15 (m, 2H), 1.18-1.03 (m, 4H). Column: CHIRALPAK IG-3, 4.6*50 mm, 3 μm; Mobile Phase A: Hexane:DCM=3:1 (0.1% DEA), Mobile Phase B: EtOH; Flow rate: 1.0 mL/min; Gradient: 50% B to 50% B for 4 min; 254 nm; RT: 2.866 min.

Example 265: N-((1r,3r)-3-(2-hydroxypropan-2-yl)cyclobutyl)-5-(1H-imidazol-1-yl)-1H-pyrazolo[4,3-d]pyrimidine-7-carboxamide

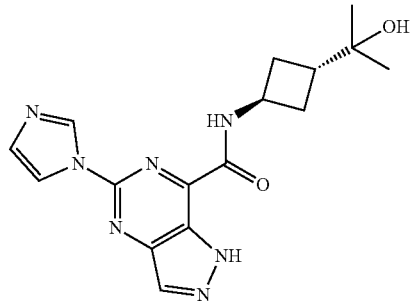 [SMILES: CC(C)(O)[C@H]1C[C@H](NC(=O)c2nc(-n3ccnc3)nc3cn[nH]c23)C1]

A solution of 5-(1H-imidazol-1-yl)-1H-pyrazolo[4,3-d]pyrimidine-7-carboxylic acid (115 mg, 0.50 mmol, 1 eq), DIEA (193.7 mg, 1.50 mmol, 3 eq), T3P (476.8 mg, 1.5 mmol, 3 eq), and 2-((1r,3r)-3-aminocyclobutyl)propan-2-ol hydrochloride (82.8 mg, 0.5 mmol, 1 eq) in DMF (2 mL) was stirred for 1 h at RT. After concentrated under vacuum, the crude product was purified by C18 reverse phase eluting with H$_2$O/CH$_3$CN (31:69) to afford the title compound (40.9 mg, 24% yield) as a light yellow solid. LCMS: [M+H]$^+$ 342.05. $^1$H NMR (400 MHz, DMSO-d6) δ 14.21 (s, 1H), 9.43 (d, J=7.9 Hz, 1H), 9.08 (t, J=1.1 Hz, 1H), 8.51 (s, 1H), 8.27 (t, J=1.4 Hz, 1H), 7.18 (t, J=1.2 Hz, 1H), 4.55-4.47 (m, 1H), 4.32 (s, 1H), 2.37-2.21 (m, 5H), 1.19-1.03 (m, 6H).

Example 266: N-((1r,3r)-3-(2-hydroxypropan-2-yl)cyclobutyl)-5-(1H-imidazol-1-yl)-1H-pyrazolo[3,4-c]pyridine-7-carboxamide

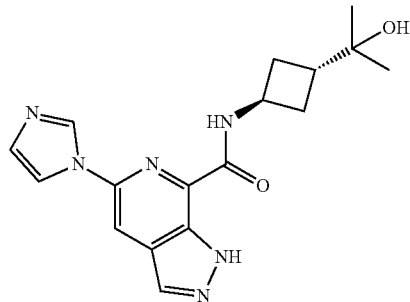 [SMILES: CC(C)(O)[C@H]1C[C@H](NC(=O)c2nc(-n3ccnc3)cc3cn[nH]c23)C1]

A solution of 5-(1H-imidazol-1-yl)-1H-pyrazolo[3,4-c]pyridine-7-carboxylic acid (80 mg, 0.35 mmol, 1 eq), DIEA (135 mg, 1.05 mmol, 3 eq), T3P (333 mg, 1.05 mmol, 3 eq), and 2-((1r,3r)-3-aminocyclobutyl)propan-2-ol hydrochloride (57.8 mg, 0.35 mmol, 1 eq) in DMF (2 mL) was stirred for 1 h at RT. After concentrated under vacuum, the crude product was purified by C18 reverse phase eluting with H$_2$O/CH$_3$CN (23:27) to afford the title compound (53.6 mg 45.1% yield) as a white solid. LCMS: [M+H]$^+$ 341.05. $^1$H NMR (400 MHz, DMSO-d6) δ 13.82 (s, 1H), 9.10 (d, J=8.0 Hz, 1H), 8.96 (t, J=1.2 Hz, 1H), 8.36 (d, J=1.7 Hz, 2H), 8.25 (t, J=1.4 Hz, 1H), 7.15 (t, J=1.2 Hz, 1H), 4.55-4.47 (m, 1H), 4.29 (s, 1H), 2.39-2.25 (m, 5H), 1.19-1.03 (m, 6H).

Example 267a and 267b: N-((1R,4r)-4-((R)-1-hydroxyethyl)cyclohexyl)-2-(1H-imidazol-1-yl)thieno[3,2-d]pyrimidine-4-carboxamide and N-((1S,4r)-4-((S)-1-hydroxyethyl)cyclohexyl)-2-(1H-imidazol-1-yl)thieno[3,2-d]pyrimidine-4-carboxamide

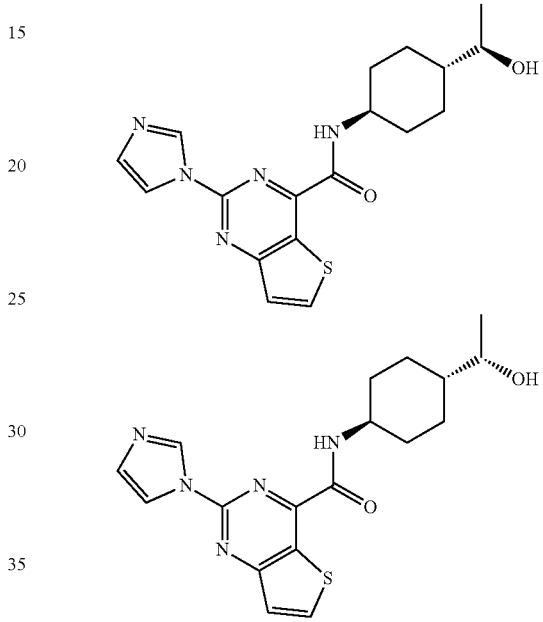

A solution of 2-(1H-imidazol-1-yl)thieno[3,2-d]pyrimidine-4-carboxylic acid (250 mg, 1.02 mmol, 1 eq), 1-(4-aminocyclohexyl)ethanol (290 mg, 2.03 mmol, 2 eq), HATU (463 mg, 1.22 mmol, 1.2 eq), and 4-methylmorpholine (205 mg, 2.03 mmol, 2 eq) in DMF (5 mL) was stirred for 4 h at RT. After completion, the resulting mixture was quenched by 50 mL of water and extracted with 2×20 mL of ethyl acetate, the organic layers combined and concentrated. The residue was applied onto a silica gel column with ACN/H$_2$O (52/48) and further purified by Prep-CHIRAL-HPLC with the following conditions (Column: CHIRAL ART Cellulose-SB, 3*25 cm, 5 μm. Mobile Phase A: Hexane:DCM=3:1 (0.5% 2M NH$_3$-MeOH), Mobile Phase B:EtOH. Flow rate: 45 mL/min; Gradient: maintaining 10% B for 12 min; 220/254 nm) to afford title compounds with retention times of 9.2 minutes (Example 267a) and 10.6 minutes (Example 267b). The absolute stereochemistry of Example 267a and Example 267b was not confirmed.

Example 267a: Isolated as a light brown solid (57.3 mg 15% yield). LCMS: [M+H]$^+$ 372.10. $^1$H NMR (300 MHz, DMSO-d6) δ 9.13 (d, J=8.6 Hz, 1H), 9.09 (s, 1H), 8.69 (d, J=5.7 Hz, 1H), 8.28 (s, 1H), 7.65 (d, J=5.4 Hz, 1H), 7.17 (s, 1H), 4.34 (t, J=5.1 Hz, 1H), 3.92-3.78 (m, 1H), 3.44-3.33 (m, 1H), 1.95-1.82 (m, 3H), 1.72-1.69 (m, 1H), 1.60-1.48 (m, 2H), 1.28-1.01 (m, 6H) (Column: CHIRAL ART Cellulose-SB, 4.6*100 mm, 3 μm. Mobile Phase A: (Hexane:DCM=3:1 (0.1% DEA)): EtOH=85:15, Mobile Phase B: EtOH. Flow rate:1 mL/min). Retention time: 3.31 min Example 267b: Isolated as a light brown solid (55.2 mg, 15% yield). LCMS: [M+H]$^+$ 372.10. $^1$H NMR (300 MHz, DMSO-d6) δ 9.10 (d, J=8.7 Hz, 1H), 9.08 (s, 1H), 8.69 (d, J=5.4 Hz, 1H), 8.28 (s, 1H), 7.65 (d, J=5.7 Hz, 1H), 7.17 (s, 1H), 4.35 (d, J=4.8 Hz, 1H), 3.92-3.76 (m, 1H), 3.44-3.32 (m, 1H), 1.98-1.82 (m, 3H), 1.75-1.68 (m, 1H), 1.65-1.40 (m, 2H), 1.27-1.16 (m, 2H), 1.15-1.01 (m, 4H). (Column: CHIRAL ART Cellulose-SB, 4.6*100 mm, 3 μm. Mobile Phase A: (Hexane:DCM=3:1 (0.1% DEA)): EtOH=85:15, Mobile Phase B: EtOH. Flow rate: 1 mL/min). Retention time: 3.752 min Example 268: 2-(1H-imidazol-1-yl)-N-((1r,4r)-4-(2-methoxyethoxy)cyclohexyl)-7-methyl-5H-pyrrolo[3,2-d]pyrimidine-4-carboxamide

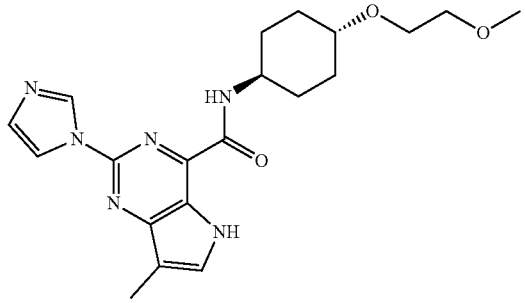 [SMILES: COCCO[C@H]1CC[C@H](NC(=O)c2nc(-n3ccnc3)nc3c(C)c[nH]c23)CC1]

Step 1: 4-(1-ethoxyvinyl)-2-(1H-imidazol-1-yl)-7-iodo-5H-pyrrolo[3,2-d]pyrimidine A solution of 4-(1-ethoxyvinyl)-2-(1H-imidazol-1-yl)-5H-pyrrolo[3,2-d]pyrimidine (2.0 g, 7.84 mmol, 1 eq), KOH (0.44 g, 7.84 mmol, 1 eq), and I$_2$ (2 g, 7.84 mmol, 1 eq) in DMF (10 mL) was stirred for 3 h at RT. The reaction was then quenched by the addition of 5 mL of saturated NaHSO$_3$ aqueous. The resulting solution was extracted with ethyl acetate (3×10 mL.) The organic layers were combined, dried over anhydrous sodium sulfate and concentrated under vacuum. The residue was applied onto a silica gel column with dichloromethane/methanol (96:4) to afford title compound (1 g, 33.5% yield) as yellow solid. LCMS: [M+H]$^+$ 382.20.

Step 2: 4-(1-ethoxyvinyl)-2-(1H-imidazol-1-yl)-7-iodo-5-((2-(trimethylsilyl)ethoxy)methyl)-5H-pyrrolo[3,2-d]pyrimidine A solution of 4-(1-ethoxyvinyl)-2-(1H-imidazol-1-yl)-7-iodo-5H-pyrrolo[3,2-d]pyrimidine (980.0 mg, 2.57 mmol, 1 eq), and NaH (123.4 mg, 5.14 mmol, 2 eq) in DMF (6 mL) was stirred for 20 min at 0° C., Then SEM-Cl (428.6 mg, 2.57 mmol, 1 eq) was added and the resulting solution was stirred for 30 min at RT. The reaction was quenched by the addition of 5 mL of water. The resulting solution was extracted with ethyl acetate (3×10 mL.) The organic layers were combined, dried over anhydrous sodium sulfate, and concentrated under vacuum to afford the title compound (960 mg, 73.0% yield) as brown oil. LCMS: [M+H]$^+$ 512.20.

Step 3: ethyl 2-(1H-imidazol-1-yl)-7-iodo-5-((2-(trimethylsilyl)ethoxy)methyl)-5H-pyrrolo[3,2-d]pyrimidine-4-carboxylate A solution of 4-(1-ethoxyvinyl)-2-(1H-imidazol-1-yl)-7-iodo-5-((2-(trimethylsilyl)ethoxy)methyl)-5H-pyrrolo[3,2-d]pyrimidine (1.1 g, 2.15 mmol, 1 eq), H$_2$O (160 mL), NaIO$_4$ (0.92 g, 4.30 mmol, 2 eq), and KMnO$_4$ (0.20 g, 1.29 mmol, 0.60 eq) in dioxane (160 mL) was stirred for 1 h at 0° C. The solids were filtered out. The resulting solution was extracted with ethyl acetate (3×200 mL.) The organic layers were combined, dried over anhydrous sodium sulfate, and concentrated under vacuum to afford the title compound (600 mg, 54.3% yield) as brown oil. LCMS: [M+H]$^+$ 514.20.

Step 4: ethyl 2-(1H-imidazol-1-yl)-7-methyl-5-((2-(trimethylsilyl)ethoxy)methyl)-5H-pyrrolo[3,2-d]pyrimidine-4-carboxylate Under atmosphere of nitrogen, a solution of ethyl 2-(1H-imidazol-1-yl)-7-iodo-5-((2-(trimethylsilyl)ethoxy)methyl)-5H-pyrrolo[3,2-d]pyrimidine-4-carboxylate (350.0 mg, 0.68 mmol, 1 eq), Pd(dppf)Cl$_2$ (49.9 mg, 0.068 mmol, 0.10 eq), and dimethylzinc (130.1 mg, 1.36 mmol, 2 eq) in dioxane (4 mL) was stirred for 4 h at 80° C. The reaction was then quenched by the addition of 5 mL of water. The resulting solution was extracted with dichloromethane (3×10 mL.) The organic layers were combined, dried over anhydrous sodium sulfate, and concentrated under vacuum. The residue was applied onto a silica gel column with ethyl acetate/petroleum ether (85:15) to afford the title compound (100 mg, 36.5% yield) as a yellow solid. LCMS: [M+H]$^+$ 402.15.

Step 5: ethyl 2-(1H-imidazol-1-yl)-7-methyl-5H-pyrrolo[3,2-d]pyrimidine-4-carboxylate A solution of ethyl 2-(1H-imidazol-1-yl)-7-methyl-5-((2-(trimethylsilyl)ethoxy)methyl)-5H-pyrrolo[3,2-d]pyrimidine-4-carboxylate (120.0 mg, 0.29 mmol, 1 eq), and TFA (2 mL) in DCM (8 mL) was stirred for 1 h at RT. The resulting mixture was concentrated under vacuum. The residue was stirred in TEA (4 mL) for 1 h at RT. The resulting solution was concentrated to afford the title compound (80 mg, 98.7% yield) as a yellow crude solid. LCMS: [M+H]$^+$ 272.20.

Step 6: 2-(1H-imidazol-1-yl)-7-methyl-5H-pyrrolo[3,2-d]pyrimidine-4-carboxylic acid A solution of ethyl 2-(1H-imidazol-1-yl)-7-methyl-5H-pyrrolo[3,2-d]pyrimidine-4-carboxylate (80 mg, 0.29 mmol, 1 eq), H$_2$O (1 mL), and NaOH (35.4 mg, 0.89 mmol, 3 eq) in MeOH (4 mL) was stirred for 1 h at RT. The reaction was diluted with 5 mL of water. The pH value of the solution was adjusted to 4 with HCl aqueous (1 M). The resulting solution was extracted with dichloromethane (3×10 mL.) The organic layers were combined, dried over anhydrous sodium sulfate, and concentrated under vacuum to afford the title compound (60 mg, 83.7% yield) as a light yellow solid. LCMS: [M+H]$^+$ 244.20.

Step 7: 2-(1H-imidazol-1-yl)-N-((1r,4r)-4-(2-methoxyethoxy)cyclohexyl)-7-methyl-5H-pyrrolo[3,2-d]pyrimidine-4-carboxamide A solution of 2-(1H-imidazol-1-yl)-7-methyl-5H-pyrrolo[3,2-d]pyrimidine-4-carboxylic acid (55.0 mg, 0.23 mmol, 1 eq), (1r,4r)-4-(2-methoxyethoxy)cyclohexan-1-amine (47.0 mg, 0.27 mmol, 1.2 eq), DIEA (87.7 mg, 0.68 mmol, 3 eq), and HATU (128.9 mg, 0.34 mmol, 1.5 eq) in DMF (2 mL)

was stirred for 1 h at RT. The resulting solution was quenched with 10 mL of water. The resulting solution was extracted with DCM (3×20 mL.) The organic layers were combined and concentrated. The crude product was purified by Flash-Prep-HPLC with the following conditions: (Column: YMC-Actus Triart C18 ExRS, 30*150 mm, 5 μm. Mobile Phase A: Water (10 mM NH₄HCO₃), Mobile Phase B: ACN. Flow rate:60 mL/min; Gradient: 29% B to 53% B in 8 min; 254/220 nm) to afford the title compound (30.3 mg, 33.6% yield) as a white solid. LCMS: [M+H]⁺ 399.15. ¹H NMR (400 MHz, DMSO-d6) δ 11.75 (s, 1H), 9.00 (s, 1H), 8.87 (d, J=8.6 Hz, 1H), 8.23 (s, 1H), 7.83 (s, 1H), 7.13 (s, 1H), 3.95-3.80 (m, 1H), 3.60-3.53 (m, 2H), 3.48-3.41 (m, 2H), 3.30-3.26 (m, 1H), 3.25 (s, 3H), 2.31 (s, 3H), 2.11-2.05 (m, 2H), 1.90-1.81 (m, 2H), 1.66-1.60 (m, 2H), 1.31-1.21 (m, 2H).

The following Examples in Table 5 were prepared according to the methods described for the previous Examples.

TABLE 5

| Example # | Structure and name | Prepared according to example # | LCMS (M + H)⁺ |
|---|---|---|---|
| 269 | 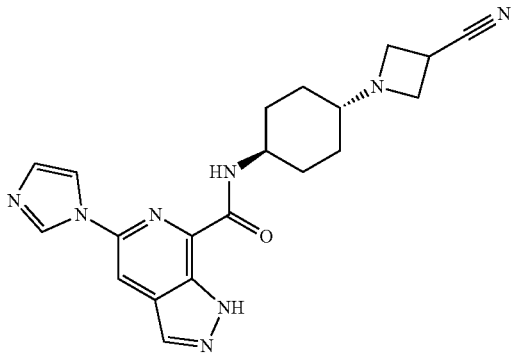 [SMILES: N#CC1CN([C@H]2CC[C@H](NC(=O)c3nc(-n4ccnc4)cc4cn[nH]c34)CC2)C1]<br>N-((1r,4r)-4-(3-cyanoazetidin-1-yl)cyclohexyl)-5-(1H-imidazol-1-yl)-1H-pyrazolo[3,4-c]pyridine-7-carboxamide | 101 | 391.15 |
| 270 | 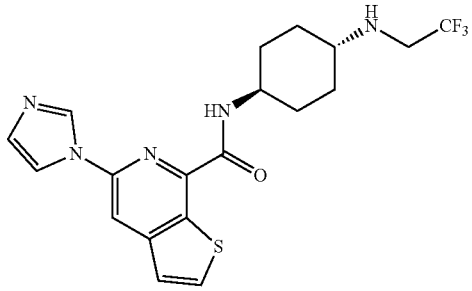 [SMILES: O=C(N[C@H]1CC[C@H](NCC(F)(F)F)CC1)c1nc(-n2ccnc2)cc2ccsc12]<br>5-(1H-imidazol-1-yl)-N-((1r,4r)-4-((2,2,2-trifluoroethyl)amino)cyclohexyl)thieno[2,3-c]pyridine-7-carboxamide | 7 | 424.15 |
| 271 | 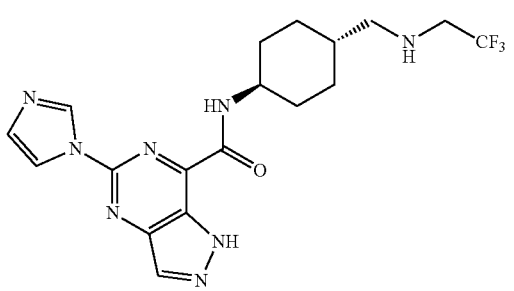 [SMILES: O=C(N[C@H]1CC[C@H](CNCC(F)(F)F)CC1)c1nc(-n2ccnc2)nc2cn[nH]c12]<br>5-(1H)-imidazol-1-yl)-N-((1r,4r)-4-(((2,2,2-trifluoroethyl)amino)methyl)cyclohexyl)-1H-pyrazolo[4,3-d]pyrimidine-7-carboxamide | 101 step 1 | 423.20 |

TABLE 5-continued

| Example # | Structure and name | Prepared according to example # | LCMS (M + H)+ |
|---|---|---|---|
| 272 | 2-(1H-imidazol-1-yl)-N-((1r,4r)-4-((1,1,1-trifluoro-2-methylpropan-2-yl)amino)cyclohexyl)-5H-pyrrolo[3,2-d]pyrimidine-4-carboxamide | 7 | 436.20 |
| 273 | N-((1r,4r)-4-((1,1-difluoro-2-methylpropan-2-yl)amino)cyclohexyl)-2-(1H-imidazol-1-yl)-5H-pyrrolo[3,2-d]pyrimidine-4-carboxamide | 7 | 418.20 |
| 274 | 5-(1H-imidazol-1-yl)-N-((1s,4s)-4-methyl-4-((2,2,2-trifluoroethyl)amino)cyclohexyl)-1H-pyrazolo[4,3-d]pyrimidine-7-carboxamide | 101 step 1 | 423.15 |
| 275 | | 101 step 1 | 423.15 |

TABLE 5-continued

| Example # | Structure and name | Prepared according to example # | LCMS (M + H)+ |
|---|---|---|---|
| 276 | 5-(1H-imidazol-1-yl)-N-((1r,4r)-4-methyl-4-((2,2,2-trifluoroethyl)amino)cyclohexyl)-1H-pyrazolo[4,3-d]pyrimidine-7-carboxamide<br><br>[structure]<br><br>5-(1H-imidazol-1-yl)-N-((1r,4r)-4-((1,1,1-trifluoro-2-methylpropan-2-yl)amino)cyclohexyl)-1H-pyrazolo[4,3-d]pyrimidine-7-carboxamide | 7 | 437.15 |
| 277 | [structure]<br><br>5-(1H-imidazol-1-yl)-N-((1s,4s)-4-((1,1,1-trifluoro-2-methylpropan-2-yl)amino)cyclohexyl)-1H-pyrazolo[4,3-d]pyrimidine-7-carboxamide | 7 | 437.15 |

Example A

CD38 Enzyme Assay

The CD38 enzyme assay was performed as described previously (Becherer, J D, et al. J. Med. Chem. 2015, 58, 7021-7056). Briefly, 200 nL of a dose response titration of each test compound dissolved in 100% DMSO was spotted in clear polystyrene 384-well plate (Thermo #-264704) using a Mosquito (FTP Labtech). A 10 µL solution of 2 nM CD38 (BPS Biosciences #71227) suspended in 100 mM HEPES ((4-(2-hydroxyethyl)-1-piperazineethanesulfonic acid, pH=7.5), 4 mM EDTA (2,2',2",2'''-(ethane-1,2-diyldinitrilo)tetraacetic acid) and 1 mM CHAPS (3-[(3-cholamidopropyl)dimethylammonio]-1-propanesulfonate) was incubated with test compound at 25° C. for 30 min. The enzyme reaction was initiated by adding 10 µL. of 400 µM nicotinamide adenine dinucleotide (NAD-), 1000 µM (E)-2-(2-(pyridin-4-ylmethylene)hydrazineyl)pyridine in buffer containing 5 mM sodium acetate (pH=5.2) and 1 mM CHAPS. The reactions were incubated at 25° C. and the absorbance at 405 nm was measured after 15 minutes and 60 min on an Envision plate reader (Perkin Elmer) The absorbance values from the 15 min timepoint were subtracted from the absorbance value from the 60 min timepoint.

The compound 4-(((1r,4r)-4-(2-methoxyethoxy)cyclohexyl)amino)-1-methyl-6-(thiazol-5-yl)quinolin-2(1H)-one was synthesized as previously described (Haffner C D, et al. J. Med. Chem. 2015, 58, 3548-3571). Control wells containing a negative control of 1% DMSO vehicle or a positive control of 100 µM 4-(((1r,4r)-4-(2-methoxyethoxy)cyclohexyl)amino)-1-methyl-6-(thiazol-5-yl)quinolin-2(1H)-one were used to calculate the % inhibition as described below.

$$\% \text{ inhibition} = 100 \times \frac{SUB_{cmpd} - SUB_{min}}{SUB_{max} - SUB_{min}}$$

where SUB$_{cmpd}$ is the subtracted value for the individual compound treated well, SUB$_{min}$ is the average of the subtracted values of the 4-(((1r,4r)-4-(2-methoxyethoxy)cyclohexyl)amino)-1-methyl-6-(thiazol-5-yl)quinolin-2(1H)-one positive control wells and SUB$_{max}$ is the average of the subtracted values of the DMSO negative control wells.

The % inhibition values were plotted as a function of compound concentration and the following 4-parameter fit was applied to derive the IC$_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

where top and bottom are normally allowed to float, but nay be fixed at 100 or 0 respectively in a 3-parameter fit. The Hill Coefficient is normally allowed to float but may also be fixed at 1 in a 3-parameter fit. Y is the % inhibition and X is the compound concentration.

IC$_{50}$ data for the compounds of the invention according to this assay are provided in Table A-1 below ("+" is <0.01 μM; "++" is ≥0.01 and <0.1 μM; "+++" is ≥0.1 μM and <1 μM; and "++++" is ≥1 μM).

TABLE A-1

| Example No. | Human CD38 IC50 (μM) |
|---|---|
| 1 | +++ |
| 2 | ++++ |
| 3 | +++ |
| 4 | +++ |
| 5 | +++ |
| 6 | +++ |
| 7 | ++ |
| 8 | +++ |
| 9 | +++ |
| 10 | ++ |
| 11 | ++ |
| 12 | ++ |
| 13 | +++ |
| 14 | ++ |
| 15 | +++ |
| 16 | ++ |
| 17 | +++ |
| 18 | ++ |
| 19 | ++ |
| 20 | +++ |
| 21 | +++ |
| 22 | ++ |
| 23 | ++ |
| 24 | ++ |
| 25 | +++ |
| 26 | ++ |
| 27 | + |
| 28a | ++ |
| 28b | + |
| 29 | +++ |
| 30 | +++ |
| 31 | ++ |
| 32 | ++ |
| 33 | ++++ |
| 34 | ++++ |
| 35 | ++++ |
| 36 | ++ |
| 37 | ++++ |
| 38 | ++++ |
| 39a | + |
| 39b | + |
| 41 | +++ |
| 42 | +++ |
| 43 | +++ |
| 44 | ++ |
| 45 | +++ |
| 46 | ++ |
| 47 | ++++ |
| 48 | ++ |
| 49 | ++ |
| 50 | ++ |
| 51 | ++ |
| 52 | ++ |
| 53 | +++ |
| 54 | ++++ |
| 55 | ++ |
| 56 | ++ |
| 57 | ++ |
| 58 | + |
| 59 | + |
| 60 | ++++ |
| 61 | ++ |
| 62 | ++ |
| 63 | + |
| 64 | ++ |
| 65 | ++ |
| 66 | ++ |
| 67 | ++ |
| 68 | ++ |
| 69 | ++ |
| 70 | +++ |
| 71 | ++ |
| 72 | ++ |
| 73 | +++ |
| 74 | +++ |
| 75 | + |
| 76 | ++ |
| 77 | + |
| 78 | ++ |
| 79 | +++ |
| 80 | ++ |
| 81 | + |
| 82 | + |
| 83 | + |
| 84 | + |
| 85 | + |
| 86 | + |
| 87 | + |
| 88 | + |
| 89 | + |
| 90 | + |
| 91 | + |
| 92 | + |
| 93 | ++ |
| 94 | + |
| 95 | ++ |
| 96 | + |
| 97 | ++ |
| 98 | + |
| 99 | + |
| 100 | + |
| 101 | ++ |
| 102 | ++ |
| 103 | ++ |
| 104 | + |
| 105 | ++ |
| 106 | +++ |
| 107 | + |
| 108 | ++ |
| 109 | + |
| 110 | ++ |
| 111 | +++ |
| 112 | ++ |
| 113 | ++ |
| 114 | + |
| 115 | ++ |
| 116 | ++ |
| 117 | ++ |
| 118 | + |
| 119a | ++ |
| 119b | ++ |
| 120a | + |

TABLE A-1-continued

| Example No. | Human CD38 IC50 (μM) |
|---|---|
| 120b | ++ |
| 121 | + |
| 122 | + |
| 123a | ++ |
| 123b | +++ |
| 124a | ++ |
| 124b | ++ |
| 125a | ++ |
| 125b | ++ |
| 126a | ++ |
| 126b | ++ |
| 127a | ++ |
| 127b | ++ |
| 128a | + |
| 128b | ++ |
| 129 | ++ |
| 130 | + |
| 131 | + |
| 132 | + |
| 133 | ++ |
| 134 | + |
| 135 | ++ |
| 136 | + |
| 137 | + |
| 138 | + |
| 139 | ++ |
| 140 | + |
| 141 | + |
| 142 | + |
| 143 | ++ |
| 144 | + |
| 145 | + |
| 146 | ++ |
| 147 | ++ |
| 148 | + |
| 149 | + |
| 150 | + |
| 151 | + |
| 152 | ++ |
| 153 | + |
| 154 | + |
| 155 | ++ |
| 156 | + |
| 157 | ++ |
| 158 | ++ |
| 159 | + |
| 160 | ++ |
| 161 | ++ |
| 162 | + |
| 163 | ++ |
| 164 | ++ |
| 165 | ++ |
| 166 | ++ |
| 167 | ++ |
| 168 | ++ |
| 169 | +++ |
| 170 | ++ |
| 171 | + |
| 172 | ++ |
| 173 | + |
| 174 | + |
| 175 | + |
| 176 | ++ |
| 177 | + |
| 178 | ++ |
| 179 | ++ |
| 180 | ++ |
| 181 | +++ |
| 182 | + |
| 183 | + |
| 184 | + |
| 185 | + |
| 186 | ++ |
| 187 | ++ |
| 188 | +++ |
| 189 | ++ |
| 190 | + |

TABLE A-1-continued

| Example No. | Human CD38 IC50 (μM) |
|---|---|
| 191 | ++ |
| 192a | + |
| 192b | + |
| 193 | ++ |
| 194 | +++ |
| 195 | ++ |
| 196 | ++ |
| 197 | ++ |
| 198 | ++ |
| 199 | ++ |
| 200 | + |
| 201 | ++ |
| 202 | ++ |
| 203 | ++ |
| 204 | ++ |
| 205 | + |
| 206 | ++ |
| 207 | ++ |
| 208 | ++ |
| 209 | ++ |
| 210 | + |
| 211 | + |
| 212 | + |
| 213 | ++ |
| 214 | + |
| 215 | + |
| 216 | ++ |
| 217 | + |
| 218 | ++ |
| 219 | + |
| 220 | ++ |
| 221 | ++ |
| 222 | ++ |
| 223 | ++ |
| 224 | + |
| 225 | + |
| 226 | ++ |
| 227 | ++ |
| 228 | + |
| 229 | + |
| 230 | ++ |
| 231 | + |
| 232 | ++ |
| 233 | ++ |
| 234 | ++ |
| 235 | ++ |
| 236 | + |
| 237 | + |
| 238 | + |
| 239 | + |
| 240 | +++ |
| 241 | ++ |
| 242 | ++ |
| 243 | ++ |
| 244 | ++ |
| 245 | ++ |
| 246 | ++ |
| 247 | + |
| 248 | ++ |
| 249 | + |
| 250 | ++ |
| 251 | ++ |
| 252 | ++ |
| 253 | ++ |
| 254 | +++ |
| 255 | ++ |
| 256 | +++ |
| 257 | ++ |
| 258 | ++ |
| 259 | +++ |
| 260 | + |
| 261 | + |
| 262 | ++ |
| 263 | + |
| 264a | + |
| 264b | ++ |
| 265 | ++ |

TABLE A-1-continued

| Example No. | Human CD38 IC50 (μM) |
|---|---|
| 266 | ++ |
| 267a | + |
| 267b | ++ |
| 268 | ++ |
| 269 | ++ |
| 270 | ++ |
| 271 | ++ |
| 272 | ++ |
| 273 | ++ |
| 274 | ++ |
| 275 | +++ |
| 276 | ++ |
| 277 | +++ |

Example B. Treatment with CD38 Inhibitors in Dose Response In Vivo PD Study

Quantification of $NAD^+$

A bioanalytical method for the quantification of $NAD^+$ was developed and utilized for PK/PD studies. The method uses a protein-precipitation (PP) extraction of samples using 0.5M perchloric acid followed by LC/MS/MS analysis and demonstrated a linear assay range from 5 to 500 μmol/L, utilizing a 0.02 mL sample volume. This assay was successfully applied to the analysis of samples such as spleen and liver.

Carbamazepine was used for the internal standard (IS) solution preparation, as shown in the table below:

| Compound ID | MW | FW | Storage Condition |
|---|---|---|---|
| $NAD^+$ | 663.43 | 663.43 | −20° C. |
| Carbamazepine | 236.27 | 236.27 | −20° C. |

The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC/MS/MS mass spectrometer.

Chromatographic separation was performed on a Waters Atlantis T3 3 um 4.6×100 mm at room temperature. The mobile phase was composed of A: 100% water (0.1% formic acid); B: 100% acetonitrile (0.1% formic acid). The flow rate was 0.7 mL/min.

Positive mode electrospray ionization (ESI) was performed on a Turbo V® ion source to obtain a protonated ion of $NAD^+$ and Carbamazepine (IS). A multiple reaction monitoring (MRM) method was selected for quantitative analysis. The optimized transitions were 664.038–427.9 and 237.146→194.2 for $NAD^+$ and Carbamazepine, respectively. The instrument parameters were set as follows: ion spray voltage: 5500 V; curtain gas: 40 psi; nebulizer gas: 50 psi; turbo gas: 50 psi; collision gas: 10 psi; temperature: 400° C. The compound dependent parameters are listed in the following table:

| Compound ID | $NAD^+$ | Carbamazepine (IS) |
|---|---|---|
| Transition | 664.038 → 427.9 | 237.146 → 194.2 |
| DP | 61 | 101 |
| CE | 35 | 25 |
| CXP | 14 | 18 |

$NAD^+$ was prepared in water with vortex at 10 mmol/L (free form) as standard stock solution. Calibration standard working solutions were prepared at concentrations of 50,100,200, 500, 1000, 2000 and 5000 umol/L by serial dilution of the standard stock solution by water. Quality control working solutions at concentrations of 20, 50, 100, 200, 500 and 4000 umol/L were prepared by serial dilution of the standard stock solution by water. These QC samples were prepared on the day of analysis in the same way as calibration standards. Carbamazepine was prepared in DMSO with vortex at 1 mg/mL (free form) as standard stock solution. Then final concentration of the IS at 20 ng/mL was prepared by dilution of IS stock by water.

2 μL of each calibration standard working solution (50, 100, 200, 500, 1000, 2000, 5000 μM) were added to 20 μL of the blank matrix to achieve calibration standards of 5~500 μM (5, 10, 20, 50, 100, 200, 500 μM) in a total volume of 22 μL. Five quality control samples at 5 μM, M, 20 μM, 50 μM and 400 μM were prepared independently of those used for the calibration curves. These QC samples were prepared on the day of analysis in the same way as calibration standards.

22 μL standards, 22 μL QC samples were added to 200 μL of 0.5 N perchloric acid and L of water containing IS mixture for precipitating protein, and 22 μL unknown samples (20 μL of "spleen: 0.5 N perchloric acid=1:4" with 2 μL blank solution) were added to 184 μL of 0.5 N perchloric acid, 16 μL of water and 30 μL of water containing IS mixture for precipitating protein. Then the samples were vortexed for 30 s. After centrifugation at 4 degree Celsius, 4000 rpm for 15 min. The supernatant was diluted 4 times with 5 mM ammonium formate. 3 μL of the diluted supernatant was injected into the LC/MS/MS system for quantitative analysis.

The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC/MS/MS mass spectrometer.

Chromatographic separation was performed on a Waters Atlantis T3 3 um 4.6×100 mm at room temperature. The mobile phase was composed of A: 100% water (0.1% formic acid); B: 100% acetonitrile (0.1% formic acid). The flow rate was 0.7 mL/min. The injection volume was 3 μL. The elution gradient is listed in the following table:

| Time (min) | A (%) | B (%) |
|---|---|---|
| 0.01 | 100 | 0.00 |
| 0.50 | 100 | 0.00 |
| 3.40 | 0.00 | 100 |
| 5.00 | 0.00 | 100 |
| 5.01 | 100 | 0.00 |
| 5.50 | 100 | 0.00 |

Positive mode electrospray ionization (ESI) was performed on a Turbo V® ion source to obtain a protonated ion of $NAD^+$ and carbamazepine (IS). A multiple reaction monitoring (MRM) method was selected for quantitative analysis. The optimized transitions were 664.038-427.9 and 237.146→194.2 for $NAD^+$ and carbamazepine, respectively.

The instrument parameters were set as follows: ion spray voltage: 5500 V; curtain gas: 40 psi; nebulizer gas: 50 psi; turbo gas: 50 psi; collision gas: 10 psi; temperature: 400° C. The compound dependent parameters are listed in the following table:

| Compound ID | NAD+ | Carbamazepine (IS) |
|---|---|---|
| Transition | 664.038 → 427.9 | 237.146 → 194.2 |
| DP | 61 | 101 |
| CE | 35 | 25 |
| CXP | 14 | 18 |

Quantification of ADPr

Bioanalytical method for the quantification of ADPr was developed and utilized for PK/PD studies. The method uses a protein-precipitation (PP) extraction of samples using acetonitrile followed by LC/MS/MS analysis and demonstrated a linear assay range from 5 to 5000 ng/mL, utilizing a 0.01 mL sample volume. This assay was successfully applied to the analysis of samples such as spleen and liver.

D5-Adenosine was used for the internal standard (IS) solution preparation. These compounds information is listed in the table below:

| Compound ID | MW | FW | Storage Condition |
|---|---|---|---|
| ADPr | 559.1 | 559.1 | −20° C. |
| D5-Adenosine | 282.16 | 282.16 | −20° C. |

The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC/MS/MS mass spectrometer.

Chromatographic separation was performed on a Waters Atlantis T3 4 um 3×100 mm at room temperature. The mobile phase was composed of A: 5% acetonitrile (0.1% formic acid) in water; B: 95% acetonitrile (0.1% formic acid) in water. The flow rate was 0.6 mL/min.

Positive mode electrospray ionization (ESI) was performed on a Turbo V® ion source to obtain a protonated ion of ADPr and dexamethasone (IS). A multiple reaction monitoring (MRM) method was selected for quantitative analysis. The optimized transitions were 560.105→136.1 and 283.163→145.9 for ADPr and D5-Adenosine, respectively. The instrument parameters were set as follows: ion spray voltage: 5500 V; curtain gas: 40 psi; nebulizer gas: 50 psi; turbo gas: 50 psi; collision gas: 10 psi; temperature: 400° C. The compound dependent parameters are listed in the table below:

| Compound ID | ADPR | D5-Adenosine (IS) |
|---|---|---|
| Transition | 560.105 → 136.1 | 283.163 → 145.9 |
| DP | 76 | 72 |
| CE | 47 | 25 |
| CXP | 8 | 20 |

ADPr was prepared in 0.5M perchloric acid with vortex at 1 mg/mL (free form) as standard stock solution. Calibration standard working solutions were prepared at concentrations of 5, 10, 20, 50, 100, 200, 500, 1000, 2000 and 5000 ng/mL by serial dilution of the standard stock solution by 50% MeOH (0.1% formic acid) in water. Quality control working solutions at concentrations of 10, 20, 50, 500, 1600 and 4000 ng/mL were prepared by serial dilution of the standard stock solution by 50% MeOH (0.1% formic acid) in water. These QC samples were prepared on the day of analysis in the same way as calibration standards.

D5-Adenosine was prepared in MeoH with vortex at 0.1 mg/mL (free form) as standard stock solution. Then final concentration of the IS at 50 ng/mL was prepared by dilution of IS stock by MeoH with 0.1% formic acid.

20 μL of each calibration standard working solution (5, 10, 20, 50, 100, 200, 500, 1000, 2000 and 5000 ng/mL) was added to 20 μL of blank 0.05M perchloric acid to achieve calibration standards of 5-5000 ng/mL (5, 10, 20, 50, 100, 200, 500, 1000, 2000 and 5000 ng/mL) in a total volume of 40 μL. Quality Control (QC) samples at 10 (low-1), 20, (low-2) 50 (low-3), 500 (mid-1), 1600 (mid-2) and 4000 (high) ng/mL in 0.05M PA were prepared independently from those used for the calibration curves. These QC samples were prepared on the day of analysis in the same way as calibration standards. 40 μL standards, 40 μL QC samples were added to 200 μL of methanol and 0.1% Formic acid containing IS mixture for precipitating protein, and 40 μL unknown samples (20 μL of liver/spleen with 20 μL "50% methanol in water solution (0.1% Formic acid)" were added to 200 μL methanol and 0.1% Formic acid containing IS mixture for precipitating protein. Then the samples were vortexed for 30 s. After centrifugation at 4 degree Celsius, 4000 rpm for 5 min. The supernatant was diluted 2 times with DI water. 15 μL of the diluted supernatant was injected into the LC/MS/MS system for quantitative analysis LC-MS/MS conditions The LC-MS/MS system consisted of Degasser DGU-20A5R, C, Liquid Chromatograph LC-30AD, Communications Bus Module CBM-20A, Auto Sampler SIL-30AC, Rack changer II and an AB Sciex Triple Quads 5500 LC/MS/MS mass spectrometer.

Chromatographic separation was performed on an Waters Atlantis T3 4 um 3×10 mm at room temperature. The mobile phase was composed of A: 5% acetonitrile (0.1% formic acid) in water; B: 95% acetonitrile (0.1% formic acid) in water. The flow rate was 0.6 mL/min. The injection volume was 15 μL. The elution gradient is listed in the table below:

| Time (min) | A (%) | B (%) |
|---|---|---|
| 0.01 | 100 | 0.00 |
| 0.20 | 100 | 0.00 |
| 2.60 | 70.0 | 30.0 |
| 3.50 | 10.0 | 90.0 |
| 3.80 | 10.0 | 90.0 |
| 3.81 | 100 | 0.00 |
| 4.30 | 100 | 0.00 |

Positive mode electrospray ionization (ESI) was performed on a Turbo V® ion source to obtain a protonated ion of ADPr and dexamethasone (IS). A multiple reaction monitoring (MRM) method was selected for quantitative analysis. The optimized transitions were 559.326→497.20 and 393.128→373.200 for ERAS-601 and dexamethasone, respectively. The instrument parameters were set as follows: ion spray voltage: 5500 V; curtain gas: 40 psi; nebulizer gas: 50 psi; turbo gas: 50 psi; collision gas: 10 psi; temperature: 400° C. The compound dependent parameters are listed in the table below:

| Compound ID | ERAS-601 (PO) | Dexamethasone (IS) |
|---|---|---|
| Transition | 560.105 → 136.1 | 283.163 → 145.9 |
| DP | 76 | 72 |
| CE | 47 | 25 |
| CXP | 8 | 20 |

In Vivo PD Study

C57BL/6 mice were dosed with vehicle and the dose range of each CD38 inhibitor in a formulation of 0.5% hydroxypropyl methylcelluslose (HPMC)+0.1% Tween 80 adjusted to pH~3.5 with citric acid buffer. Plasma PK samples were collected at the endpoint. About 500 μL whole blood was collected into a 1.5 mL tube containing 20 μL of 15% dipotassium ethylenediaminetetraacetic acid (EDTA-2K) solution. The sample was centrifuged at 6000 rpm, 4° C. for 5 minutes to isolate about 200 μL plasma and sent to bioanalysis. Whole spleen and left lobes of liver samples were collected at endpoint for $NAD^+$ or ADPR measurement. Liver and spleen samples were cut down to 100-400 mg/each with the wet weights recorded and placed in a tube containing 0.5 N perchloric acid (1:4 ratio, (mg/μL)) within 30 seconds. The samples were snap frozen in dry ice and stored at −80° C.

Samples were stored at −80° C. with sample preparation performed immediately after removal from the freezer due to instability of $NAD^+$ in matrixes at room temperature. Medal bead Lysing matrix was added to each tube along with a 4 fold dilution of the sample with 80:20 acetonitrile: water containing a CD38 inhibitor and $O18NAD^+$. Samples were homogenized on a MP FastPrep-24 at 6 m/see for 60 seconds. The homogenate was centrifuged at 13,000 rpm for 5 minutes with the supernatant transferred to 96 well plate and diluted 1:10 with water. Analysis of $NAD^+$ was performed by injecting 10 μL on a Zorbax Hillic Plus column on an Agilent 1290 HPLC and a Sciex API4000 Mass Spectrometer monitoring the 664-428 transition for $NAD^+$ and 668-136 for $O18NAD^+$ internal standard. The LC separation was achieved with mobile phase A—water with 0.1% ammonium acetate and mobile phase B—acetonitrile w/0.1% formic acid starting with 98% mobile phase A followed by 0.5 min gradient to 5% mobile phase. Data was reported as an area ratio of $NAD^+$ to the $O18NAD^+$ internal standard.

Figure 1B:
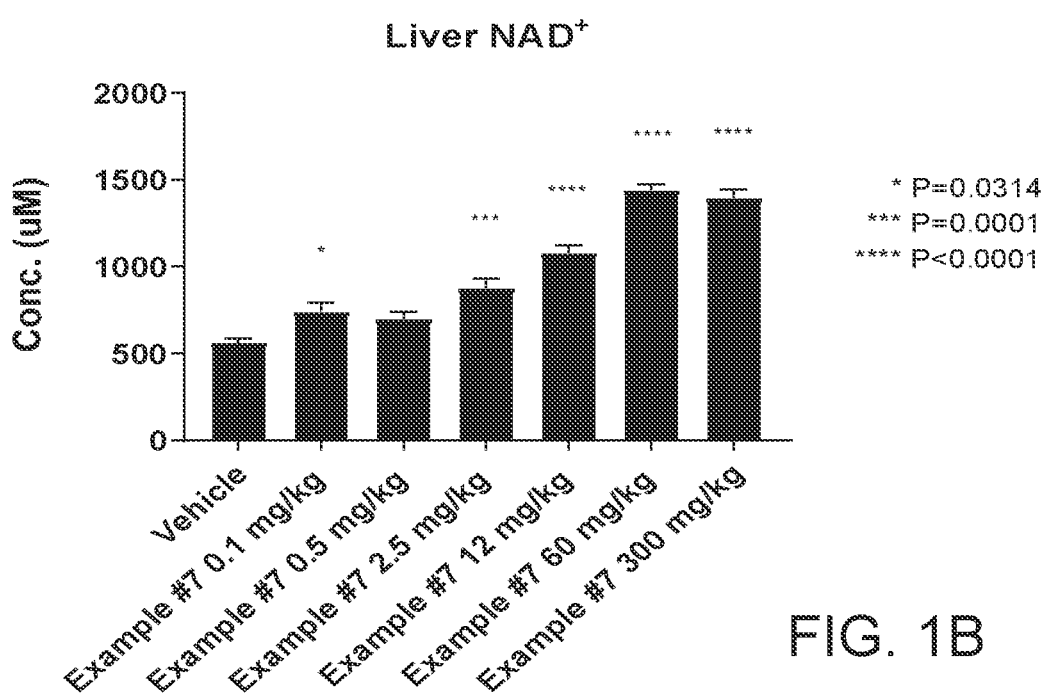
FIG. 1B is a graph of the concentration of $NAD^+$ in the liver at a single time point after dosing with various amounts of Example 7.

FIG. 1A is a graph of the concentration of $NAD^+$ in the spleen at a single time point after dosing with various amounts of Example 7. FIG. 1B is a graph of the concentration of $NAD^+$ in the liver at a single time point after dosing with various amounts of Example 7.

Figure 2A:
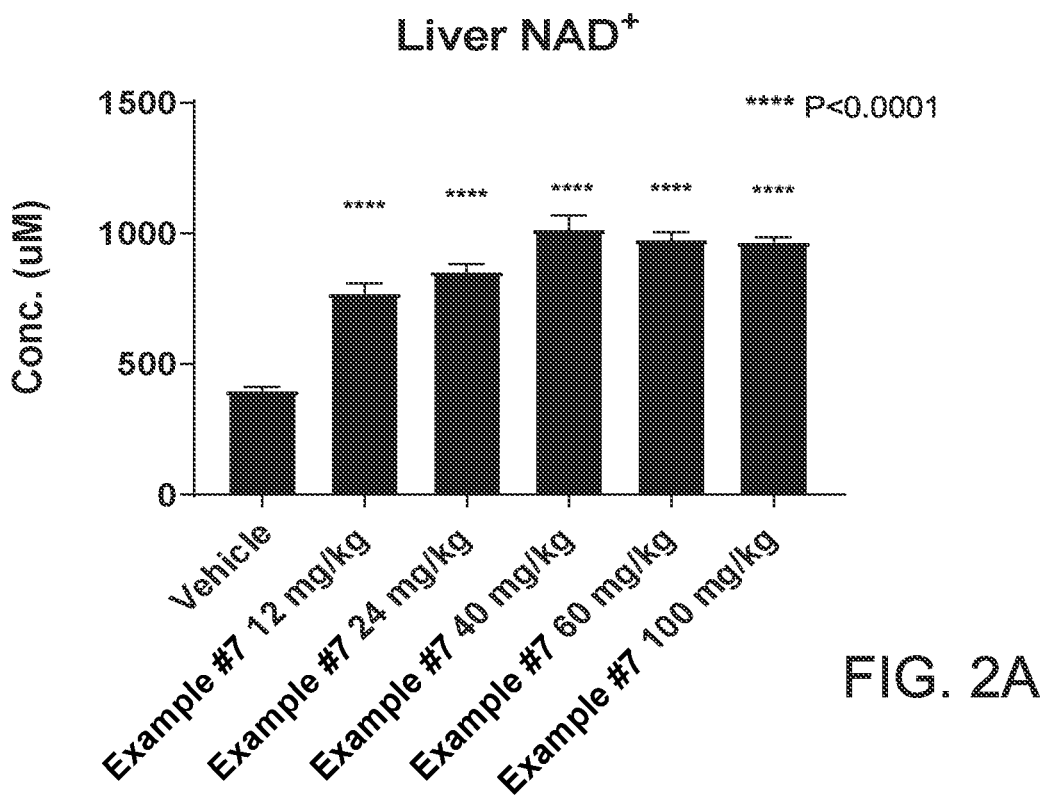
FIG. 2A is a graph of the concentration of $NAD^+$ in the liver at a single time point after dosing with various amounts of Example 7.
Figure 2B:
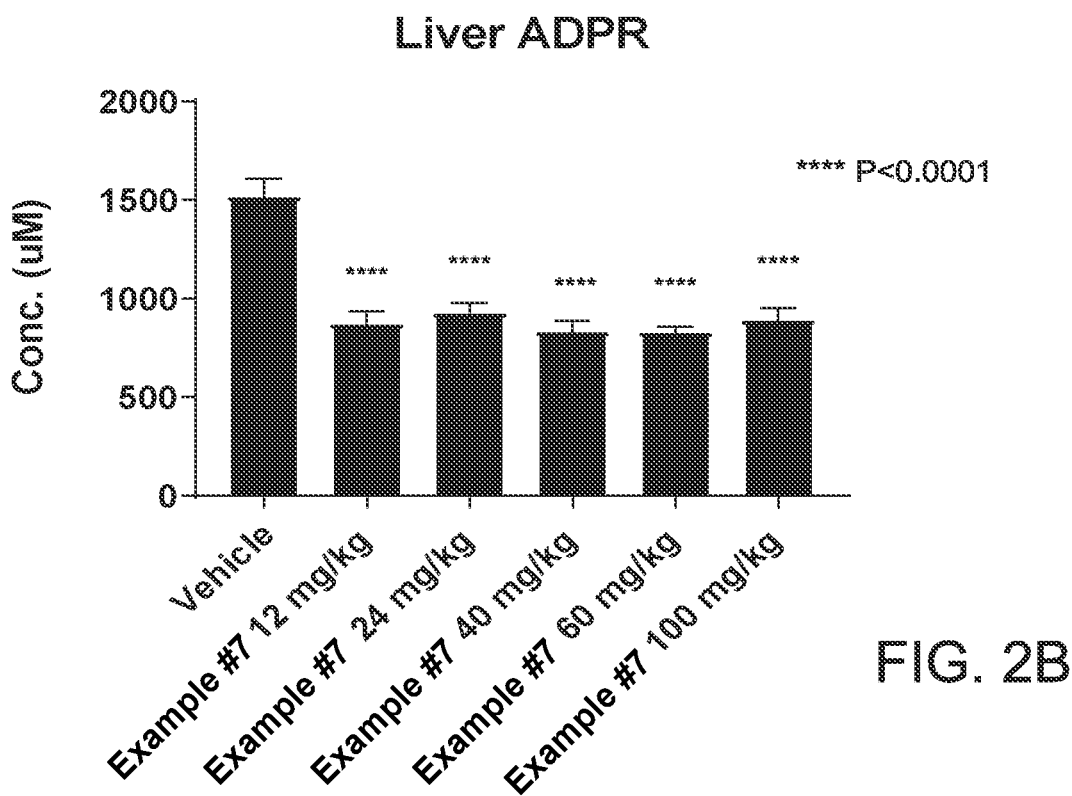
FIG. 2B is a graph of the concentration of ADPR in the liver at a single time point after dosing with various amounts of Example 7.
Figure 3A:
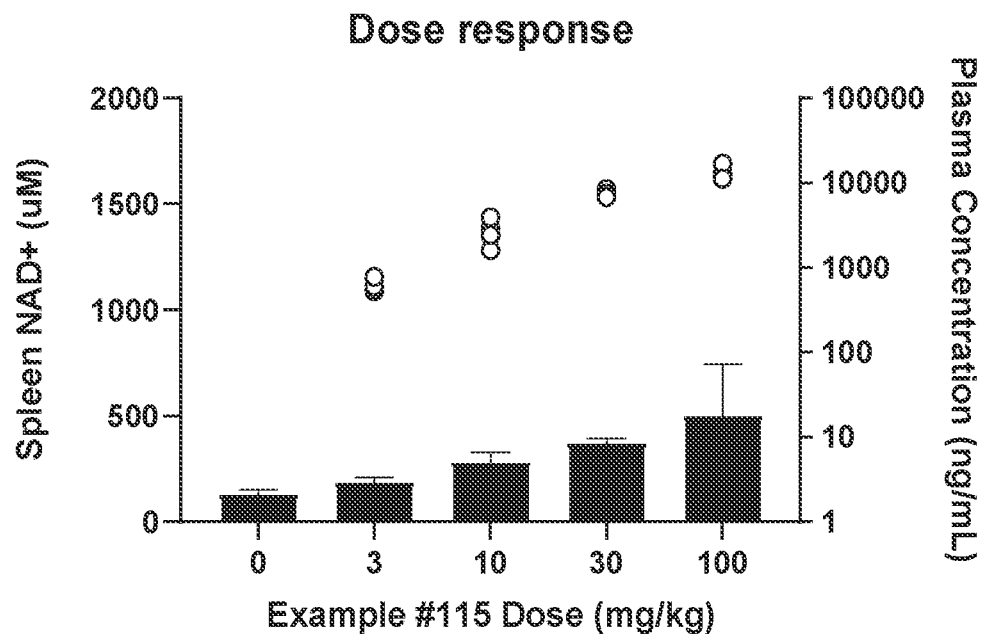
FIG. 3A is a graph of the concentration of $NAD^+$ in the spleen at a single time point after dosing with various amounts of Example 115.
Figure 3B:
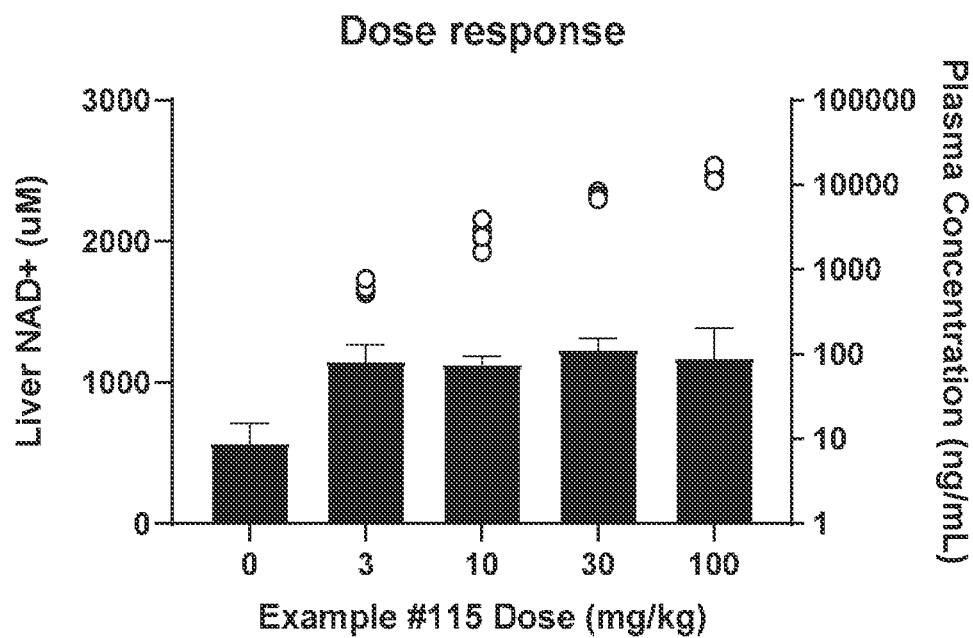
FIG. 3B is a graph of the concentration of $NAD^+$ in the liver at a single time point after dosing with various amounts of Example 115.

FIG. 2A is a graph of the concentration of $NAD^+$ in the liver at a single time point after dosing with various amounts of Example 7. FIG. 2B is a graph of the concentration of ADPR in the liver at a single time point after dosing with various amounts of Example 7 FIG. 3A is a graph of the concentration of $NAD^+$ in the spleen at a single time point after dosing with various amounts of Example 115. FIG. 3B is a graph of the concentration of $NAD^+$ in the liver at a single time point after dosing with various amounts of Example 115.

Figure 4A:
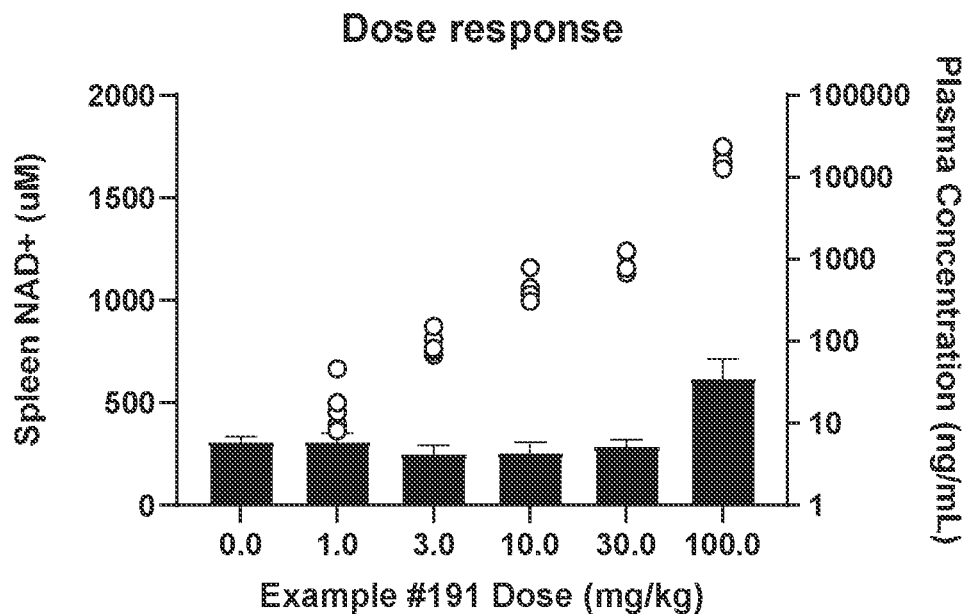
FIG. 4A is a graph of the concentration of $NAD^+$ in the spleen at a single time point after dosing with various amounts of Example 191.
Figure 4B:
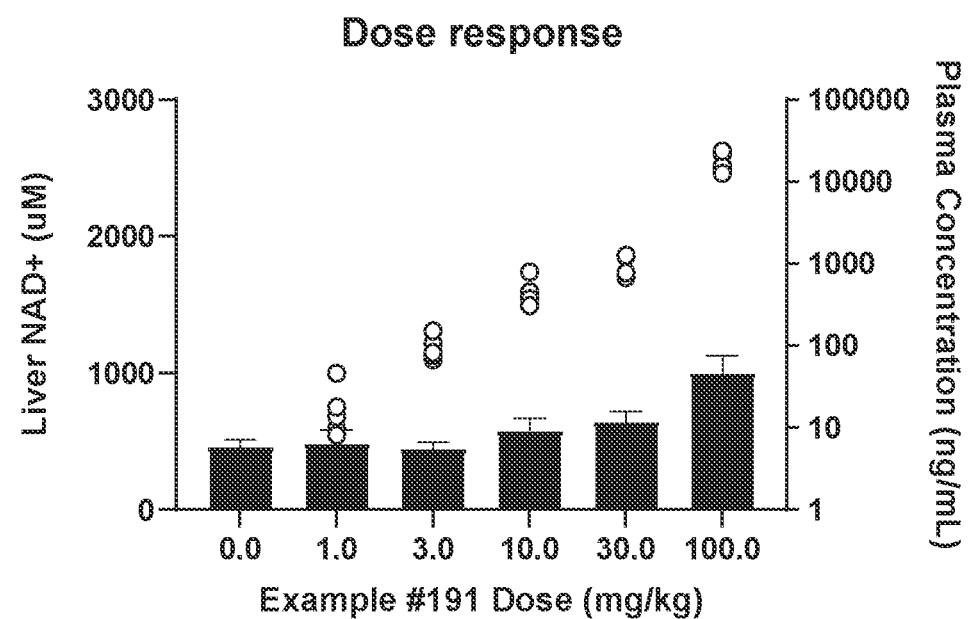
FIG. 4B is a graph of the concentration of $NAD^+$ in the liver at a single time point after dosing with various amounts of Example 191.

FIG. 4A is a graph of the concentration of $NAD^+$ in the spleen at a single time point after dosing with various amounts of Example 191. FIG. 4B is a graph of the concentration of $NAD^+$ in the liver at a single time point after dosing with various amounts of Example 191.

Figure 5A:
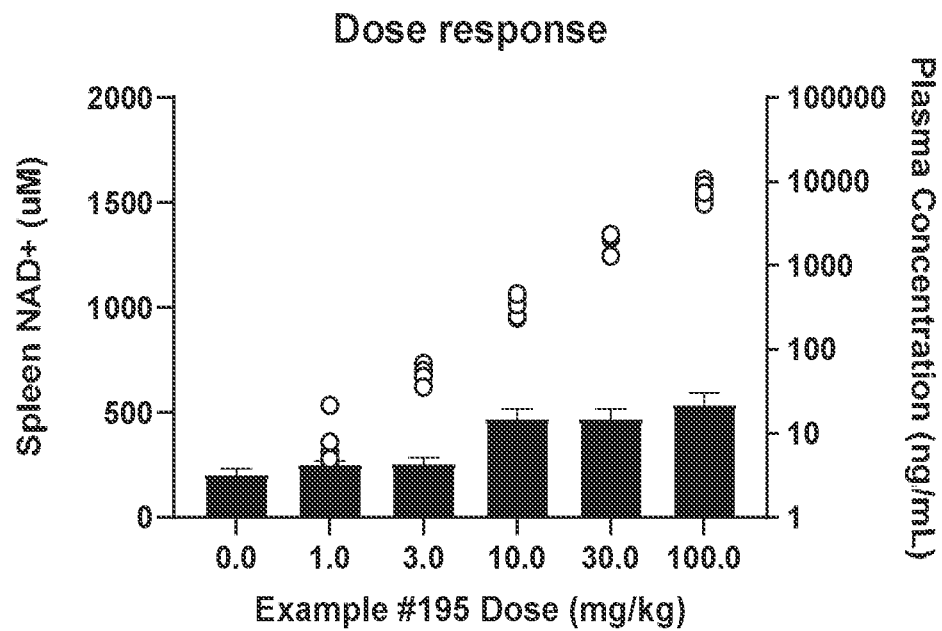
FIG. 5A is a graph of the concentration of $NAD^+$ in the spleen at a single time point after dosing with various amounts of Example 195.
Figure 5B:
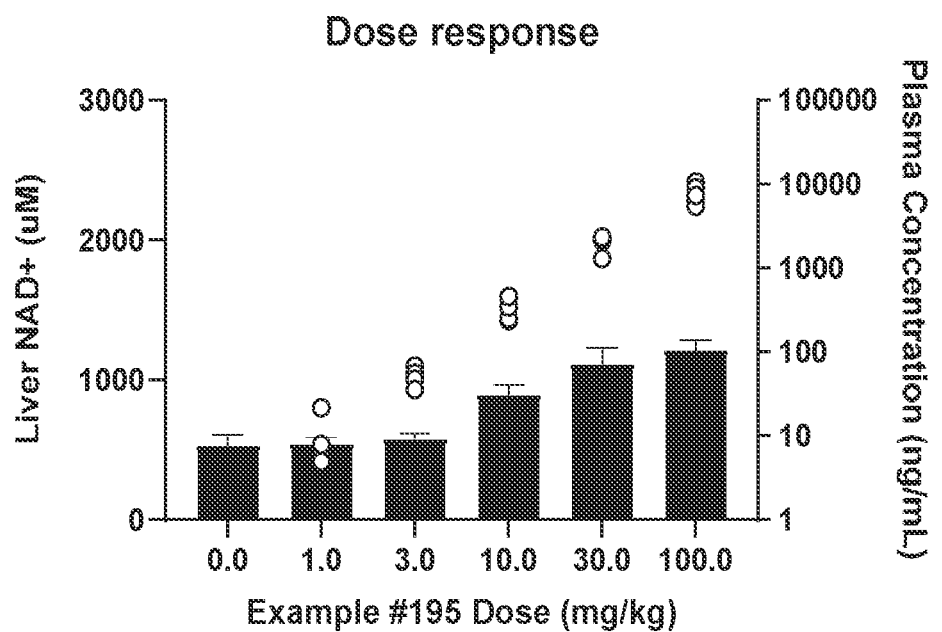
FIG. 5B is a graph of the concentration of $NAD^+$ in the liver at a single time point after dosing with various amounts of Example 195.

FIG. 5A is a graph of the concentration of $NAD^+$ in the spleen at a single time point after dosing with various amounts of Example 195. FIG. 5B is a graph of the concentration of $NAD^+$ in the liver at a single time point after dosing with various amounts of Example 195.

Figure 6A:
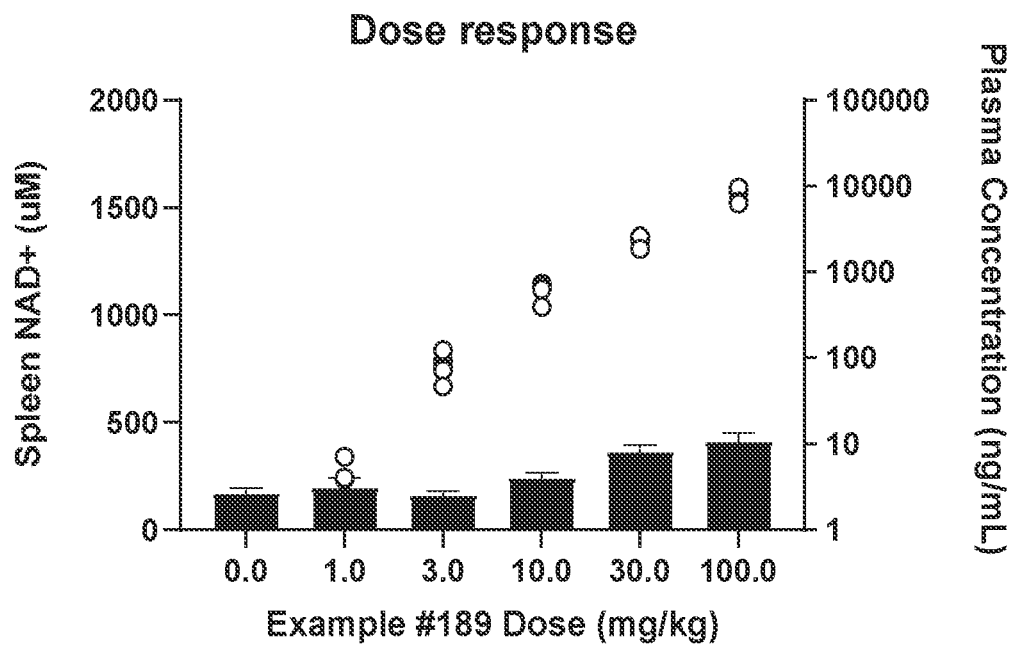
FIG. 6A is a graph of the concentration of $NAD^+$ in the spleen at a single time point after dosing with various amounts of Example 189.
Figure 6B:
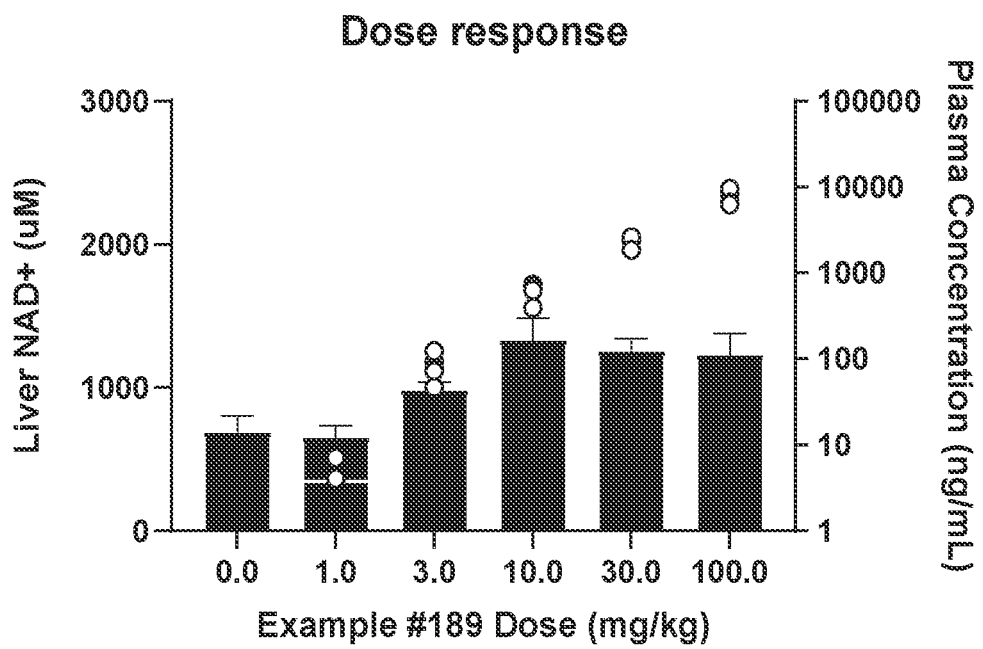
FIG. 6B is a graph of the concentration of $NAD^+$ in the liver at a single time point after dosing with various amounts of Example 189.

FIG. 6A is a graph of the concentration of $NAD^+$ in the spleen at a single time point after dosing with various amounts of Example 189. FIG. 6B is a graph of the concentration of $NAD^+$ in the liver at a single time point after dosing with various amounts of Example 189.

Figure 7A:
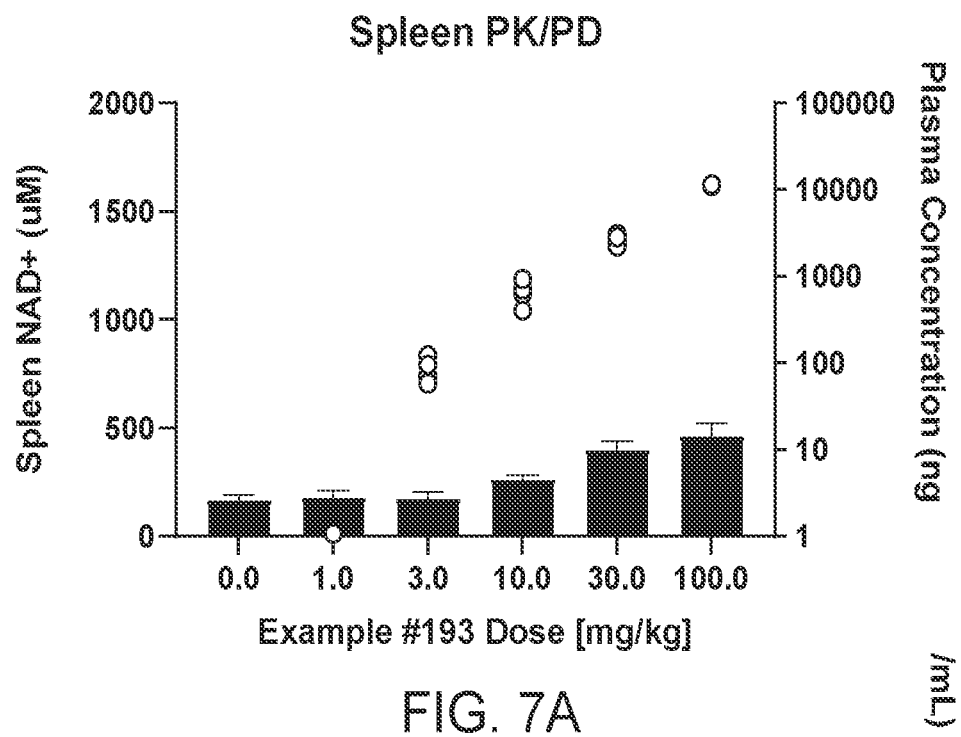
FIG. 7A is a graph of the concentration of $NAD^+$ in the spleen at a single time point after dosing with various amounts of Example 193.
Figure 7B:
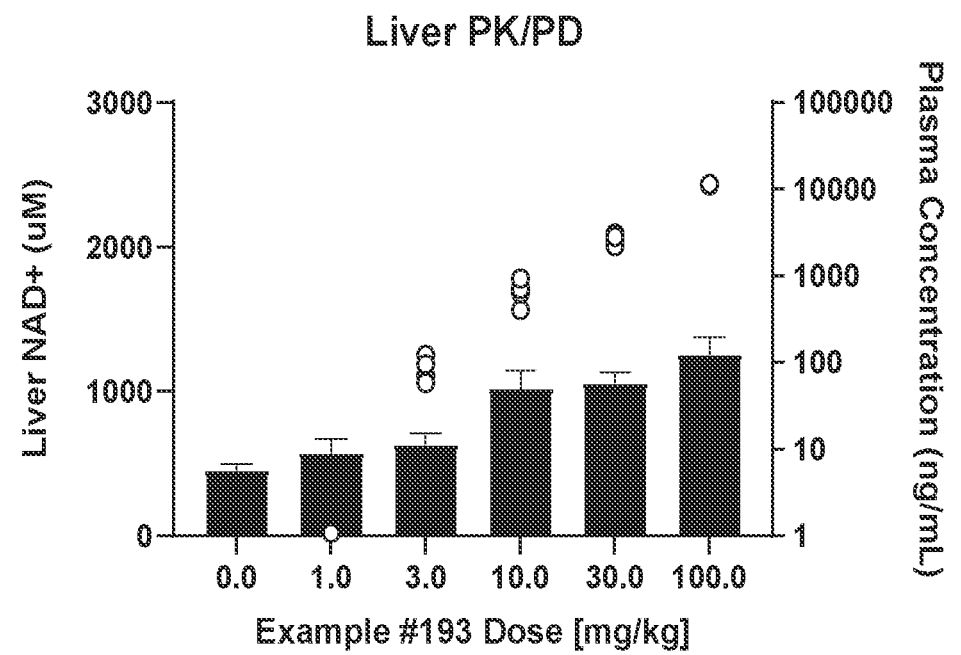
FIG. 7B is a graph of the concentration of $NAD^+$ in the liver at a single time point after dosing with various amounts of Example 193.

FIG. 7A is a graph of the concentration of $NAD^+$ in the spleen at a single time point after dosing with various amounts of Example 193. FIG. 7B is a graph of the concentration of $NAD^+$ in the liver at a single time point after dosing with various amounts of Example 193.

Figure 8A:
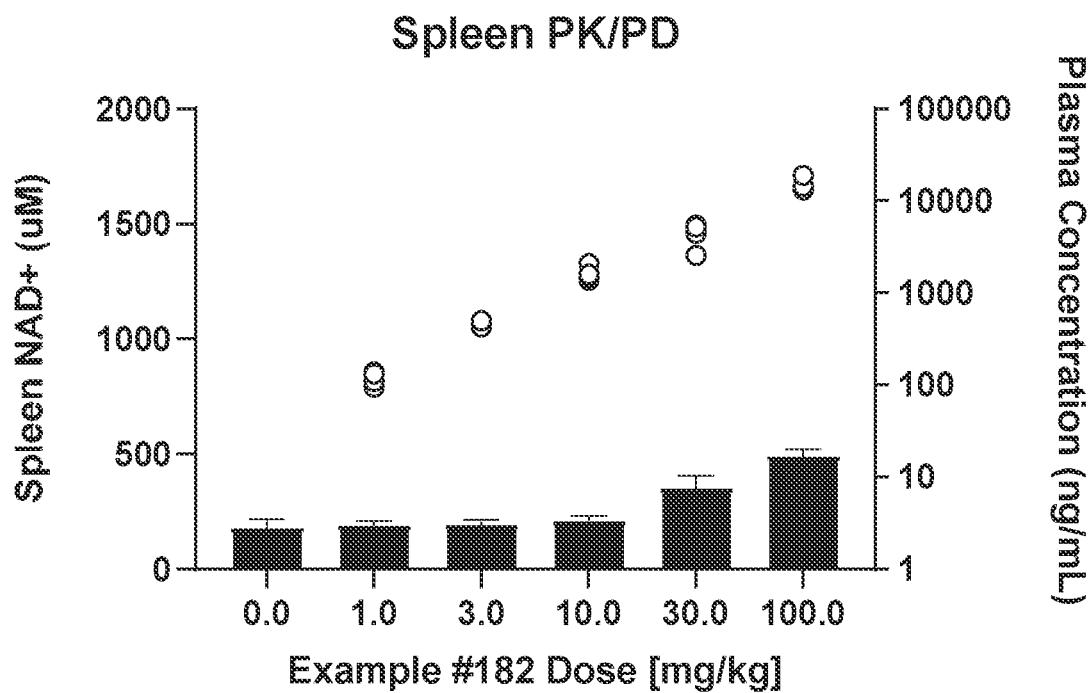
FIG. 8A is a graph of the concentration of $NAD^+$ in the spleen at a single time point after dosing with various amounts of Example 182.
Figure 8B:
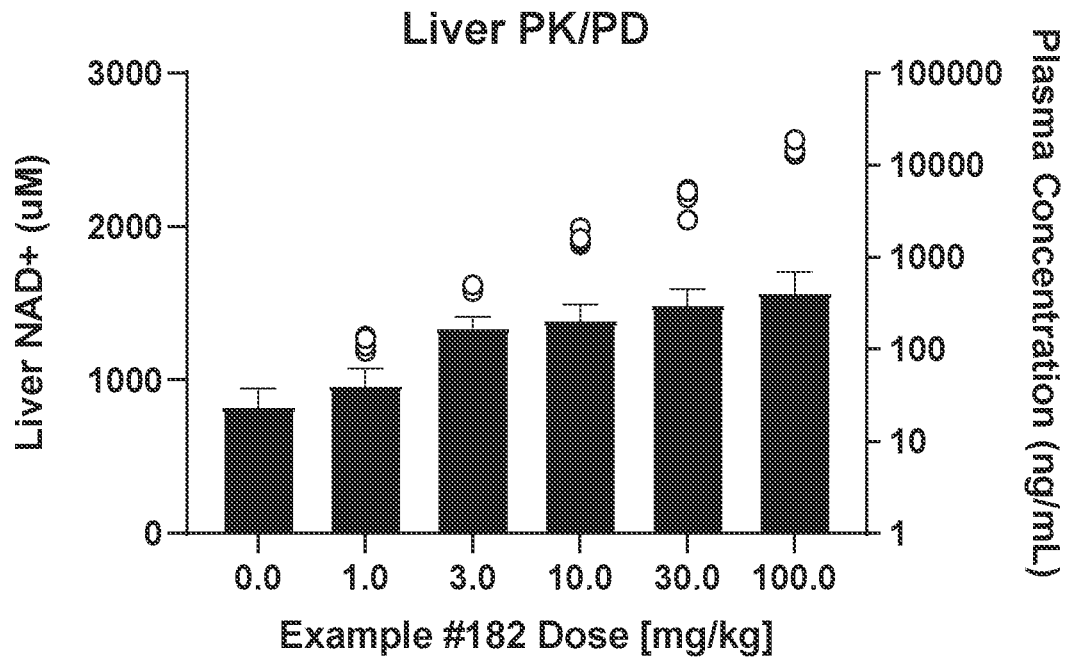
FIG. 8B is a graph of the concentration of $NAD^+$ in the liver at a single time point after dosing with various amounts of Example 182.

FIG. 8A is a graph of the concentration of $NAD^+$ in the spleen at a single time point after dosing with various amounts of Example 182. FIG. 8B is a graph of the concentration of $NAD^+$ in the liver at a single time point after dosing with various amounts of Example 182.

Example C. Efficacy Study in a B16F10 Model

B16-F10 tumor cells (ATCC, Cat #CRL-6475) were maintained in vitro as a monolayer culture in DMEM medium (Gibco, Cat #11995-040) supplemented with 10% heat inactivated fetal bovine serum (Biological Industries, Cat #04-002-1A), 100 U/mL penicillin and 100 g/mL streptomycin (Hyclone, Cat #SV30010) at 37° C. in an atmosphere of 5% $CO_2$ in air. The tumor cells were routinely subcultured twice weekly by trypsin-EDTA (Gibco, Cat #25200-072) treatment. The cells growing to a confluency around 70%-80% were harvested and counted for tumor inoculation. The cultured B16-F10 cells were harvested, re-suspended in base medium at a density of $2 \times 10^7$ cells/mL with viability>90%. 6-8 weeks of Female C57BL/6 mouse (Shanghai LingChang Biotech Co., LTD) was inoculated subcutaneously at the right flank with $1 \times 10^6$ in 0.05 mL base medium for tumor development. Tumors were calipered in two dimensions to monitor growth as the mean volume approached the desired range. Tumor volume (TV) was calculated using the formula: TV=0.5 a×b2 where a and b are the long and short diameters of the tumor.

Mice were assigned into 4 groups with 12 mice per group. The treatments were started on the second day after inoculation (defined as D1) and mice were treated with Vehicle (p.o. QD), Example 7 (300 mg/kg, p.o. QD), Vehicle+anti-mPD-L1 (10 mg/kg, i.p., QW), Example 7 (300 mg/kg, p.o. QD)+anti-mPD-L1 (10 mg/kg, i.p., QW), respectively. The tumor sizes were measured three times per week during the treatment. Survival was monitored with tumor volume exceeding 2000 mm3 as endpoint. Anti-mPD-L1 was obtained from BioXCell (catalogue number BE0101, lot number 696618M).

A 60 μL sample of whole blood was collected into a tube containing 8 μL of 15% dipotassium ethylenediaminetetraacetic acid (EDTA-2K) solution at Day 1 and endpoint. The samples were centrifuged at 4° C., 5000 rpm for 5 minutes to isolate 20 μL plasma and sent to bioanalysis. Whole spleen, left lobes of liver and tumor samples were collected at endpoint for $NAD^+$ or ADPR measurement. Tissue samples were cut down to 100-400 mg/each with the wet weights recorded and placed in a tube containing 0.5 N perchloric acid (1:4 ratio, (mg/μL)) within 1 min 30 seconds. The samples were snap frozen in dry ice and stored at −80° C. Example 7 compound levels were determined by HPLC-MS/MS analysis. A stock solution of Example 7 was prepared at 1 mg/mL in DMSO. For undiluted plasma samples, an aliquot of 10 μL sample was added to 200 μL internal standard (IS) (Diclofenac, 400 ng/mL) in acetonitrile (ACN). The mixture was vortexed for 10 minutes at 750 rpm and centrifuged at 6000 rpm for 10 minutes. An aliquot of 1.0 µL supernatant was injected for LC-MS/MS analysis. For 10-fold diluted plasma samples, an aliquot of 3 µL sample was added with 27 µL blank plasma, then added to 600 µL IS (Diclofenac, 100 ng/mL) in ACN. The mixture was vortexed for 5 minutes at 750 rpm and centrifuged at 14,000 rpm for 5 minutes. An aliquot of 1.0 µL supernatant was injected for LC-MS/MS analysis.

Figure 9A:
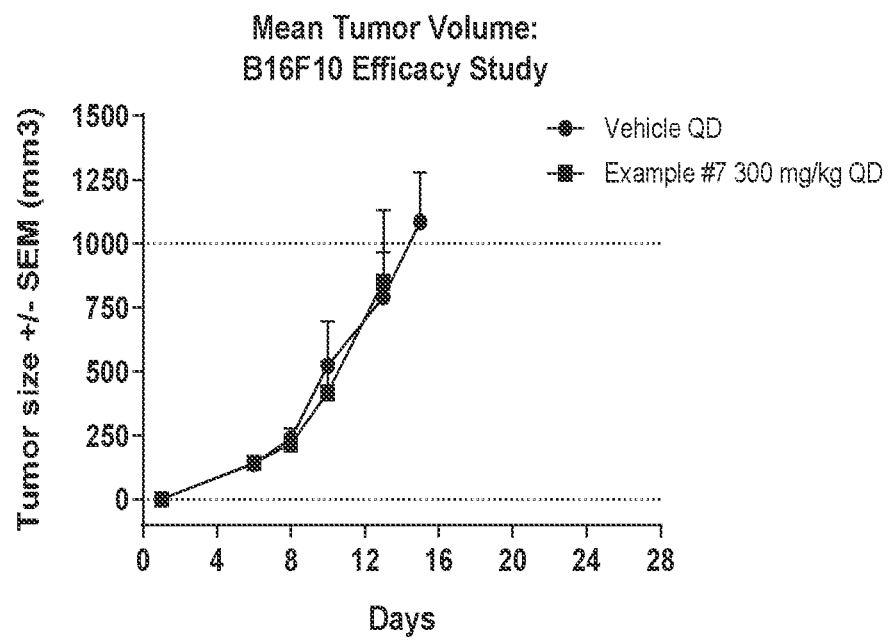
FIG. 9A is a plot of the mean B16-F10 tumor volume in mice dosed with Example 7.

FIG. 9A is a plot of the mean B16-F10 tumor volume in mice dosed with Example 7.

Figure 9B:
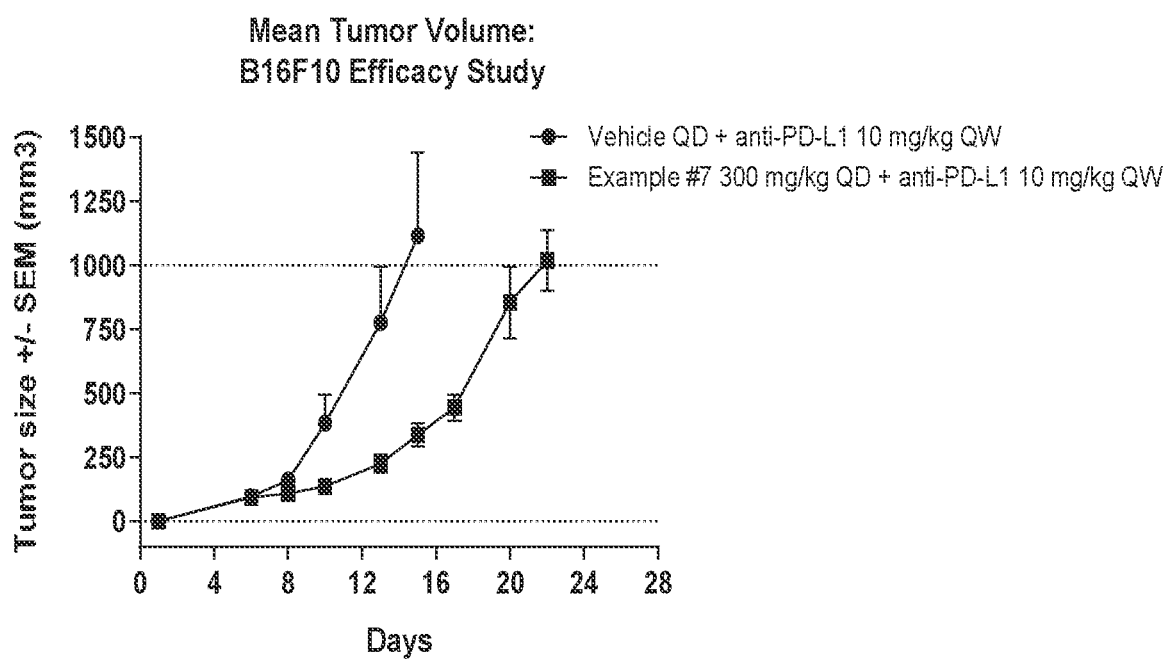
FIG. 9B is a plot of the mean B16-F10 tumor volume in mice dosed with Example 7 and anti-mPD-L1.

FIG. 9B is a plot of the mean B16-F10 tumor volume in mice dosed with Example 7 and anti-mPD-L1.

Figure 10:
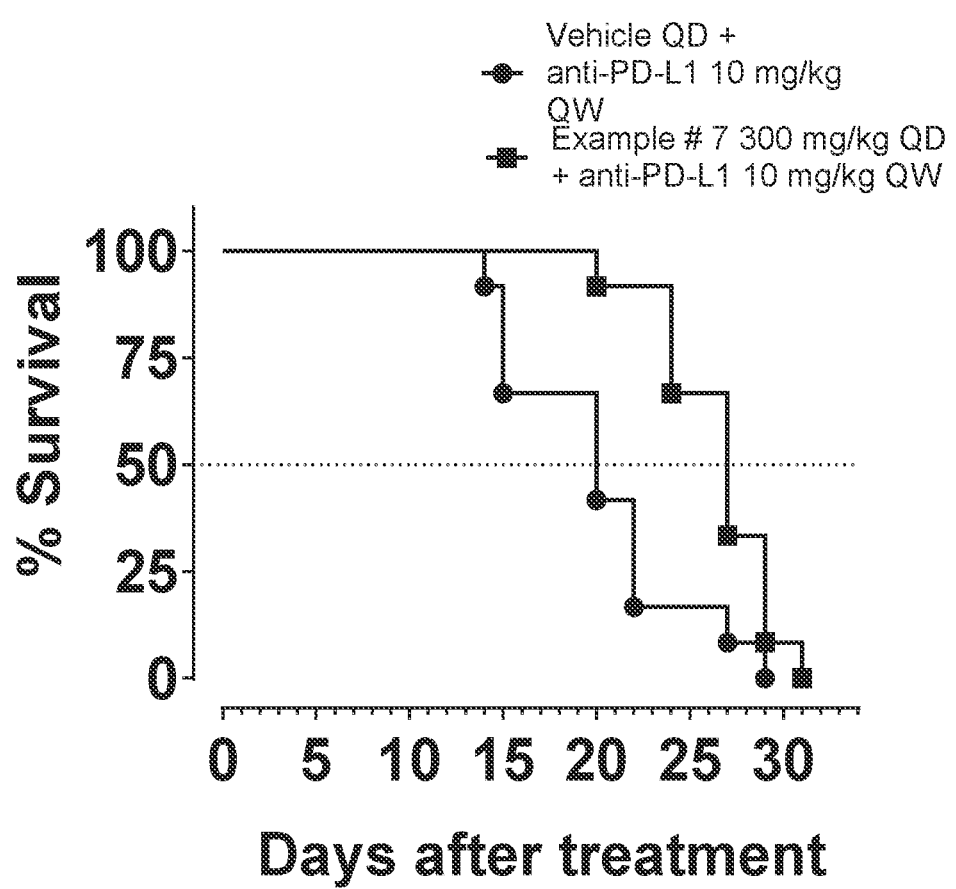
FIG. 10 is a plot of the percent survival of the B16-F10 tumor bearing mice treated with anti-mPD-L1 (10 mg/kg) and treated with Example 7 (300 mg/kg) in combination with anti-mPD-L1 (10 mg/kg).

FIG. 10 is a plot of the percent survival of the B16-F10 tumor bearing mice treated with anti-mPD-L1 (10 mg/kg) and treated with Example 7 (300 mg/kg) in combination with anti-mPD-L1 (10 mg/kg). Example 7 in combination with anti-mPD-L1 conferred significant survival benefit over vehicle or anti-mPD-L1 treated mice (p value<0.0001).

Example D. Efficacy Study in a MC-38 Model

MC-38 tumor cells (NCI) were maintained in vitro as a monolayer culture in DMEM medium (Gibco, Cat #11995-065) supplemented with 10% heat inactivated fetal bovine serum (Gibco, Cat #10099-141), 100 U/mL penicillin and 100 µg/mL streptomycin (Hyclone, Cat #SV30010) at 37° C. in an atmosphere of 5% $CO_2$ in air. The tumor cells were routinely subcultured twice weekly by trypsin-EDTA (Gibco, Cat #25200-072) treatment. The cells growing to a confluency around 70%-80% were harvested and counted for tumor inoculation. The cultured MC-38 cells were harvested, re-suspended in base medium at a density of $1\times10^7$ cells/mL with viability>90%. 6-8 weeks of Female C57BL/6 mouse (Shanghai LingChang Biotech Co., LTD) was inoculated subcutaneously at the right flank with $1\times10^6$ in 0.1 mL base medium for tumor development. Tumors were calipered in two dimensions to monitor growth as the mean volume approached the desired range. Tumor volume (TV) was calculated using the formula: TV=0.5 a×b2 where a and b are the long and short diameters of the tumor. Anti-mPD-1 from BioXCell (catalogue number BE0146, lot number 73501901) was used.

The mice were assigned into 4 groups with 12 mice per group. The treatments were started on the second day after inoculation (defined as Day 0) and mice were treated with Vehicle (0.5% HPMC+0.1% Tween 80 in pH 3.5 Citric Buffer) (0.2 mL/20 g, p.o., BID), Example 7 (60 mg/kg, p.o., BID), Vehicle+Anti-mPD-1 (0.2 mL/20 g, p.o., BID+5 mg/kg, i.p., BIW), Example 7+Anti-mPD-1 (60 mg/kg, p.o., BID+5 mg/kg, i.p., BIW), respectively. On Day 1, Day 7, Day 15 and Day 22, the mice were measured body temperature. The tumor sizes were measured three times per week during the treatment. Survival was monitored with tumor volume exceeding 2000 $mm^3$ as endpoint. The entire study was terminated on Day 28.

A 60 µL sample of whole blood was collected into a tube containing 8 µL of 15% dipotassium ethylenediaminetetraacetic acid (EDTA-2K) solution. The sample was centrifuged at 4° C., 5000 rpm for 5 minutes to isolate 20 uL plasma and sent to bioanalysis. Whole spleen, left lobes of liver and tumor samples were collected at endpoint for $NAD^+$ or ADPR measurement. Tissue samples were cut down to 100-400 mg/each with the wet weights recorded and placed in a tube containing 0.5 N perchloric acid (1:4 ratio, (mg/µL)) within 1 min 30 seconds. The samples were snap frozen in dry ice and stored at −80° C.

Example 7 compound levels were determined by HPLC-MS/MS analysis. A stock solution of Example 7 was prepared at 3 mg/mL in DMSO. For undiluted plasma samples, an aliquot of 10 µL sample was added to 200 µL internal standard (IS) (Diclofenac, 400 ng/mL) in acetonitrile (ACN). For diluted samples, an aliquot of 1 µL sample was added with 9 µL blank plasma and the dilution factor was 10. The mixture was vortexed for 10 minutes and centrifuged at 5800 rpm for 10 minutes. An aliquot of 0.5 µL supernatant was injected for LC-MS/MS analysis.

Figure 11A:
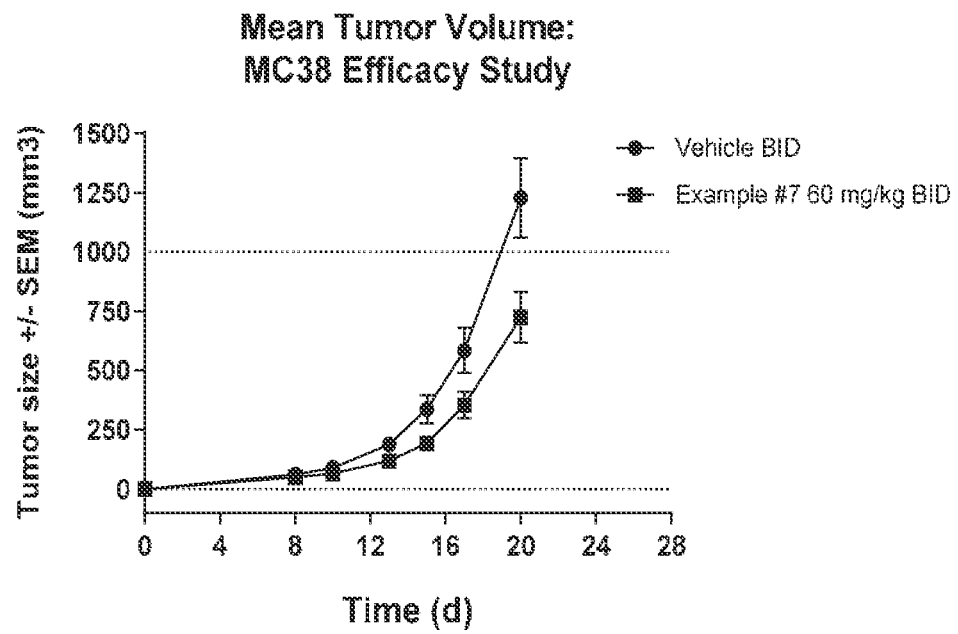
FIG. 11A is a plot of the mean MC-38 tumor volume in mice dosed with Example 7.

FIG. 11A is a plot of the mean MC-38 tumor volume in mice dosed with Example 7.

Figure 11B:
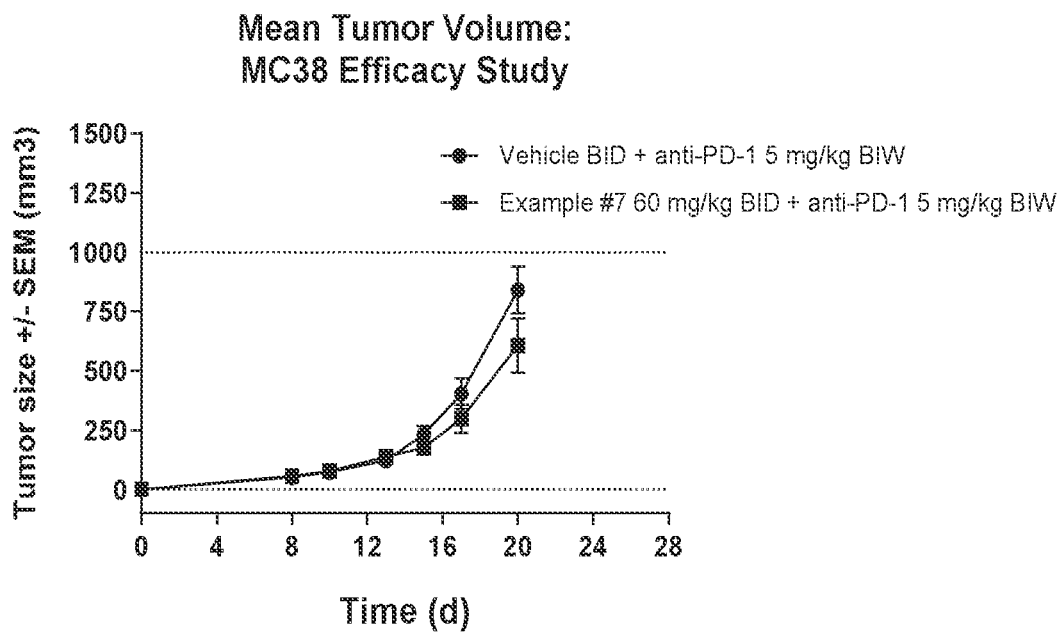
FIG. 11B is a plot of the mean MC-38 tumor volume in mice dosed with Example 7 and anti-mPD-L1.

FIG. 11B is a plot of the mean MC-38 tumor volume in mice dosed with Example 7 and anti-mPD-L1.

Figure 12:
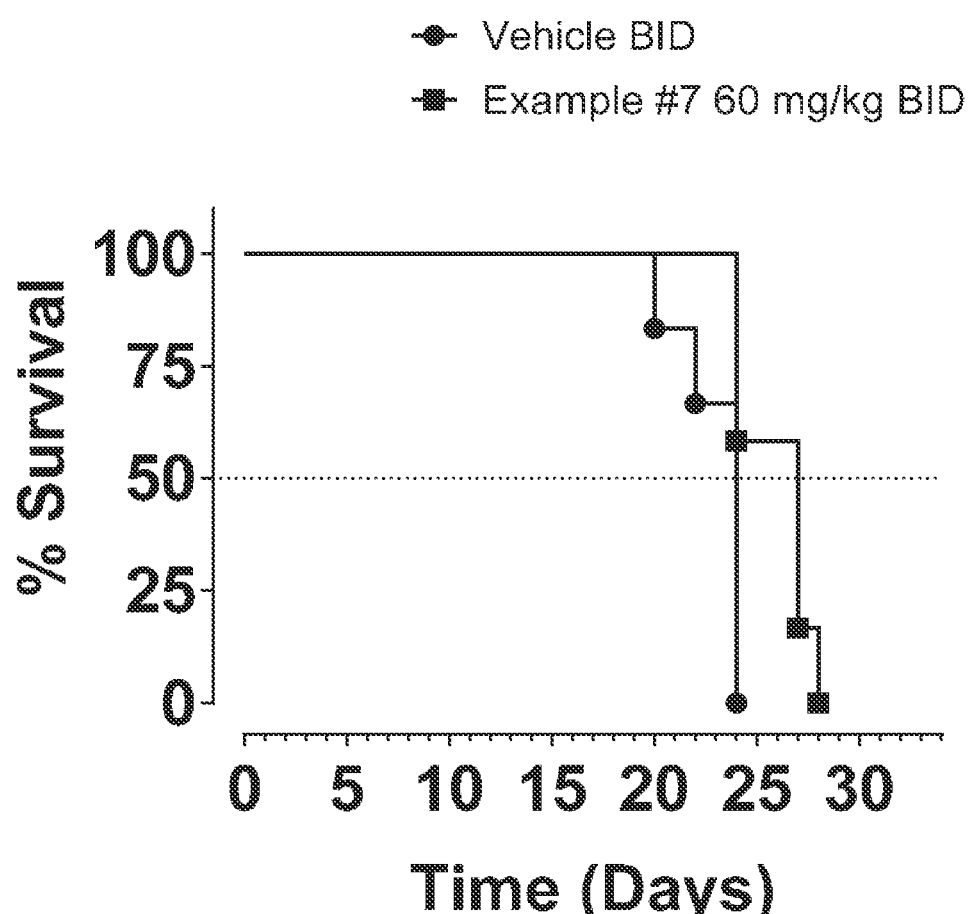
FIG. 12 is a plot of the percent survival of the MC-38 tumor bearing mice treated with Example 7 (60 mg/kg).

FIG. 12 is a plot of the percent survival of the MC-38 tumor bearing mice treated with Example 7 (60 mg/kg).

Figure 13:
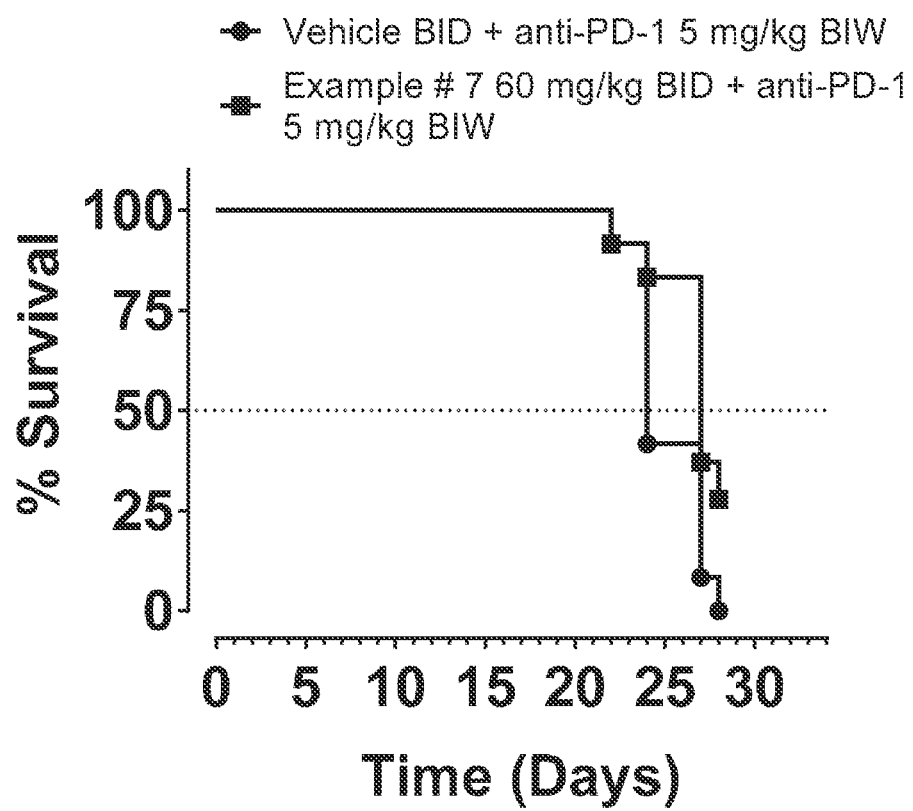
FIG. 13 is a plot of the percent survival of the MC-38 tumor bearing mice treated with anti-mPD-L1 (5 mg/kg) and treated with Example 7 (60 mg/kg) in combination with anti-mPD-L1 (5 mg/kg).

FIG. 13 is a plot of the percent survival of the MC-38 tumor bearing mice treated with anti-mPD-L1 (5 mg/kg) and treated with Example 7 (60 mg/kg) in combination with anti-mPD-L1 (5 mg/kg).

Example E. Efficacy Study in a Cloudman S91 Model

Cloudman S91 (ATCC, CCL-53.1™) cells were maintained in vitro as a monolayer culture in F12K medium (Gibco, #21127-002) supplemented with 2.5% heat inactivated fetal bovine serum (Gibco, Cat #10099-141) and 15% horse serum (Biological Industries, #04-004-1A), 100 U/mL penicillin and 100 µg/mL streptomycin (Hyclone, Cat #SV30010) at 37° C. in an atmosphere of 5% $CO_2$ in air. The tumor cells were routinely subcultured twice weekly by trypsin-EDTA (Gibco, Cat #25200-072) treatment. The cells growing to a confluency around 70%-80% were harvested and counted for tumor inoculation. The cultured Cloudman S91 cells were harvested, re-suspended in base medium at a density of $5\times10^7$ cells/mL with viability>90%. 8-10 weeks of female DBA/2 mice (Vital River) were inoculated subcutaneously at the right flank with $5\times10^6$ in 0.1 mL base medium for tumor development. Tumors were calipered in two dimensions to monitor growth as the mean volume approached the desired range. Tumor volume (TV) was calculated using the formula: TV=0.5 a×$b^2$ where a and b are the long and short diameters of the tumor. Anti-mPD-1 from BioXCell (catalogue number BE0146, lot number 73501901) was used.

The mice were assigned into 4 groups with 12 mice per group. The treatments were started on the second day after inoculation (defined as Day 1) and mice were treated with Vehicle (0.5% HPMC+0.1% Tween 80 in pH 3.5 Citric Buffer) (0.2 mL/20 g, p.o., BID), Example 7 (60 mg/kg, p.o., BID), Vehicle+Anti-mPD-1 (0.2 mL/20 g, p.o., BID+5 mg/kg, i.p., BIW), Example 7+Anti-mPD-1 (60 mg/kg, p.o., BID+5 mg/kg, i.p., BIW), respectively. On Day 1, Day 8, Day 15 and Day 22, the mice were measured body temperature. The tumor sizes were measured three times per week during the treatment. Survival was monitored with tumor volume exceeding 2000 $mm^3$ as endpoint. The entire study was terminated on Day 29. A 60 µL sample of whole blood was collected into a tube containing 5 µL of 15% dipotassium ethylenediaminetetraacetic acid (EDTA-2K) solution. The sample was centrifuged at 4° C., 6000 rpm for 5 minutes to isolate 20 µL plasma and sent to bioanalysis. Whole spleens, left lobes of liver and tumor samples were collected at endpoint for $NAD^+$ or ADPR measurement. Tissue samples were cut down to 100-400 mg/each with the wet weights recorded and placed in a tube containing 0.5 N perchloric acid (1:4 ratio, (mg/μL)) within 1 min 30 seconds. The samples were snap frozen in dry ice and stored at −80° C.

Example 7 compound levels were determined by HPLC-MS/MS analysis. A stock solution of Example 7 was prepared at 1 mg/mL in DMSO. For undiluted plasma samples, an aliquot of 10 μL sample was added to 200 μL internal standard (IS) (Diclofenac, 400 ng/mL) in acetonitrile (ACN). For diluted samples, an aliquot of 1 μL sample was diluted with 9 μL blank matrix and the dilution factor was 10. The mixture was vortexed for 10 minutes and centrifuged at 5800 rpm for 10 minutes. An aliquot of 0.5 μL supernatant was injected for LC-MS/MS analysis.

Figure 14A:
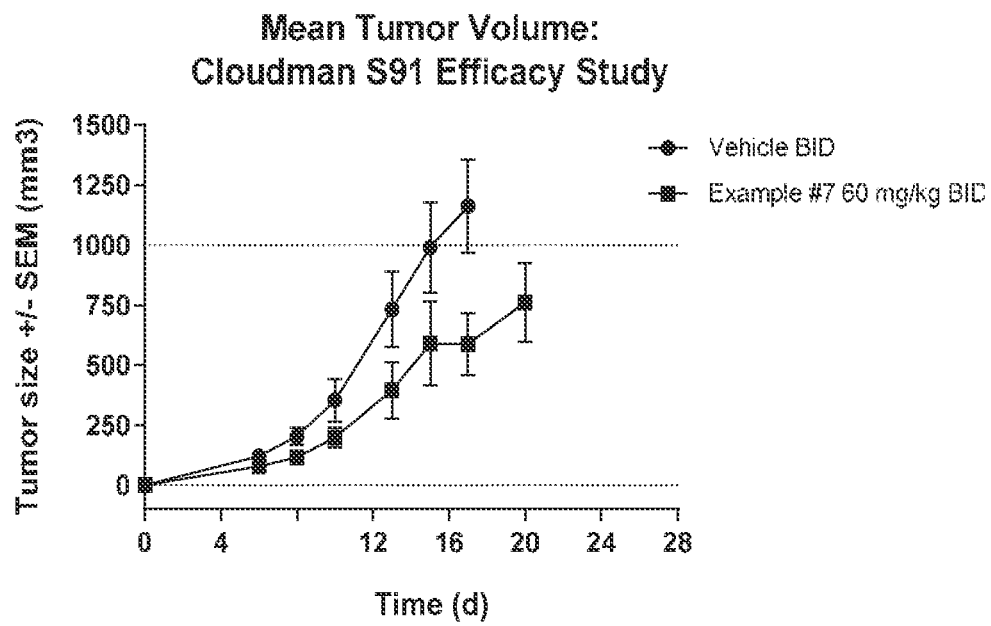
FIG. 14A is a plot of the mean Cloudman S91 tumor volume in mice dosed with Example 7.

FIG. 14A is a plot of the mean Cloudman S91 tumor volume in mice dosed with Example 7.

Figure 14B:
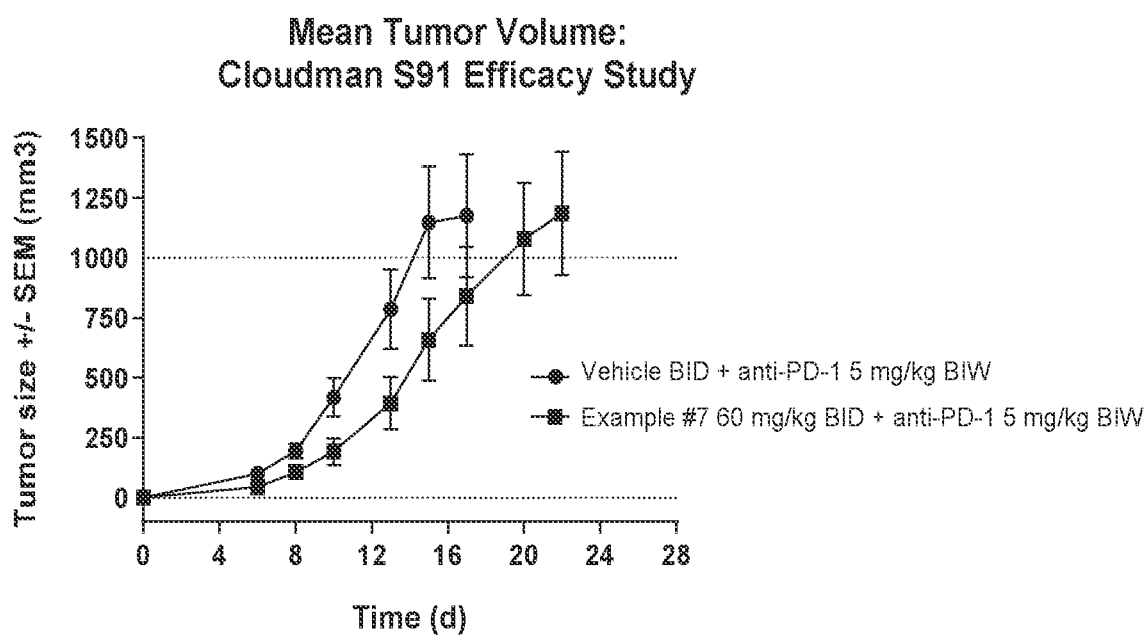
FIG. 14B is a plot of the mean Cloudman S91 tumor volume in mice dosed with Example 7 and anti-mPD-L1.

FIG. 14B is a plot of the mean Cloudman S91 tumor volume in mice dosed with Example 7 and anti-mPD-L1.

Figure 15:
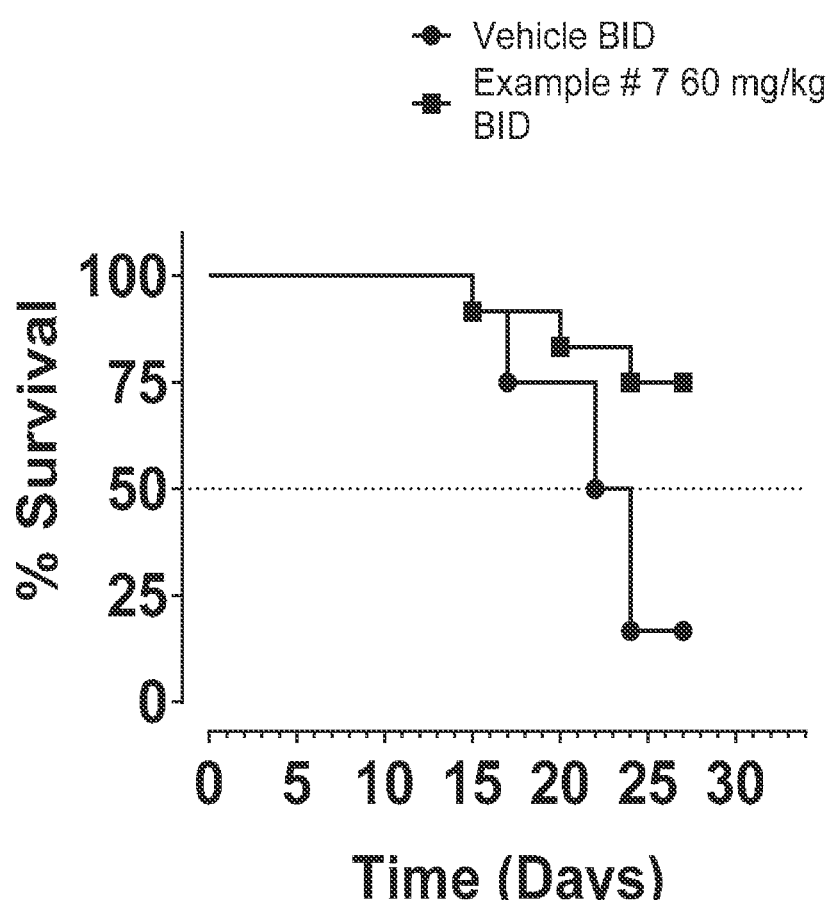
FIG. 15 is a plot of the percent survival of the Cloudman S91 tumor bearing mice treated with Example 7 (60 mg/kg).

FIG. 15 is a plot of the percent survival of the Cloudman S91 tumor bearing mice treated with Example 7 (60 mg/kg).

Figure 16:
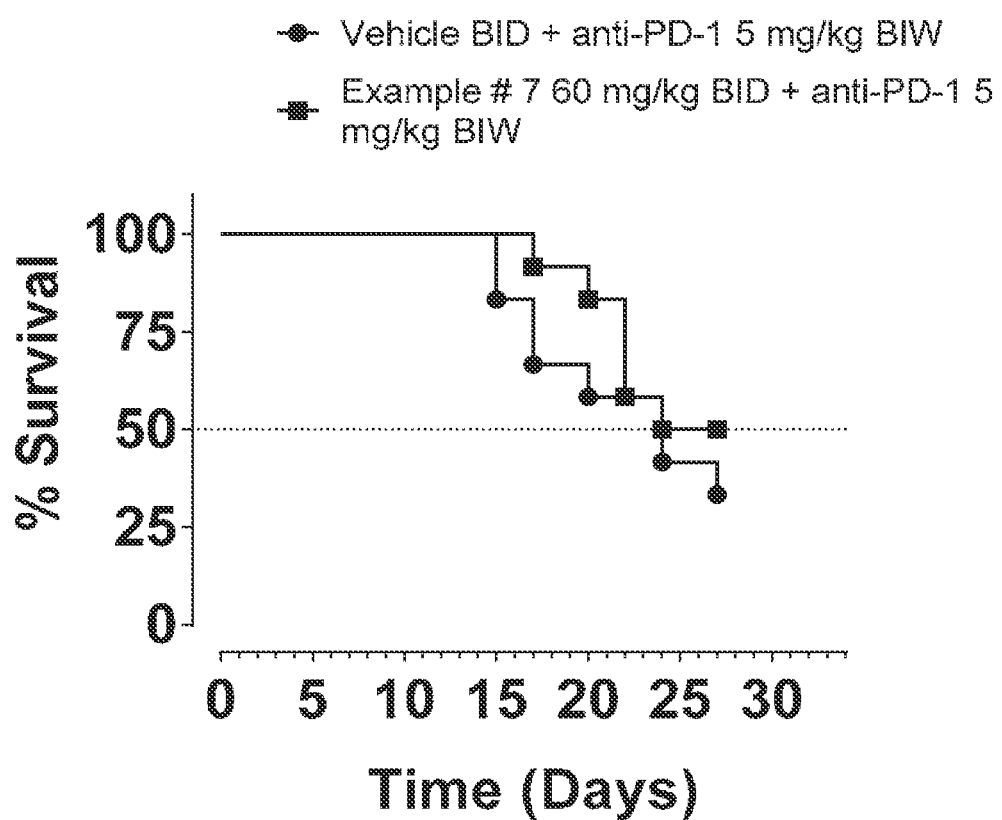
FIG. 16 is a plot of the percent survival of the Cloudman S91 tumor bearing mice treated with anti-mPD-L1 (5 mg/kg) and treated with Example 7 (60 mg/kg) in combination with anti-mPD-L1 (5 mg/kg).

FIG. 16 is a plot of the percent survival of the Cloudman S91 tumor bearing mice treated with anti-mPD-L1 (5 mg/kg) and treated with Example 7 (60 mg/kg) in combination with anti-mPD-L1 (5 mg/kg).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound of Formula I:

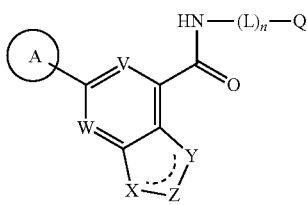

or a pharmaceutically acceptable salt thereof, wherein:

V is N or $CR^V$, wherein $R^V$ is H, halo, or $C_{1-4}$ alkyl;
W is N or $CR^W$, wherein $R^W$ is H, halo, or $C_{1-4}$ alkyl;
the moiety represented by:

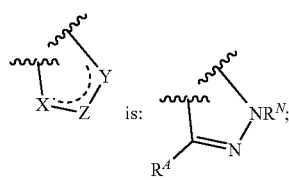

is:

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and $C_{1-4}$ alkyl;

$R^N$ is selected from H, $C_{1-4}$ alkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^N$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$, $R^A$ is selected from H, halo, $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^A$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NRCS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$, L is a $C_{1-4}$ alkylene linker;

n is 0 or 1;

Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, and $C_{2-6}$ alkynyl are optionally substituted by 1, 2, or 3 substituents independently selected from $Cy^1$, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

wherein Q is other than H when n is 0;

each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$, each Cy$^1$ is independently selected from C$_{6-10}$ aryl, C$_{3-7}$ cycloalkyl, 5-10 membered heteroaryl, and 4-10 membered heterocycloalkyl, each optionally substituted by 1, 2, 3, or 4 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$ NR$^{c2}$R$^{d2}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, and R$^{d2}$ is optionally substituted with 1, 2, 3, 4, or 5 substituents independently selected from Cy$^2$, Cy$^2$-C$_{1-4}$ alkyl, halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^c$ and R$^d$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^{c1}$ and R$^{d1}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

or R$^{c2}$ and R$^{d2}$ together with the N atom to which they are attached form a 4-7 membered heterocycloalkyl group optionally substituted with 1, 2, or 3 substituents independently selected from halo, C$_{1-4}$ alkyl, C$_{1-4}$ haloalkyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$;

each Cy$^2$ is C$_{6-10}$ aryl, C$_{3-7}$ cycloalkyl, 5-10 membered heteroaryl, or 4-10 membered heterocycloalkyl, each optionally substituted by 1, 2, 3, or 4 substituents independently selected from halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)NR$^{c3}$R$^{d3}$, NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$, each R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl are each optionally substituted with 1, 2, or 3 substituents independently selected from OH, CN, amino, halo, C$_{1-6}$ alkyl, C$_{1-6}$ alkylamino, di(C$_{1-6}$ alkyl)amino, C$_{1-6}$ alkoxy, C$_{1-6}$ haloalkyl, and C$_{1-6}$ haloalkoxy;

each R$^e$, R$^{e1}$, R$^{e2}$, and R$^{e3}$ is independently selected from H, C$_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

2. The compound of claim 1, or a pharmaceutically acceptable salt thereof, wherein:

V is N or CR$^V$, wherein R$^V$ is H, halo, or C$_{1-4}$ alkyl;

W is N or CR$^W$, wherein R$^W$ is H, halo, or C$_{1-4}$ alkyl;

the moiety represented by:

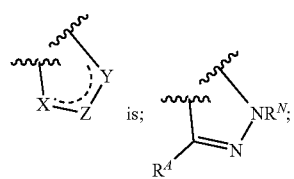

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and C$_{1-4}$ alkyl;

each R$^N$ is independently selected from H, C$_{1-4}$ alkyl, C$_{6-10}$ aryl, C$_{3-7}$ cycloalkyl, 5-10 membered heteroaryl, or 4-10 membered heterocycloalkyl, wherein said C$_{1-4}$ alkyl, C$_{2-6}$ alkenyl, C$_{2-6}$ alkynyl, C$_{1-6}$ haloalkyl, C$_{6-10}$ aryl, C$_{3-7}$ cycloalkyl, 5-10 membered heteroaryl, and 4-10 membered heterocycloalkyl of R$^N$ are each optionally substituted with 1, 2, 3, 4, or 5 substituents independently selected from Cy, Cy-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^a$, SR$^a$, C(O)R$^b$, C(O)NR$^c$R$^d$, C(O)OR$^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

$R^A$ is selected from H, halo, $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^A$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NRCS(O)R^b$, $NRCS(O)_2R^b$, $NR^cS(O)_2NR^cR^d$, $S(O)R^b$, $S(O)NR^cR^d$, $S(O)_2R^b$, and $S(O)_2NR^cR^d$;

L is a $C_{1-4}$ alkylene linker;

n is 0 or 1;

Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$;

wherein Q is other than H when n is 0;

each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NRCS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{c3})NR^{c3}R^{d3}$, $NR^{c3}C(=NR^{c3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{c3})NR^{c3}R^{d3}$, $NR^{c3}C(=NR^{c3})NR^{c3}R^{d3}$, $S(O)R^{b3}$, $S(O)NR^{c3}R^{d3}$, $S(O)_2R^{b3}$, $NR^{c3}S(O)_2R^{b3}$ $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{c3})NR^{c3}R^{d3}$, $NR^{c3}C(=NR^{c3})NR^{c3}R^{d3}$, $S(O)R^{b3}$, $S(O)NR^{c3}R^{d3}$, $S(O)_2R^{b3}$, $NR^{c3}S(O)_2R^{b3}$ $NR^{c3}S(O)_2NR^{c3}R^{d3}$, and $S(O)_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkylamino, di($C_{1-6}$ alkyl)amino, $C_{1-6}$ alkoxy, $C_{1-6}$ haloalkyl, and $C_{1-6}$ haloalkoxy;

each $R^e$, $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

3. The compound of claim 1, or a pharmaceutically acceptable salt thereof, wherein:

V is N or $CR^V$, wherein $R^V$ is H, halo, or $C_{1-4}$ alkyl;
W is N or $CR^W$, wherein $R^W$ is H, halo, or $C_{1-4}$ alkyl;
the moiety represented by:

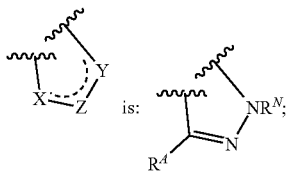

Ring A is a 5-membered heteroaryl group having 1, 2 or 3 ring-forming heteroatoms selected from N, O, and S, wherein the 5-membered heteroaryl group of Ring A is optionally substituted by 1, 2, or 3 substituents independently selected from halo and $C_{1-4}$ alkyl;

each $R^N$ is independently selected from H, $C_{1-4}$ alkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^N$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

each $R^A$ is selected from H, halo, $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, or 4-10 membered heterocycloalkyl, wherein said $C_{1-4}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, and 4-10 membered heterocycloalkyl of $R^A$ are each optionally substituted with 1, 2, 3, 4, or 5 substituents independently selected from Cy, Cy-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NRCS(O)_2R^b$, $NR^cS(O)NR^cR^d$, $S(O)R^b$, $S(O)NR^cR^d$, $S(O)_2R^b$, and $S(O)_2NR^cR^d$;

L is a $C_{1-4}$ alkylene linker;
n is 0 or 1;
Q is H, $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{2-10}$ alkenyl, $C_{2-10}$ alkynyl, $C_{1-10}$ haloalkyl, $C_{6-10}$ aryl, $C_{3-14}$ cycloalkyl, 5-14 membered heteroaryl, and 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$ $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2$ $NR^{c1}R^{d1}$;

wherein Q is other than H when n is 0;
each Cy is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $C(=NR^e)NR^cR^d$, $NR^cC(=NR^e)NR^cR^d$, $NR^cR^d$, $NR^cC(O)R^b$, $NR^cC(O)OR^a$, $NR^cC(O)NR^cR^d$, $NR^cS(O)R^b$, $NRCS(O)_2R^b$, $NRCS(O)_2NR^cR^d$, $S(O)R^b$, $S(O)NR^cR^d$, $S(O)_2R^b$, and $S(O)_2NR^cR^d$;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR 2R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^a$, $R^b$, $R^c$, $R^d$, $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ $NR^{c3}S(O)_2NR^{c3}R^{d3}$, and $S(O)_2NR^{c3}R^{d3}$;

or $R^c$ and $R^d$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

4. The compound of claim 1, or a pharmaceutically acceptable salt thereof, wherein $R^A$ is selected from H and $C_{1-4}$ alkyl.

5. The compound of claim 1, or a pharmaceutically acceptable salt thereof, wherein $R^A$ is H.

6. The compound of claim 1, or a pharmaceutically acceptable salt thereof, wherein V is N.

7. The compound of claim 1, or a pharmaceutically acceptable salt thereof, wherein V is $CR^V$.

8. The compound of claim 1, or a pharmaceutically acceptable salt thereof, wherein W is N.

9. The compound of claim 1, or a pharmaceutically acceptable salt thereof, wherein W is $CR^W$.

10. The compound of claim 1, or a pharmaceutically acceptable salt thereof, wherein Ring A is selected from:

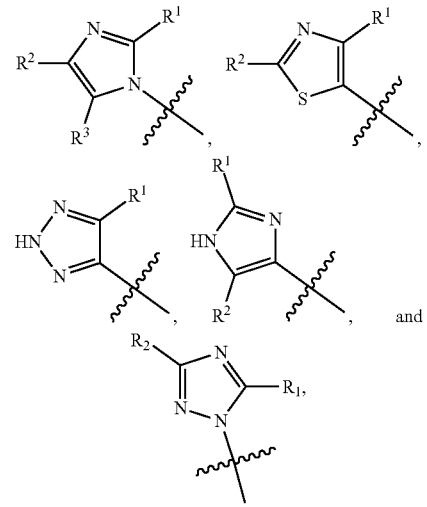

wherein $R^1$, $R^2$, and $R^3$ are each independently selected from H and $C_{1-4}$ alkyl.

11. The compound of claim 1, or a pharmaceutically acceptable salt thereof, wherein Q is $C_{1-10}$ alkyl, $C_{1-10}$ haloalkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl and $C_{2-6}$ alkynyl are optionally substituted by 1, 2, or 3 substituents independently selected from OH, CN, $C_{1-6}$ alkoxy, and $NR^{c1}C(O)R^{b1}$.

12. The compound of claim 1, or a pharmaceutically acceptable salt thereof, wherein Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$ $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

13. The compound of claim 1, or a pharmaceutically acceptable salt thereof, wherein Q is $C_{1-10}$ alkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{e1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

14. The compound of claim 1, or a pharmaceutically acceptable salt thereof, wherein Q is $C_{1-4}$ alkyl.

15. The compound of claim 1, or a pharmaceutically acceptable salt thereof, wherein Q is selected from $C_{1-4}$ alkyl and $C_{1-4}$ haloalkyl.

16. The compound of claim 1, or a pharmaceutically acceptable salt thereof, wherein Q is phenyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})$ $NR^{c1}R^{d1}$, $NR^{c1}R^{d1}$, $NR^{c1}C(O)R^{b1}$, $NR^{c1}C(O)OR^{a1}$ $NR^{c1}C(O)NR^{c1}R^{d1}$, $NR^{c1}S(O)R^{b1}$, $NR^{c1}S(O)_2R^{b1}$, $NR^{e1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

17. The compound of claim 1, or a pharmaceutically acceptable salt thereof, wherein Q is phenyl optionally substituted with 1 or 2 substituents independently selected from halo, $C_{1-6}$ alkyl, $C_{1-6}$ haloalkyl, CN, and $OR^{a1}$, wherein the $C_{1-6}$ alkyl is optionally substituted by CN.

18. The compound of claim 1, or a pharmaceutically acceptable salt thereof, wherein Q is $C_{3-14}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})$ $NR^{c1}R^{d1}$, $NR^{c1}R^{d1}$, $NR^{e1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{e1}S(O)_2NR^{c1}R^{d1}$, $S(O)R^{b1}$, $S(O)NR^{c1}R^{d1}$, $S(O)_2R^{b1}$, and $S(O)_2NR^{e1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

19. The compound of claim 1, or a pharmaceutically acceptable salt thereof, wherein Q is $C_{4-7}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})$ $NR^{c1}R^{d1}$, $NR^{c1}R^{d1}$, $NR^{c1}C(O)R^{b1}$, $NR^{e1}C(O)OR^{a1}$, $NR^{c1}C(O)NR^{c1}R^{d1}$, $NR^{c1}S(O)R^{b1}$, $NR^{c1}S(O)_2R^{b1}$, $NR^{e1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

20. The compound of claim 1, or a pharmaceutically acceptable salt thereof, wherein Q is $C_{4-7}$ cycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})$ $NR^{c1}R^{d1}$, $NR^{c1}R^{d1}$, $NR^{c1}C(O)R^{b1}$, $NR^{e1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$, and $NR^{c1}C(O)R^{b1}$.

21. The compound of claim 1, or a pharmaceutically acceptable salt thereof, wherein Q is $C_{4-7}$ cycloalkyl optionally substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$, and $NR^{c1}C(O)R^{b1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

22. The compound of claim 1, or a pharmaceutically acceptable salt thereof, wherein Q is $C_{4-7}$ cycloalkyl optionally substituted with 1 or 2 substituents independently selected from $Cy^1$, halo, $C_{1-6}$ alkyl, $C_{1-6}$ haloalkyl, CN, $OR^{a1}$, $NR^{c1}R^{d1}$, $C(O)NR^{c1}R^{d1}$ $NR^{c1}C(O)R^{b1}$, and $S(O)_2R^{b1}$, wherein the $C_{1-6}$ alkyl is optionally substituted by 1, 2, or 3 substituents independently selected from OH, CN, $C_{1-6}$ alkoxy, $C(O)NR^{c1}R^{d1}$, $NR^{c1}R^{d1}$ and $NR^{c1}C(O)R^{b1}$.

23. The compound of claim 1, or a pharmaceutically acceptable salt thereof, wherein Q is 5-14 membered heteroaryl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{e1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

24. The compound of claim 1, or a pharmaceutically acceptable salt thereof, wherein Q is 5-14 membered heteroaryl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$ $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl and $C_{2-6}$ alkynyl are optionally substituted by 1, 2, or 3 substituents independently selected from OH, CN, $C_{1-6}$ alkoxy, $NR^{c1}R^{d1}$, and $NR^{c1}C(O)R^{b1}$.

25. The compound of claim 1, or a pharmaceutically acceptable salt thereof, wherein Q is 5- or 6-membered heteroaryl optionally substituted with $Cy^1$, halo, $C_{1-6}$ alkyl, or $OR^{a1}$, wherein the $C_{1-6}$ alkyl is optionally substituted by $C_{1-6}$ alkoxy.

26. The compound of claim 1, or a pharmaceutically acceptable salt thereof, wherein Q is 5- or 6-membered heteroaryl optionally substituted with $Cy^1$, halo, $C_{1-6}$ alkyl, $C_{1-6}$ haloalkyl, or $OR^{a1}$, wherein the $C_{1-6}$ alkyl is optionally substituted by $C_{1-6}$ alkoxy or $NR^{c1}R^{d1}$.

27. The compound of claim 1, or a pharmaceutically acceptable salt thereof, wherein Q is 4-14 membered heterocycloalkyl optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$.

28. The compound of claim 1, or a pharmaceutically acceptable salt thereof, wherein Q is 5-10-membered heterocycloalkyl optionally substituted with 1 or 2 substituents independently selected from $Cy^1$, halo, $C_{1-6}$ alkyl, $C_{1-6}$ haloalkyl, $C(O)R^{b1}$, and $S(O)_2R^{b1}$.

29. The compound of claim 1, or a pharmaceutically acceptable salt thereof, wherein Q is 5- or 6-membered heterocycloalkyl optionally substituted with 1 or 2 substituents independently selected from $Cy^1$, halo, $C_{1-6}$ alkyl, $C_{1-6}$ haloalkyl, $C(O)R^{b1}$, and $S(O)_2R^{b1}$.

30. The compound of claim 1, or a pharmaceutically acceptable salt thereof, wherein L is a methylene linker.

31. The compound of claim 1, or a pharmaceutically acceptable salt thereof, wherein n is 0.

32. The compound of claim 1, or a pharmaceutically acceptable salt thereof, wherein n is 1.

33. The compound of claim 1, or a pharmaceutically acceptable salt thereof, wherein:

V is N or CRY, wherein $R^V$ is H, halo, or $C_{1-4}$ alkyl;
W is N or $CR^W$, wherein $R^W$ is H, halo, or $C_{1-4}$ alkyl;
the moiety represented by:

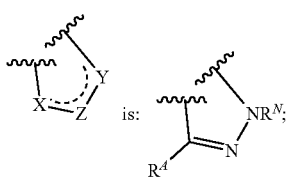

is:

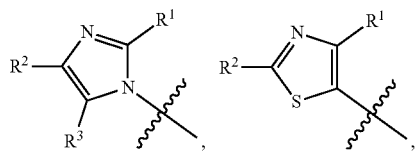

each $R^N$ is independently selected from H and $C_{1-4}$ alkyl;
$R^A$ is selected from H and $C_{1-4}$ alkyl;
Ring A is selected from:

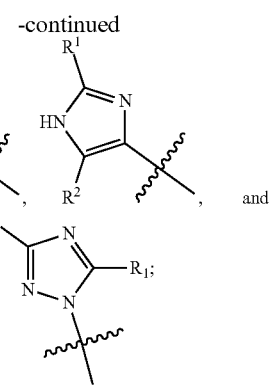

$R^1$, $R^2$, and $R^3$ are each independently selected from H and $C_{1-4}$ alkyl;

L is methylene;

n is 0 or 1;

Q is $C_{1-10}$ alkyl, $C_{6-10}$ aryl, $C_{3-14}$ cycloalkyl, 5-14 membered heteroaryl, or 4-14 membered heterocycloalkyl, wherein said $C_{1-10}$ alkyl, $C_{6-10}$ aryl, $C_{3-14}$ cycloalkyl, 5-14 membered heteroaryl, or 4-14 membered heterocycloalkyl of Q are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the $C_{1-6}$ alkyl is optionally substituted by 1, 2, or 3 substituents independently selected from OH, CN, $C_{1-6}$ alkoxy, and $NR^{c1}C(O)R^{b1}$;

wherein Q is other than H when n is 0;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{a1}$, $R^{b1}$, $R^{c1}$, $R^{d1}$, $R^{a2}$, $R^{b2}$, $R^{c2}$, and $R^{d2}$ is optionally substituted with 1, 2, 3, 4, or 5 substituents independently selected from $Cy^2$, $Cy^2$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)$ $NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$ $S(O)NR^{c3}R^{d3}$, $S(O)_2R^{b3}$, $NR^{c3}S(O)_2 R^{b3}$, $NR^{c3}S(O)_2NR^{c3}R^{d3}$, and $S(O)_2NR^{c3}R^{d3}$;

or $R^{c1}$ and $R^{d1}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$ $NR^{c3}S(O)_2NR^{c3}R^{d3}$, and $S(O)_2NR^{c3}R^{d3}$;

or $R^{c2}$ and $R^{d2}$ together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^2$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, each $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkylamino, di($C_{1-6}$ alkyl)amino, $C_{1-6}$ alkoxy, $C_{1-6}$ haloalkyl, and $C_{1-6}$ haloalkoxy;

each $R^{e1}$, $R^{e2}$, and $R^{e3}$ is independently selected from H, $C_{1-4}$ alkyl, and CN;

wherein one or more ring-forming C or N atoms of any aforementioned heterocycloalkyl group is optionally substituted by an oxo (=O) group; and wherein one or more ring-forming S atoms of any aforementioned heterocycloalkyl group is optionally substituted by one or two oxo (=O) groups.

34. The compound of claim 1, selected from:
5-(1H-Imidazol-1-yl)-N-((1r,4r)-4-(2-methoxyethoxy)cyclohexyl)-1H-indazole-7-carboxamide;
N-(2-Fluoro-6-(trifluoromethyl)benzyl)-5-(1H-imidazol-1-yl)-1H-pyrazolo[4,3-b]pyridine-7-carboxamide;
5-(1H-Imidazol-1-yl)-N-((1r,4r)-4-(2-methoxyethoxy)cyclohexyl)-1H-pyrazolo[3,4-c]pyridine-7-carboxamide;
N-((1r,4r)-4-(2-Methoxyethoxy)cyclohexyl)-5-(thiazol-5-yl)-1H-pyrazolo[4,3-b]pyridine-7-carboxamide;
N-((1r,4r)-4-(2-Methoxyethoxy)cyclohexyl)-5-(thiazol-5-yl)-1H-pyrazolo[3,4-c]pyridine-7-carboxamide;
5-(1H-Imidazol-1-yl)-N-((1r,4r)-4-(2-methoxyethoxy)cyclohexyl)-1H-pyrazolo[4,3-d]pyrimidine-7-carboxamide; and
N-(2-Fluoro-6-(trifluoromethyl)benzyl)-5-(1H-imidazol-1-yl)-1H-pyrazolo[3,4-c]pyridine-7-carboxamide;
or a pharmaceutically acceptable salt of any of the aforementioned.

35. The compound of claim 1, selected from:
N-(4,4-difluorocyclohexyl)-5-(1H-imidazol-1-yl)-1H-pyrazolo[3,4-c]pyridine-7-carboxamide;
N-((1r,4r)-4-(2-hydroxypropan-2-yl)cyclohexyl)-5-(1H-imidazol-1-yl)-1H-pyrazolo[3,4-c]pyridine-7-carboxamide;
5-(1H-imidazol-1-yl)-N-((1r,4r)-4-((2,2,2-trifluoroethyl)amino)cyclohexyl)-1H-pyrazolo[3,4-c]pyridine-7-carboxamide;
5-(1H-imidazol-1-yl)-N-((1s,4s)-4-((2,2,2-trifluoroethyl)amino)cyclohexyl)-1H-pyrazolo[3,4-c]pyridine-7-carboxamide;
N-(4,4-difluorocyclohexyl)-5-(1H-imidazol-1-yl)-1H-pyrazolo[4,3-d]pyrimidine-7-carboxamide;
5-(1H-imidazol-1-yl)-N-((1r,4r)-4-(trifluoromethyl)cyclohexyl)-1H-pyrazolo[4,3-d]pyrimidine-7-carboxamide;
5-(1H-imidazol-1-yl)-N-((1s,4s)-4-(trifluoromethyl)cyclohexyl)-1H-pyrazolo[4,3-d]pyrimidine-7-carboxamide;
5-(1H-imidazol-1-yl)-N-((1r,4r)-4-(trifluoromethyl)cyclohexyl)-1H-pyrazolo[3,4-c]pyridine-7-carboxamide;
N-((1r,4r)-4-(2-hydroxypropan-2-yl)cyclohexyl)-5-(1H-imidazol-1-yl)-1H-pyrazolo[4,3-d]pyrimidine-7-carboxamide;
5-(1H-imidazol-1-yl)-N-((1r,4r)-4-methoxycyclohexyl)-1H-pyrazolo[4,3-d]pyrimidine-7-carboxamide;
5-(1H-imidazol-1-yl)-N-((1s,4s)-4-((3,3,3-trifluoropropyl)amino)cyclohexyl)-1H-pyrazolo[3,4-c]pyridine-7-carboxamide; and
5-(1H-imidazol-1-yl)-N-((1r,4r)-4-((3,3,3-trifluoropropyl)amino)cyclohexyl)-1H-pyrazolo[3,4-c]pyridine-7-carboxamide;
or a pharmaceutically acceptable salt of any of the aforementioned.

36. The compound of claim 1, selected from:
5-(1H-imidazol-1-yl)-N-((1r,4r)-4-((2,2,2-trifluoroethyl)amino)cyclohexyl)-1H-pyrazolo[4,3-d]pyrimidine-7-carboxamide;
N-((1S,4r)-4-((S)-1-hydroxyethyl)cyclohexyl)-5-(1H-imidazol-1-yl)-1H-pyrazolo[3,4-c]pyridine-7-carboxamide;
N-((1R,4r)-4-((R)-1-hydroxyethyl)cyclohexyl)-5-(1H-imidazol-1-yl)-1H-pyrazolo[3,4-c]pyridine-7-carboxamide;
N-((1r,4r)-4-((2,2-difluoropropyl)amino)cyclohexyl)-5-(1H-imidazol-1-yl)-1H-pyrazolo[3,4-c]pyridine-7-carboxamide;
N-((1s,4s)-4-((2,2-difluoropropyl)amino)cyclohexyl)-5-(1H-imidazol-1-yl)-1H-pyrazolo[3,4-c]pyridine-7-carboxamide;

N-((1r,4r)-4-((2,2-difluoroethyl)amino)cyclohexyl)-5-(1H-imidazol-1-yl)-1H-pyrazolo[3,4-c]pyridine-7-carboxamide;

5-(1H-imidazol-1-yl)-N-((1r,4r)-4-(2-methoxyethoxy)cyclohexyl)-2-methyl-2H-pyrazolo[3,4-c]pyridine-7-carboxamide;

5-(1H-imidazol-1-yl)-N-((1r,4r)-4-(2-methoxyethoxy)cyclohexyl)-1-methyl-1H-pyrazolo[3,4-c]pyridine-7-carboxamide;

5-(1H-imidazol-1-yl)-N-((1r,4r)-4-(2-(methylamino)-2-oxoethyl)cyclohexyl)-1H-pyrazolo[3,4-c]pyridine-7-carboxamide;

N-((1r,4r)-4-(2-(dimethylamino)-2-oxoethoxy)cyclohexyl)-5-(1H-imidazol-1-yl)-1H-pyrazolo[4,3-d]pyrimidine-7-carboxamide;

N-((1r,4r)-4-(2-(dimethylamino)-2-oxoethoxy)cyclohexyl)-5-(1H-imidazol-1-yl)-1H-pyrazolo[3,4-c]pyridine-7-carboxamide;

5-(1H-imidazol-1-yl)-N-(6-(2-(pyrrolidin-1-yl) ethoxy)pyridin-3-yl)-1H-pyrazolo[3,4-c]pyridine-7-carboxamide;

N-(4-cyanophenyl)-5-(1H-imidazol-1-yl)-1H-pyrazolo[3,4-c]pyridine-7-carboxamide;

N-((1r,4r)-4-(2,2-difluoroethylamino)cyclohexyl)-5-(1H-imidazol-1-yl)-1H-pyrazolo[4,3-d]pyrimidine-7-carboxamide;

N-((1S,4r)-4-((S)-2-hydroxypropoxy)cyclohexyl)-5-(1H-imidazol-1-yl)-1H-pyrazolo[3,4-c]pyridine-7-carboxamide;

N-((1R,4r)-4-((R)-2-hydroxypropoxy)cyclohexyl)-5-(1H-imidazol-1-yl)-1H-pyrazolo[3,4-c]pyridine-7-carboxamide;

N-((1r,4r)-4-(acetamidomethyl)cyclohexyl)-5-(1H-imidazol-1-yl)-1H-pyrazolo[3,4-c]pyridine-7-carboxamide;

N-((1r,4r)-4-(cyanomethoxy)cyclohexyl)-5-(1H-imidazol-1-yl)-1H-pyrazolo[4,3-d]pyrimidine-7-carboxamide;

N-((1r,4r)-4-(cyanomethoxy)cyclohexyl)-5-(1H-imidazol-1-yl)-1H-pyrazolo[3,4-c]pyridine-7-carboxamide;

5-(1H-imidazol-1-yl)-N-((1r,4r)-4-(methylcarbamoyl)cyclohexyl)-1H-pyrazolo[3,4-c]pyridine-7-carboxamide;

5-(1H-imidazol-1-yl)-N-((1r,4r)-4-(methyl (2,2,2-trifluoroethyl)amino)cyclohexyl)-1H-pyrazolo[3,4-c]pyridine-7-carboxamide;

N-((1r,4r)-4-(cyanomethyl)cyclohexyl)-5-(1H-imidazol-1-yl)-1H-pyrazolo[3,4-c]pyridine-7-carboxamide;

N-(6-(2-(dimethylamino) ethoxy)pyridin-3-yl)-5-(1H-imidazol-1-yl)-1H-pyrazolo[3,4-c]pyridine-7-carboxamide;

5-(1H-imidazol-1-yl)-N-(6-(piperazin-1-yl)pyridin-3-yl)-1H-pyrazolo[3,4-c]pyridine-7-carboxamide;

N-((1r,4r)-4-(hydroxymethyl)cyclohexyl)-5-(1H-imidazol-1-yl)-1H-pyrazolo[3,4-c]pyridine-7-carboxamide;

N-((1s,4s)-4-hydroxy-4-methylcyclohexyl)-5-(1H-imidazol-1-yl)-1H-pyrazolo[3,4-c]pyridine-7-carboxamide;

N-((1r,4r)-4-(3,3-difluoroazetidin-1-yl)cyclohexyl)-5-(1H-imidazol-1-yl)-1H-pyrazolo[3,4-c]pyridine-7-carboxamide;

N-((1r,4r)-4-(1-hydroxycyclopropyl)cyclohexyl)-5-(1H-imidazol-1-yl)-1H-pyrazolo[3,4-c]pyridine-7-carboxamide;

5-(1H-imidazol-1-yl)-N-(6-(trifluoromethyl)pyridin-3-yl)-1H-pyrazolo[3,4-c]pyridine-7-carboxamide;

N-(6-(2-(2-oxa-6-azaspiro [3.3]heptan-6-yl) ethoxy)pyridin-3-yl)-5-(1H-imidazol-1-yl)-1H-pyrazolo[3,4-c]pyridine-7-carboxamide;

5-(1H-imidazol-1-yl)-N-(6-(2,2,2-trifluoroethoxy)pyridin-3-yl)-1H-pyrazolo[3,4-c]pyridine-7-carboxamide;

N-((1r,4r)-4-(3,3-difluoropyrrolidin-1-yl)cyclohexyl)-5-(1H-imidazol-1-yl)-1H-pyrazolo[3,4-c]pyridine-7-carboxamide;

5-(1H-imidazol-1-yl)-N-((1r,4r)-4-(oxetan-3-ylamino)cyclohexyl)-1H-pyrazolo[3,4-c]pyridine-7-carboxamide;

5-(1H-imidazol-1-yl)-N-((1r,4r)-4-(3-(trifluoromethyl)azetidin-1-yl)cyclohexyl)-1H-pyrazolo[3,4-c]pyridine-7-carboxamide;

5-(1H-imidazol-1-yl)-N-(isoindolin-5-yl)-1H-pyrazolo[3,4-c]pyridine-7-carboxamide;

N-(2-acetylisoindolin-5-yl)-5-(1H-imidazol-1-yl)-1H-pyrazolo[3,4-c]pyridine-7-carboxamide;

N-((1r,4r)-4-(1-hydroxycyclopropyl)cyclohexyl)-5-(1H-imidazol-1-yl)-1H-pyrazolo[4,3-d]pyrimidine-7-carboxamide;

5-(1H-imidazol-1-yl)-N-((1s,4s)-4-methyl-4-((2,2,2-trifluoroethyl)amino)cyclohexyl)-1H-pyrazolo[3,4-c]pyridine-7-carboxamide;

5-(1H-imidazol-1-yl)-N-((1r,4r)-4-methyl-4-((2,2,2-trifluoroethyl)amino)cyclohexyl)-1H-pyrazolo[3,4-c]pyridine-7-carboxamide;

5-(1H-imidazol-1-yl)-N-((1r,4r)-4-(3-(trifluoromethyl)azetidin-1-yl)cyclohexyl)-1H-pyrazolo[4,3-d]pyrimidine-7-carboxamide;

5-(1H-imidazol-1-yl)-N-((1r,4r)-4-(methylcarbamoyl)cyclohexyl)-1H-pyrazolo[4,3-d]pyrimidine-7-carboxamide;

N-((1r,4r)-4-(acetamidomethyl)cyclohexyl)-5-(1H-imidazol-1-yl)-1H-pyrazolo[4,3-d]pyrimidine-7-carboxamide;

N-((1r,4r)-4-((2,2-difluoropropyl)amino)cyclohexyl)-5-(1H-imidazol-1-yl)-1H-pyrazolo[4,3-d]pyrimidine-7-carboxamide;

N-(3,3-difluoropropyl)-5-(1H-imidazol-1-yl)-1H-pyrazolo[3,4-c]pyridine-7-carboxamide;

5-(1H-imidazol-1-yl)-N-((1s,4s)-4-methyl-4-((2,2,2-trifluoroethyl)amino)cyclohexyl)-1H-pyrazolo[3,4-c]pyridine-7-carboxamide;

5-(1H-imidazol-1-yl)-N-((1r,4r)-4-(methyl (2,2,2-trifluoroethyl)amino)cyclohexyl)-1H-pyrazolo[4,3-d]pyrimidine-7-carboxamide;

5-(1H-imidazol-1-yl)-N-((1r,4r)-4-(3,3,3-trifluoropropoxy)cyclohexyl)-1H-pyrazolo[3,4-c]pyridine-7-carboxamide;

5-(1H-imidazol-1-yl)-N-((1r,4r)-4-(((2,2,2-trifluoroethyl)amino)methyl)cyclohexyl)-1H-pyrazolo[3,4-c]pyridine-7-carboxamide;

5-(1H-imidazol-1-yl)-N-((1s,4s)-4-(2,2,2-trifluoroethoxy)cyclohexyl)-1H-pyrazolo[3,4-c]pyridine-7-carboxamide;

5-(1H-imidazol-1-yl)-N-((1r,4r)-4-(2,2,2-trifluoroethoxy)cyclohexyl)-1H-pyrazolo[3,4-c]pyridine-7-carboxamide;

N-((1r,4r)-4-((1,1-difluoro-2-methylpropan-2-yl)amino)cyclohexyl)-5-(1H-imidazol-1-yl)-1H-pyrazolo[3,4-c]pyridine-7-carboxamide; and N-((1s,4s)-4-((1,1-difluoro-2-methylpropan-2-yl)amino)cyclohexyl)-5-(1H-imidazol-1-yl)-1H-pyrazolo[3,4-c]pyridine-7-carboxamide;

or a pharmaceutically acceptable salt of any of the aforementioned.

37. The compound of claim 1, selected from:

N-((1r,4r)-4-(3,3-difluoroazetidin-1-yl)cyclohexyl)-5-(1H-imidazol-1-yl)-1H-pyrazolo[4,3-d]pyrimidine-7-carboxamide;

N-((1s,4s)-4-(3-fluoro-3-methylazetidin-1-yl)cyclohexyl)-5-(1H-imidazol-1-yl)-1H-pyrazolo[4,3-d]pyrimidine-7-carboxamide;

N-((1r,4r)-4-(3-fluoro-3-methylazetidin-1-yl)cyclohexyl)-5-(1H-imidazol-1-yl)-1H-pyrazolo[4,3-d]pyrimidine-7-carboxamide;

N-((1r,4r)-4-(3-cyano-3-methylazetidin-1-yl)cyclohexyl)-5-(1H-imidazol-1-yl)-1H-pyrazolo[3,4-c]pyridine-7-carboxamide;

N-((1s,4s)-4-(3-cyano-3-methylazetidin-1-yl)cyclohexyl)-5-(1H-imidazol-1-yl)-1H-pyrazolo[3,4-c]pyridine-7-carboxamide;

N-((1r,3r)-3-(2-hydroxypropan-2-yl)cyclobutyl)-5-(1H-imidazol-1-yl)-1H-pyrazolo[4,3-d]pyrimidine-7-carboxamide;

N-((1r,3r)-3-(2-hydroxypropan-2-yl)cyclobutyl)-5-(1H-imidazol-1-yl)-1H-pyrazolo[3,4-c]pyridine-7-carboxamide;

N-((1r,4r)-4-(3-cyanoazetidin-1-yl)cyclohexyl)-5-(1H-imidazol-1-yl)-1H-pyrazolo[3,4-c]pyridine-7-carboxamide;

5-(1H-imidazol-1-yl)-N-((1r,4r)-4-(((2,2,2-trifluoroethyl)amino)methyl)cyclohexyl)-1H-pyrazolo[4,3-d]pyrimidine-7-carboxamide;

5-(1H-imidazol-1-yl)-N-((1s,4s)-4-methyl-4-((2,2,2-trifluoroethyl)amino)cyclohexyl)-1H-pyrazolo[4,3-d]pyrimidine-7-carboxamide;

5-(1H-imidazol-1-yl)-N-((1r,4r)-4-methyl-4-((2,2,2-trifluoroethyl)amino)cyclohexyl)-1H-pyrazolo[4,3-d]pyrimidine-7-carboxamide;

5-(1H-imidazol-1-yl)-N-((1r,4r)-4-((1,1,1-trifluoro-2-methylpropan-2-yl)amino)cyclohexyl)-1H-pyrazolo[4,3-d]pyrimidine-7-carboxamide; and 5-(1H-imidazol-1-yl)-N-((1s,4s)-4-((1,1,1-trifluoro-2-methylpropan-2-yl)amino)cyclohexyl)-1H-pyrazolo[4,3-d]pyrimidine-7-carboxamide;

or a pharmaceutically acceptable salt of any of the aforementioned.

38. A pharmaceutical composition comprising a compound of claim 1, or a pharmaceutically acceptable salt thereof, and at least one pharmaceutically acceptable excipient.

39. A method of inhibiting a function of CD38 comprising contacting a compound of claim 1, or a pharmaceutically acceptable salt thereof, with the CD38.

40. The method of claim 39, wherein the CD38 is in a cell.

41. The method of claim 39, wherein the contacting occurs in vitro.

42. The method of claim 39, wherein the contacting occurs in vivo.

43. A method of treating cancer in a patient in need thereof comprising administering to the patient a therapeutically effective amount of a compound of claim 1, or a pharmaceutically acceptable salt thereof, wherein the cancer is lung cancer, melanoma, or colon cancer.

44. The method of claim 43, wherein the cancer is lung cancer.

45. The method of claim 43, wherein the cancer is melanoma.

46. The method of claim 43, wherein the cancer is colon cancer.

47. The compound of claim 1, or a pharmaceutically acceptable salt thereof, wherein $R^N$ is H.

48. The compound of claim 1, wherein the compound is N-((1r,4r)-4-(2-hydroxypropan-2-yl)cyclohexyl)-5-(1H-imidazol-1-yl)-1H-pyrazolo[3,4-c]pyridine-7-carboxamide, or a pharmaceutically acceptable salt thereof.

49. The compound of claim 1, wherein the compound is 5-(1H-imidazol-1-yl)-N-((1r,4r)-4-((2,2,2-trifluoroethyl)amino)cyclohexyl)-1H-pyrazolo[3,4-c]pyridine-7-carboxamide, or a pharmaceutically acceptable salt thereof.

50. The compound of claim 1, wherein the compound is 5-(1H-imidazol-1-yl)-N-((1r,4r)-4-((3,3,3-trifluoropropyl)amino)cyclohexyl)-1H-pyrazolo[3,4-c]pyridine-7-carboxamide, or a pharmaceutically acceptable salt thereof.

51. The compound of claim 1, wherein the compound is 5-(1H-imidazol-1-yl)-N-((1r,4r)-4-((2,2,2-trifluoroethyl)amino)cyclohexyl)-1H-pyrazolo[4,3-d]pyrimidine-7-carboxamide, or a pharmaceutically acceptable salt thereof.

52. The compound of claim 1, wherein the compound is N-((1r,4r)-4-((2,2-difluoropropyl)amino)cyclohexyl)-5-(1H-imidazol-1-yl)-1H-pyrazolo[3,4-c]pyridine-7-carboxamide, or a pharmaceutically acceptable salt thereof.

53. The compound of claim 1, wherein the compound is N-((1r,4r)-4-((2,2-difluoroethyl)amino)cyclohexyl)-5-(1H-imidazol-1-yl)-1H-pyrazolo[3,4-c]pyridine-7-carboxamide, or a pharmaceutically acceptable salt thereof.

* * * * *